(12) United States Patent
Hall et al.

(10) Patent No.: US 11,325,905 B2
(45) Date of Patent: May 10, 2022

(54) IMIDOPIPERIDINE COMPOUNDS AS INHIBITORS OF HUMAN POLYNUCLEOTIDE KINASE PHOSPHATASE

(71) Applicant: THE GOVERNORS OF THE UNIVERSITY OF ALBERTA, Edmonton (CA)

(72) Inventors: Dennis Hall, Edmonton (CA); Michael Weinfeld, Edmonton (CA); Sylvain Bernard, Longueuil (CA); Tristan Verdelet, Fontenay Aux Roses (FR); Timothy Morgan, Edmonton (CA); Vikie Lamontagne, Longueuil (CA); Zahra Shire, Edmonton (CA); Afsaneh Lavasanifar, Edmonton (CA)

(73) Assignee: The Governors of the University of Alberta, Edmonton (CA)

( * ) Notice: Subject to any disclaimer, the term of this patent is extended or adjusted under 35 U.S.C. 154(b) by 0 days.

(21) Appl. No.: 16/500,885

(22) PCT Filed: Apr. 5, 2018

(86) PCT No.: PCT/CA2018/050422
§ 371 (c)(1),
(2) Date: Oct. 4, 2019

(87) PCT Pub. No.: WO2018/184113
PCT Pub. Date: Oct. 11, 2018

(65) Prior Publication Data
US 2020/0148675 A1 May 14, 2020

Related U.S. Application Data

(60) Provisional application No. 62/482,060, filed on Apr. 5, 2017, provisional application No. 62/590,322, filed on Nov. 23, 2017, provisional application No. 62/590,490, filed on Nov. 24, 2017.

(51) Int. Cl.
| | | |
|---|---|---|
| *C07D 471/04* | (2006.01) |
| *A61K 47/62* | (2017.01) |
| *A61P 35/00* | (2006.01) |
| *A61K 9/107* | (2006.01) |
| *A61K 47/34* | (2017.01) |
| *A61K 31/4745* | (2006.01) |

(52) U.S. Cl.
CPC ........... *C07D 471/04* (2013.01); *A61K 9/107* (2013.01); *A61K 47/34* (2013.01); *A61K 47/62* (2017.08); *A61P 35/00* (2018.01); *A61K 31/4745* (2013.01)

(58) Field of Classification Search
CPC .. C07D 471/04; A61K 9/107; A61K 31/4745; A61K 47/62; A61K 47/34; A61P 35/00
See application file for complete search history.

(56) References Cited

U.S. PATENT DOCUMENTS

2012/0040916 A1* 2/2012 Moon ................ A61P 43/00
514/21.1

FOREIGN PATENT DOCUMENTS

| WO | WO-2010/075282 A1 | 7/2010 |
| WO | WO-2010/139069 A1 | 12/2010 |
| WO | WO-2012/058763 A1 | 5/2012 |

OTHER PUBLICATIONS

Journal of Combinatorial Chemistry 2007, 9, 695-703. (Year: 2007).*
Tailor et al. Organic Letters 2000, 2, 3715-3718. (Year: 2000).*
Ulaczyk-Lesanko et al. Journal of Combinatorial Chemistry 2007, 9, 695-703. (Year: 2007).*
CAS RN: 1004283-04-4; 111H-Pyrrolo[3,4-b]pyridine-5,7(2H,6H)-dione,4a,7a-dihydro-2-(l-hydroxy-3-phenyl-2-propyn-l-yl)-6-methyl-1-( 1-piperidinyl)-11 (1 Page).
CAS RN: 1005102-34-0; 111H-Pyrrolo[3,4-b]pyridine-5,7(2H,6H)-dione,4a,7a-dihydro-2-(l-hydroxy-2-methylpropyl)-6-methyl-l-(1-piperidinyl)-11 (1 Page).
CAS RN: 1005153-30-9; 111H-Pyrrolo[3,4-b]pyridine-5,7(2H,6H)-dione,4a,7a-dihydro-2-[l-hydroxy-3-(4-nitrophenyl)-2-propen-l-yl]-6-(phenylmethyl)-l-( 4H-l,2,4-triazol-4-yl)-11 (1 Page).
CAS RN: 1005153-28-5; 111H-Pyrrolo[3,4-b]pyrldine-5,7(2H,6H)-dlone,4a,7a-dlhydro-2-(l-hydroxy-2-phenylethyl)-6-(phenylmethyl)-l-(4H-l,2,4-triazol-4-yl)-11 (1 Page).
CAS RN: 1005153-25-2; 111H-Pyrrolo[3,4-b]pyridine-5,7(2H,6H)-dione,4a,7a-dihydro-2-(l-hydroxy-2-phenylpropyl)-6-(phenylmethyl)-1-( 4H-1,2,4-triazol-4-yl)-11 (1 Page).
CAS RN: 1005102-80-6; 111H-Pyrrolo[3,4-b]pyridine-5,7(2H,6H)-dione,4a,7a-dihydro-2-(l-hydroxy-2,2-diphenylethyl)-6-(phenylmethyl)-l-( 4H-1,2,4-triazol-4-yl)-11 (1 Page).
CAS RN: 1005153-27-4; 111H-Pyrrolo[3,4-b]pyridine-5,7(2H,6H)-dione,4a,7a-dihydro-2-[l-hydroxy-3-(5-methyl-2-furanyl)butyl]-6-(phenylmethyl)-l-(4H-l ,2,4-triazol-4-yl)1-1 (1 Page).
CAS RN: 1005153-07-0; 111H-Pyrrolo[3,4-b]pyridine-5,7(2H,6H)-dione,4a,7a-dihydro-2-(1-hydroxyundecyl)-6-(phenylmethyl)-1-(4H-l ,2,4-triazol-4-yl)-11 (1 Page).
CAS RN: 1005153-06-9; 111H-Pyrrolo[3,4-b]pyridine-5,7(2H,6H)-dione,4a,7a-dihydro-2-(l-hydroxypentyl)-6-(phenylmethyl)-l-(4H-l ,2,4-triazol-4-yl)-11 (1 Page).
CAS RN: 1005128-98-2; 111H-Pyrrolo[3,4-b]pyridine-5,7(2H,6H)-dione,2-(2-ethyl-l-hydroxyhexyl)-4a,7a-dihydro-6-(phenylmethyl)-1-(4H-l ,2,4-triazol-4-yl)-11 (1 Page).
CAS RN: 1005153-05-8; 111H-Pyrrolo[3,4-b]pyrldine-5,7(2H,6H)-dlone,4a,7a-dihydro-2-(l-hydroxyundecyl)-6-methyl-l-(l-piperidinyl)-11 (1 Page).
CAS RN: 1005144-98-8; 111H-Pyrrolo[3,4-b]pyridine-5,7(2H,6H)-dione,2-(2-ethyl-l-hydroxybutyl)-4a,7a-dihydro-6-methyl-l-(1-piperidinyl)-11 (1 Page).
CAS RN: 1005144-70-6; 111H-Pyrrolo[3,4-b]pyridine-5,7(2H,6H)-dione,4a,7a-dihydro-2-(l-hydroxypentyl)-6-methyl-l-(l-piperidinyl)-11 (1 Page).

(Continued)

*Primary Examiner* — D Margaret M Seaman
(74) *Attorney, Agent, or Firm* — Clark & Elbing LLP

(57) ABSTRACT

There is described herein imidopiperidine compounds as inhibitors of human polynucleotide kinase phosphatase.

15 Claims, 38 Drawing Sheets
(27 of 38 Drawing Sheet(s) Filed in Color)
Specification includes a Sequence Listing.

(56) References Cited

OTHER PUBLICATIONS

CAS RN: 1005145-62-9; 111H-Pyrrolo[3,4-b]pyridine-5,7(2H,6H)-dione,4a,7a-dihydro-2-(l-hydroxypentyl)-6-methyl-l-(phenylamlno)-11 (1 Page).
CAS RN: 1005145-41-4; 111H-Pyrrolo[3,4-b]pyridine-5,7(2H,6H)-dione,4a,7a-dihydro-2-(l-hydroxy-2,2-dimethylpropyl)-6-methyl-l-(phenylamino)-11 (1 Page).
CAS RN: 1005145-21-0; 111H-Pyrrolo[3,4-b]pyridine-5,7(2H,6H)-dione,2-(2-ethyl-l-hydroxyhexyl)-4a,7a-dihydro-6-methyl-l-(phenylamino)-11 (1 Page).
CAS RN: 1005144-76-2; 111H-Pyrrolo[3,4-b]pyridine-5,7(2H,6H)-dione,4a,7a-dihydro-2-[l-hydroxy-3-(5-methyl-2-furanyl)butyl]-6-methyl-l-(phenylamino)-11 (1 Page).
CAS RN: 1005129-74-7; 111H-Pyrrolo[3,4-b]pyridine-5,7(2H,6H)-dione,1-[(2,4-dinitrophenyl)amino]-4a,7a-dihydro-2-(l-hydroxyundecyl)-6-methyl-11 (1 Page).
CAS RN: 1005129-31-6; 111H-Pyrrolo[3,4-b]pyridine-5,7(2H,6H)-dione,4a,7a-dihydro-2-(l-hydroxy-2-methylpropyl)-6-methyl-l-(phenylamino)-11 (1 Page).
CAS RN: 1005102-73-7; 11 H-Pyrrolo[3,4-b]pyridine-5,7(2H,6H)-dione,1-(diphenylamino)-4a,7a-dihydro-2-(l-hydroxypentyl)-6-methyl-11 (1 Page).
CAS RN: 1005102-35-1; 111H-Pyrrolo[3,4-b]pyridine-5,7(2H,6H)-dione,2-(2-ethyl-l-hydroxybutyl)-4a,7a-dihydro-6-methyl-l-(phenylamino)-11 (1 Page).
CAS RN: 1005098-79-2; 111H-Pyrrolo[3,4-b]pyridine-5,7(2H,6H)-dione,4a,7a-dihydro-2-(l-hydroxyundecyl)-6-methyl-l-[ (3,4,5-trimethoxyphenyl)amino]-11 (1 Page).
CAS RN: 1005129-69-0; N-[2,4a,5,6,7,7a-hexahydro-2-[l-hydroxy-3-(5-methyl-2-furanyl)butyl]-6-methyl-5,7-dioxo-1 H-pyrrolo[3,4-b]pyridin-l-yl]-, 1,1-dimethylethyl ester (1 Page).
CAS RN: 1005128-91-5; Carbamic acid,N-[2,4a,5,6,7,7a-hexahydro-2-(l-hydroxyundecyl)-6-methyl-5,7-dioxo-1H-pyrrolo[3,4-b]pyridin-1-yl]-, 1,1-dimethylethyl ester (1 Page).
CAS RN: 1005145-38-9; 1H-Pyrrolo[3,4-b]pyridine-5,7(2H,6H)-dione,4a,7a-dihydro-2-[l-hydroxy-2-(phenylmethoxy)ethyl]-6-methyl-l-(phenylamino)-(1 Page).
CAS RN: 1005144-82-0; 1H-Pyrrolo[3,4-b]pyridine-5,7(2H,6H)-dione,1-[(2,4-dinitrophenyl)amino]-4a,7a-dihydro-2-[ 1-hydroxy-2-(phenylmethoxy)ethyl]-6-methyl-(1 Page).
CAS RN: 1005103-03-6; 1H-Pyrrolo[3,4-b]pyridine-5,7(2H,6H)-dione,1-(diphenylamino)-4a,7a-dihydro-2-[l-hydroxy-2-(phenylmethoxy)ethyl]-6-methyl-(1 Page).
CAS RN: 1005144-97-7; 1H-Pyrrolo[3,4-b]pyridine-5,7(2H,6H)-dione,4a,7a-dihydro-2-(l-hydroxy-2,2-dlphenylethyl)-6-methyl-l-(phenylamino)-(1 Page).
CAS RN: 1005103-00-3; 1H-Pyrrolo[3,4-b]pyridine-5,7(2H,6H)-dione,1-(diphenylamino)-4a,7a-dihydro-2-(l-hydroxy-2-phenylethyl)-6-methyl-(1 Page).
CAS RN: 1005102-42-0; 1H-Pyrrolo[3,4-b]pyridine-5,7(2H,6H)-dione,4a,7a-dihydro-2-(l-hydroxy-2-phenylpropyl)-6-methyl-l-(phenylamino)-(1 Page).
CAS RN: 1005102-13-5; 1H-Pyrrolo[3,4-b]pyrldlne-5,7(2H,6H)-dione,1-(diphenylamino)-4a,7a-dihydro-2-(l-hydroxy-2-phenylpropyl)-6-methyl-(1 Page).
CAS RN: 1005144-96-6; 1H-Pyrrolo[3,4-b]pyridine-5,7(2H,6H)-dione,4a,7a-dihydro-2-[l-hydroxy-3-(4-nitrophenyl)-2-propen-l-yl]-6-methyl-1-(1-piperidinyl)-(1 Page).
CAS RN: 1005129-18-9; 1H-Pyrrolo[3,4-b]pyridine-5,7(2H,6H)-dione,4a,7a-dihydro-2-(l-hydroxy-2-buten-l-yl)-6-methyl-l-(1-piperidinyl)-(1 Page).
CAS RN: 1005144-80-8; 1H-Pyrrolo[3,4-b]pyrldlne-5,7(2H,6H)-dione,1-[(2,4-dinitrophenyl)amino]-4a,7a-dihydro-2-(l-hydroxy-2-buten-l-yl)-6-methyl-(1 Page).
CAS RN: 1005129-17-8; 1H-Pyrrolo[3,4-b]pyridine-5,7(2H,6H)-dione,4a,7a-dihydro-2-[l-hydroxy-3-(4-nitrophenyl)-2-propen-l-yl]-6-methyl-l-(phenylamino)-(1 Page).
CAS RN: 1005102-63-5; 1H-Pyrrolo[3,4-b]pyridine-5,7(2H,6H)-dione,1-(diphenylamino)-4a,7a-dihydro-2-(l-hydroxy-2-buten-l-yl)-6-methyl-(1 Page).
CAS RN: 1005102-38-4; Carbamic acid,N-[2,4a,5,6,7,7a-hexahydro-2-(l-hydroxy-2-buten-l-yl)-6-methyl-5,7-dioxo-IH-pyrrolo[3,4-b]pyridin-l-yl]-, 1,1-dimethylethyl ester (1 Page).
CAS RN: 1005144-69-3; 1H-Pyrrolo[3,4-b]pyridine-5,7(2H,6H)-dione,4a,7a-dihydro-2-(l-hydroxy-3-phenyl-2-propyn-l-yl)-6-methyl-l-(phenylamino)-(1 Page).
Adams et al., "Amphiphilic Block Copolymers for Drug Delivery," J Pharm Sci. 92(7):1343-1355 (2003).
Aliabadi et al., "Micelles of Methoxy Poly(Ethylene Oxide)-b-Poly(ε-caprolactone) as Vehicles for the Solubilization and Controlled Delivery of Cyclosporine A," J Control Release. 104(2): 301-311 (2005).
Andres et al., "Recognition and Repair of Chemically Heterogeneous Structures at DNA Ends," Environ Mol Mutagen. 56(1):1-21. (2015).
Bernstein et al., "The Molecular Architecture of the Mammalian DNA Repair Enzyme, Polynucleotide Kinase," Mol Cell. 17(5): 657-670 (2005).
Brown et al., "Targeting DNA Repair in Cancer: Beyond PARP Inhibitors," Cancer Discov. 7(1): 20-37 (2017).
Colzani et al., "Design of Smart GE11-PLGA/PEG-PLGA Blend Nanoparticulate Platforms for Parenteral Administration of Hydrophilic Macromolecular Drugs: Synthesis, Preparation and in Vitro/ex Vivo Characterization," Int J Pharm. 511(2):1112-1123 (2016).
Curtin et al., "Inhibiting the DNA Damage Response as a Therapeutic Manoeuvre in Cancer," Br J Pharmacol. 169(8):1745-1765 (2013).
Dai et al., "Combination Antitumor Therapy With Targeted Dual-Nanomedicines," Adv Drug Deliv Rev. 115:23-45 (2017).
Fan et al., "Design and Biological Activity of Epidermal Growth Factor Receptor-Targeted Peptide Doxorubicin Conjugate," Biomed Pharmacother.70: 268-73 (2015).
Fanta et al., "Production, Characterization, and Epitope Mapping of Monoclonal Antibodies Against Human Polydeoxyribonucleotide Kinase," Hybridoma. 20(4):237-242 (2001).
Freschauf et al., "Identification of a Small Molecule Inhibitor of the Human DNA Repair Enzyme Polynucleotide Kinase/Phosphatase," Cancer Res. 69(19):7739-7746 (2009).
Garg et al., "Polymeric Micelles Based on Poly(Ethylene Oxide) and α-carbon Substituted Poly(ε-caprolactone): an in Vitro Study on the Effect of Core Forming Block on Polymeric Micellar Stability, Biocompatibility, and Immunogenicity," Colloids Surf B Biointerfaces. 132: 161-170 (2015).
Gauthier et al., "In Vivo and In Vitro Antitumor Activity of Oxaliplatin in Combination With Cetuximab in Human Colorectal Tumor Cell Lines Expressing Different Level of EGFR," Cancer Chemother Pharmacol. 57(6): 709-718 (2006).
Gavande et al., "DNA Repair Targeted Therapy: the Pastor Future of Cancer Treatment?," Pharmacol Ther. 160:65-83 (2016).
Herrero et al., "Advanced Targeted Therapies in Cancer: Drug Nanocarriers, the Future of Chemotherapy," Eur J Pharm Biopharm. 93: 52-79. (2015).
Honary et al., "The Effect of Self-Assembly Conditions on the Size of Di- and Tri-block Copolymer Micelles: Solicitation From Response Surface Methodology," Pharm Dev Technol. 20(8): 957-965 (2015).
Houdaihed et al., "Overcoming the Road Blocks: Advancement of Block Copolymer Micelles for Cancer Therapy in the Clinic," Mol Pharm.14(8):2503-2517 (2017).
Hsu et al., "The Role of HER2, EGFR, and Other Receptor Tyrosine Kinases in Breast Cancer," Cancer Metastasis Rev. 35(4):575-588 (2016).
Hung et al., "Epidermal Growth Factor Receptor Mutation Enhances Expression of Vascular Endothelial Growth Factor in Lung Cancer," Oncol Lett. 12(6): 4598-4604 (2016).
International Preliminary Report on Patentability for International Application No. PCT/CA2018/050422, dated Oct. 8, 2019 (11 pages).
International Search Report and Written Opinion for International Application No. PCT/CA2018/050422, dated Jul. 10, 2018 (22 pages).

(56) References Cited

OTHER PUBLICATIONS

Jackson et al., "Synthetic Lethal Approaches for Assessing Combinatorial Efficacy of Chemotherapeutic Drugs," Pharma Ther. 162: 69-85 (2016).
Jilani et al., "Molecular Cloning of the Human Gene, PNKP, Encoding a Polynucleotide Kinase 3'-Phosphatase and Evidence for Its Role In Repair of DNA Strand Breaks Caused by Oxidative Damage," J Biol Chem. 274 (34):24176-24186 (1999).
Karimi-Busheri et al., "Molecular Characterization of a Human DNA Kinase," J Biol Chem. 274(34): 24187-24194 (1999).
Lavasanifar et al., "The Effect of Fatty Acid Substitution on the in Vitro Release of Amphotericin B From Micelles Composed of Poly(Ethylene Oxide)-Block-Poly(N-hexyl Stearate-I-Aspartamide)," J Control Release. 79(1-3): 165-172 (2002).
Leung et al.,"Synthetic Lethality in Lung Cancer and Translation to Clinical Therapies," Mol Cancer. 15(1):61 (2016).
Liu et al., "Targeting Tumor Suppressor Genes for Cancer Therapy," Bioessays. 37(12):1277-1286 (2015).
Lu et al., "Polymeric Micelles and Alternative Nanonized Delivery Vehicles for Poorly Soluble Drugs," Int J Pharma. 453(1): 198-214 (2013).
Mahmud et al., "The Effect of Block Copolymer Structure on the Internalization of Polymeric Micelles by Human Breast Cancer Cells," Colloids Surf B Biointerfaces. 45(2):82-89 (2005).
Mahmud et al., "Novel Self-Associating Poly(Ethylene Oxide)-Block-Poly(e-caprolactone) Block Copolymers With Functional Side Groups on the Polyester Block for Drug Delivery," Macromolecules. 39(26): 9419-9428 (2006).
Marmol et al., "Colorectal Carcinoma: A General Overview and Future Perspectives in Colorectal Cancer," Int J Mol Sci. 18(1):197 (2017).
Marzbali et al., "Polymeric Micelles as Mighty Nanocarriers for Cancer Gene Therapy A Review," Cancer Chemotherapy Pharmacol. 79(4): 637-649 (2017).
Mathews et al., "Peptide Modified Polymeric Micelles Specific for Breast Cancer Cells," Bioconjug Chem. 24(4):560-570 (2013).
Matsumura et al., "Polymeric Micellar Delivery Systems In Oncology," Jpn J Clin Oncol. 38(12): 793-802 (2008).
Mereniuk et al., "Genetic Screening for Synthetic Lethal Partners of Polynucleotide Kinase/Phosphatase: Potential for Targeting SHP-1-depleted Cancers," Cancer Res. 72(22):5934-5944 (2012).
Mereniuk et al., "Synthetic Lethal Targeting of PTEN-Deficient Cancer Cells using Selective Disruption of Polynucleotide Kinase/Phosphatase," Mol Cancer Ther. 12 (10): 2135-44, (2013).
Nijman "Synthetic Lethality: General Principles, Utility and Detection Using Genetic Screens in Human Cells," FEBS Lett. 585 (1): 1-6 (2011).
Nishiyama et al., "Development of Polymeric Micelles for Targeting Intractable Cancers," Cancer Sci. 107(7): 867-874 (2016).
Rasouli-Nia et al., "Stable Down-Regulation of Human Polynucleotide Kinase Enhances Spontaneous Mutation Frequency and Sensitizes Cells to Genotoxic Agents," Proc Natl Acad Sci U S A.101(18): 6905-6910 (2004).
Shire et al. "Processing Strand Break Termini in the DNA Single-Strand Break Repair Pathway. In: Wilson III DM, Editor. The Base Excision Repair Pathway: Molecular Mechanisms and Role in Disease Development and Therapeutic Design," World Scientific, London, 281-321 (2017).
Srinivasan et al., "Multifunctional Nanomaterials and Their Applications in Drug Delivery and Cancer Therapy," Nanomaterials. 5(4):1690-1703 (2015).
Stover et al., "Biomarkers of Response and Resistance to DNA Repair Targeted Therapies," Clin Cancer Res. 22(23): 5651-5660 (2016).
Talelli et al., "Core-Crosslinked Polymeric Micelles: Principles, Preparation, Biomedical Applications and Clinical Translation," Nano Today. 10(1): 93-117 (2015).
Tang et al., "Effects of Surface Displayed Targeting Ligand Ge11 on Liposome Distribution and Extravasation in Tumor," Mol Pharma. 11(10): 3242-3250 (2014).
Toure et al., "A Three-Component Reaction for Diversity-oriented Synthesis of Polysubstituted Piperidines: Solution and Solid-phase Optimization of the First Tandem Aza[4+2]/allylboration," Chemistry. 9(2):466-474 (2003).
Ulbrich et al., "Targeted Drug Delivery With Polymers and Magnetic Nanoparticles: Covalent and Noncovalent Approaches, Release Control, and Clinical Studies," Chem Rev. 116(9): 5338-5431 (2016).
Weinfield et al., "Tidying Up Loose Ends: the Role of Polynucleotide Kinase/phosphatase in DNA Strand Break Repair," Trends Biochem Sci. 36 (5):262-271 (2011).
Xiong et al., "Conjugation of Arginine-Glycine-Aspartic Acid Peptides to Poly(Ethylene Oxide)-b-Poly(e-caprolactone) Micelles for Enhanced Intracellular Drug Delivery to Metastatic Tumor Cells," Biomacromolecules.8(3): 874-884 (2007).
Xiong et al., "Engineering of Amphiphilic Block Copolymers for Polymeric Micellar Drug and Gene Delivery," J Control Release. 155(2):248-261 (2011).
Zhang et al., "Strategies for Improving the Payload of Small Molecular Drugs in Polymeric Micelles," J Control Release.261:352-366 (2017).
Srivas et al., "A Network of Conserved Synthetic Lethal Interactions for Exploration of Precision Cancer Therapy," Molecular Cell, 63(3), 514-525. (2016).
Freschauf et al., "Mechanism of Action of an Imidopiperidine Inhibitor of Human Polynucleotide Kinase/Phosphatase," J Biol Chem. 285 (4): 2351-2360 (2010).
Hu et al., "GE11 Peptide Modified and Reduction-responsive Hyaluronic Acid-based Nanoparticles Induced Higher Efficacy of Doxorubicin for Breast Carcinoma Therapy," Int J Nanomedicine. 11:5125-5147 (2016).

* cited by examiner

| log(inhibitor) vs. response -- Variable slope (four parameters) | |
| --- | --- |
| Best-fit values | |
| Bottom | 0.02055 |
| Top | 1.013 |
| LogIC50 | 1.276 |
| HillSlope | -1.596 |
| IC50 | 18.9 |
| Span | 0.9925 |
| Std. Error | |
| Bottom | 0.07714 |
| Top | 0.03265 |
| LogIC50 | 0.06286 |
| HillSlope | 0.303 |
| Span | 0.0924 |
| 95% Confidence Intervals | |
| Bottom | -0.1430 to 0.1841 |
| Top | 0.9438 to 1.082 |
| LogIC50 | 1.145 to 1.408 |
| HillSlope | -2.239 to -0.9539 |
| IC50 | 13.97 to 25.56 |
| Span | 0.7966 to 1.188 |
| Goodness of Fit | |
| Degrees of Freedom | 16 |
| R square | 0.9714 |
| Absolute Sum of Squares | 0.07022 |
| Sy.x | 0.06625 |
| Number of points Analyzed | 20 |

2-(1-hydroxyundecyl)-1-[(4-nitrophenyl)amino]-6-[4-(piperazin-1-yl)phenyl]-2H,4aH,7aH-pyrrolo[3,4-b]pyridine-5,7-dione: $^1$H NMR (500 MHz; CD$_3$OD): δ 8.01 (d, $J$ = 9.1, 2H), 7.15-7.13 (m, 2H), 7.07 (d, $J$ = 9.1, 2H), 6.89-6.84 (m, 2H), 6.18-6.14 (m, 1H), 6.07 (dt, $J$ = 10.3, 2.1, 1H), 4.00-3.98 (m, 1H), 3.85-3.82 (m, 1H), 3.68-3.65 (m, 1H), 3.50-3.48 (m, 1H), 3.46-3.43 (m, 4H), 3.36-3.33 (m, 4H), 1.63-1.57 (m, 2H), 1.42-1.38 (m, 2H), 1.34-1.25 (m, 4H), 1.22-1.15 (m, 10H), 0.88 (t, $J$ = 7.1, 3H); $^{13}$C NMR (125 MHz; CD3OD): δ 176.8, 174.8, 156.1, 151.4, 139.6, 129.1, 128.5, 126.9, 126.0, 120.5, 117.8, 111.5, 71.5, 68.7, 63.9, 47.4, 44.6, 43.4, 33.0, 32.7, 30.66, 30.65, 30.62, 30.45, 30.44, 27.2, 23.7, 19.3, 14.4; IR (microscope, cm$^{-1}$): 3292.42 (br), 3050.96, 2924.75, 2853.00, 1713.48, 1598.98, 1517.12, 1456.24, 1376.98, 1323.37; HRMS (ESI) for C$_{34}$H$_{47}$N$_6$O$_5$: calcd. 619.3602; found 619.3600.

A83B4C63

Compound: A12B4C53
Ref: SBH-05-127
Molecular Formula: C₃₀H₃₀N₅O₉
Formula Weight: 601.70
HPLC Purity: 96%
Vial: 12 x 25 mg Structure:

K_d and IC_50 log(inhibitor) vs. response -- Variable slope
(four parameters)
Best-fit values
Bottom           0.1288
Top              0.8982
HillSlope        -1.722
IC50             5.301
Span             0.7694
95% Confidence Intervals
Bottom           0.09510 to 0.1624
Top              0.8598 to 0.9366
IC50             4.571 to 6.148
Goodness of Fit
R square         0.9919

Kd: 170 nM
IC50: 5.3 µM

IMIDOPIPERIDINE COMPOUNDS AS INHIBITORS OF HUMAN POLYNUCLEOTIDE KINASE PHOSPHATASE

CROSS REFERENCE TO RELATED APPLICATIONS

This application claims priority to U.S. 62/482,060, filed Apr. 5, 2017, U.S. 62/590,322, filed Nov. 23, 2017, and U.S. 62/590,490, filed Nov. 24, 2017 the entire contents all of which are incorporated by reference.

FIELD

The present disclosure relates generally to imidopiperidine compounds as inhibitors of human polynucleotide kinase phosphatase.

BACKGROUND

Radiation and systemic chemotherapy are important therapeutic modalities for treatment of cancer. Nuclear DNA is considered to be a major cellular target responsible for cytotoxicity of ionizing radiation and many conventional antineoplastic drugs. As a consequence, levels of DNA damage and its repair are likely to influence cell survival and affect clinical outcome (1).

Manipulation of DNA repair systems is a focus for enhancing efficacy of radio- and chemotherapy. Particular emphasis has been placed on single and double-strand break repair pathways (2). Small molecule inhibitors have been developed that target enzymes such as poly(ADP-ribose) polymerase (PARP) and apurinic/apyrimidinic endonuclease (APE 1), which are involved in the repair of damaged bases and single-strand breaks induced by many agents including ionizing radiation and alkylating agents (1,3,4); tyrosyl DNA-phosphodiesterase (Tdp1), which is required for the repair of strand breaks introduced by topoisomerase 1 inhibitors such as camptothecin and irinotecan (5); and ATM and DNA-PK, which regulate the response to DNA double-strand breaks (6,7). Inhibitors of PARP are now in clinical trial (8).

Ionizing radiation and other genotoxic agents often generate strand breaks with incompatible termini that must be processed in order for single and double-strand break repair pathways to complete repair. Among frequently observed termini are 3'-phosphate and phosphoglycolate and 5'-hydroxyl groups (9,10). These lesions create a barrier for DNA polymerases and ligases to replace missing bases and seal breaks because these enzymes have a strict requirement for the presence of a 3'-hydroxyl group and in addition DNA ligases require a 5'-phosphate group (11,12).

A major enzyme responsible for the phosphorylation of 5'-hydroxyl termini and dephosphorylation of 3'-phosphate termini in human cells is polynucleotide kinase/phosphatase (hPNKP) (13,14). In the single-strand break (SSB) repair pathway, hPNKP acts in concert with XRCC1, DNA polymerase β and DNA ligase III (15-17). PNKP-mediated DNA end-processing at double-strand breaks is a component of the nonhomologous end-joining (NHEJ) pathway and is dependent on DNA-PKcs and XRCC4 (18-20). In addition to its role in the repair of strand breaks produced directly by genotoxic agents, hPNKP has been implicated in the repair of strand breaks produced by enzymatic processes, including strand breaks introduced by the βδ-AP lyase activity of DNA glycosylases such as NEIL1 and NEIL2 (21, 22), which generate 3'-phosphate termini. Similarly, hPNKP is required to process termini generated by the topoisomerase I inhibitor camptothecin (23). Treatment with camptothecin stalls topoisomerase I while it is covalently attached to a 3'-phosphate group in the course of its nicking-resealing activity. The stalled enzyme can be cleaved from the DNA by Tdp1 leaving a strand break with 3'-phosphate and 5'-hydroxyl termini, which necessitates the subsequent action of PNKP. Down-regulation of hPNKP by RNAi sensitized cells to a variety of genotoxic agents including ionizing radiation, camptothecin, methyl methanesulfonate and hydrogen peroxide (24). It remains to be determined which of hPNKP's activities, 5'-kinase or 3'-phosphatase (or both), is responsible for sensitization to each agent. The two activities are independent with separate DNA binding domains (25), but the phosphatase reaction appears to proceed ahead of the kinase reaction (26).

Synthetic lethality occurs when a combination of two protein knockouts is lethal, however the corresponding single mutations are viable. The original concept of synthetic lethality as it relates to DNA repair was discovered in 2005. The Ashworth and Helleday groups published two papers back to back in Nature, outlining synthetic lethality between BRCA−/− cells and inhibition of poly(ADP-ribose) polymerase (PARP).

This background information is provided for the purpose of making known information believed by the applicant to be of possible relevance to the present invention. No admission is necessarily intended, nor should it be construed, that any of the preceding information constitutes prior art against the present invention.

SUMMARY

In an aspect of the present application, there is provided a compound of formula (I)

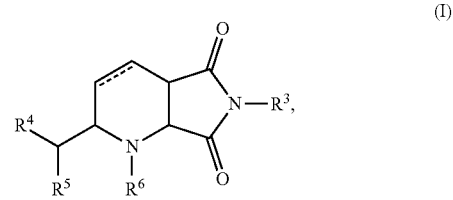

(I)

or a stereoisomer, a racemate, a pharmaceutically acceptable salt, a solvate, or a functional derivative thereof,
wherein
$R^3$ is independently $C_1$-$C_6$ alkyl, $C_2$-$C_6$ alkenyl, $C_2$-$C_6$ alkynyl, $C_3$-$C_{20}$ carbocycle, aryl, benzyl, heterocycle, $C_1$-$C_6$ alkoxy, alcohol, ether, polyether, ketone, ester, thiol, thioether, sulfone, amine, carbamate, amide, cyano, each of which is optionally substituted;
$R^4$ is independently $C_1$-$C_{10}$ alkyl, $C_{10}$-$C_{20}$ alkyl, $C_2$-$C_{10}$ alkenyl, $C_{10}$-$C_{20}$ alkenyl, $C_2$-$C_{10}$ alkynyl, $C_{10}$-$C_{20}$ alkynyl, $C_3$-$C_{20}$ carbocycle, aryl, benzyl, heterocycle, $C_1$-$C_{10}$ alkoxy, $C_{10}$-$C_{20}$ alkoxy, alcohol, ether, polyether, ketone, ester, thiol, thioether, sulfone, amine, carbamate, amide, each of which is optionally substituted;
$R^5$ is independently OH, or ester which is optionally substituted;
$R^6$ is H, or $C_1$-$C_6$ alkyl, $C_2$-$C_6$ alkenyl, $C_2$-$C_6$ alkynyl, $C_3$-$C_6$ carbocycle, aryl, benzyl, heterocycle, or ketone, each of which is optionally substituted, or ($NR^1R^2$) where $R^1$ and $R^2$ are each independently H, or $C_1$-$C_6$ alkyl, $C_2$-$C_6$ alkenyl, $C_2$-$C_6$ alkynyl, $C_3$-$C_6$ carbocycle, aryl, benzyl, or heterocycle, each of which is optionally substituted;

where the dashed line represents an optional double bond; and with the proviso that, when the double bond is present and
(i) $R^3$ is —$C_6H_5$, $R^5$ is —OH, and $R^6$ is ($NR^1R^2$), where $R^1$ is H and $R^2$ is —$C_6H_4$-4-$NO_2$, $R^4$ is not —$C_{10}H_{21}$;
(ii) $R^3$ is —$C_6H_5$, $R^5$ is —OH, and $R^6$ is ($NR^1R^2$), where $R^1$ is H and $R^2$ is —$C_6H_4$-4-$NO_2$, $R^4$ is not —$C_6H_5$;
(iii) $R^3$ is —$C_6H_5$, $R^5$ is —OH, and $R^6$ is ($NR^1R^2$), where $R^1$ is H and $R^2$ is —$C_6H_4$-4-$NO_2$, $R^4$ is not —$C_6H_2$-3,4,5-$(OCH_3)_3$;
(iv) $R^5$ is —OH, $R^6$ is ($NR^1R^2$), where $R^1$ is H and $R^2$ is —BOC, and $R^4$ is —$CH(C_6H_5)_2$, $R^3$ is not —$CH_3$; and
(v) $R^5$ is —OH, $R^6$ is ($NR^1R^2$), where $R^1$ is H and $R^2$ is —$C_6H_5$, and $R^4$ is -(2-thienyl), $R^3$ is not —$CH_3$.

In an embodiment of the present application, there is provided a compound of formula (I) with the proviso that a compound of formula (I) does not have the structure

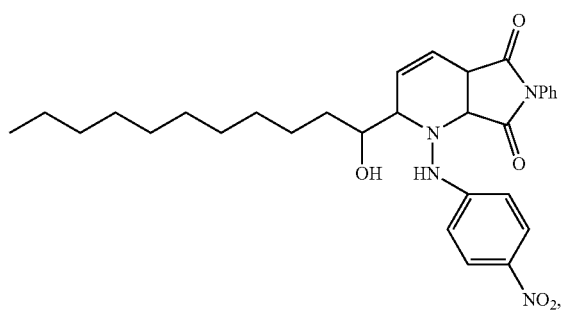

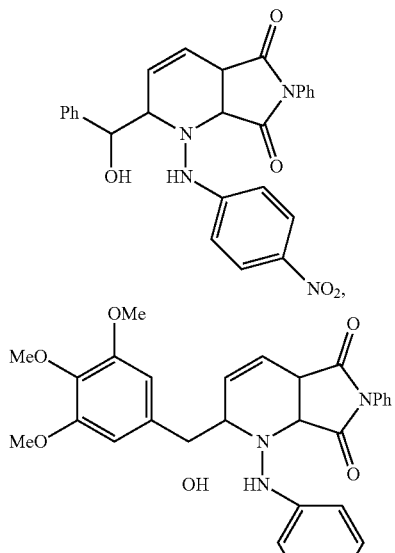

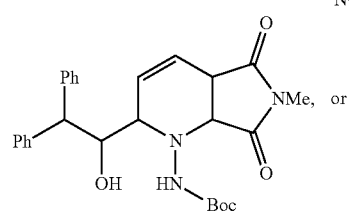

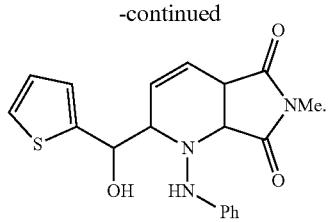

In another embodiment, there is provided a compound of formula (I) wherein $R^4$ is independently $C_6$-$C_{10}$ alkyl, $C_{10}$-$C_{20}$ alkyl, $C_6$-$C_{10}$ alkenyl, $C_{10}$-$C_{20}$ alkenyl, $C_6$-$C_{10}$ alkynyl, $C_{10}$-$C_{20}$ alkynyl, $C_6$-$C_{20}$ carbocycle, aryl, benzyl, heterocycle, $C_6$-$C_{10}$ alkoxy, $C_{10}$-$C_{20}$ alkoxy, alcohol, ether, polyether, ketone, ester, thiol, thioether, sulfone, amine, carbamate, amide, each of which is optionally substituted.

In an embodiment of the present application, there is provided a compound of formula (II)

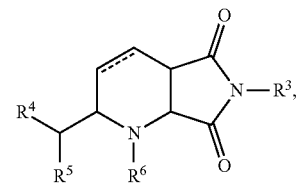

a stereoisomer, a racemate, a tautomer, a pharmaceutically acceptable salt, a solvate, or a functional derivative thereof, wherein $R^3$ is independently

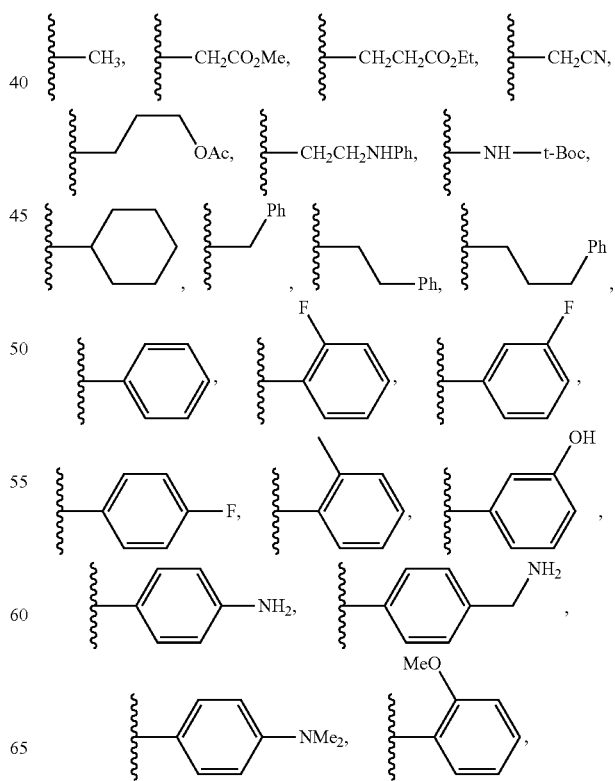

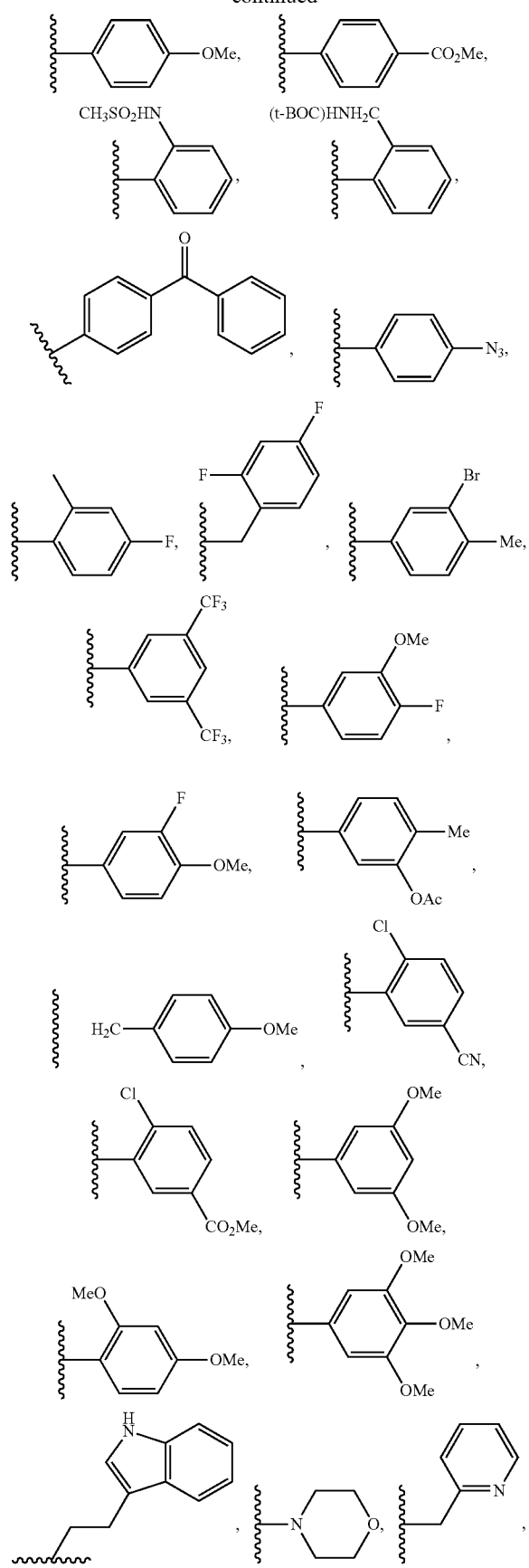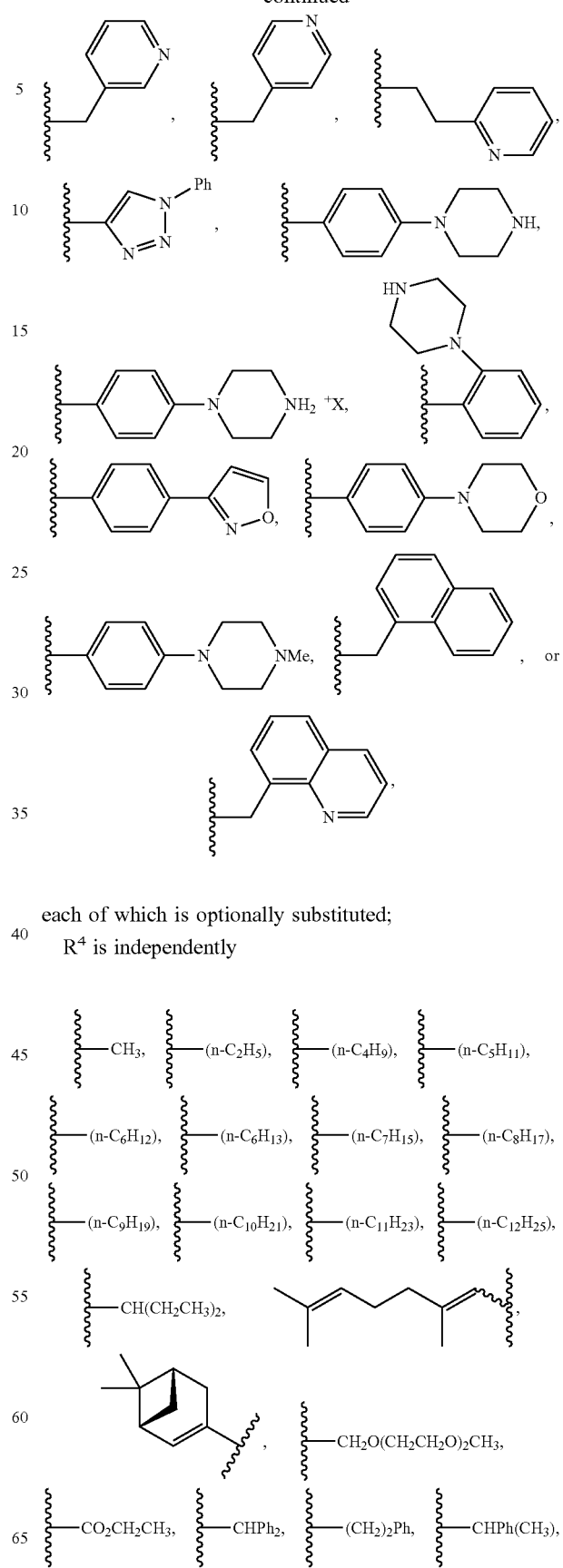
each of which is optionally substituted;
$R^4$ is independently -continued

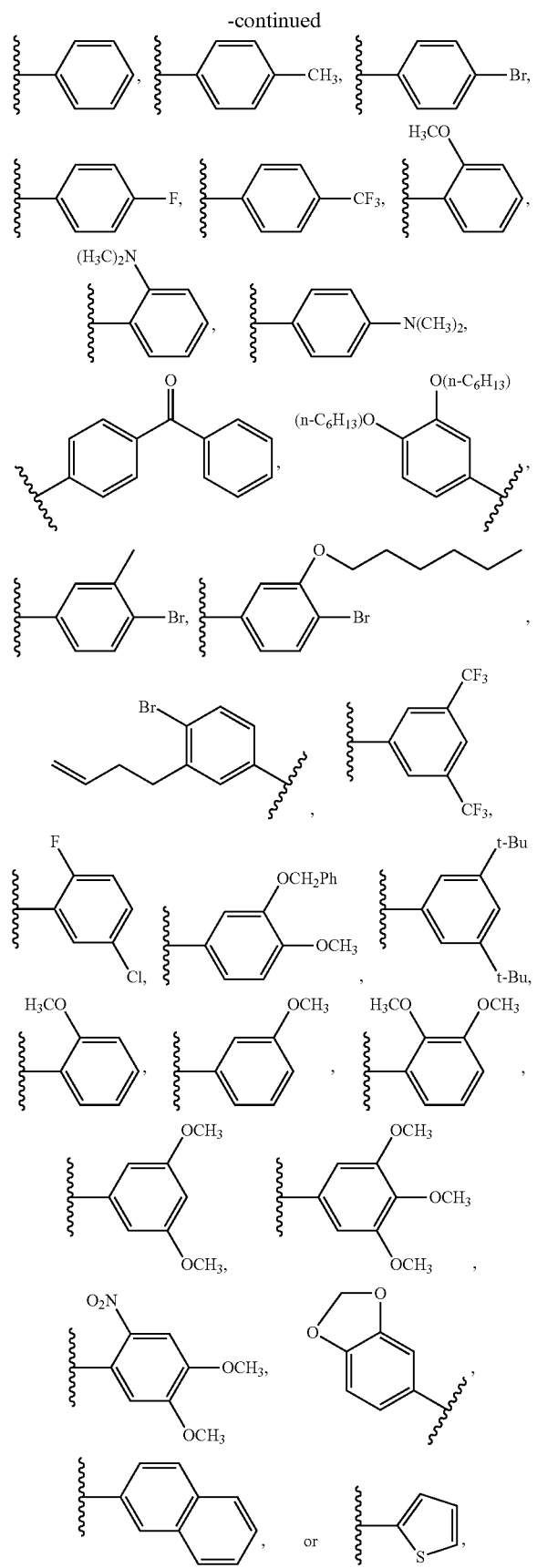

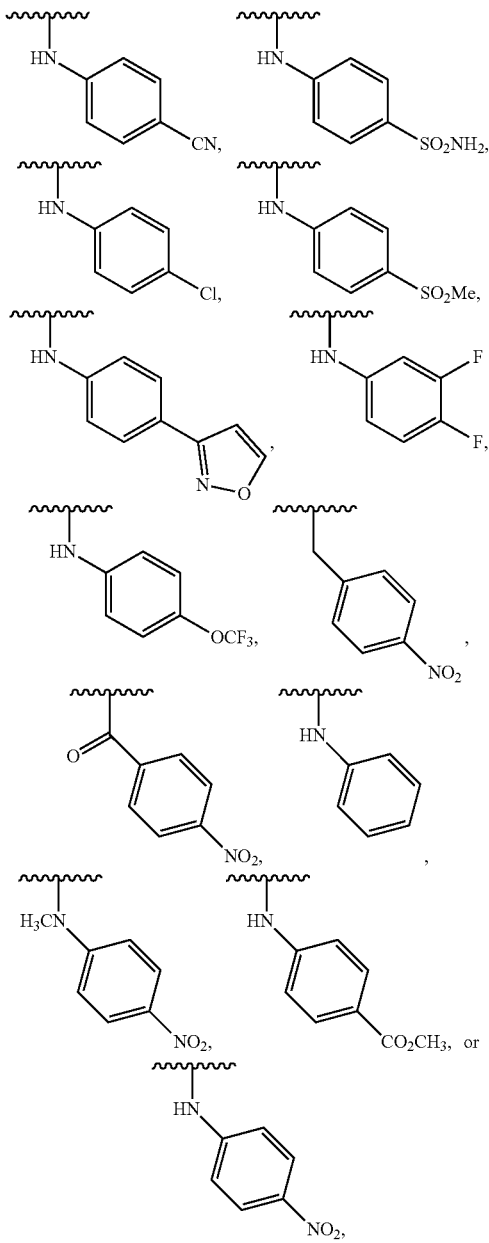

each of which is optionally substituted;
R$^5$ is independently OH, CO$_2$CF$_3$, or ester which is optionally substituted;
R$^6$ is H, or (NR$^1$R$^2$), where R$^1$ and R$^2$ together are each of which is optionally substituted;
where the dashed line represents an optional double bond; and
with the proviso that, when the double bond is present and
(i) R$^3$ is —C$_6$H$_5$, R$^5$ is —OH, and R$^6$ is (NR$^1$R$^2$), where R$^1$ is H and R$^2$ is —C$_6$H$_4$-4-NO$_2$, R$^4$ is not —C$_{10}$H$_{21}$;
(ii) R$^3$ is —C$_6$H$_5$, R$^5$ is —OH, and R$^6$ is (NR$^1$R$^2$), where R$^1$ is H and R$^2$ is —C$_6$H$_4$-4-NO$_2$, R$^4$ is not —C$_6$H$_5$;
(iii) R$^3$ is —C$_6$H$_5$, R$^5$ is —OH, and R$^6$ is (NR$^1$R$^2$), where R$^1$ is H and R$^2$ is —C$_6$H$_4$-4-NO$_2$, R$^4$ is not —C$_6$H$_2$-3,4,5-(OCH$_3$)$_3$;
(iv) R$^5$ is —OH, R$^6$ is (NR$^1$R$^2$), where R$^1$ is H and R$^2$ is —BOC, and R$^4$ is —CH(C$_6$H$_5$)$_2$, R$^3$ is not —CH$_3$; and (v) $R^5$ is —OH, $R^6$ is $(NR^1R^2)$, where $R^1$ is H and $R^2$ is —$C_6H_5$, and $R^4$ is -(2-thienyl), $R^3$ is not —$CH_3$.

In an embodiment of the present application, there is provided a compound of formula (II) with the proviso that a compound of formula (II) does not have the structure

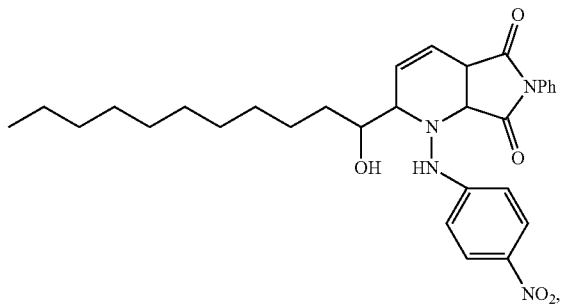

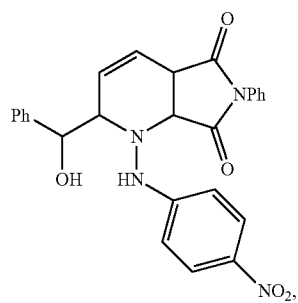

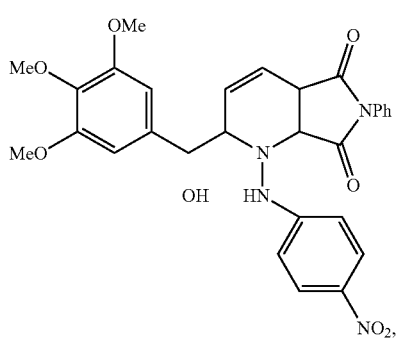

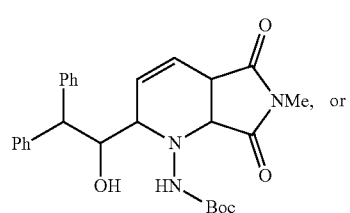

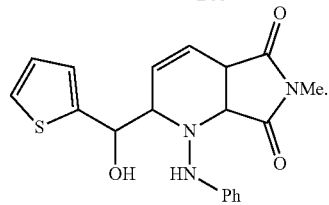

In an embodiment of the present application, there is provided a compound of formula (IIa)

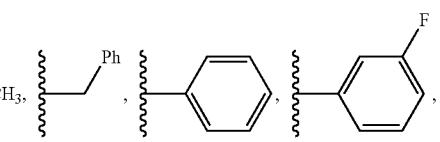

or a stereoisomer, a racemate, a tautomer, a pharmaceutically acceptable salt, a solvate, or a functional derivative thereof, wherein $R^3$ is independently

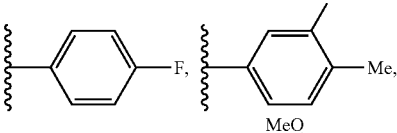

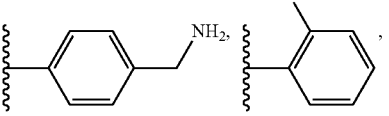

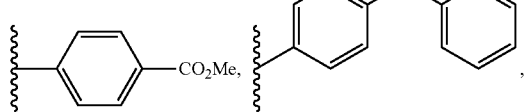

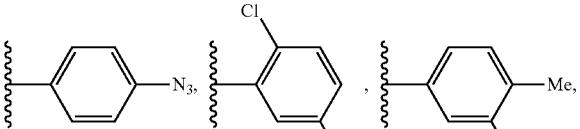

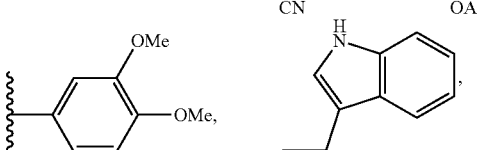

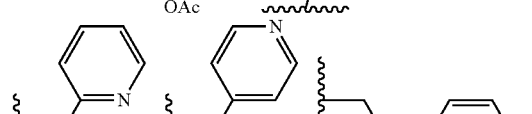

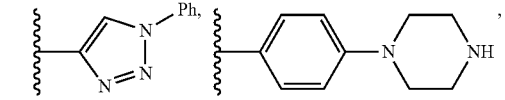

-continued

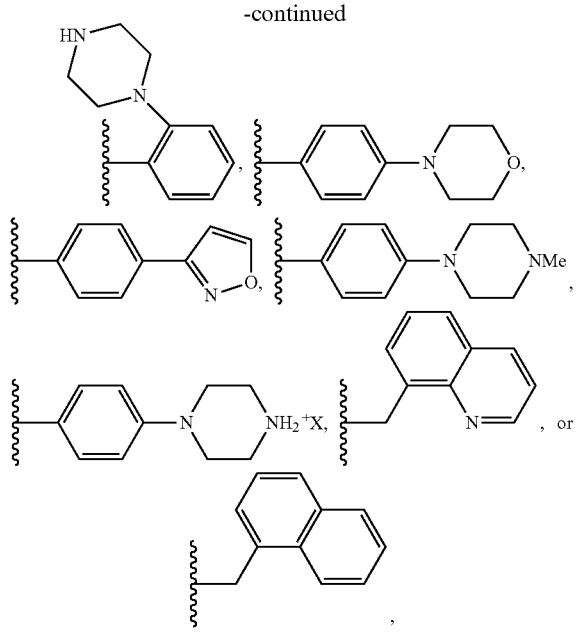

each of which is optionally substituted;
R⁴ is independently,

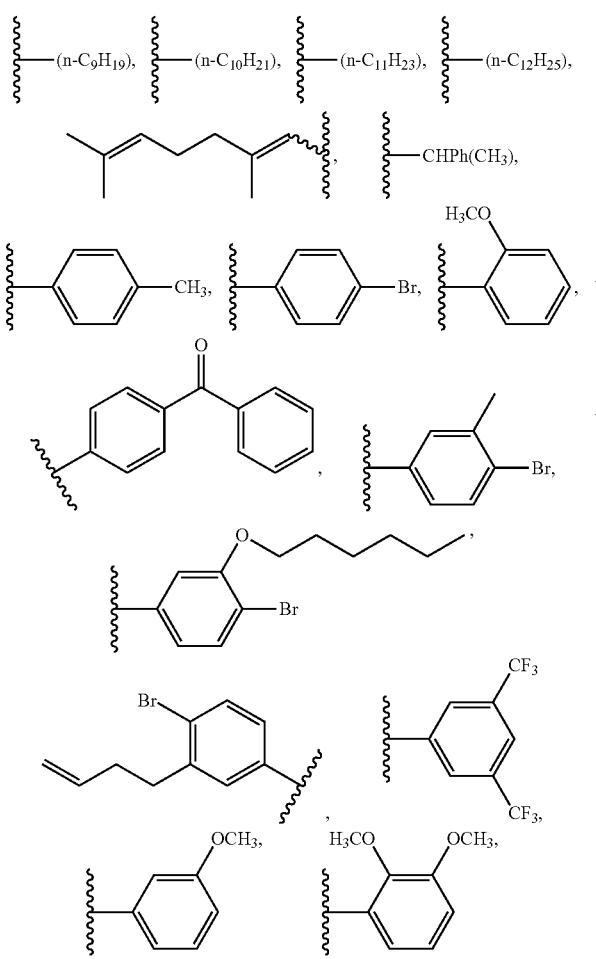

each of which is optionally substituted;

$R^5$ is OH, $CO_2CF_3$, or ester which is optionally substituted;

$R^6$ is H, or ($NR^1R^2$), where $R^1$ and $R^2$ together are

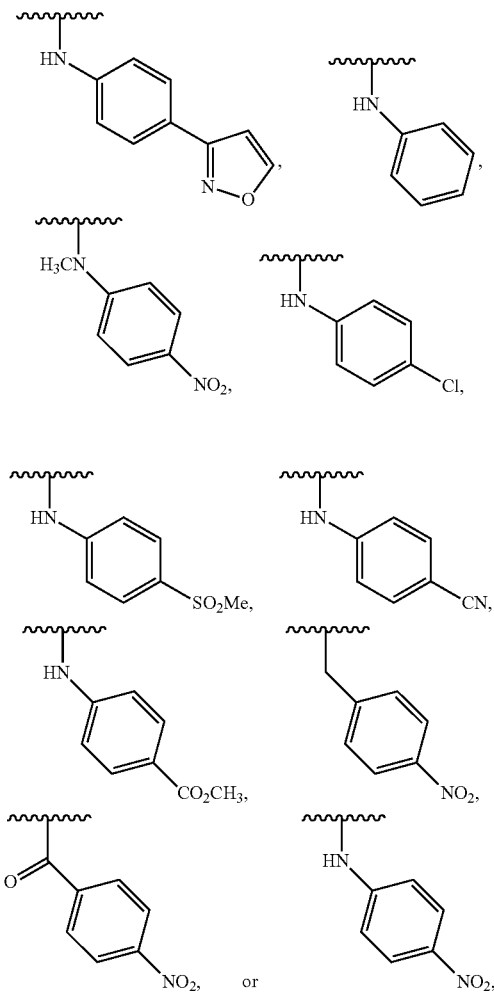

each of which is optionally substituted;

where the dashed line represents an optional double bond; and with the proviso that, when the double bond is present and
(i) $R^3$ is —$C_6H_5$, $R^5$ is —OH, and $R^6$ is ($NR^1R^2$), where $R^1$ is H and $R^2$ is —$C_6H_4$-4-$NO_2$, $R^4$ is not —$C_{10}H_{21}$;
(ii) $R^3$ is —$C_6H_5$, $R^5$ is —OH, and $R^6$ is ($NR^1R^2$), where $R^1$ is H and $R^2$ is —$C_6H_4$-4-$NO_2$, $R^4$ is not —$C_6H_5$;
(iii) $R^3$ is —$C_6H_5$, $R^5$ is —OH, and $R^6$ is ($NR^1R^2$), where $R^1$ is H and $R^2$ is —$C_6H_4$-4-$NO_2$, $R^4$ is not —$C_6H_2$-3,4,5-$(OCH_3)_3$;
(iv) $R^5$ is —OH, $R^6$ is ($NR^1R^2$), where $R^1$ is H and $R^2$ is —BOC, and $R^4$ is —$CH(C_6H_5)_2$, $R^3$ is not —$CH_3$; or
(v) $R^5$ is —OH, $R^6$ is ($NR^1R^2$), where $R^1$ is H and $R^2$ is —$C_6H_5$, and $R^4$ is -(2-thienyl), $R^3$ is not —$CH_3$.

In an embodiment of the present application, there is provided a compound of formula (IIa) with the proviso that a compound of formula (IIa) does not have the structure

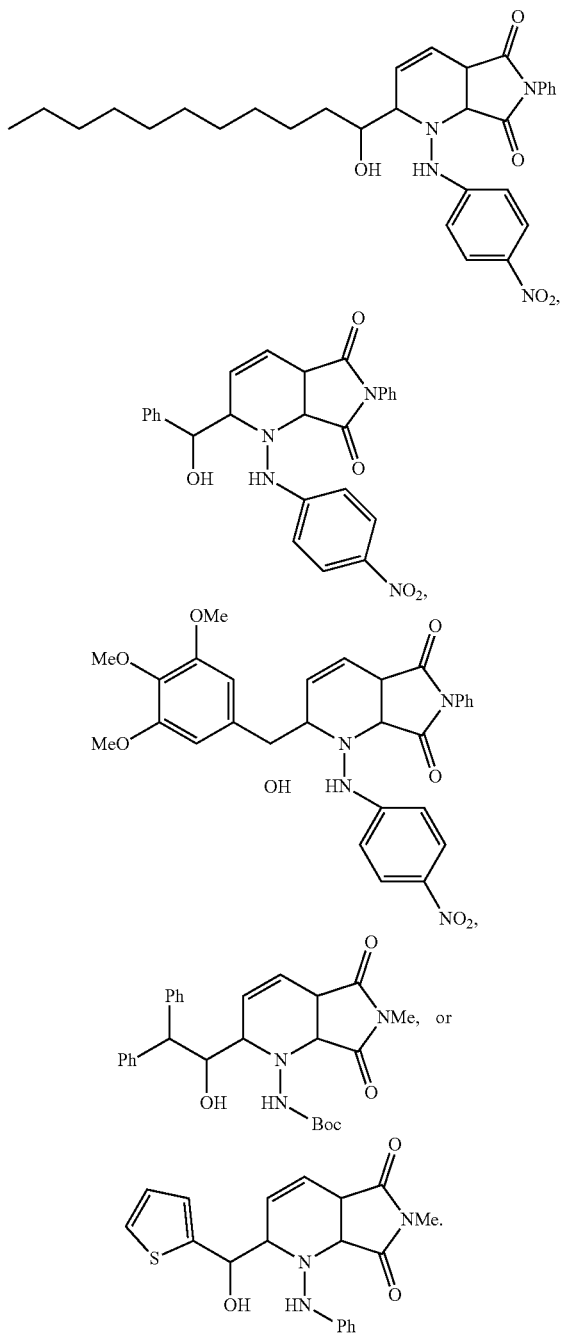
In an embodiment of the present application, there is provided a compound of formula (IIb)
(IIb)
or
a stereoisomer, a racemate, a tautomer, a pharmaceutically acceptable salt, a solvate, or a functional derivative thereof, wherein
$R^3$ is independently
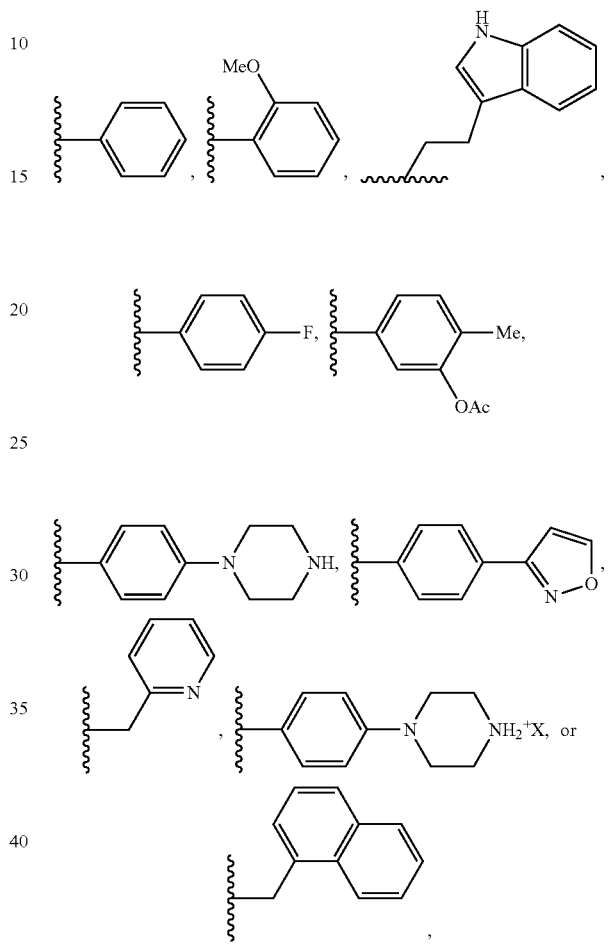
each of which is optionally substituted;
$R^4$ is independently, each of which is optionally substituted;

$R^5$ is OH;

$R^6$ is ($NR^1R^2$), where $R^1$ and $R^2$ together are

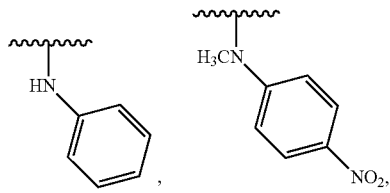

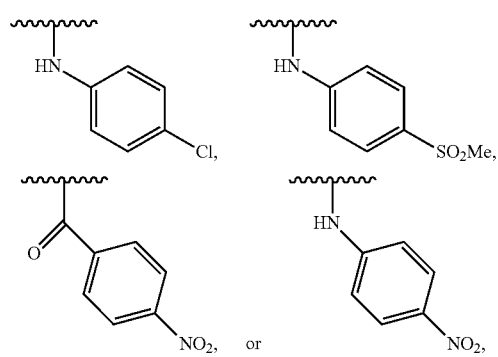

each of which is optionally substituted;

where the dashed line represents an optional double bond; and with the proviso that, when the double bond is present and
(i) $R^3$ is —$C_6H_5$, $R^5$ is —OH, and $R^6$ is ($NR^1R^2$), where $R^1$ is H and $R^2$ is —$C_6H_4$-4-$NO_2$, $R^4$ is not —$C_{10}H_{21}$;
(ii) $R^3$ is —$C_6H_5$, $R^5$ is —OH, and $R^6$ is ($NR^1R^2$), where $R^1$ is H and $R^2$ is —$C_6H_4$-4-$NO_2$, $R^4$ is not —$C_6H_5$;
(iii) $R^3$ is —$C_6H_5$, $R^5$ is —OH, and $R^6$ is ($NR^1R^2$), where $R^1$ is H and $R^2$ is —$C_6H_4$-4-$NO_2$, $R^4$ is not —$C_6H_2$-3,4,5-$(OCH_3)_3$;
(iv) $R^5$ is —OH, $R^6$ is ($NR^1R^2$), where $R^1$ is H and $R^2$ is —BOC, and $R^4$ is —$CH(C_6H_5)_2$, $R^3$ is not —$CH_3$; or
(v) $R^5$ is —OH, $R^6$ is ($NR^1R^2$), where $R^1$ is H and $R^2$ is —$C_6H_5$, and $R^4$ is -(2-thienyl), $R^3$ is not —$CH_3$.

In an embodiment of the present application, there is provided a compound of formula (IIa) with the proviso that a compound of formula (IIb) does not have the structure

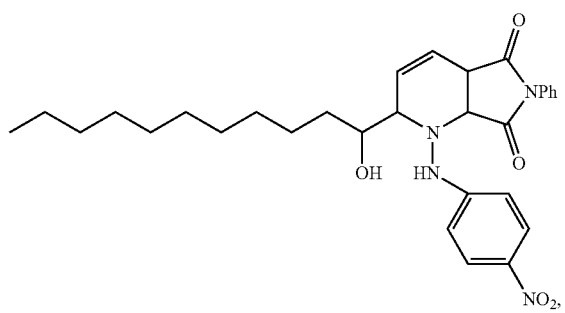

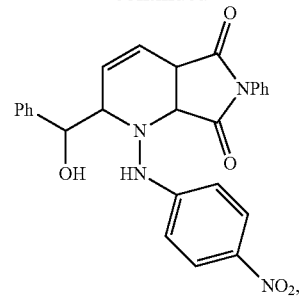

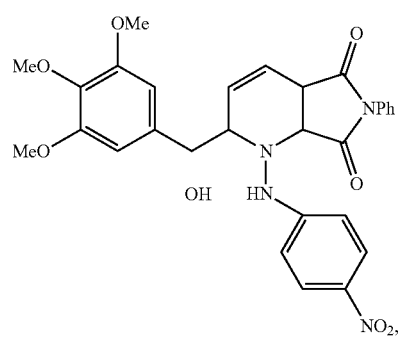

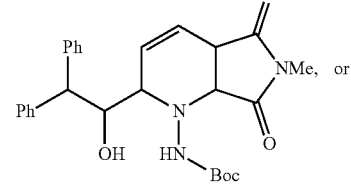

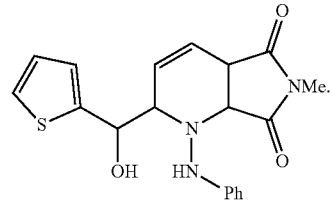

In an embodiment of the present application, there is provided a compound of formula (III)

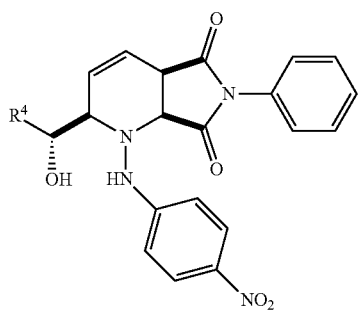

(III)

or a stereoisomer, a racemate, a tautomer, a pharmaceutically acceptable salt, a solvate, or a functional derivative thereof, wherein
R⁴ is independently

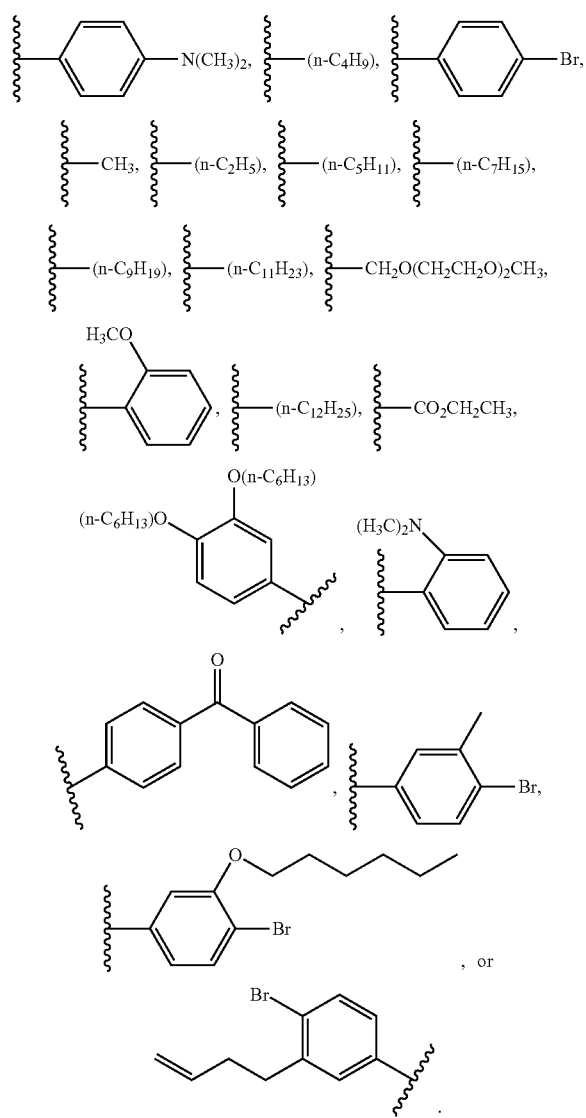

In an embodiment of the present application, there is provided a compound of formula (IIIa)

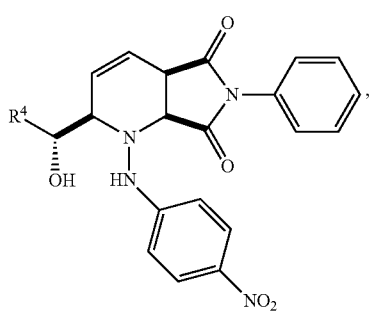

(IIIa)

or
a stereoisomer, a racemate, a tautomer, a pharmaceutically acceptable salt, a solvate, or a functional derivative thereof,
wherein
R⁴ is independently

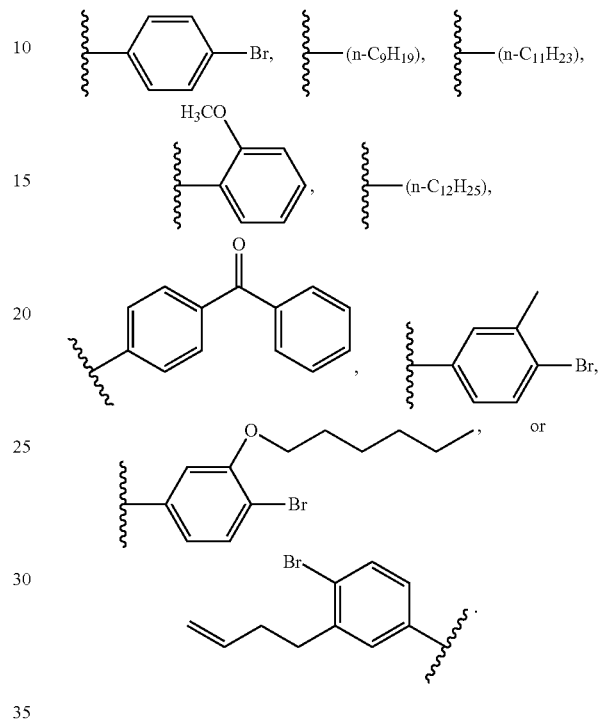

In an embodiment of the present application, there is provided a compound of formula (IIIb)

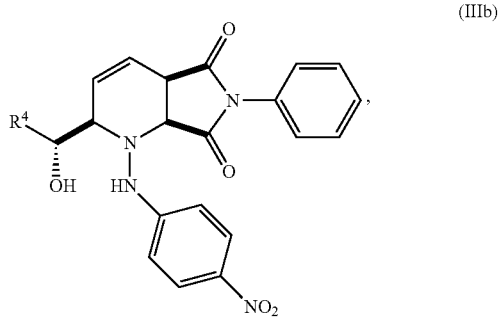

(IIIb)

or
a stereoisomer, a racemate, a tautomer, a pharmaceutically acceptable salt, a solvate, or a functional derivative thereof,
wherein
R⁴ is independently

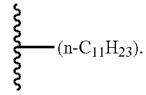

In an embodiment of the present application, there is provided a compound of formula (IV)

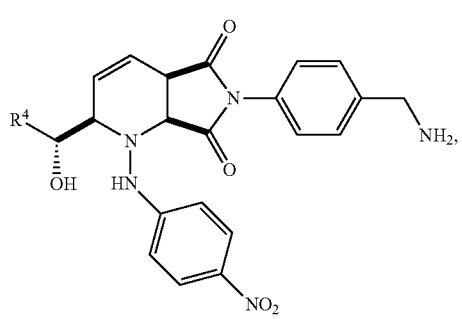

(IV)

or
a stereoisomer, a racemate, a tautomer, a pharmaceutically acceptable salt, a solvate, or a functional derivative thereof,
wherein
R⁴ is independently

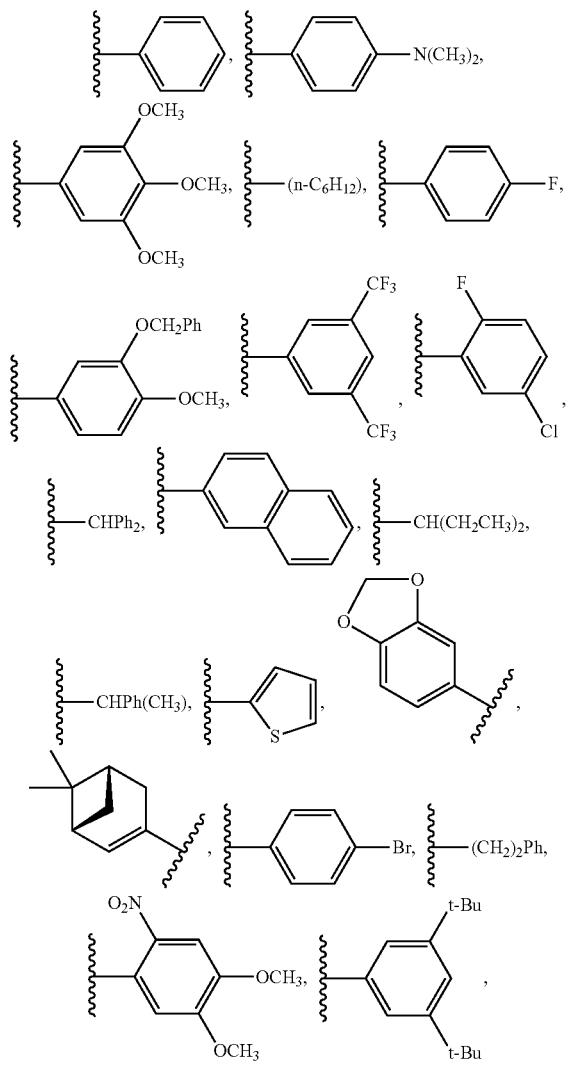

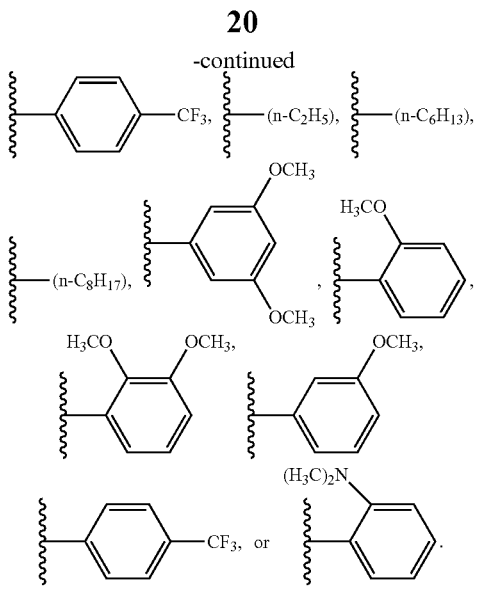

In an embodiment of the present application, there is provided a compound of formula (IVa)

(IVa)

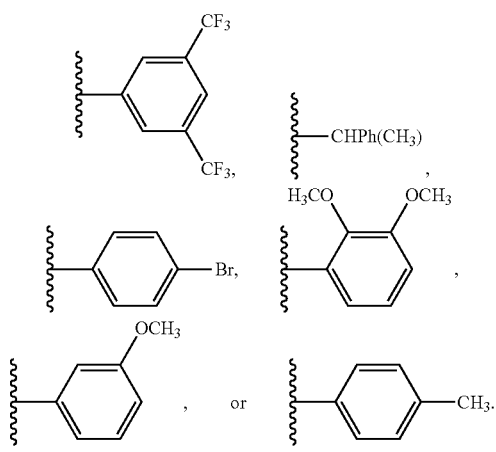

or
a stereoisomer, a racemate, a tautomer, a pharmaceutically acceptable salt, a solvate, or a functional derivative thereof,
wherein
R⁴ is independently In an embodiment of the present application, there is provided a compound of formula (IVb)

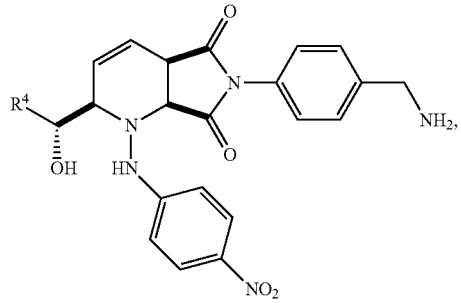

(IVb)

or a stereoisomer, a racemate, a tautomer, a pharmaceutically acceptable salt, a solvate, or a functional derivative thereof,
wherein
$R^4$ is

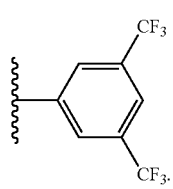 [SMILES: *c1cc(C(F)(F)F)cc(C(F)(F)F)c1]

In an embodiment of the present application, there is provided a compound of formula (V)

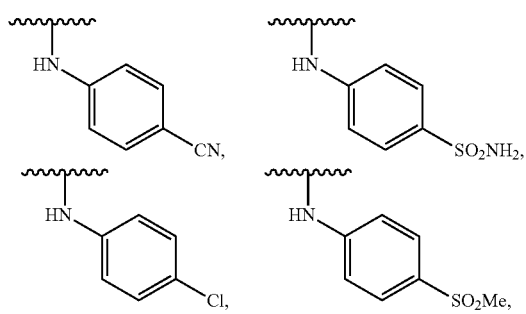

(V)

or a stereoisomer, a racemate, a tautomer, a pharmaceutically acceptable salt, a solvate, or a functional derivative thereof,
wherein
$R^1$ and $R^2$ together are

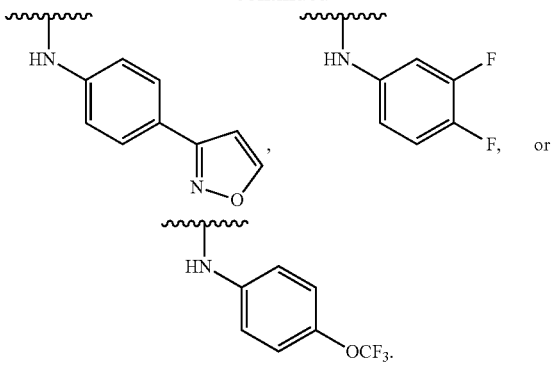

-continued

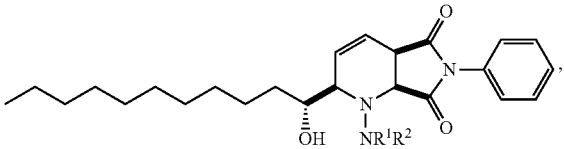

, or

In an embodiment of the present application, there is provided a compound of formula (Va)

(Va)

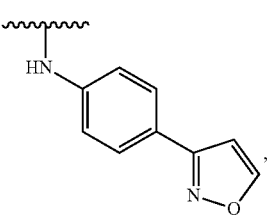

or a stereoisomer, a racemate, a tautomer, a pharmaceutically acceptable salt, a solvate, or a functional derivative thereof,
wherein
$R^1$ and $R^2$ together are In an embodiment of the present application, there is provided a compound of formula (Vb)

(Vb)

or a stereoisomer, a racemate, a tautomer, a pharmaceutically acceptable salt, a solvate, or a functional derivative thereof, wherein
R¹ and R² together are
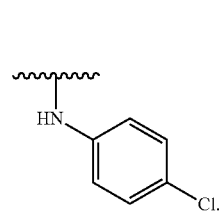 [SMILES: *Nc1ccc(Cl)cc1]
In an embodiment of the present application, there is provided a compound having the structure
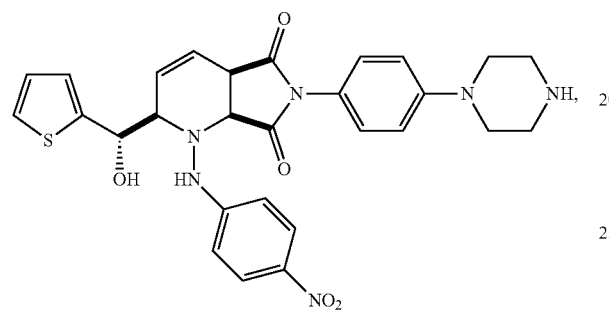
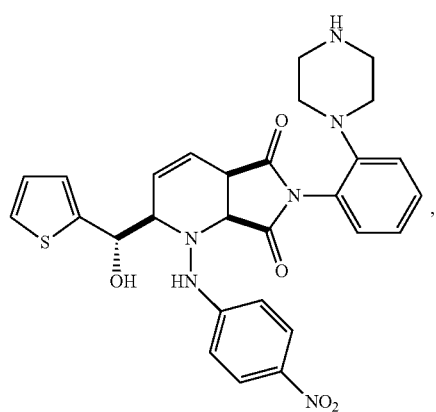
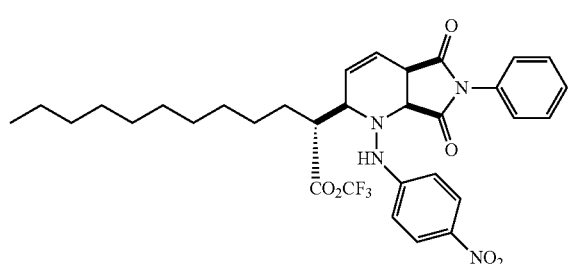
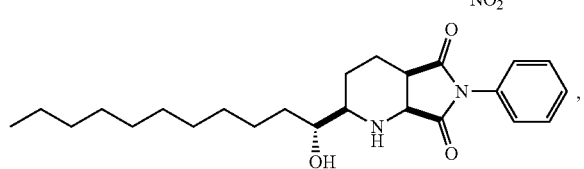
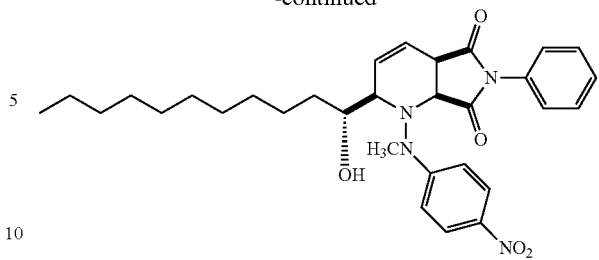
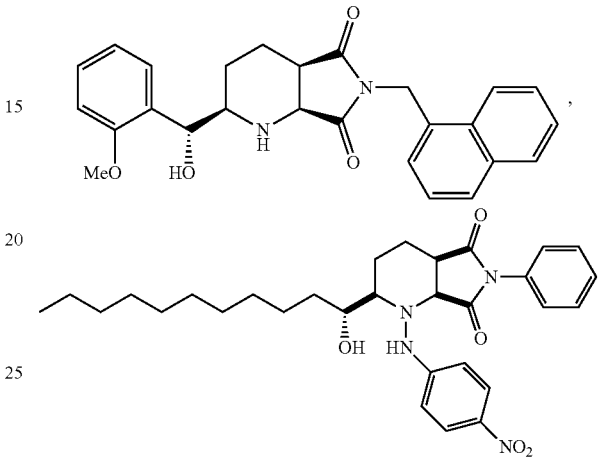
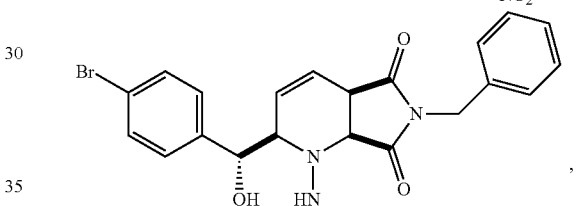
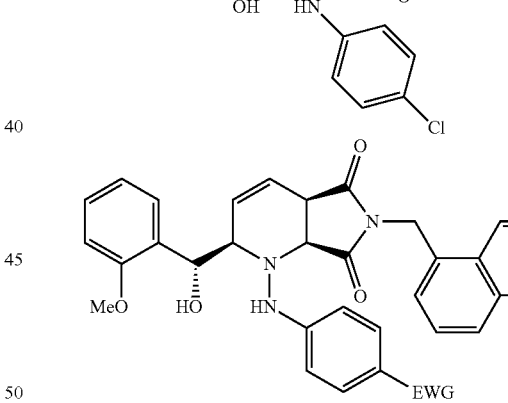
where EWG=CN, $CO_2CH_3$,
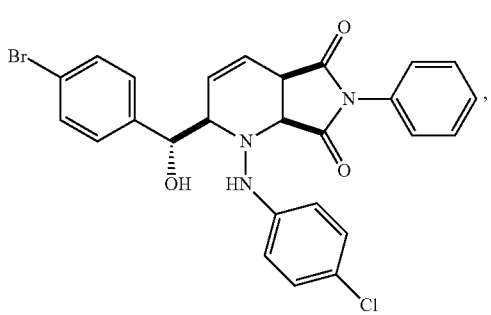

25
-continued
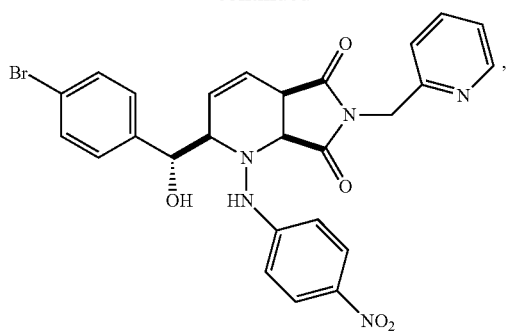
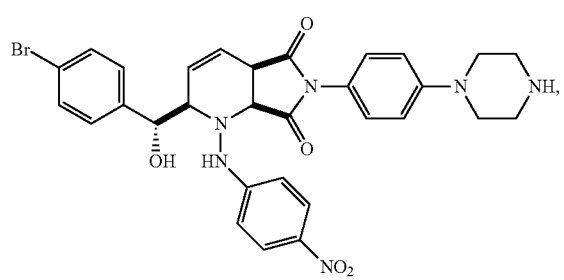
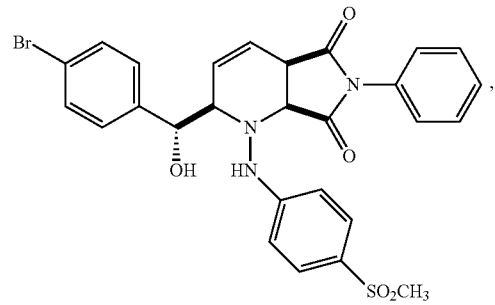
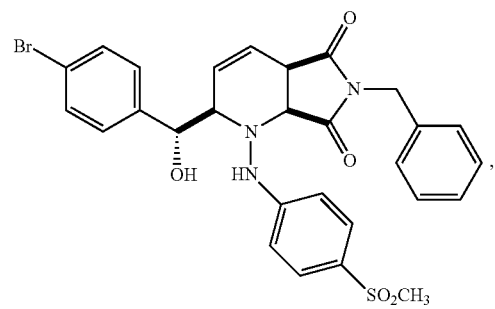
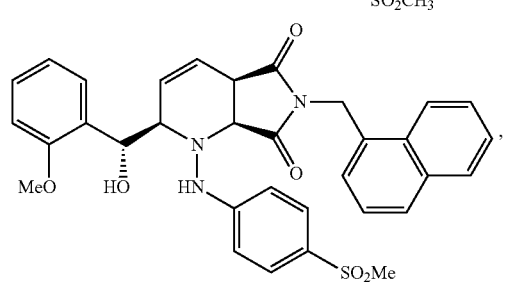
26
-continued
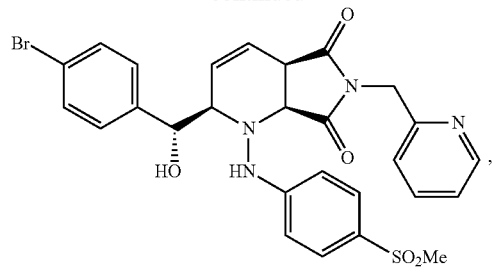
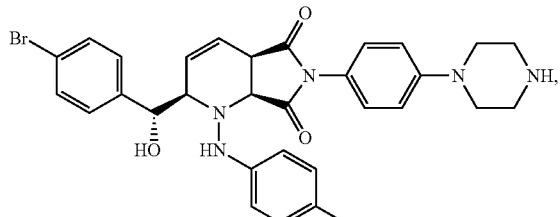
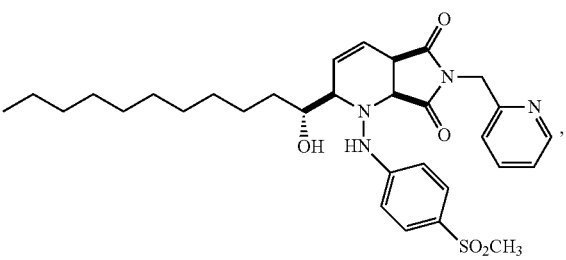
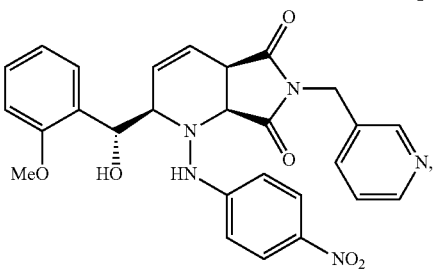
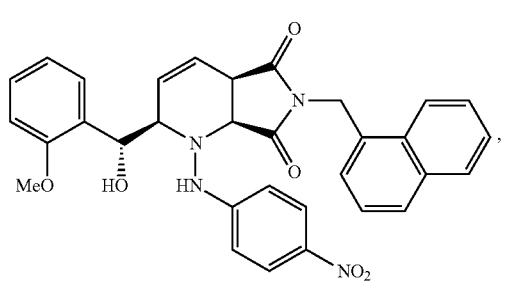
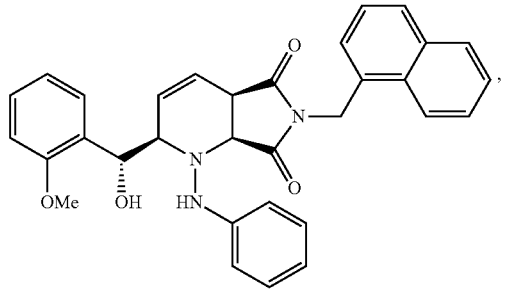 [SMILES: COc1ccccc1[C@@H](O)[C@H]1C=C[C@H]2C(=O)N(Cc3cccc4ccccc34)C(=O)[C@H]2N1Nc1ccccc1]

27
-continued
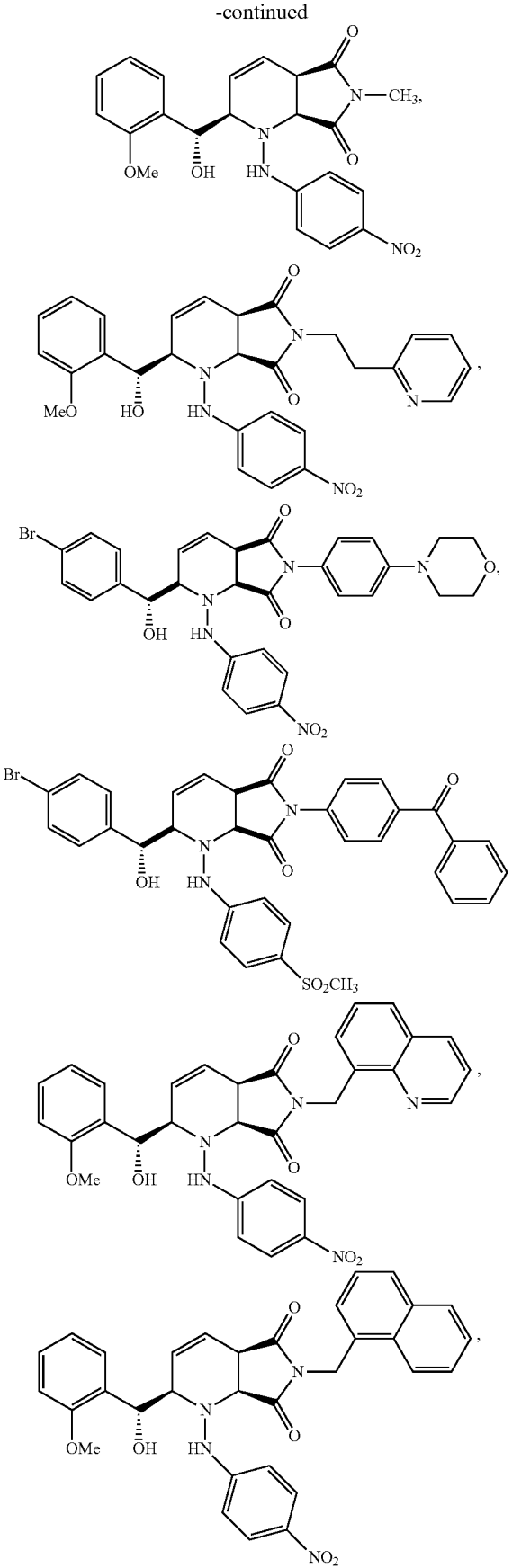
28
-continued
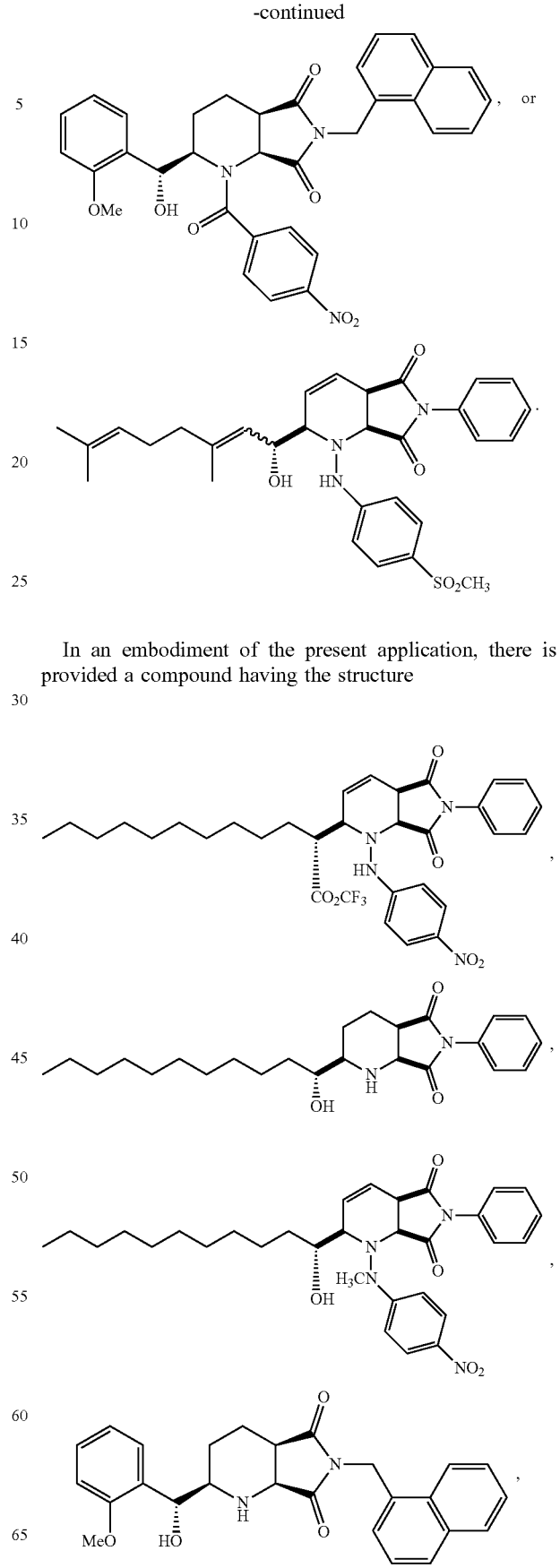
In an embodiment of the present application, there is provided a compound having the structure

29
-continued
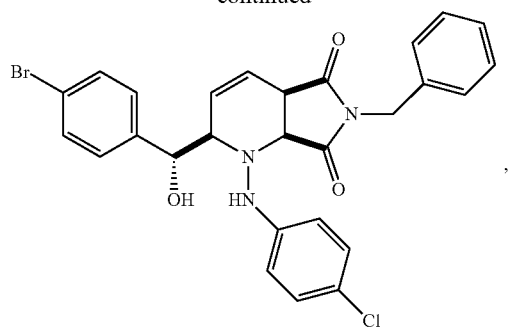
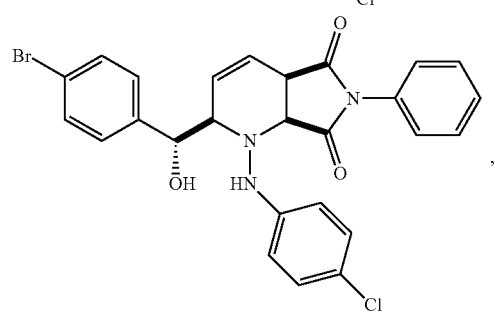
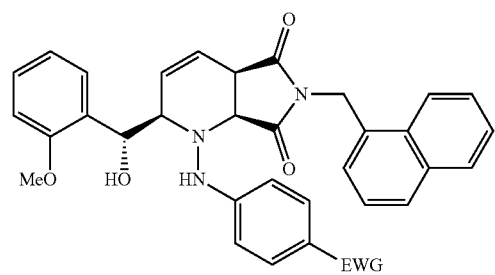
where EWG=CN, CO$_2$CH$_3$,
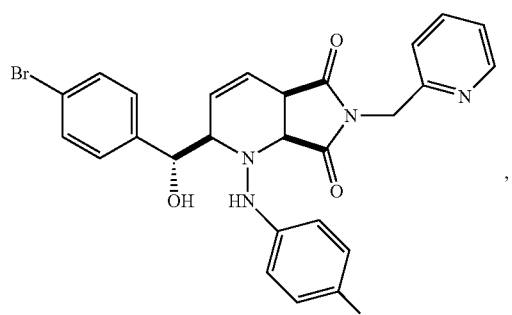
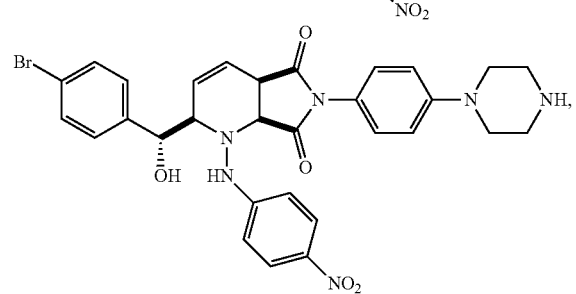
30
-continued
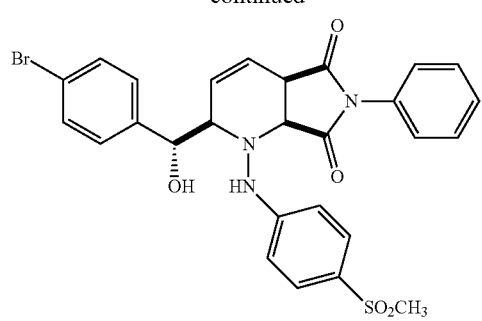
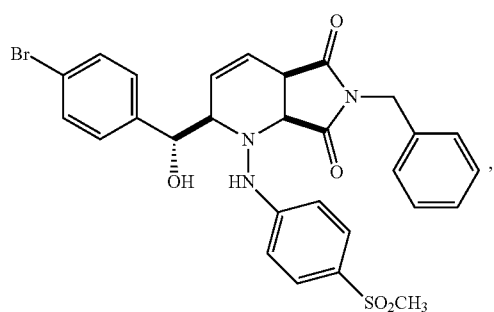
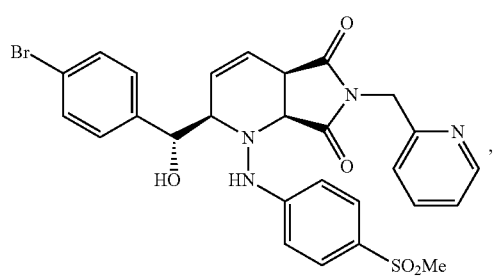
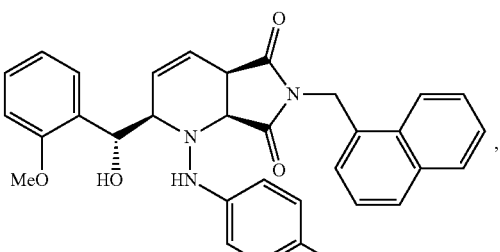
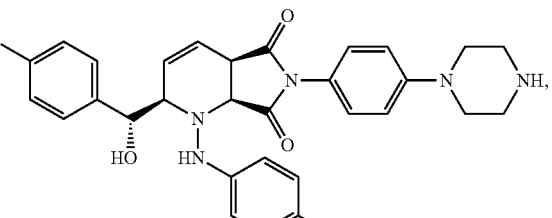
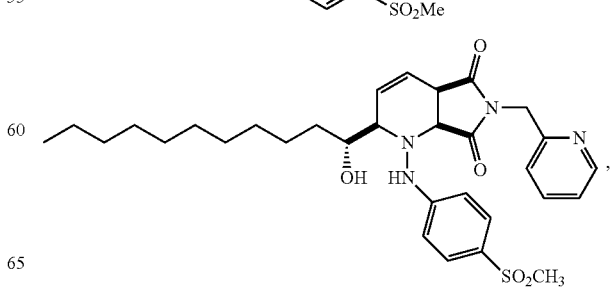

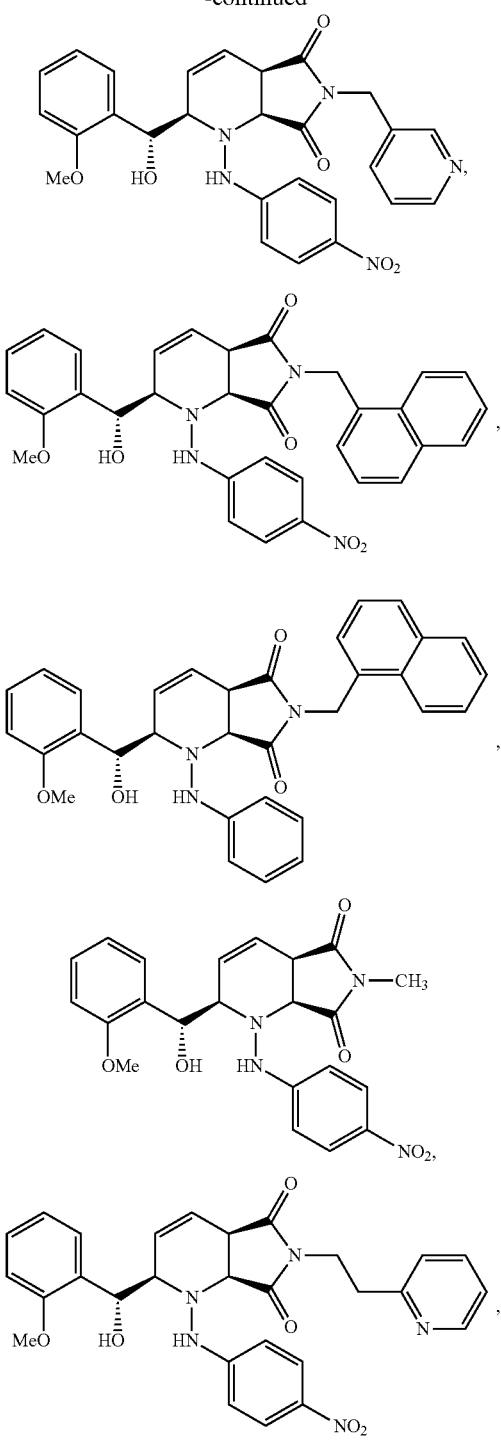
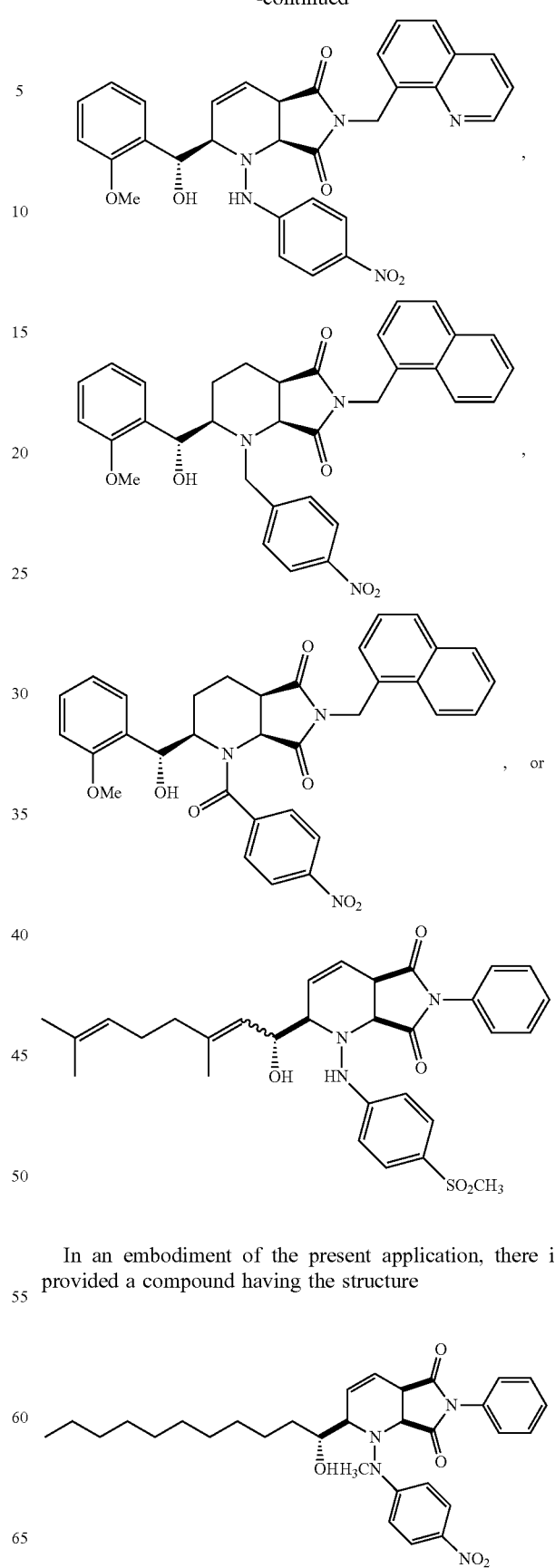
In an embodiment of the present application, there is provided a compound having the structure -continued
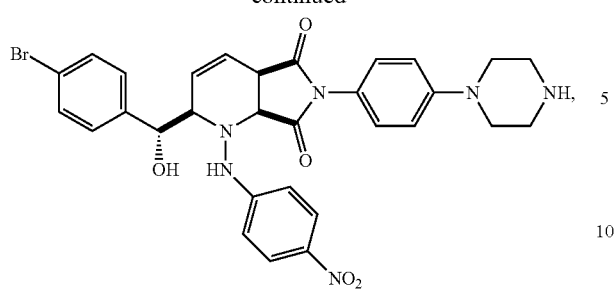
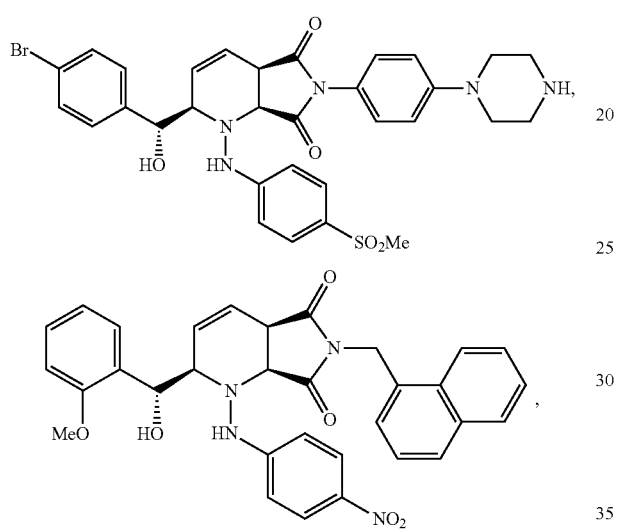
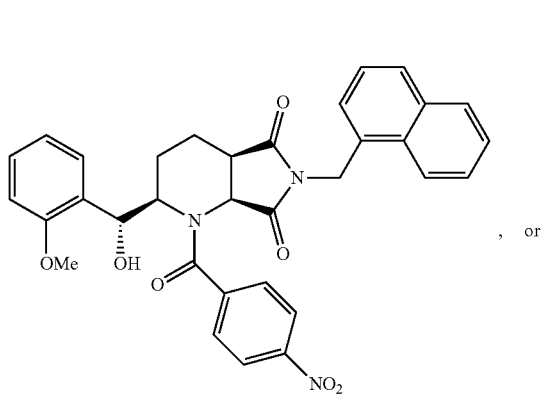
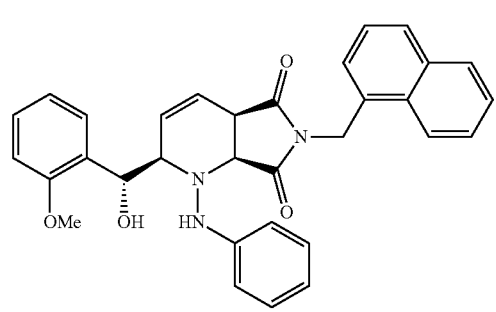, or
In an embodiment of the present application, there is provided a compound having the structure
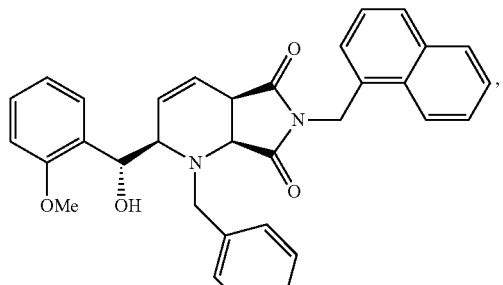
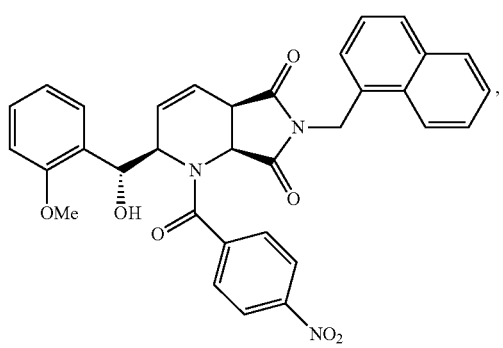
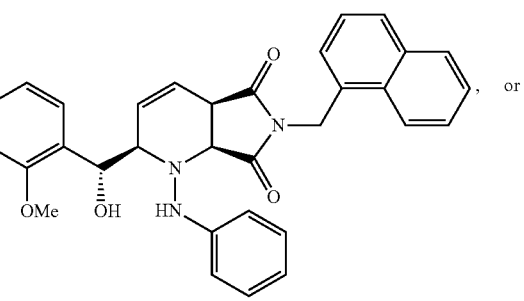, or
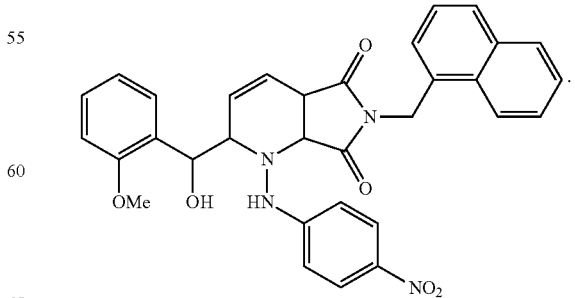.

In an embodiment of the present application, there is provided a compound of formula (VI)
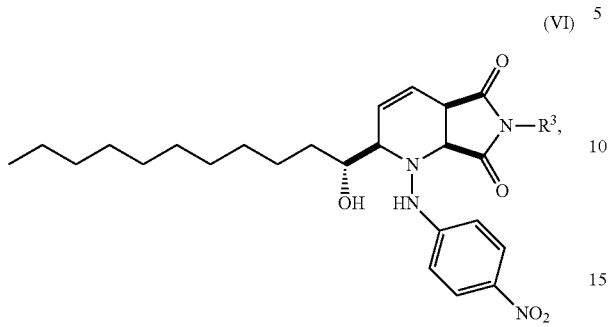
or
a stereoisomer, a racemate, a tautomer, a pharmaceutically acceptable salt, a solvate, or a functional derivative thereof,
wherein
$R^3$ is independently
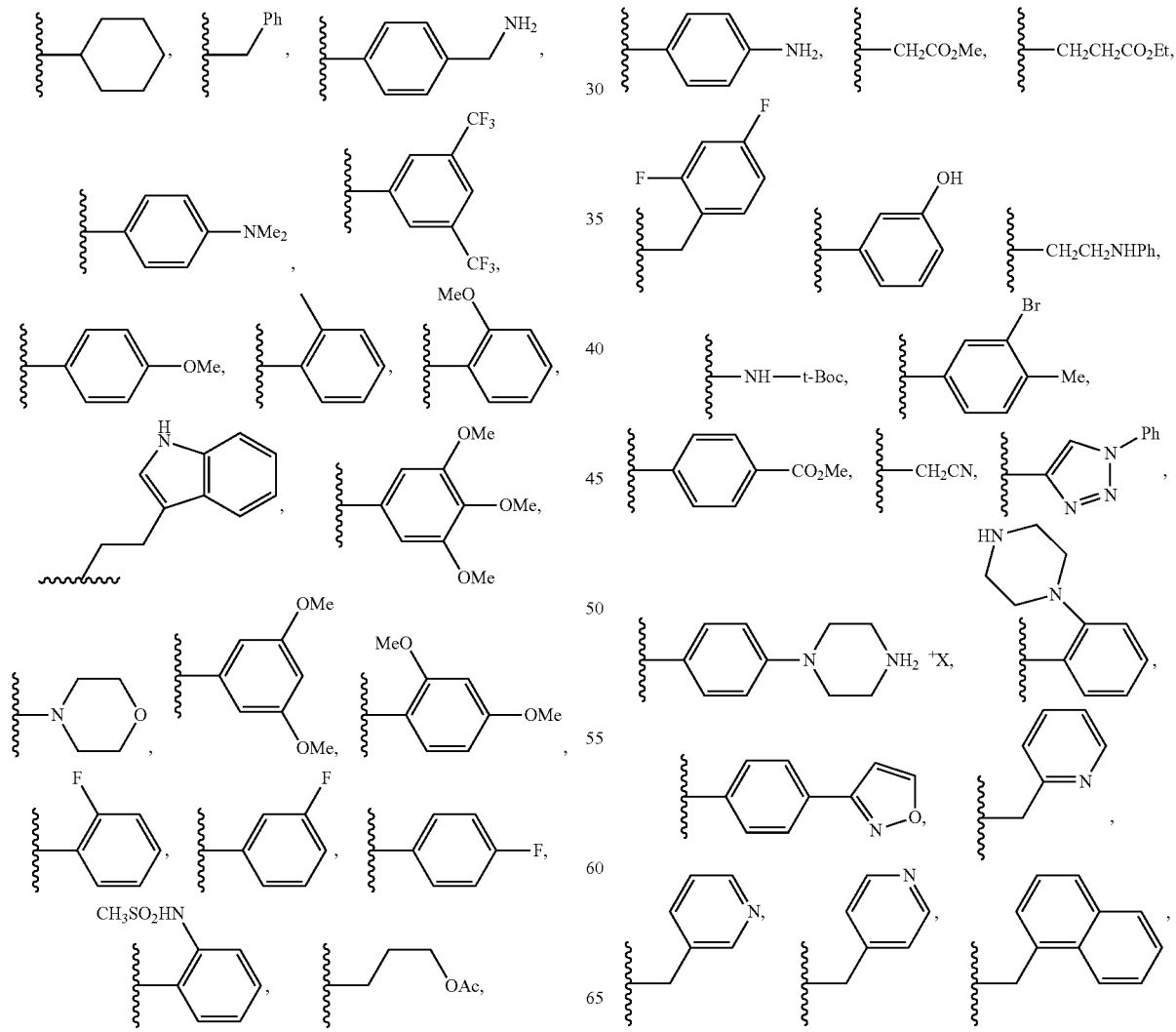

-continued

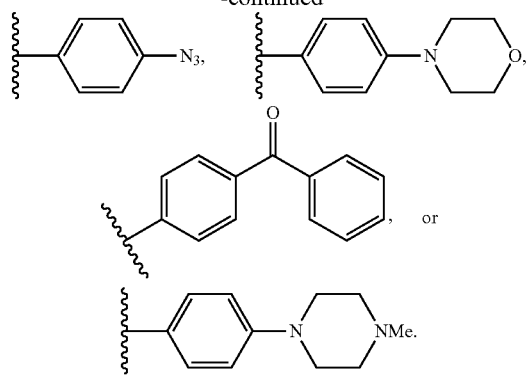

In an embodiment of the present application, there is provided a compound of formula (VIa)

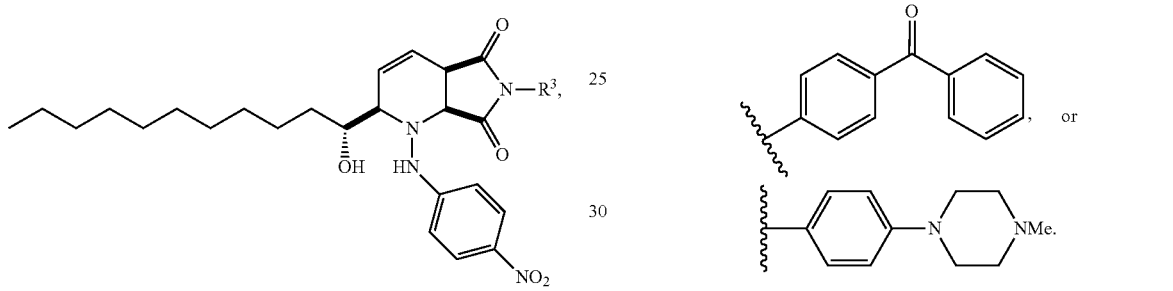
(VIa)

or
a stereoisomer, a racemate, a tautomer, a pharmaceutically acceptable salt, a solvate, or a functional derivative thereof, wherein
R³ is independently

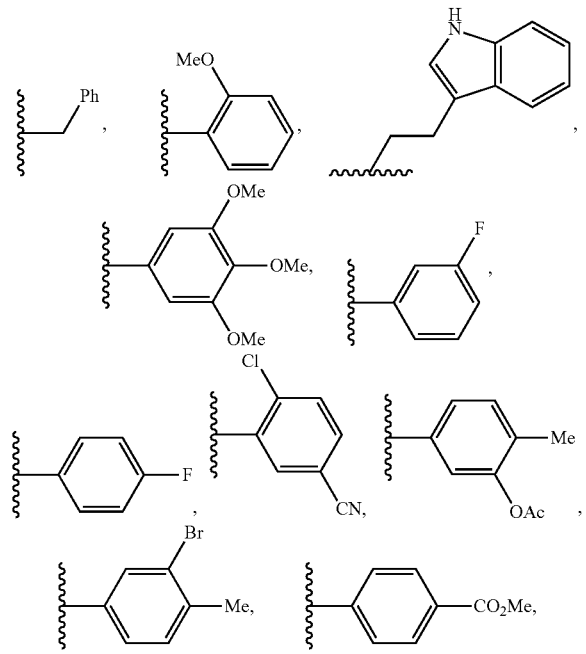

-continued

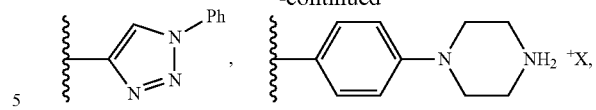

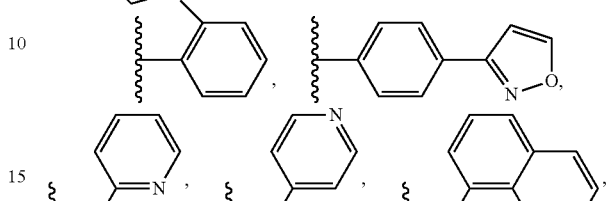

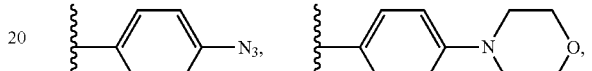

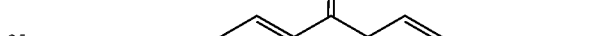

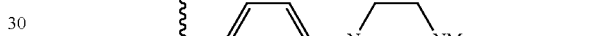

In an embodiment of the present application, there is provided a compound of formula (VIb)

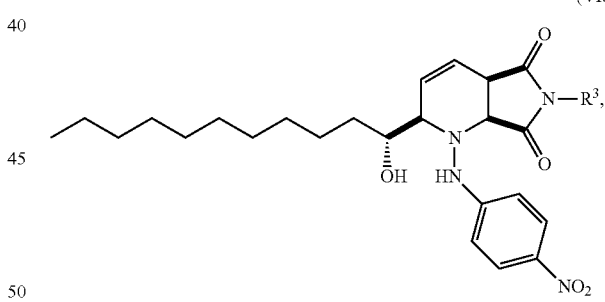
(VIb)

or
a stereoisomer, a racemate, a tautomer, a pharmaceutically acceptable salt, a solvate, or a functional derivative thereof, wherein
R³ is independently

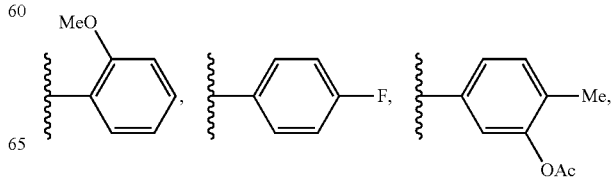

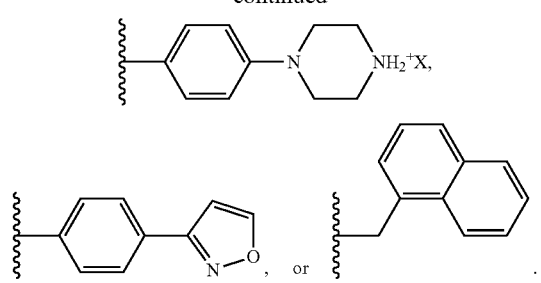
In an embodiment of the present application, there is provided a compound having the structure
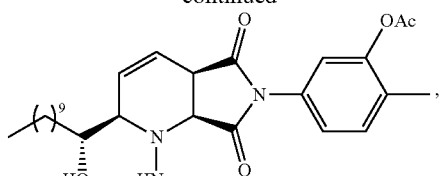
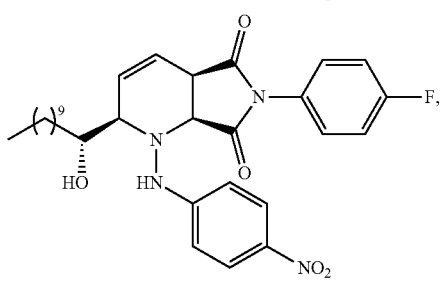
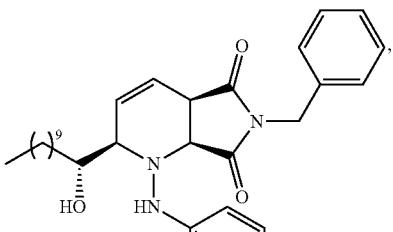
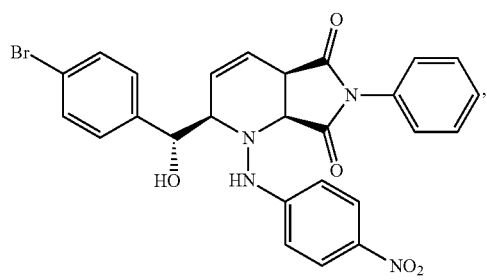
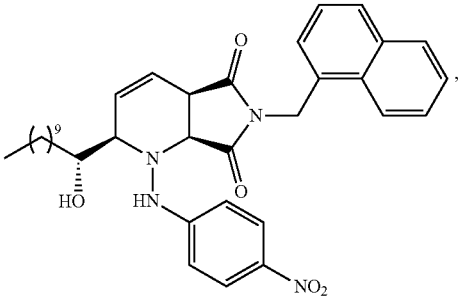
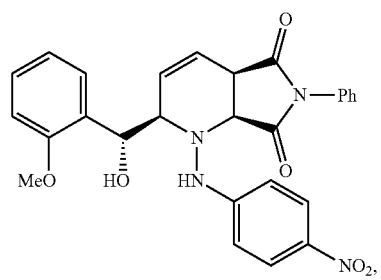
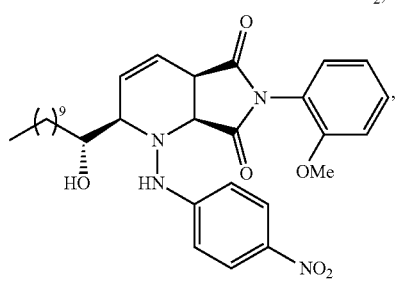
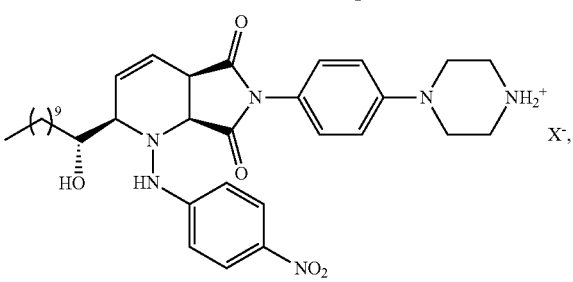

41
-continued
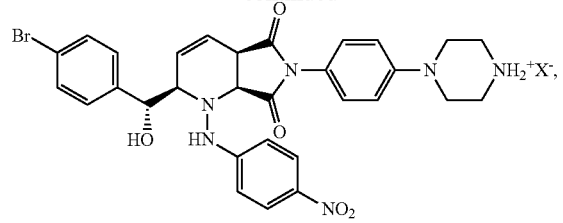
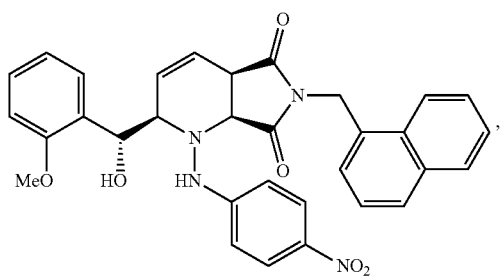
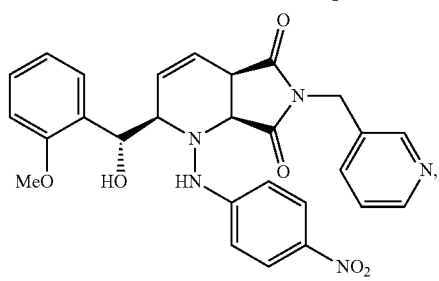
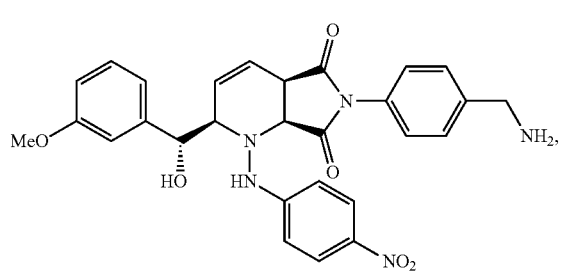
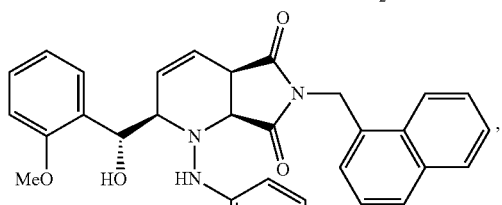
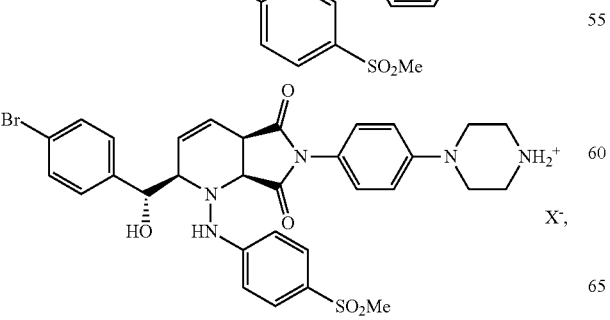
42
-continued
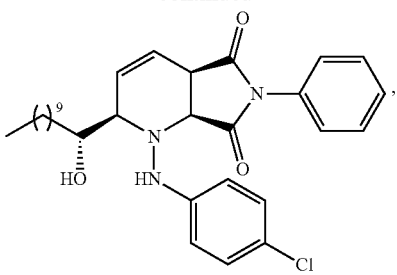
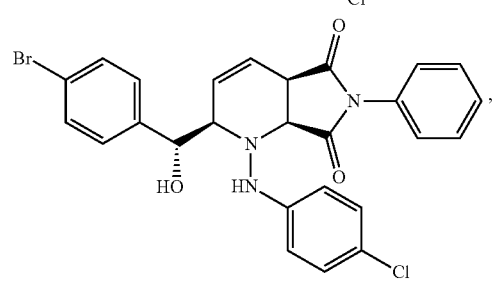
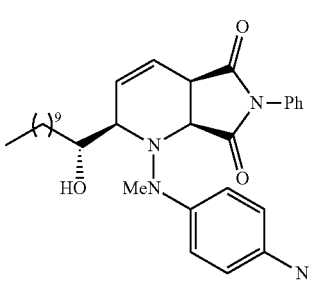
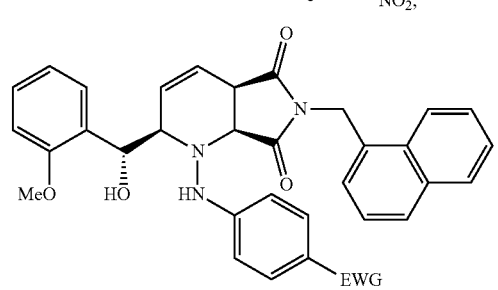
where EWG=CN, CO₂Me,
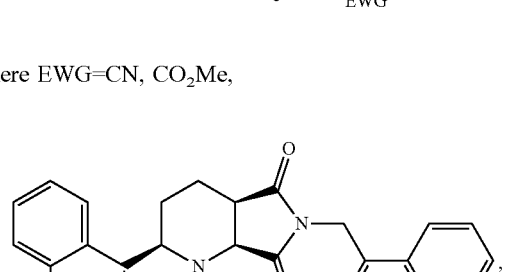
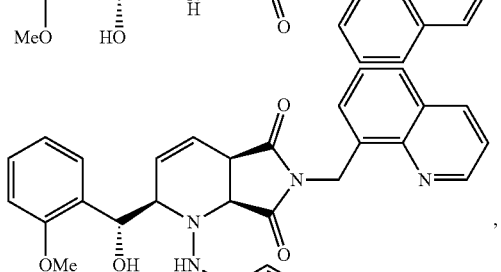

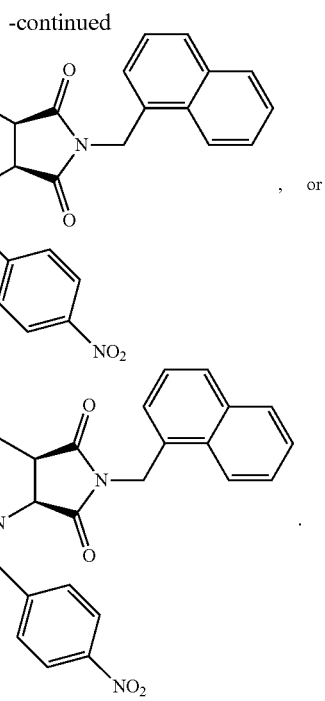

In an aspect of the present application, there is provided a pharmaceutical composition comprising a compound as described herein, and a pharmaceutically acceptable carrier, diluent, or vehicle.

In another aspect of the present application, there is provided a use of a compound as described herein, or a composition as described herein for treating a subject with, or suspected of having, a cancer.

In another aspect of the present application, there is provided a use of a compound as described herein, or a composition as described herein in the manufacture of a medicament for treating a subject with, or suspected of having a cancer.

In another aspect of the present application, there is provided a method of treating a subject having or suspected of having a cancer, comprising: administering a therapeutically effective amount of a compound as described herein, or a composition as described herein.

In another aspect of the present application, there is provided a compound as described herein, or a composition as described herein for inhibiting polynucleotide kinase phosphatase.

In another aspect of the present application, there is provided a compound as described herein, or a composition as described herein for increasing the sensitivity of a cancerous cell of a subject to a chemotherapeutic agent or radiation therapy.

In another aspect of the present application, there is provided a method of chemosensitizing or radiosensitizing a cancerous cell in a subject in need of chemotherapy or radiation therapy, comprising: administering to said subject a compound as described herein, or a composition as described herein.

In another aspect of the present application, there is provided an improved method for radiation therapy of a patient with a cancer employing a radiation sensitizer, wherein the improvement comprises treating said patient with an effective amount of a compound as described herein, or a composition as described herein as the radiation sensitizer.

In another aspect of the present application, there is provided an improved method for chemotherapy therapy of a patient with a cancer employing a chemosensitizer, wherein the improvement comprises treating said patient with an effective amount of a compound as described herein, or a composition as described herein as the chemosensitizer.

In another aspect of the present application, there is provided a kit for increasing the sensitivity of a cancerous cell to a chemotherapeutic agent or radiation therapy said kit comprising: a compound as described herein, or a composition as described herein; and instructions for the use thereof.

In another aspect of the present application, there is provided a compound for increasing the sensitivity of a cell and/or tumour to a chemotherapeutic agent and/or ionizing radiation, the compound comprising a compound as described herein.

In another aspect of the present application, there is provided a chemosensitization and/or radiosensitization method to treat a cell in vitro and/or in vivo comprising administering to said cell a compound as described herein, or a composition as described herein.

In another aspect of the present application, there is provided a method of radiosensitizing tumor cells in a subject in need of radiation therapy, comprising administering to said subject a compound as described herein, or a composition as described herein.

In another aspect of the present application, there is provided a use of a compound selected from a compound as described herein in the preparation of a pharmaceutical composition for use as a radiosensitizer.

In another aspect of the present application, there is provided a use of a compound selected from a compound as described herein in the preparation of a pharmaceutical composition for use as a chemosensitizer.

In another aspect of the present application, there is provided a method of inhibiting the phosphatase activity of PNKP, comprising: contacting a cell with a compound as described herein or pharmaceutically acceptable salt thereof, or a composition as described herein.

In another aspect of the present application, there is provided a method of treating a subject suffering from a disorder associated with a defect in DNA polymerase β, comprising administering to said subject an inhibitor of PNKP comprising a compound as described herein, or a composition as described herein.

In another aspect of the present application, there is provided a use of a compound as described herein, or a composition as described herein as an inhibitor of PNKP for treating a subject with, or suspected of having a disorder associated with a defect in DNA polymerase β.

In another aspect of the present application, there is provided a use of a compound as described herein in the preparation of a pharmaceutical composition for use as an inhibitor of the phosphatase activity of PNKP.

In an embodiment of the present application, there is provided a use wherein the phosphatase activity of PNKP is selected from human PNKP or mouse PNKP.

In another aspect of the present application, there is provided a PNKP phosphatase inhibitor selected from a compound as described herein to prepare a pharmaceutical composition to prevent or treat a cancer in a subject, wherein the pharmaceutical composition is intended for administration in combination with a chemotherapeutic agent and/or ionizing radiation used in a treatment of a cancer.

In another aspect of the present application, there is provided a pharmaceutical composition comprising: a first amount of a topoisomerase I inhibitor and a second amount of a PNKP inhibitor selected from a compound as described herein, and a pharmaceutically acceptable carrier.

In another aspect of the present application, there is provided a combination comprising a topoisomerase I inhibitor and a PNKP inhibitor selected from a compound as described herein, or a composition as described herein.

In another aspect of the present application, there is provided a method of treating a subject diagnosed with cancer, said method comprising administering to said subject a therapeutically effective amount of a pharmacological composition comprising a compound as described herein, wherein said composition contacts a cancer cell or tumour in said subject, thereby making said cancer cell or tumour more susceptible to the effects of chemotherapy and/or ionizing radiation.

In another aspect of the present application, there is provided a method for the treatment of a subject suffering from a disorder, such as cancer, associated with a defect in DNA polymerase β, comprising administering to said subject an inhibitor of PNKP selected from a compound as described herein, or a composition as described herein.

In another aspect of the present application, there is provided a method for the treatment of a subject suffering from a disorder, such as cancer, associated with a defect in PNKP or DNA-PK, comprising administering to said subject an inhibitor of PARP selected from a compound as described herein, or a composition as described herein.

In another aspect of the present application, there is provided a kit for increasing the sensitivity of a cell(s) and/or tumour(s) to a chemotherapeutic agent and/or ionizing radiation or for inhibiting the phosphatase activity of PNKP, said kit comprising: (i) a compound selected from a compound as described herein; and (ii) instructions for the use thereof.

In another aspect of the present application, there is provided a compound of formula (I), wherein formula (I) has the structure,

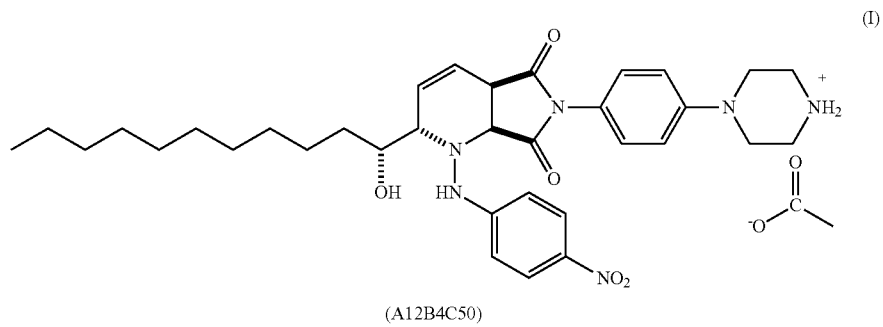

(A12B4C50)

or enantiomers, prodrugs, derivatives, and pharmaceutically acceptable salts thereof.

In another aspect of the present application, there is provided a compound of formula (II), wherein formula (II) has the structure,

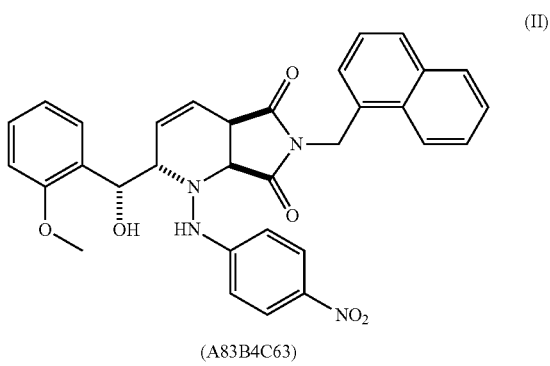

(A83B4C63)

or enantiomers, prodrugs, derivatives, and pharmaceutically acceptable salts thereof.

In another aspect of the present application, there is provided a pharmaceutical composition comprising a compound as described herein, and a pharmaceutically acceptable excipient or carrier.

In another aspect of the present application, there is provided a pharmaceutical composition, comprising a micelle and a compound as described herein.

In another aspect of the present application, there is provided a pharmaceutical composition, comprising a micelle, wherein said micelle comprises PEO-b-PBCL, PEO-PCL, PEO-PDLA, and/or PEO-PLGA; and a compound as described herein.

In another aspect of the present application, there is provided a pharmaceutical composition, comprising a micelle, wherein said micelle comprises PEO-b-PBCL, PEO-PCL, PEO-PDLA, and/or PEO-PLGA; and a compound as described herein.

In an embodiment of the present application, there is provided a pharmaceutical composition wherein said micelle further comprises a targeting ligand.

In another embodiment of the present application, there is provided a pharmaceutical composition, wherein said targeting ligand is an antibody, a polypeptide, a small molecule, or an aptamer.

In another embodiment, there is provided a pharmaceutical composition, wherein said targeting ligand comprises or consists of polypeptide is YHWYGYTPQNVI (SEQ ID NO: 3; GE11).

In another embodiment of the present application, there is provided a pharmaceutical composition further comprising a topoisomerase I inhibitor.

In another embodiment, there is provided a pharmaceutical composition wherein said topoisomerase I inhibitor is irinotecan.

In another embodiment, there is provided a pharmaceutical composition wherein the size of each said micelle is between 20-100 nm.

In another aspect of the present application, there is provided a method of inhibiting PNKP protein activity in a cell, comprising, contacting a cell with a compound as described herein, or a pharmaceutical composition as described herein.

In an embodiment of the present application, there is provided a method wherein said contacting is in vitro or in vivo.

In another embodiment, there is provided a method wherein said PNKP is human PNKP.

In another aspect of the present application, there is provided a use of a compound as described herein, or a pharmaceutical composition as described herein for inhibiting PNKP protein activity in a cell.

In another aspect of the present application, there is provided a use of a compound as described herein, or a pharmaceutical composition as described herein in the manufacture of a medicament for inhibiting PNKP protein activity in a cell.

In an embodiment of the present application, there is provided a use wherein said use is in vitro or in vivo.

In another embodiment, there is provided a use wherein said PNKP is human PNKP.

In another aspect of the present application, there is provided a method of chemosensitizing or radio sensitizing a cancer cell is a mammal in need of chemotherapy or radiation therapy, comprising: administering to said mammal a compound as described herein, or a pharmaceutical composition as described herein.

In another embodiment of the present application, there is provided a method wherein said chemotherapy is treatment with a topoisomerase I inhibitor.

In another embodiment, there is provided a method, wherein said topoisomerase I inhibitor is irinotecan.

In another embodiment, there is provided a method wherein said radiation therapy is external radiation therapy, internal radiation therapy or systemic radiation therapy.

In another embodiment, there is provided a method wherein said patient has or is suspected of having a colorectal cancer.

In another embodiment, there is provided a method wherein said mammal is a human.

In another aspect of the present application, there is provided a use of a compound as described herein, or a pharmaceutical composition as described herein for chemosensitizing or radio sensitizing a cancer cell is a mammal.

In another embodiment of the present application, there is provided a use wherein said chemotherapy is use of a topoisomerase I inhibitor.

In another embodiment, there is provided a use wherein said topoisomerase I inhibitor is irinotecan.

In another embodiment, there is provided a use wherein said radiation therapy is external radiation therapy, internal radiation therapy or systemic radiation therapy.

In another embodiment, there is provided a use of wherein said patient has or is suspected of having colorectal cancer.

In another embodiment, there is provided a use wherein said mammal is a human.

In another aspect of the present application, there is provided a method of treating a subject having a cancer, or suspected of having a cancer, said cancer associated with a defect in a tumor suppressor, comprising: administering to said subject a compound as described herein, or a pharmaceutical composition as described herein.

In another embodiment of the present application, there is provided a method wherein said tumour suppressor is ING3, CDKN3, PTPN6, PTEN, or SMG1.

In another embodiment, there is provided a method wherein said tumour suppressor is PTEN.

In another embodiment, there is provided a method wherein said subject is a human.

In another embodiment, there is provided a method wherein said cancer is colorectal cancer.

In another aspect of the present application, there is provided a use of a compound as described herein, or a pharmaceutical composition as described herein for treating a subject having a cancer, or suspected of having a cancer, said cancer associated with a defect in a tumor suppressor.

In another embodiment of the present application, there is provided a use wherein said tumour suppressor is ING3, CDKN3, PTPN6, PTEN, or SMG1.

In another embodiment, there is provided a use wherein said tumour suppressor is PTEN.

In another embodiment, there is provided a use wherein said subject is a human.

In another embodiment, there is provided a use wherein said cancer is colorectal cancer.

In another aspect of the present application, there is provided a method of identifying a subject having cancer, or suspected of having cancer, that will benefit from treatment with an inhibitor of PNKP, comprising: determining the presence of a defect in a tumour suppressor in a cancerous within said sample, wherein said defect reduces or abolishes the expression or activity of said tumour suppressor, wherein a defect in said tumour suppressor indicates said subject has a cancer which is suitable for treatment with said inhibitor of PNKP, wherein said inhibitor of PNKP is a compound as described herein, or a pharmaceutical composition as described herein.

In another embodiment, there is provided a method wherein said tumour suppressor is ING3, CDKN3, PTPN6, PTEN, or SMG1.

In another embodiment, there is provided a method wherein said tumour suppressor is PTEN.

In another embodiment, there is provided a method wherein said cancer is colorectal cancer.

In another embodiment, there is provided a method wherein said subject is a human.

In another embodiment, there is provided a method further comprising administering a compound as described herein, or a pharmaceutical composition as described herein.

In another aspect of the present application, there is provided a kit comprising one or more of a compound as described herein, or a pharmaceutical composition as described herein, optionally a carrier or excipient, optionally a container, and optionally instructions for use thereof.

BRIEF DESCRIPTION OF THE FIGURES

The application file contains at least one drawing executed in color. Copies of this patent or patent application with color drawings will be provided by the Office upon request and payment of the necessary fee.

Embodiments of the present disclosure will now be described, by way of example only, with reference to the attached Figures.

FIG. 4 depicts tabulated nonlinear regression data sheet from Prism.

DETAILED DESCRIPTION

Figure 1:
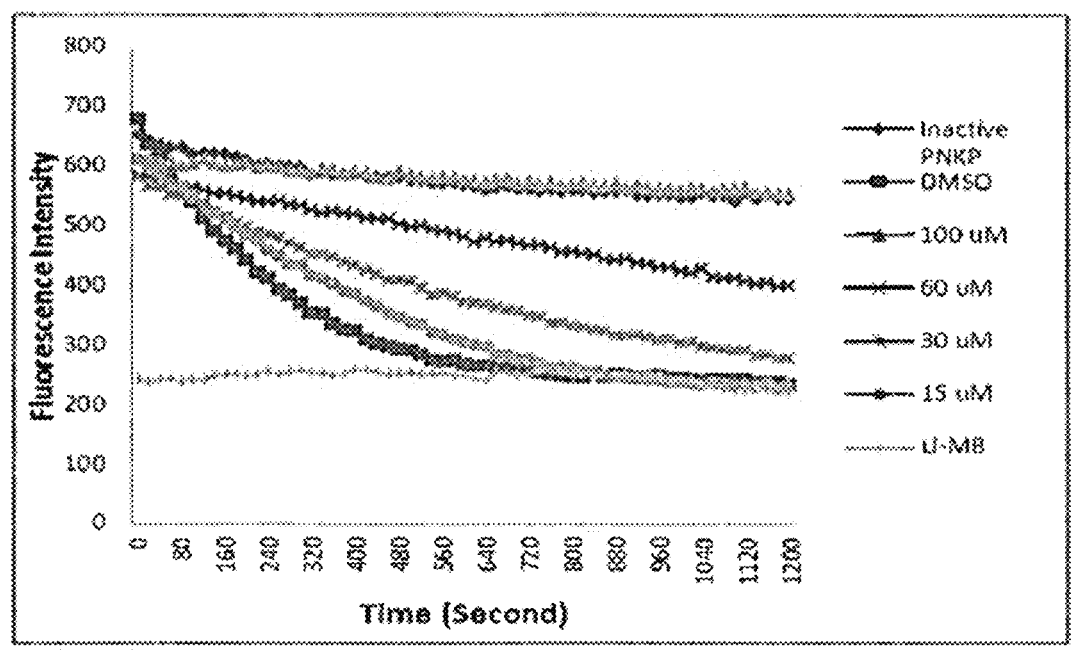
FIG. 1 is a graph depicting inhibition of PNKP Phosphatase activity by A96B4C3.

Unless defined otherwise, all technical and scientific terms used herein have the same meaning as commonly understood by one of ordinary skill in the art to which this invention belongs.

As used in the specification and claims, the singular forms "a", "an" and "the" include plural references unless the context clearly dictates otherwise.

The term "comprising" as used herein will be understood to mean that the list following is non-exhaustive and may or may not include any other additional suitable items, for example one or more further feature(s), component(s) and/or ingredient(s) as appropriate.

As described herein, in one aspect, there is described compounds, compositions, methods and kits for treating a subject suspect of having cancer or having cancer.

In one aspect, there is described compounds, compositions, methods and kits for increasing sensitivity of cells and/or tumours to chemotherapeutic agents and/or ionizing radiation.

As further described herein, the present application relates to inhibitors of polynucleotide kinase/phosphatase and poly (ADP-ribose) polymerase.

As used herein, the term 'optionally substituted' refers to being substituted or unsubstituted.

As used herein, the term "unsubstituted" refers to any open valence of an atom being occupied by hydrogen. Also, if an occupant of an open valence position on an atom is not specified then it is hydrogen.

As used herein, the term "substituted" refers to having one or more substituents or substituent moieties whose presence either facilitates or improves a desired reaction/property, or does not impede a desired reaction/property. A "substituent" is an atom or group of bonded atoms that can be considered to have replaced one or more hydrogen atoms attached to a parent molecular entity; and, whose presence either facilitates or improves desired reactions, properties, and/or functions of an invention, or does not impede desired reactions, properties, and/or functions of an invention. Examples of substituents include alkyl, alkenyl, alkynyl, aryl, polycyclic aryl, benzyl, polycyclic benzyl, fused aromatic rings, arylhalide, heterocycle, heteroaryl, polycyclic heteroaryl, fused heteroaromatic rings, cycloalkyl (non-aromatic ring), halo, alkoxyl, perfluoronated alkoxyl, amino, alkylamino, alkenylamino, amide, amidine, hydroxyl, thioether, alkylcarbonyl, alkylcarbonyloxy, arylcarbonyloxy, alkoxycarbonyloxy, aryloxycarbonyloxy, carbonate, alkoxycarbonyl, aminocarbonyl, alkylthiocarbonyl, phosphate, phosphate ester, phosphonato, phosphinato, cyano, acylamino, imino, sulfhydryl, alkylthio, arylthio, thiocarboxylate, dithiocarboxylate, sulfate, sulfato, sulfonate, sulfamoyl, sulfone, sulfonyl, sulfonamide, Si(alkyl)$_3$, Si(alkoxy)$_3$, nitro, nitrile, azido, heterocyclyl, ether, ester, silicon-containing moieties, thioester, or a combination thereof. The substituents may themselves be substituted. For instance, an amino substituent may itself be mono or independently disubstituted by further substituents provided above, such as alkyl, alkenyl, alkynyl, aryl, arylhalide, heteroaryl, cycloalkyl (non-aromatic ring).

As used herein, "alkyl" refers to a linear or branched saturated hydrocarbon moiety that consists solely of single-bonded carbon and hydrogen atoms, which can be unsubstituted or substituted with one or more substituents. Examples of saturated straight or branched chain alkyl groups include, but are not limited to, methyl, ethyl, 1-propyl, 2-propyl, 1-butyl, 2-butyl, 2-methyl-1-propyl, 2-methyl-2-propyl, 1-pentyl, 2-pentyl, 3-pentyl, 2-methyl-1-butyl, 3-methyl-1-butyl, 2-methyl-3-butyl, 2,2-dimethyl-1-propyl, 1-hexyl, 2-hexyl, 3-hexyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl and 2-ethyl-1-butyl, 1-heptyl, and 1-octyl.

As used herein, "alkenyl" refers to a linear or branched hydrocarbon moiety that comprises at least one carbon to carbon double bond, which can be unsubstituted or substituted with one or more substituents. "Alkynyl" refers to a linear or branched hydrocarbon moiety that comprises at least one carbon to carbon triple bond, which can be unsubstituted or substituted with one or more substituents.

The term "carbocycle" as used herein refers to a non-aromatic, saturated or partially saturated monocyclic or polycyclic hydrocarbon ring moiety containing at least 3 carbon atoms. Examples of $C_3$-$C_n$ carbocycles include, but are not limited to, cyclopropyl, cyclobutyl, cyclopentyl, cyclohexyl, cycloheptyl, cyclooctyl, norbornyl, adamantyl, bicyclo[2.2.2]oct-2-enyl, and bicyclo[2.2.2]octyl.

As used herein, "aryl" and/or "aromatic ring" refers to an aromatic (unsaturated cyclic) hydrocarbon moiety having 6 to 100 atoms, or 6 to 50 atoms, or 6 to 25 atoms, or 6 to 15 atoms, which can be unsubstituted or substituted with one or more substituents. The aromatic hydrocarbon moiety may be derived from benzene or a benzene derivative; may be monocyclic or polycyclic, where polycyclic may include a fused ring system. Examples include, but are not limited to, phenyl, naphthyl, xylene, phenyl ethane, substituted phenyl, substituted naphthyl, substituted xylene, substituted 4-ethylphenyl, benzyl, etc.

As used herein, "heteroaryl" or "heteroaromatic" refers to an aryl (including fused aryl rings) that includes heteroatoms selected from oxygen, nitrogen, sulfur, and phosphorus. A "heteroatom" refers to an atom that is not carbon or hydrogen, such as nitrogen, oxygen, sulfur, or phosphorus. Heteroaryl or heteroaromatic groups include, for example, furanyl, thiophenyl, pyrrolyl, imidazoyl, benzamidazoyl, 1,2- or 1,3-oxazolyl, 1,2- or 1,3-diazolyl, 1,2,3- or 1,2,4-triazolyl, and the like.

As used herein, a "heterocycle" is an aromatic or non-aromatic monocyclic, polycyclic, or fused ring moiety of carbon atoms and at least one heteroatom, or 1 to 4 heteroatoms, or 1 to 10 heteroatoms. A "heteroatom" refers to an atom that is not carbon or hydrogen, such as nitrogen, oxygen, sulfur, or phosphorus. Included within the term "heterocycle" is "heteroaryl", which refers to an aromatic (unsaturated cyclic) moiety of carbon atoms and at least one heteroatom, or 1 to 4 heteroatoms, or 1 to 10 heteroatoms, having a total of 6 to 100 atoms, or 6 to 50 atoms, or 6 to 25 atoms, or 6 to 15 atoms, which can be unsubstituted or substituted with one or more substituents. Also included within this term are monocyclic and bicyclic rings that include one or more double and/or triple bonds within the ring. Examples of 3- to 9-membered heterocycles include, but are not limited to, furanyl, thiophenyl, pyrrolyl, imidazoyl, benzamidazoyl, 1,2- or 1,3-oxazolyl, 1,2- or 1,3-diazolyl, 1,2,3- or 1,2,4-triazolyl, aziridinyl, oxiranyl, thiiranyl, azirinyl, diaziridinyl, diazirinyl, oxaziridinyl, azetidinyl, azetidinonyl, oxetanyl, thietanyl, piperidinyl, piperazinyl, morpholinyl, pyrrolyl, oxazinyl, thiazinyl, diazinyl, triazinyl, tetrazinyl, imidazolyl, benzimidazolyl, tetrazolyl, indolyl, isoquinolinyl, quinolinyl, quinazolinyl, pyrrolidinyl, purinyl, isoxazolyl, benzisoxazolyl, furanyl, furazanyl, pyridinyl, oxazolyl, benzoxazolyl, thiazolyl, benzthiazolyl, thiophenyl, pyrazolyl, triazolyl, benzodiazolyl, benzotriazolyl, pyrimidinyl, isoindolyl and indazolyl.

As used herein, "halo" refers to F, Cl, Br, I.

As used herein, "BOC/Boc" or "t-BOC/Boc" refers to a tert-butyloxycarbonyl group.

As used herein, the term "inhibit" with respect to phosphatase activity is intended to include partial or complete inhibition of phosphatase activity.

The term "radiosensitizer", as used herein refers to an agent, molecule, compound or composition that enhances the sensitivity of a neoplastic cell, a cancer cell and/or a tumour to the effects of radiation. The "sensitivity" of a neoplastic cell, a cancer cell, and/or a tumour to radiation is the susceptibility of the neoplastic cell, cancer cell, and/or tumour to the inhibitory effects of radiation on the cell's or tumour's growth and/or viability.

The term "chemosensitizer", as used herein, refers to an agent, molecule, compound or composition that enhances the sensitivity of a neoplastic cell, a cancer cell and/or a tumor to the effects of a chemotherapeutic agent. The "sensitivity" of a neoplastic cell, a cancer cell, and/or a tumour to a chemotherapeutic agent is the susceptibility of the neoplastic cell, cancer cell, and/or tumour to the inhibitory effects of a chemotherapeutic agent on the cell's or tumour's growth and/or viability.

The term "topoisomerase I inhibitor" as used herein includes, but is not limited to topotecan (HYCAMTIN®), gimatecan, irinotecan (CAMPTOSAR®), camptothecin and its analogues.

The term "subject", as used herein, refers to any human or non-human animal whom would benefit from treatment with a chemosensitizer and/or a radiosensitizer, and/or has a disorder associated with PNKP. Non-limiting examples of a subject include humans, non-human mammal, primates, rodents, companion animals (including but not limited to dogs, cats, mice, rats), livestock (including but not limited to horses, sheep, cattle, pigs), reptiles, amphibians, and the like. In a specific example, the subject is a human.

The term "cancer" refers to or describes the physiological conditions in a subject generally characterized by inappropriate cellular proliferation, abnormal or excessive cellular proliferation. Cancers may be solid or non-solid cancers. Cancers may be a primary cancer and/or metastatic cancer. Cancers include, but are not limited to, a solid cancer, a non-solid cancer, a primary cancer, a metastatic cancer, breast cancer, uterine cancer, ovarian cancer, prostate cancer, lung cancer, colorectal cancer, cervical cancer, liver cancer, head and neck cancer, oesophageal cancer, pancreatic cancer, renal cancer, stomach cancer and cerebral cancer, lymphoma, NK lymphoma, T cell lymphoma, leukemia, lymphoid malignancies, sarcomas, carcinomas skin cancer, bladder cancer, a carcinoma, a melanoma, endometrial carcinoma, astrocytoma, malignant astrocytoma, colorectal cancer, familial cancer, or sporadic cancer.

The term "sample" as used herein encompasses a variety of cell-containing bodily fluids and/or secretions as well as tissues including, but not limited to, a cell(s), tissue, whole blood, blood-derived cells, plasma, serum, sputum, mucous, bodily discharge, and the like, and combinations thereof. Methods of obtaining such samples from subject are known to the skilled worker.

By the terms "treating" or "lessening the severity", it is to be understood that any reduction using the methods, compounds and composition disclosed herein, is to be considered encompassed by the invention. Treating or lessening in severity, may, in one embodiment comprise enhancement of survival, or in another embodiment, halting disease progression, or in another embodiment, delay in disease progression, or in another embodiment, diminishment of pain, or in another embodiment, delay in disease spread to alternate sites, organs or systems. Treating or lessening in severity, may, in one embodiment, comprise a reduction in the amount/dosage of radiotherapy and/or chemotherapy otherwise required to treat a subject, thereby resulting in a reduction of normal tissue damage. It is to be understood that any clinically beneficial effect that arises from the methods, compounds and compositions disclosed herein, is to be considered to be encompassed by the invention.

In a specific example, treatment is carried out in vivo.

In a specific example, treatment is carried out in vitro, including but not limited to, in test tube, in cultured cells (both adherent cells and non-adherent cells), and the like.

In a specific example, treatment is carried out ex vivo, including but not limited to, in test tube, in cultured cells (both adherent cells and non-adherent cells), and the like.

The term "prognosis" as used herein refers to the prediction of the likelihood of cancer-attributable death or progression, including recurrence, metastatic spread, and drug resistance, of a neoplastic disease.

The term "pharmaceutically effective amount" as used herein refers to the amount of a drug or pharmaceutical agent that will elicit the biological or medical response of a tissue, system, animal or human that is being sought by a researcher or clinician. This amount can be a therapeutically effective amount.

The term "pharmaceutically acceptable" as used herein refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The term "pharmaceutically acceptable carrier" as used herein refers to a pharmaceutically acceptable material, composition or vehicle, such as a liquid or solid filler, diluent, excipient, solvent or encapsulating material, involved in carrying or transporting the subject agents from one organ, or portion of the body, to another organ, or portion of the body. Each carrier must be "acceptable" in the sense of being compatible with the other ingredients of the formulation, for example the carrier does not decrease the impact of the agent on the treatment. In other words, a carrier is pharmaceutically inert. The terms "physiologically tolerable carriers" and "biocompatible delivery vehicles" are used interchangeably. Thus, the term "carrier" or "excipient" may refer to a non-toxic solid, semi-solid or liquid filler, diluent. The term includes solvents, dispersion, media, coatings, isotonic agents, and adsorption delaying agents, and the like. The use of such media and agents for pharmaceutically active substances is well known in the art.

As used herein, the term "pharmaceutically-acceptable salts" refers to the conventional nontoxic salts or quaternary ammonium salt. These salts can be prepared in situ in the administration vehicle or the dosage form manufacturing process, or by separately reacting a compound in its free base or acid form with a suitable organic or inorganic acid or base, and isolating the salt thus formed during subsequent purification. Conventional nontoxic salts include those derived from inorganic acids such as sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like.

A "pharmaceutical composition" as used herein refers to a chemical or biological composition suitable for administration to a mammalian subject. Such compositions may be specifically formulated for administration via one or more of a number of routes, including but not limited to, oral, parenteral, intravenous, intraarterial, subcutaneous, intranasal, sublingual, intraspinal, intracerebroventricular, and the like.

The term "functional derivative" as used herein refers to a molecule that retains a biological activity (either function or structural) that is substantially similar to that of the original compound. A functional derivative or equivalent may be a natural derivative or is prepared synthetically. For example, the term "derivative"" as used herein may refer to a chemical substance related structurally to another, i.e., an "original" substance, which can be referred to as a "parent" compound. A "derivative" can be made from the structurally-related parent compound in one or more steps. The general physical and chemical properties of a derivative are also similar to the parent compound.

Also encompassed is prodrug or "physiologically functional derivative". The term "physiologically functional derivative" as used herein refers to compounds which are not pharmaceutically active themselves but which are transformed into their pharmaceutically active form in vivo, i.e. in the subject to which the compound is administered.

As used herein, a "prodrug" refers to a compound that can be converted via some chemical or physiological process (e.g., enzymatic processes and metabolic hydrolysis). The term "prodrug" also refers to a precursor of a biologically active compound that is pharmaceutically acceptable. A prodrug may be inactive when administered to a subject, i.e. an ester, but is converted in vivo to an active compound, for example, by hydrolysis to the free carboxylic acid or free hydroxyl. The prodrug compound often offers advantages of solubility, tissue compatibility or delayed release in an organism. The term "prodrug" is also meant to include any covalently bonded carriers, which release the active compound in vivo when such prodrug is administered to a subject. Prodrugs of an active compound may be prepared by modifying functional groups present in the active compound in such a way that the modifications are cleaved, either in routine manipulation or in vivo, to the parent active compound.

Described herein is the design, and synthesis of new imidopiperidine compounds and the identification of potent inhibitors of the DNA repair enzyme, human polynucleotide kinase phosphatase (PNKP).

The term "enantiomer" is used to describe one of a pair of molecular isomers which are mirror images of each other and non-superimposable.

Radiation and many of the current chemotherapeutic agents used to treat cancer kill cancer cells by damaging the DNA in the cells. Because cells contain enzymes that repair DNA damage, small molecules have been developed that inhibit DNA repair enzymes like polynucleotide kinase/phosphatase (PNKP) and improve the ability of radiation and drugs to kill cancer cells. Previously, a small group of chemical compounds, as described in U.S. Pat. No. 9,040,551 (the entire contents of which is incorporated by reference), were identified that inhibited PNKP. These were the first compounds reported to inhibit human PNKP. In vivo studies have also demonstrated the validity of PNKP as a drug target.

Damage to cellular DNA is the principle cause of cell death induced by many chemotherapeutic drugs and ionizing radiation (IR). Drugs such as the topoisomerase I poisons irinotecan and topotecan, as well as IR, induce multiple forms of DNA damage, including DNA strand breaks with strand break termini that require action from a DNA repair enzyme termed polynucleotide kinase/phosphatase (PNKP). In both the metastatic and curative settings, a significant number of patients do not benefit from chemotherapy and radiotherapy because their tumors possess robust DNA repair capacity or they develop resistance over time through upregulation of DNA repair pathways. Inhibiting the capacity of cancer cells to repair their DNA following irradiation or treatment with drugs has potential to improve the therapeutic benefit of these treatments, or to reduce the dosage and the adverse effects associated with treatment. In addition, synthetic lethality offers the potential for the use of DNA repair inhibitors as single agents in cancer treatment of selected individuals. It also offers the potential to combine inhibitors of PNKP with inhibitors of the synthetic lethal partner, e.g. PTEN or PARP inhibitors.

As described herein, new inhibitors of the PNKP DNA repair enzyme have been developed to enhance killing of cancer cells by the standard therapeutic agents, and through synthetic lethality. This approach was based on evidence that DNA repair affects clinical outcomes. DNA repair systems are emerging as therapeutic targets to enhance cytotoxicity of radiation and genotoxic drugs, fueled by commercialization of inhibitors of one such DNA repair enzyme, PARP. Targeting of PNKP offers an alternative to use of PARP inhibitors when used together with radiation. This is beneficial under circumstances where cancer cells develop resistance to the PARP inhibitors and also increases the scope of synthetic lethal interactions.

Compound(s)/Composition(s)

In an aspect of the present application, there is provided compound(s) and composition(s) that inhibit PNKP phosphatase activity. In examples of the present application, the compound(s) and composition(s) inhibit DNA phosphatase activity of human PNKP or mouse PNKP.

In an aspect of the present application, compound(s) as described herein increase radiosensitivity and/or chemosensitivity of a cell(s) and/or tumour(s). In another aspect, compound(s) as described herein reduce cell survival of cells depleted with DNA polymerase β or PARP. In another aspect, compound(s) as described herein inhibit the phosphatase activity of PNKP.

In an example of the present application, a PNKP inhibitor is A83B4C64.

Compounds as described herein are capable of forming a variety of different salts with various inorganic and organic acids. Such salts are pharmaceutically acceptable for administration to a subject.

In an example of the present application, the compound(s) and composition(s) as described herein increase sensitivity of a cell and/or tumour to radiation.

About half of patients with cancer are treated with radiation therapy, either alone or in combination with other types of cancer treatment. Radiation therapy (also referred to as radiotherapy, X-ray therapy, or irradiation) may be external, internal and systemic. External radiation is delivered from a machine outside the body; internal radiation is implanted into or near the tumour(s); systemic radiation utilizes unsealed radiation sources.

External radiation therapy is used to treat most types of cancer, including but not limited to, cancer of the bladder, brain, breast, cervix, larynx, lung, prostate, and vagina. Intraoperative radiation therapy (IORT) is a form of external radiation that is given during surgery, and can be used to treat localized cancers that cannot be completely removed or that have a high risk of recurring in nearby tissues, including, but not limited to treatment of thyroid and colorectal cancers, gynecological cancers, cancer of the small intestine, and cancer of the pancreas. Prophylactic cranial irradiation (PCI) is another type of external radiation given to the brain when the primary cancer (for example, small cell lung cancer) has a high risk of spreading to the brain.

Internal radiation therapy (or brachytherapy) typically uses radiation source sealed in a small holder called an implant. Implants may be in the form of thin wires, plastic tubes called catheters, ribbons, capsules, or seeds. Interstitial radiation therapy, a type of internal radiation therapy, is inserted into tissue at or near the tumour site. It is used to treat tumors of the head and neck, prostate, cervix, ovary, breast, and perianal and pelvic regions. Intracavitary or intraluminal radiation therapy is inserted into the body with an applicator. It is commonly used in the treatment of uterine cancer, and may have application in other cancers, including breast, bronchial, cervical, gallbladder, oral, rectal, tracheal, uterine, and vaginal.

Systemic radiation therapy uses materials such as iodine 131 and strontium 89, and may be taken by mouth or injected. Such therapy may be used in the treatment of cancers of the thyroid and adult non-Hodgkin lymphoma.

In an example of the present application, the radiation is γ-radiation. In another example, the ionizing radiation is X-rays generated by a linear accelerator (Linac).

In another example, the compound(s) and composition(s) as described herein increases sensitivity of a cell(s) and/or tumour(s) to a chemotherapeutic agent. In one example, the chemotherapeutic agent is a topoisomerase I inhibitor. In another example, the topoisomerase I inhibitor is camptothecin.

Indications, routes and methods of administration, and the like, of topoisomerase I inhibitors are known to the skilled worker. CAMPTOSAR® injection, for example, is indicated as a component of first-line therapy in combination with 5-fluorouracil and leucovorin for patients with metastatic carcinoma of the colon or rectum. CAMPTOSAR is also indicated for patients with metastatic carcinoma of the colon or rectum whose disease has recurred or progressed following initial fluorouracil-based therapy. HYCAMTIN for Injection, for example, is indicated for: metastatic carcinoma of the ovary after failure of initial or subsequent chemotherapy, small cell lung cancer sensitive disease after failure of first-line chemotherapy, combination therapy with cisplatin for stage IV-B, recurrent, or persistent carcinoma of the cervix which is not amenable to curative treatment with surgery and/or radiation therapy. HYCAMTIN capsules, for example, is indicated for treatment of patients with relapsed small cell lung cancer In another aspect of the present application, there are provided pharmaceutical compositions and methods of treatment using such pharmaceutical compositions for therapeutic uses. In an example of the present application, there is provided a pharmaceutical composition comprising a compound as described herein together with pharmaceutically acceptable diluents or carriers. Suitable pharmaceutical carriers include inert diluents or fillers, water and various organic solvents. The pharmaceutical composition may, if desired, contain additional ingredients such as flavorings, binders, excipients and the like.

In another aspect of the present application, inhibitors of PNKP are used to reduce survival of cells depleted in DNA polymerase β. Accordingly, there is provided a potential synthetic lethal therapeutic strategy for the treatment of cancers with specific DNA-repair defects, including those arising in carriers of a DNA Polymerase β mutation.

In another aspect of the present application, inhibitors of PARP are used to reduce survival of cells depleted in PNKP or DNA-PK. PARP inhibitors may be useful in the treatment of pancreatic cancer, solid tumours, melanoma, colorectal cancer, breast cancer, ovarian cancer, non-small cell lung cell cancer, sarcoma, glioblastoma multiforme. Additional examples of PARP inhibitors include, but are not limited to, BSI401 (BiPar Science Inc.); CPH101 with CPH102 (Crimson Pharma); GPI21016 (Eisai Co.); ABT888 and ABT888 with Temozolomide (Abbott Laboratories); AZD2281 and AZD2281 with Avastin, Caelyx, Carboplatin, Carboplatin/paclitaxel, Dacarbazine, gemcitabine or paclitaxel (AstraZeneca Plc); MK4827 (Merk & Co. Inc); AZD2281 and AZD2281 with cisplatin or paclitaxel (AstraZeneca Plc); BSI201 and BSI201 with carboplatin/paclitaxel, chemotherapy, irinotecan, Temodar and radiation; or topotecan (BiPar Science Inc); AG014699 or AG14699 with temozolomide (Pfizer Inc); BSI201 with gencitabine and carboplatin; PARP 1 Sentineal (Sentinel oncology).

The following table depicts examples non-limiting example PARP inhibitors, the phase of testing and indication(s):

| Company | Product | Phase | Indication |
| --- | --- | --- | --- |
| BiPar Sciences, Inc. | BSI401 | PC | Pancreatic Cancer |
| Crimson Pharma | CPH101 with CPH102 | PC | Cancer |
| Eisai Co. | GPI21016 | PC | Cancer (Cancer Chemosensitization and Radiosensitization) |
| Abbott Laboratories | ABT888 | I | Cancer |
| | ABT888 with Temozolomide | I | Solid Tumors |

-continued

| Company | Product | Phase | Indication |
|---|---|---|---|
| AstraZeneca Plc | AZD2281 with Avastin | I | Solid Tumors (Advanced Solid Tumors) |
| | AZD2281 with Caelyx | I | Solid Tumors (Advanced Solid Tumors) |
| | AZD2281 with Carboplatin | I | Solid Tumors (Advanced Solid Tumors) |
| | AZD2281 with Carboplatin, Paclitaxel | I | Solid Tumors (Advanced Solid Tumors) |
| | AZD2281 with Dacarbazine | I | Melanoma (Advanced Melanoma) |
| | AZD2281 with Gemcitabine | I | Pancreatic Cancer |
| | AZD2281 with Paclitaxel | I | Solid Tumors (Advanced Solid Tumors) |
| BiPar Sciences, Inc. | BSI201 | I | Solid Tumors (Solid Tumors (Monotherapy)) |
| | BSI201 | I | Solid Tumors |
| Cephalon Inc | CEP9722 | I | Solid Tumors |
| Merck & Co Inc | MK4827 | I | Solid Tumors (Ovarian Neoplasm) |
| AstraZeneca Plc | AZD2281 | II | Colorectal Cancer |
| | AZD2281 | II | Breast Cancer (Advanced Breast Cancer) |
| | AZD2281 | II | Ovarian Cancer (BRCA Deficient Advanced Ovarian Cancer) |
| | AZD2281 with Cisplatin | II | Breast Cancer (Triple Negative Breast Cancer) |
| | AZD2281 with Paclitaxel | II | Breast Cancer (Metastatic Triple Negative Breast Cancer) |
| BiPar Sciences, Inc. | BSI201 | II | Pancreatic Cancer (BRCA-Negative Pancreatic Cancer) |
| | BSI201 | II | Ovarian Cancer (BRCA-Negative Ovarian Cancer (Monotherapy)) |
| | BSI201 with Carboplatin, Paclitaxel | II | Cancer (Uterine Carcinosarcoma) |
| | BSI201 with Carboplatin, Paclitaxel | II | Non-Small-Cell Lung Cancer |
| | BSI201 with Chemotherapy | II | Sarcoma |
| | BSI201 with Irinotecan | II | Breast Cancer (Metastatic Breast Cancer) |
| | BSI201 with Temodar and Radiation Therapy | II | Brain Tumor (Newly Diagnosed Glioblastoma Multiforme) |
| | BSI201 with Topotecan | II | Ovarian Cancer (Advanced Ovarian Cancer) |
| Pfizer Inc (PFE) | AG014699 | II | Breast Cancer |
| | AG14699 | II | Cancer |
| | AG14699 | II | Ovarian Cancer |
| | AG14699 with Temozolomide | II | Melanoma (Metastatic Malignant Melanoma) |
| BiPar Sciences, Inc. (Private) | BSI201 with Gemcitabine and Carboplatin | III | Breast Cancer (Metastatic Triple Negative Breast Cancer) |
| LEAD Therapeutics, Inc. (Private) | PARP Inhibitor Program LEAD THERAPEUTICS | NA | Cancer |
| Sentinel Oncology | PARP 1 SENTINEL | NA | Solid Tumors (Tumors) |

Thus, in an aspect of the present application there is provided a potential synthetic lethal therapeutic strategy for the treatment of cancers with specific DNA-repair defects, including those arising in carriers of a PNKP or DNA-PK mutation.

Compound(s) of the present application may be administered with a physiologically acceptable carrier. A physiologically acceptable carrier is a formulation to which the compound can be added to dissolve it or otherwise facilitate its administration. Non limiting examples include, but are not limited to, water, saline, physiologically buffered saline.

Solid dosage forms for oral administration can include capsules, tablets, pills, powders, and granules. In such forms, the compound(s) as described herein may be combined with one or more adjuvants, as indicated by the route of administration. Compound(s) as described herein can be admixed with, for example, lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets can contain a controlled-release formulation as can be provided in a dispersion of active compound in hydroxypropylmethyl cellulose. In the case of capsules, tablets, and pills, the dosage forms can also comprise buffering agents such as sodium citrate, magnesium or calcium carbonate or bicarbonate. Tablets and pills can additionally be prepared with enteric coatings.

Compound(s) and pharmaceutically acceptable composition(s) as described herein can be administered by parenteral administration, in the form of aqueous or non-aqueous isotonic sterile injection solutions or suspensions. These solutions and suspensions can be prepared from sterile powders or granules having one or more of the carriers or diluents mentioned for use in the formulations for oral administration. Compound(s) as described herein can be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art, as know by the skilled worker.

Liquid dosage forms for oral administration include pharmaceutically acceptable emulsions, solutions, suspensions, syrups, and elixirs containing inert diluents commonly used in the art, such as water. Such compositions can also comprise adjuvants, such as wetting agents, emulsifying and suspending agents, and sweetening, flavoring, and perfuming agents.

It will be appreciated that the amount of active ingredient that can be combined with the carrier materials to produce a single dosage form varies depending upon the mammalian host treated and the particular mode of administration.

Compound(s) and composition(s) as described herein are suitable for combination. Combination therapy as used herein includes administration of the therapeutic agents in a sequential manner, wherein each therapeutic agent is administered at a different time, as well as administration of the therapeutic agents at the same time. As used herein, the therapeutic agents are administered in a sequential manner, wherein each therapeutic agent is administered at a different time, or administered in a generally simultaneous manner. The generally simultaneous administration can be accomplished, for example, by administering to the subject a single capsule having a fixed ratio of each therapeutic agent or in multiple, single capsules for each of the therapeutic agents.

Administration of each therapeutic agent, whether sequential or generally simultaneous, can be effected by any appropriate route including, but not limited to, oral routes, intravenous routes, intramuscular routes, and direct absorption through mucous membrane tissues, etc. The therapeutic agents can be administered by the same route or by different routes.

Combination therapy also includes administration of the therapeutic agents in combination with other biologically active ingredients (such as, but not limited to, a second and different antineoplastic agent) and non-drug therapies (such as, but not limited to, surgery or radiation therapy).

Where the combination therapy further comprises radiation therapy, the radiation therapy may be conducted at a suitable time so long as a beneficial effect from the co-action of the combination of the therapeutic agents and radiation treatment is achieved.

Method(s)

In accordance with another aspect of the present application, there is provided a method(s) for increasing the sensitivity of a cell(s) and/or tumour(s) to chemotherapeutic agents and/or ionizing radiation. In another aspect, there is provided a method(s) for inhibiting PNKP phosphatase activity.

Compound(s) and composition(s) as described herein are chemosensitizers and/or radiosensitizers useful for the treatment of cancer. In an aspect of the present application, the methods, compound(s) and composition(s) of the present invention may be used for the treatment of neoplasia disorders including benign, metastatic and malignant neoplasias. An embodiment of the present application relates to treating or lessening the severity of one or more diseases in which PNKP is known to play a role. In an example, the disease is cancer.

In some example, the compound(s) and composition(s) described herein increase radiosensitivity and/or chemosensitivity of a cell(s) and/or tumour(s).

In one aspect, there is provided radiosensitizer and chemosensitizer compounds and compositions, methods and kits and the uses thereof. In a specific example, a pharmaceutical composition comprising a compound of Formula (I) (A12B4C50) or a compound of Formula (II) (A83B4C63), may be used as a radiosensitizer and/or a chemosensitizer.

In one example, a pharmaceutical composition comprising a compound of Formula (I) (A12B4C50) or a compound of Formula (II) (A83B4C63), may be used as a radiosensitizer and/or a chemosensitizer, for the treatment of a subject having, or suspected of having a cancer.

The term "radiosensitizer", as used herein, refers to an agent, molecule, compound or composition that enhances the sensitivity of a neoplastic cell, a cancer cell and/or a tumor to the effects of radiation. The "sensitivity" of a neoplastic cell, a cancer cell, and/or a tumour to radiation is the susceptibility of the neoplastic cell, cancer cell, and/or tumour to the inhibitory effects of radiation on the cell's or tumour's growth and/or viability In a specific example, the compound(s) and composition(s) described herein increase sensitivity of a cell and/or tumour to radiation.

About half of patients with cancer are treated with radiation therapy, either alone or in combination with other types of cancer treatment.

Radiation therapy (also referred to as radiotherapy, X-ray therapy, or irradiation) may be external, internal and systemic.

External radiation is delivered from a machine outside the body; internal radiation is implanted into or near the tumour(s), systemic radiation utilizes unsealed radiation sources.

External radiation therapy is used to treat most types of cancer, including but not limited to, cancer of the bladder, brain, breast, cervix, larynx, lung, prostate, and vagina. Intraoperative radiation therapy (IORT) is a form of external radiation that is given during surgery, and can be used to treat localized cancers that cannot be completely removed or that have a high risk of recurring in nearby tissues, including, but not limited to treatment of thyroid and colorectal cancers, gynecological cancers, cancer of the small intestine, and cancer of the pancreas. Prophylactic cranial irradiation (PCI) is another type of external radiation given to the brain when the primary cancer (for example, small cell lung cancer) has a high risk of spreading to the brain.

Internal radiation therapy (or brachytherapy) typically uses radiation source sealed in a small holder called an implant. Implants may be in the form of thin wires, plastic tubes called catheters, ribbons, capsules, or seeds. Interstitial radiation therapy, a type of internal radiation therapy) is inserted into tissue at or near the tumour site. It is used to treat tumors of the head and neck, prostate, cervix, ovary, breast, and perianal and pelvic regions. Intracavitary or intraluminal radiation therapy is inserted into the body with an applicator. It is commonly used m the treatment of uterine cancer, and may have application in other cancers, including breast, bronchial, cervical, gallbladder, oral, rectal, tracheal, uterine, and vaginal.

Systemic radiation therapy uses materials such as iodine131 and strontium 89, and may be taken by mouth or injected. Such therapy may be used m the treatment of cancers of the thyroid and adult non-Hodgkin lymphoma.

In a specific example, the radiation is γ-radiation. In one example, the ionizing radiation is X-rays generated by a linear accelerator (Linac).

The term "chemosensitizer", as used herein, refers to an agent, molecule, compound or composition that enhances the sensitivity of a neoplastic cell, a cancer cell and/or a tumor to the effects of a chemotherapeutic agent. The "sensitivity" of a neoplastic cell, a cancer cell, and/or a tumour to a chemotherapeutic agent is the susceptibility of the neoplastic cell, cancer cell, and/or tumour to the inhibitory effects of a chemotherapeutic agent on the cell's or tumour's growth and/or viability.

In another example, the compound(s) and composition(s) of the present invention increases sensitivity of a cell(s) and/or tumour(s) to a chemotherapeutic agent. In one example, the chemotherapeutic agent is a topoisomerase I inhibitor.

The term "topoisomerase I inhibitor" as used herein includes, but is not limited to topotecan (HYCAMTIN®), gimatecan, irinotecan (CAMPTOSAR®), camptothecin and its analogues.

Indications, routes and methods of administration, and the like, of topoisomerase I inhibitors are known to the skilled worker.

CAMPTOSAR® injection, for example, is indicated as a component of first-line therapy in combination with 5-fluorouracil and leucovorin for patients with metastatic carcinoma of the colon or rectum. CAMPTOSAR is also indicated for patients with metastatic carcinoma of the colon or rectum whose disease has recurred or progressed following initial fluorouracil-based therapy.

HYCAMTIN for Injection, for example, is indicated for: metastatic carcinoma of the ovary after failure of initial or subsequent chemotherapy, small cell lung cancer sensitive disease after failure of first-line chemotherapy, combination therapy with cisplatin for stage IV-B, recurrent, or persistent carcinoma of the cervix which is not amenable to curative treatment with surgery and/or radiation therapy. HYCAMTIN capsules, for example, is indicated for treatment of patients with relapsed small cell lung cancer In a specific example, the topoisomerase I inhibitor is irinotecan.

The compounds and compositions of the present invention are suitable for combination. Combination therapy as used herein includes administration of the therapeutic agents in a sequential manner, wherein each therapeutic agent is administered at a different time, as well as administration of the therapeutic agents at the same time.

As used herein, the therapeutic agents are administered in a sequential manner, wherein each therapeutic agent is administered at a different time, or administered in a generally simultaneous manner. The generally simultaneous administration can be accomplished, for example, by administering to the subject a single capsule having a fixed ratio of each therapeutic agent or in multiple, single capsules for each of the therapeutic agents.

Administration of each therapeutic agent, whether sequential or generally simultaneous, can be effected by any appropriate route including, but not limited to, oral routes, intravenous routes, intramuscular routes, and direct absorption through mucous membrane tissues, etc. The therapeutic agents can be administered by the same route or by different routes.

Combination therapy also includes administration of the therapeutic agents in combination with other biologically active ingredients (such as, but not limited to, a second and different antineoplastic agent) and non-drug therapies (such as, but not limited to, surgery or radiation therapy).

Where the combination therapy further comprises radiation therapy, the radiation therapy may be conducted at a suitable time so long as a beneficial effect from the co-action of the combination of the therapeutic agents and radiation treatment is achieved.

Compounds of the present invention may be administered with a physiologically acceptable carrier. A physiologically acceptable carrier is a formulation to which the compound can be added to dissolve it or otherwise facilitate its administration. Non limiting examples include, but are not limited to, water, saline, physiologically buffered saline.

Solid dosage forms for oral administration can include capsules, tablets, pills, powders, and granules. In such forms, the compounds of the present invention may be combined with one or more adjuvants, as indicated by the route of administration. Compounds of the present invention can be admixed with, for example, lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets can contain a controlled-release formulation as can be provided in a dispersion of active compound in hydroxypropylmethyl cellulose. In the case of capsules, tablets, and pills, the dosage forms can also comprise buffering agents such as sodium citrate, magnesium or calcium carbonate or bicarbonate. Tablets and pills can additionally be prepared with enteric coatings.

Compounds and pharmaceutically acceptable compositions of the present invention may be administered by parenteral administration, in the form of aqueous or non-aqueous isotonic sterile injection solutions or suspensions. These solutions and suspensions can be prepared from sterile powders or granules having one or more of the carriers or diluents mentioned for use in the formulations for oral administration. Compounds of the present invention can be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art, as know by the skilled worker.

Liquid dosage forms for oral administration include pharmaceutically acceptable emulsions, solutions, suspensions, syrups, and elixirs containing inert diluents commonly used in the art, such as water. Such compositions can also comprise adjuvants, such as wetting agents, emulsifying and suspending agents, and sweetening, flavoring, and perfuming agents.

It will be appreciated that the amount of active ingredient that can be combined with the carrier materials to produce a single dosage form varies depending upon the mammalian host treated and the particular mode of administration.

Synthetic lethality arises when the combination of two non-essential protein disruptions in a single cell cause lethality. This phenomenon has been shown to occur between proteins involved in DNA repair, and with PNKP (see, for example, WO 2012/058763, the entire contents of which is hereby incorporated by reference).

In one aspect, there is described a synthetic lethal therapeutic strategy for the treatment or lessening the severity of a disorder arising in a subject with a defect(s) in a tumour suppressor(s). In one example the disorder is cancer. In one example, the tumour suppressor is PTEN.

In one example, there is described a method and use of treating a cancer associated with a deficiency associated with a tumour suppressor. In a specific example, the tumour suppressor is PTEN.

As used herein, the term "tumour suppressor" includes known tumour suppressors, and implicated or suspected as a tumour suppressor. Examples of tumour suppressors include, but are not limited to ING3, CDKN3, PTPN6, and PTEN. In a specific example, the tumour suppressor is PTEN.

Dysregulation of apoptosis also contributes to a variety of human diseases, such as cancer and autoimmune diseases. ING family proteins (ING1-ING5) are involved in many cellular processes, and appear to play a significant role in apoptosis. ING3 has been shown to help control cell cycle, apoptosis and modulate transcription, and displays irregular expression in human head and neck cancer and reduced expression in melanoma. Loss or downregulation of ING protein function is frequently observed in different tumour types. The mechanism of diminished ING3 expression in melanoma is not clear. ING3 has been implicated in bladder cancer, head and neck cancer, squamous cell carcinoma, lymphoma and melanoma. Although the mechanisms of action are unclear, in melanoma ING3 has been reported to undergo degradation through the ubiquitin-proteasome pathway.

CDKN3 (cyclin-dependent kinase inhibitor 3) encodes the protein KAP, which is a human dual specificity protein I phosphatase that was identified as a cyclin-dependent kinase inhibitor, and has been shown to interact with and dephosphorylate CDK2 kinase and thus prevent the activation of CDK2 kinase. The gene has been reported to be deleted, mutated, or overexpressed in several kinds of cancers. CDKN3 has been reported as an overexpressed gene in breast and prostate cancer by using a phosphatase domain-specific differential-display PCR strategy. KAP is reduced in some forms of malignant astrocytomas. CDKN3 has also been implicated in lung cancer. It has been reported that in normal cells, CDKN3 protein is primarily found in the perinuclear region, but in tumour cells, a significant portion of the protein is found in the cytoplasm.

PTPN6 (also known as SHP-1), an SH2 domain-containing protein tyrosine phosphatase, has been reported as being expressed in hematopoietic cells and behaves as a regulator controlling intracellular phosphotyrosine levels in lymphocytes. PTPN6 has been proposed as a candidate tumor suppressor gene in lymphoma, leukemia and other cancers, as it functions as an antagonist to the growth-promoting and oncogenic potentials of tyrosine kinase. PTPN6 protein has been reported as normally or over-expressed in some non-lymphocytic cell lines, such as prostate cancer, ovarian cancer and breast cancer cell lines. PTPN6 expression is also reported as decreased in some breast cancer cell lines with negative expression of estrogen receptor as well as some prostate and colorectal cancer cell lines. PTPN6 has been implicated in a variety of cancers, including lymphoma, leukemia, prostate cancer, ovarian cancer, breast cancer, NK lymphoma, T cell lymphoma, or colorectal cancer. PTPN6 expression was shown to be diminished or absent in 40/45 malignant prostate tissues, 95% of various malignant lymphomas and 100% of NK and T cell lymphomas. PTPN6 protein and mRNA have been reported to be diminished or abolished in most of the cancer cell lines and tissues examined. Similarly, growth of cancer cells was reported as being suppressed after introducing the PTPN6 gene into the corresponding cell lines.

PTEN is a tumour suppressor encoding a phosphatase. PTEN is one of the most frequently mutated or deleted genes in inherited and sporadic human cancers, including breast cancer. Deletion or inactivation of PTEN has also been reported in glioblastoma, endometrial carcinoma, and lymphoid malignancies. PTEN downregulation has been found in leukemia cells.

SMG1 protein is involved in nonsense-mediated mRNA decay (NMD) as part of the mRNA surveillance complex. The protein has kinase activity and is thought to function in NMD by phosphorylating the regulator of nonsense transcripts 1 protein.

From the foregoing it will be clear that the name of the gene and corresponding gene product (i.e. the corresponding protein encode by the gene) are used interchangeably herein. For example, the SHP-1 protein is encoded by the PTPN6 gene and the KAP protein is encoded by the CDKN3 gene.

In one example, there is described a method of treating a subject having a cancer associated with PTEN, or suspected of having cancer associated with PTEN, that will benefit from treatment with an inhibitor of PNKP, comprising: determining the presence of a defect in PTEN in a cancerous cell within said sample, wherein said defect reduces or abolishes the expression or activity of said PTEN, wherein a defect in said PTEN indicates said subject has a cancer which is suitable for treatment with said inhibitor of PNKP, wherein said inhibitor of PNKP is a compound or a pharmaceutical composition as described herein.

In one example, there is described a method of identifying a subject having cancer, or suspected of having cancer, that will benefit from treatment with an inhibitor of PNKP, comprising: determining the presence of a defect in a tumour suppressor in a cancerous within said sample, wherein said defect reduces or abolishes the expression or activity of said tumour suppressor, wherein a defect in said tumour suppressor indicates said subject has a cancer which is suitable for treatment with said inhibitor of PNKP, wherein said inhibitor of PNKP is a compound as described herein, or a pharmaceutical composition as described herein.

In some examples, a "defect" includes, sequence variations, such as mutations and polymorphisms, which reduce or abolish the expression or activity. Sequence variations may include a deletion, insertion or substitution of one or more nucleotides, relative to the wild-type nucleotide sequence, a gene amplification or an increase or decrease in methylation, for example hypermethylation. Sequence variations may be in a coding or non-coding region of the nucleic acid sequence. Mutations in the coding region of the gene encoding the component may prevent the translation of full-length active protein i.e. truncating mutations, or allow the translation of full-length but inactive or impaired function protein i.e. mis-sense mutations. Mutations or epigenetic changes, such as methylation, in non-coding regions of the gene encoding the component, for example, in a regulatory element, may prevent transcription of the gene. A nucleic acid comprising one or more sequence variations may encode a variant polypeptide which has reduced or abolished activity or may encode a wild-type polypeptide which has little or no expression within the cell, for example through the altered activity of a regulatory element. A nucleic acid comprising one or more sequence variations may have one or more mutations or polymorphisms relative to the wild-type sequence.

Determination of the presence of a defect, such as a sequence variation in a nucleic acid may be accomplished by detecting the presence of the variant nucleic acid sequence in one or more cells of a test sample or by detecting the presence of the variant polypeptide which is encoded by the nucleic acid sequence. Non-limiting example of sequence variation detection allele specific amplification, OLA, ALEX, COPS, Taqman, Molecular Beacons, RFLP, and restriction site based PCR and FRET techniques.

Determination of the presence of a defect, such as a sequence variation in a polypeptide, may be accomplished using polypeptide sequence variation techniques including, but not limited to immunoassays.

Determination of a defect, for example the detection of sequence variation, typically requires a discrimination technique, optionally an amplification reaction and optionally a signal generation system.

In some examples, nucleic acid or an amplified region thereof may be sequenced to identify or determine the presence of polymorphism or mutation therein. A polymorphism or mutation may be identified by comparing the sequence obtained with the known sequence of the component of the tumour suppressor or PNKP-mediated cellular pathway, for example as set out in sequence databases. Alternatively, it can be compared to the sequence of the corresponding nucleic acid from normal cells. In particular, the presence of one or more polymorphisms or mutations that cause abrogation or loss of function may be determined.

Sequencing may be performed using any one of a range of standard techniques. Having sequenced nucleic acid of an individual or sample, the sequence information can be retained and subsequently searched without recourse to the original nucleic acid itself. Thus, for example, scanning a database of sequence information using sequence analysis software may identify a sequence alteration or mutation.

In some examples, the determination of a defect includes determining the presence of one or more variations in a nucleic acid may comprise hybridizing one or more (e.g. two) oligonucleotides to nucleic acid obtained from a sample, for example genomic DNA, RNA or cDNA. Where the nucleic acid is double-stranded DNA, hybridization will generally be preceded by denaturation to produce single-stranded DNA. The hybridization may be as part of a PCR procedure, or as part of a probing procedure not involving PCR.

The compounds of the present application are synthesized as has been described before (12), the entire contents of this disclosure are incorporated herein by reference.

In another aspect, there is provided radiosensitizer and chemosensitizer compounds and compositions, methods and kits and the uses thereof. Methods as described herein are conveniently practiced by providing the compounds and/or compositions used in such method in the form of a kit. Such a kit preferably contains the composition. Such a kit preferably contains instructions for the use thereof.

To gain a better understanding of the invention described herein, the following examples are set forth. It should be understood that these examples are for illustrative purposes only. Therefore, they should not limit the scope of this invention in anyway.

EXAMPLES

Example 1

In 2009, we identified the first small molecule inhibitors of PNKP reported to date from a small library of drug-like, polysubstituted imidopiperidines (Freschauf G K, Karimi-Busheri F, Ulaczyk-Lesanko A, Mereniuk T R, Ahrens A, Koshy J M, Rasouli-Nia A, Pasarj P, Holmes C F, Rininsland F, Hall D G, Weinfeld M. Cancer Res. 2009 Oct. 1; 69(19): 7739-46; G. K. Freschauf, F. Karimi-Busheri, A. Ulaczyk-Lesanko, 7 co-authors, D. G. Hall, M. Weinfeld; Identification of a Small Molecule Inhibitor of the Human DNA Repair Enzyme Polynucleotide Kinase/Phosphatase; Cancer Research 2009, 69, 7749-7746.). These compounds were prepared using a new and efficient multicomponent reaction (MCR), developed in our laboratories, and based on a stereoselective tandem Diels-Alder cycloaddition between a borono-azadiene and maleimides, followed by allyboration with an aldehyde (A. Ulaczyk-Lesanko, E. Pelletier, M. Lee, H. Prinz, H. Waldmann, D. G. Hall; Optimization of Three- and Four-Component Reactions for Polysubstituted Piperidines. Application to the Synthesis and Preliminary Biological Screening of a Prototype Library, Journal of Combinatorial Chemistry 2007, 9, 695-703; B. B. Touré, H. Hoveyda, A. Ulaczyk Lesanko, J. Tailor, D. G. Hall; A Three-component Reaction for Diversity-Oriented Synthesis of Polysubstituted Piperidines: Solution and Solid-Phase Optimization of the First Tandem Aza[4+2]/Allylboration; Chemistry—A European Journal 2003, 9, 466-474; J. Tailor, D. G. Hall; Tandem Aza[4+2]/Allylboration: A Novel Multicomponent Reaction for the Stereocontrolled Synthesis of α-Hydroxyalkyl Piperidine Derivatives; Organic Letters 2000, 2, 3715-3718.). The resulting imido-piperidines possess a stereochemically-rich structure with stable functionalities such as imide, hydroxyl, and basic amino groups that can confer hydrogen bond donor/acceptor capabilities essential in promoting effective molecular interactions with proteins.

Multicomponent synthesis of imido-piperidines and initial top hit identified from a sub-library of ca. 250 members.

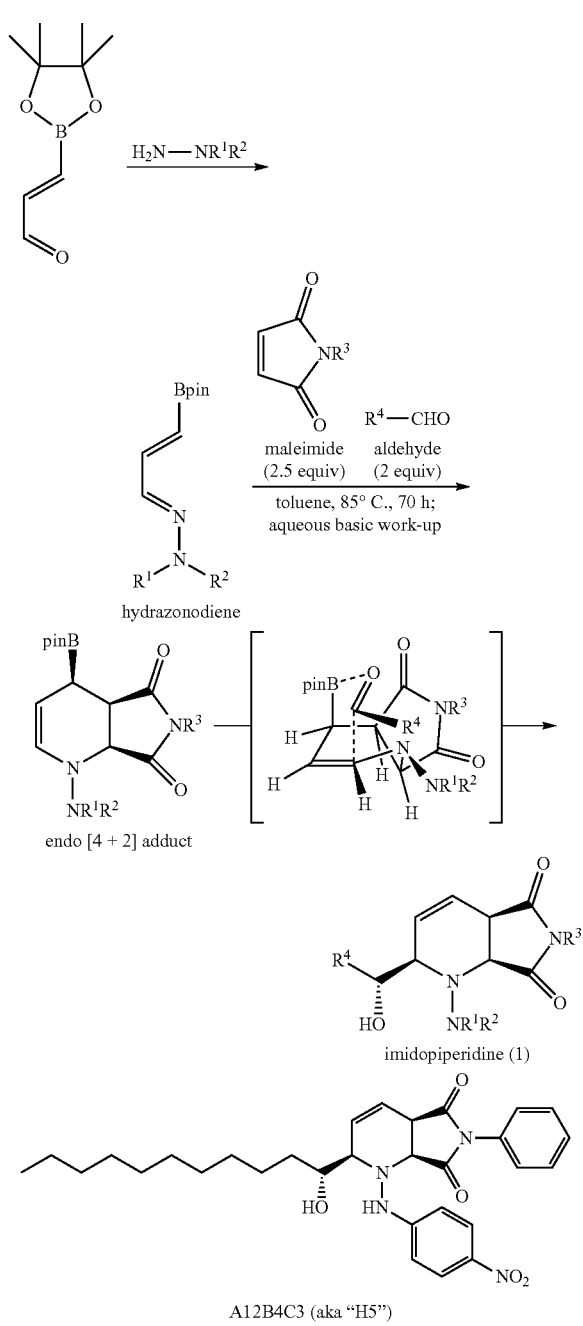

Upon screening a subset of about 250 diverse library members for inhibition of PNKP's phosphatase activity in a fluorescence-based assay, we obtained a few hits with modest micromolar IC$_{50}$ values (Freschauf G K, Karimi-Busheri F, Ulaczyk-Lesanko A, Mereniuk T R, Ahrens A, Koshy J M, Rasouli-Nia A, Pasarj P, Holmes C F, Rininsland F, Hall D G, Weinfeld M. Cancer Res. 2009 Oct. 1; 69(19):7739-46.; G. K. Freschauf, F. Karimi-Busheri, A. Ulaczyk-Lesanko, 7 co-authors, D. G. Hall, M. Weinfeld; Identification of a Small Molecule Inhibitor of the Human DNA Repair Enzyme Polynucleotide Kinase/Phosphatase; Cancer Research 2009, 69, 7749-7746.). Although the initial library did not feature extensive structural diversity with regards to the hydrazine and imide components, many of those hits possessed a hydrophobic hydroxyalkyl tail, a constant p-nitrophenylhydrazine, and a N-phenyl imide. The most promising hit was A12B4C3 (2-(1-hydroxyundecyl)-1-(4-nitrophenylamino)-6-phenyl-6,7a-dihydro-1H-pyrrolo[3,4-b]pyridine-5,7(2H, 4aH)-dione). Its PNKP inhibitory action was confirmed using a conventional radio-gel assay for 3'-phosphatase activity. A12B4C3 was thus identified as our primary hit and was studied extensively in a further series of in vitro assays. It was found to effectively inhibit the PNKP enzyme through a non-competitive inhibitory mechanism (Freschauf G K, Mani R S, Mereniuk T R, Fanta M, Virgen C A, Dianov G L, Grassot J M, Hall D G, Weinfeld M. J Biol Chem. 2010 Jan. 22; 285(4):2351-60). Circular dichroism spectroscopy indicated that A12B4C3 alters the enzyme's conformation supporting an allosteric inhibitory mechanism, and intrinsic (tryptophan) fluorescence quenching titration showed that A12B4C3 binds PNKP with a dissociation constant (Kd) of 0.34 µM. It inhibits murine PNKP with only slightly reduced efficacy, however upon testing with a limited panel of phosphatase enzymes it was found to possess specificity for PNKP (Freschauf G K, Mani R S, Mereniuk T R, Fanta M, Virgen C A, Dianov G L, Grassot J M, Hall D G, Weinfeld M. J Biol Chem. 2010 Jan. 22; 285(4):2351-60.).

A12B4C3 demonstrated low cytotoxicity at concentrations of 5-10 µM. Moreover, at such non-toxic doses it was able to sensitize human A549 lung carcinoma and MDA-MB-231 breast cancer cells to γ-radiation and to the DNA topoisomerase I poison camptothecin, which is the parental compound to the widely used chemotherapeutic agents, irinotecan and topotecan. Importantly, A12B4C3 failed to sensitize cells in which PNKP expression was down-regulated by shRNA, indicating that the primary cellular target for A12B4C3 is indeed PNKP. Other groups have shown that A12B4C3 sensitizes myeloid leukemia cells to an Auger electron-emitting radioimmunoconjugate and radioresistant prostate cancer cells to irradiation by carbon ions (The human polynucleotide kinase/phosphatase (hPNKP) inhibitor A12B4C3 radiosensitizes human myeloid leukemia cells to Auger electron-emitting anti-CD123 In-111-NLS-7G3 radioimmunoconjugates Zereshkian, A; Leyton, J V; Cai, Z; Bergstrom, D; Weinfeld, M; Reilly, R M. NUCLEAR MEDICINE AND BIOLOGY. Volume: 41. Issue: 5. Pages: 377-383. DOI: 10.1016/j.nucmedbio.2014.02.003; Targeting DNA repair with PNKP inhibition sensitizes radioresistant prostate cancer cells to high LET radiation. Srivastava P, Sarma A, Chaturvedi C M. PLoS One. 2018 Jan. 10; 13(1):e0190516. doi: 10.1371/journal.pone.0190516. eCollection 2018. PMID: 29320576).

We planned a comprehensive evaluation of structure-activity aimed at providing second-generation analogues with equal or superior potency and improved druglike attributes compared to the initial hit compound A12B4C3.

Design of Second-Generation Analogues of A12B4C3.

Because the binding site of A12B4C3 to PNKP has not yet been determined, a molecular-level drug design approach aided by computational docking techniques and crystallography is not possible at this stage. As described above, the initial small library that led to the identification of A12B4C3 did not display much diversity with regards to the hydrazine (NR$^1$R$^2$) and imide (R$^3$) components. Despite the limited set of imide components, upon first examination it appeared that N-substitution on the imide was quite variable and this site may possibly be involved in non-specific interactions (i.e., exposed to solvent). On the other hand, a larger number of aldehydes were employed to generate a more diverse set of hydroxyalkyl substituents (R$^4$), and several hit compounds bore a relatively hydrophobic side chain at this position. Based on these preliminary observations, we elected to undertake a focused library approach by dissecting the structure of A12B4C3 into four groups of analogues with the following objectives: Group A: further fine-tuning of the aldehyde side-chain (R$^4$) to identify smaller, less hydrophobic substituents and reduce the number of rotatable bonds (see compounds A70B4C3, A44B4C3, A83B4C3 of Table A below and compound H5 (A12B4C3) below); Group B: explore a larger structural diversity of N-aryl and N-benzyl imides, including nitrogen-containing heterocycles and other moieties to improve physical properties (see compounds A12B4C15, A12B4C31, A12B4C23, A12B4C5, A12B4C63, A12B4C53, A12B4C50 of Table B; compounds A44B4C50, A83B4C63, A83B4C61 of Table E; and, compound A85B4C10 of Table A2); Group C: evaluate isoelectronic nitro replacement substituents for the arylhydrazine (see compounds A83B29C63, A44B29C50, A44B27C3, A83BxxC63 of Table E; and, compound A12B27C3 of Table C); Group D: examine more profound skeletal modifications such as a saturated piperidine ring, alcohol derivatives, etc (see compounds A12B37C3, A83C63 of Table E).

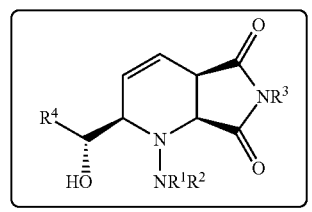

Imido-piperidine scaffold

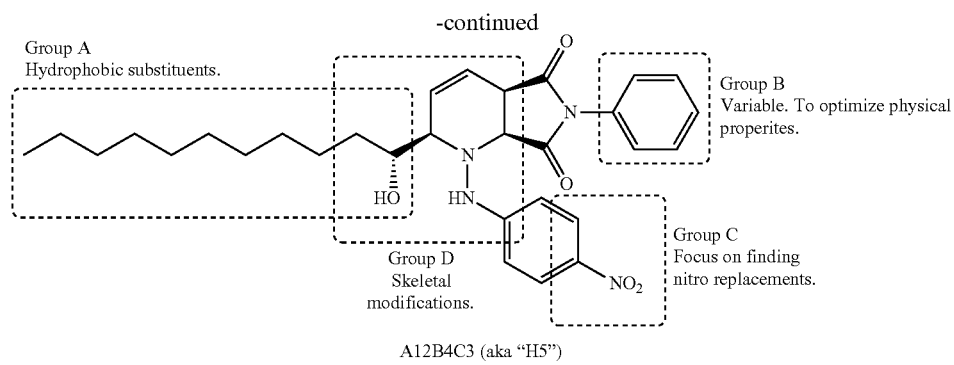

A12B4C3 (aka "H5")

Synthesis of Analogues.

The preparation of imidopiperidines by way of a three-component [4+2] cycloaddition/allylboration was achieved as described in previous synthetic studies (a) A. Ulaczyk-Lesanko, E. Pelletier, M. Lee, H. Prinz, H. Waldmann, D. G. Hall; Optimization of Three- and Four-Component Reactions for Polysubstituted Piperidines. Application to the Synthesis and Preliminary Biological Screening of a Prototype Library, Journal of Combinatorial Chemistry 2007, 9, 695-703; B. B. Touré, H. Hoveyda, A. Ulaczyk Lesanko, J. Tailor, D. G. Hall; A Three-component Reaction for Diversity-Oriented Synthesis of Polysubstituted Piperidines: Solution and Solid-Phase Optimization of the First Tandem Aza[4+2]/Allylboration; Chemistry—A European Journal 2003, 9, 466-474. [Highlighted in C&EN, Oct. 27 2003, pp. 52-54; J. Tailor, D. G. Hall; Tandem Aza[4+2]/Allylboration: A Novel Multicomponent Reaction for the Stereocontrolled Synthesis of – -Hydroxyalkyl Piperidine Derivatives; Organic Letters 2000, 2, 3715-3718.). Hydrazonodienes were reacted together under thermal conditions with the required N-substituted maleimide and the aldehyde. The resulting products were purified first by flash-chromatography to give yields of imidopiperidines typically in the nn-nn % range. When necessary, the imidopiperidines were further purified by HPLC to afford highly pure samples for biological testing.

Assays.

We chose to first rate and compare the analogues using a single-point measurement at 20 μM concentration. To this end, we modified a fluorescence-based assay using a Universal Molecular-Beacon (U-MB) approach (Song et al., 2010 Chem. Asian J. 5:1146-51). Only the top-rated analogues were further evaluated with an $IC_{50}$ and a dissociation constant (Kd) determination. Kd values were measured by steady-state fluorescence spectroscopy previously described (Freschauf G K, Mani R S, Mereniuk T R, Fanta M, Virgen C A, Dianov G L, Grassot J M, Hall D G, Weinfeld M. J Biol Chem. 2010 Jan. 22; 285(4):2351-60.). In general, we observed a good correlation between the values of Kd and $IC_{50}$; compounds that failed to provide a Kd below 0.3 μM also failed to provide good $IC_{50}$ values (data not shown). It is noteworthy that for most compounds the value of Kd and $IC_{50}$ differ by a factor of 10-20 fold. Because the compounds act as non-competitive, allosteric inhibitors, it is to be expected that tight binding, although it may help increase the compound's residence time, does not necessarily translate into effective inhibition of phosphatase activity. In the end, the most promising compounds should demonstrate a balance between potency and desirable physical properties amenable for further in vitro and in vivo studies.

Diversification of the aldehyde component in the multi-component reaction provided Group A analogues with various hydroxyalkyl side chains. Toward this end, it was found that replacement of the hydroxyalkyl decyl side chain of A12B4C3 for shorter n-alkyl groups led to an increase of the Kd values. For example, the short-chain analogue A70B4C3 displayed a Kd almost 3 times higher than that of A12B4C3. Although analogues with intermediate n-alkyl chain lengths provide decent Kd values, it was deemed necessary to reduce the number of rotatable bonds. Hence, aryl side chains were explored by using aromatic aldehydes in the three-component chemistry. Two promising analogues, A44B4C3 and A83B4C3, led to a decrease of Kd relative to A12B4C3 with similar IC50 values. These two analogues possess lower cLogP values and were indeed found to be more soluble. Other aryl substituents were examined but none led to further improvements (data not shown). Various imide N-substitutents were subsequently explored (Group B analogues). All compounds bearing the decyl hydroxyalkyl side chain provided good Kd values, with many displaying lower $IC_{50}$ values compared to A12B4C3. Use of N-aryl substituents with cationic groups, such as A12B4C50 and A44B4C50, preserved the low Kd while demonstrating lower clogP values. The IC50 values, however, were slightly higher than 10 micromolar level. The analogue A83B4C63 with the ortho-methoxyaryl hydroxyalkyl side chain and the N-naphthyl imide demonstrated a very low Kd of 90 nM with a good $IC_{50}$ value and a cLogP lower than 5. Although other combinations of aromatic aldehydes and N-substituted imides were attempted, no other analogue displayed improved characteristics. Because nitro substituents may lead to drug toxicity issues, we sought to replace this functionality with isoelectronic moieties such as a methylsulfone, carboxamide, or polar substituents like a halide atom. These Group C analogues were designed by combining some of the most promising components identified from Group A and B analogues. As shown, nitro-replacement led to a highly variable outcome. Analogue A44B29C50 with a methylsulfone replacement and a cationic N-aryl imide substituent led to excellent Kd and $IC_{50}$ values. On the other hand, the methylsulfone analogue (A83B29C63) of A83B4C63 led to a significant increase of the $IC_{50}$, suggesting that the different sites on the imidopiperidine scaffold are not independent and their effect may not be additive. Group D analogues were investigated to briefly examine the relative importance of various functional groups and substructures. The N-methylated hydrazine A12B37C3 displayed an $IC_{50}$ similar to that of A12B4C3, suggesting that the free hydrazine NH is not a critical feature of these imidopiperidine inhibitors.

Example 1A: Prepared Compounds, and Binding Affinity and Inhibitory Action Thereof Compounds as described herein were synthesized and tested (see representative procedures provided below) to determine their binding affinity ($K_d$) values and $IC_{50}$ values. Please see the tables below.

These values were compared to previously described compound A12B4C3, as described in U.S. Pat. No. 9,040,551, which was found to have a $K_d$ value of 0.37 and an $IC_{50}$ value of 14 µM, and cLogP of 7:

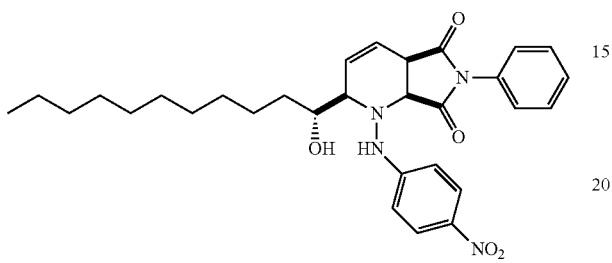

The compounds synthesized and tested were generated by modifying the following imido-piperidine scaffold, particularly at the $R^1$-$R^4$ positions:

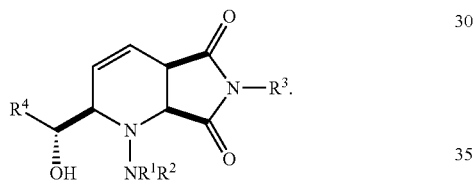

TABLE A

Modifying $R^4$ when $R^3$ is —$C_6H_5$

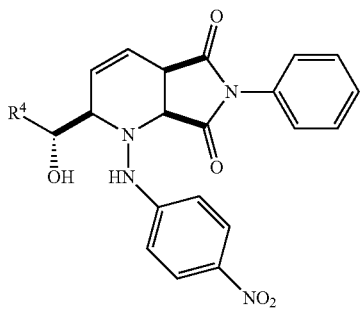

| Compound | $R^4$ | $K_d$ (µM) | $IC_{50}$ (µM) | cLogP |
|---|---|---|---|---|
| A5B4C3 | ($C_6H_4$-4-$NMe_2$) | 0.55 | — | — |
| A11B4C3 | (n-$C_4H_9$) | — | — | — |

TABLE A-continued
Modifying R⁴ when R³ is —C₆H₅
| Compound | R⁴ | $K_d$ (μM) | $IC_{50}$ (μM) | cLogP |
|---|---|---|---|---|
| A44B4C3 | —C₆H₄-4-Br ($C_6H_4$-4-Br) | 0.150 | 22 | 3.8 |
| A69B4C3 | —CH₃ | — | — | — |
| A70B4C3 | —(n-C₂H₅) | 1.05 | 48 | — |
| A72B4C3 | —(n-C₅H₁₁) | — | — | — |
| A74B4C3 | —(n-C₇H₁₅) | — | — | — |
| A76B4C3 | —(n-C₉H₁₉) | 0.20 | — | — |
| A77B4C3 | —(n-C₁₁H₂₃) | 0.24 | 3.9 | — |
| A78B4C3 | —CH₂O(CH₂CH₂O)₂CH₃ | — | — | — |
| A83B4C3 | $C_6H_4$-2-OMe | 0.22 | ~30 | — |
| A89B4C3 | —(n-C₁₂H₂₅) | 0.45 | 8 | — |

TABLE A-continued

Modifying R⁴ when R³ is —C₆H₅

| Compound | R⁴ | $K_d$ (μM) | IC$_{50}$ (μM) | cLogP |
|---|---|---|---|---|
| A90B4C3 | —CO₂CH₂CH₃ (CO₂Et) | — | — | — |
| A91B4C3 | (C₆H₃-3,4-(O-n-C₆H₁₃)₂) | — | — | — |
| A92B4C3 | (C₆H₄-2-NMe₂) | — | — | — |
| A95B4C3 | (Benzophenone) | 0.250 | — | — |
| A96B4C3 | (C₆H₃-3-Me-4-Br) | 0.160 | 19 | — |
| A98B4C3 | (C₆H₃-4-Br-3-O-n-hex) | 0.240 | — | — |

TABLE A-continued
Modifying R⁴ when R³ is —C₆H₅
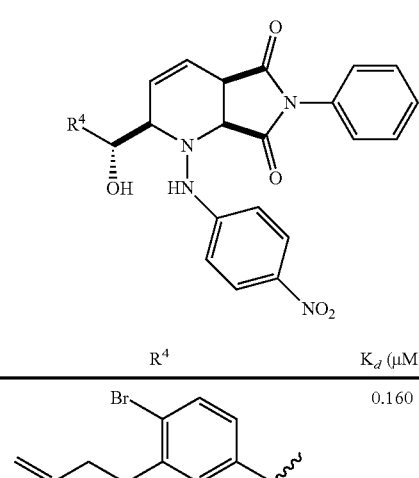
| Compound | R⁴ | $K_d$ (μM) | $IC_{50}$ (μM) | cLogP |
|---|---|---|---|---|
| A99B4C3 | (C₆H₃-4-Br-3-butenyl) | 0.160 | — | — |
TABLE A2
Modifying R⁴ when R³ is —C₆H₄-4-(CH₂NH₂)
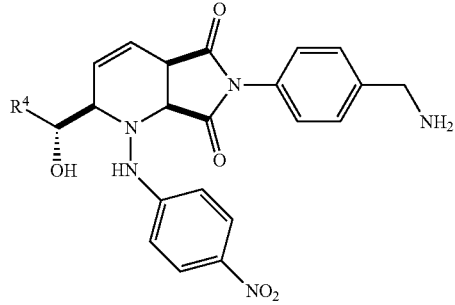
| Compound | R⁴ | $K_d$ (μM) | $IC_{50}$ (μM) | cLogP |
|---|---|---|---|---|
| A1B4C10 | (Ph) | — | — | — |
| A5B4C10 | (C₆H₄-4-NMe₂) | — | — | — |
| A6B4C10 | (C₆H₂-3,4,5-(OMe)₃) | — | — | — |
TABLE A2-continued
Modifying R⁴ when R³ is —C₆H₄-4-(CH₂NH₂)
| Compound | R⁴ | $K_d$ (μM) | $IC_{50}$ (μM) | cLogP |
|---|---|---|---|---|
| A8B4C10 | (n-C₆H₁₂) | — | — | — |
| A13B4C10 | (C₆H₄-4-F) | — | — | — |
| A16B4C10 | (C₆H₃-3-OBn-4-OMe) | — | — | — |

TABLE A2-continued

Modifying $R^4$ when $R^3$ is —$C_6H_4$-4-($CH_2NH_2$)

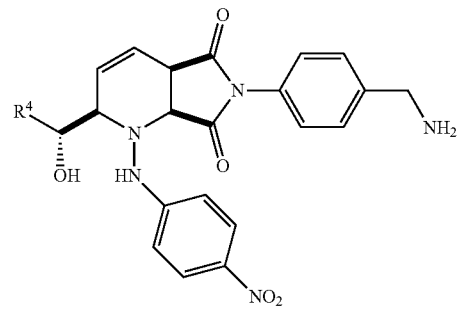

| Compound | $R^4$ | $K_d$ ($\mu M$) | $IC_{50}$ ($\mu M$) | cLogP |
|---|---|---|---|---|
| A19B4C10 | ($C_6H_3$-3,5-($CF_3$)$_2$) | 0.105 | 13.1 | — |
| A20B4C10 | ($C_6H_3$-2-F-5-Cl) | — | — | — |
| A26B4C10 | (n-$CHPh_2$) | 0.65 | — | — |
| A27B4C10 | (x-naphthyl) | — | — | — |
| A29B4C10 | (n-CH($CH_2CH_3$)$_2$) | — | — | — |
| A37B4C10 | (n-CHPh($CH_3$)) | 0.32 | — | — |

TABLE A2-continued

Modifying $R^4$ when $R^3$ is —$C_6H_4$-4-($CH_2NH_2$)

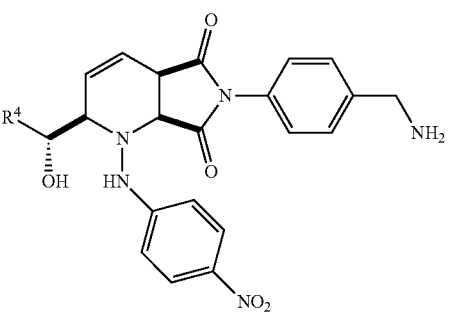

| Compound | $R^4$ | $K_d$ ($\mu M$) | $IC_{50}$ ($\mu M$) | cLogP |
|---|---|---|---|---|
| A39B4C10 | (2-thienyl) | — | — | — |
| A42B4C10 | ($C_6H_3$-3,4-[O($CH_2$)1/2]) | — | — | — |
| A43B4C10 | (pinene) | 0.45 | — | — |
| A44B4C10 | ($C_6H_4$-4-Br) | 0.140 | — | — |
| A46B4C10 | —($CH_2$)$_2$Ph | — | — | — |
| A54B4C10 | ($C_6H_2$-2-($NO_2$)-4,5-($OMe$)$_2$) | — | — | — |

TABLE A2-continued
Modifying R⁴ when R³ is —C₆H₄-4-(CH₂NH₂)
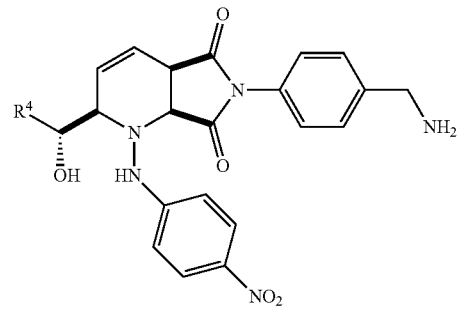
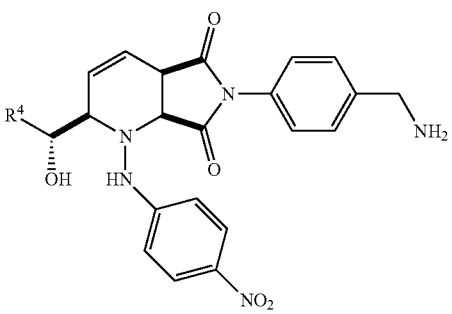
| Compound | R⁴ | $K_d$ (μM) | $IC_{50}$ (μM) | cLogP |
|---|---|---|---|---|
| A63B4C10 | (C₆H₃-3,5-(t-Bu)₂) | — | — | — |
| A67B4C10 | (C₆H₄-4-CF₃) | — | — | — |
| A70B4C10 | (n-C₂H₅) | — | — | — |
| A73B4C10 | (n-C₆H₁₃) | — | — | — |
| A75B4C10 | (n-C₈H₁₇) | — | — | — |
| A82B4C10 | (C₆H₃-3,5-(OMe)₂) | — | — | — |
| A83B4C10 | (C₆H₄-2-OMe) | — | — | — |
| A84B4C10 | (C₆H₃-2,3-(OMe)₂) | 0.25 | — | — |
| A85B4C10 | (C₆H₄-3-(OMe)) | 0.12 | 15 | — |
| A87B4C10 | (C₆H₄-4-Me) | 0.3 | — | — |
| A92B4C10 | (C₆H₄-2-NMe₂) | — | — | — |

TABLE A3

When R⁴ is 2-thienyl, or a derivative thereof

| Compound | Structure | $K_d$ (μM) | $IC_{50}$ (μM) |
|---|---|---|---|
| A39B4C50 | [structure: 2-thienyl-CH(OH) bicyclic pyrrolo-pyridine-dione with N-HN-(4-nitrophenyl) and N-(4-piperazinylphenyl) substituent] | — | — |
| A39B4C51 | [structure: 2-thienyl-CH(OH) bicyclic pyrrolo-pyridine-dione with N-HN-(4-nitrophenyl) and N-(2-piperazinylphenyl) substituent] | — | — |

TABLE B

Modifying R³ when R⁴ is —C₁₀H₂₁

[structure: C₁₀H₂₁-CH(OH) bicyclic pyrrolo-pyridine-dione with N—R³ and HN-(4-nitrophenyl)]

| Compound | R³ | $K_d$ (μM) | $IC_{50}$ (μM) | cLogP |
|---|---|---|---|---|
| A12B4C4 | cyclohexylmethyl (C₆H₁₂) | — | — | — |
| A12B4C5 (=A76B4C5) | benzyl —CH₂Ph (Bn) | 0.140 | 15 | — |

TABLE B-continued
Modifying R³ when R⁴ is —C₁₀H₂₁
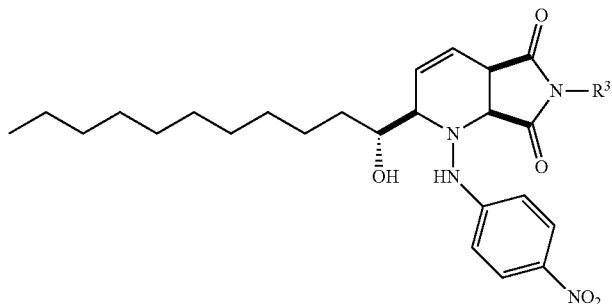
| Compound | R³ | $K_d$ (μM) | $IC_{50}$ (μM) | cLogP |
|---|---|---|---|---|
| A12B4C10 | (C₆H₄-4-CH₂NH₂) | 0.38 | 4.4 | — |
| A12B4C11 | (C₆H₄-4-NMe₂) | — | — | — |
| A12B4C12 | (C₆H₃-3,5-(CF₃)₂) | — | — | — |
| A12B4C13 | (C₆H₄-4-OMe) | — | — | — |
| A12B4C14 | (C₆H₄-2-Me) | — | — | — |
| A12B4C15 | (C₆H₄-2-OMe) | 0.16 | 9.0 | 6.3 |

TABLE B-continued
Modifying R³ when R⁴ is —C₁₀H₂₁
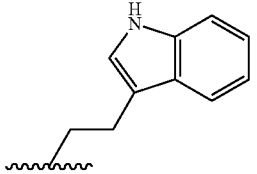
| Compound | R³ | $K_d$ (µM) | $IC_{50}$ (µM) | cLogP |
|---|---|---|---|---|
| A12B4C16 | 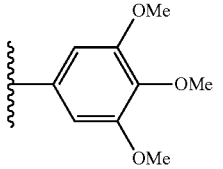<br>(CH₂)₂-3-(indolyl) | 0.26 | 3.8 | — |
| A12B4C17 | 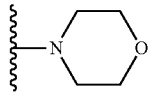<br>(C₆H₂-3,4,5-(OMe)₃) | — | 6.0 | — |
| A12B4C18 | 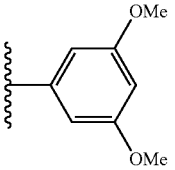<br>(morpholino) | — | — | — |
| A12B4C19 | 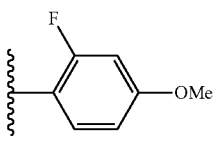<br>(C₆H₃-3,5-(OMe)₂) | — | — | — |
| A12B4C20 | 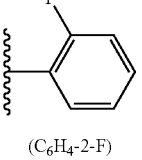<br>(C₆H₃-2,4-(OMe)₂) | — | — | — |
| A12B4C21 | <br>(C₆H₄-2-F) | — | — | — |

TABLE B-continued
Modifying R³ when R⁴ is —C₁₀H₂₁
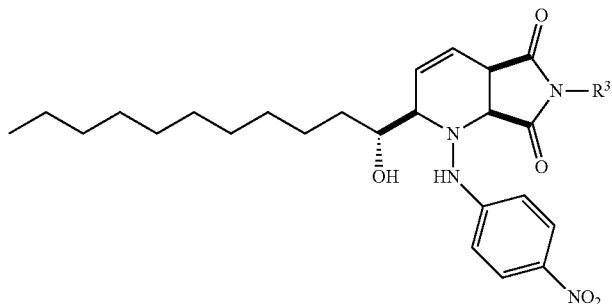
| Compound | R³ | $K_d$ (μM) | $IC_{50}$ (μM) | cLogP |
|---|---|---|---|---|
| A12B4C22 | (C₆H₄-3-F) | 0.24 | — | — |
| A12B4C23 | (C₆H₄-4-F) | 0.170 | 9.6 | 6.6 |
| A12B4C24 | (C₆H₄-2-NHSO₂Me) | — | — | — |
| A12B4C25 | ((CH₂)₂CH₂OAc) | — | — | — |
| A12B4C26 | (C₆H₃-3-OMe-4-F) | — | — | — |
| A12B4C27 | (C₆H₃-3-F-4-OMe) | — | — | — |

TABLE B-continued
Modifying R³ when R⁴ is —C₁₀H₂₁
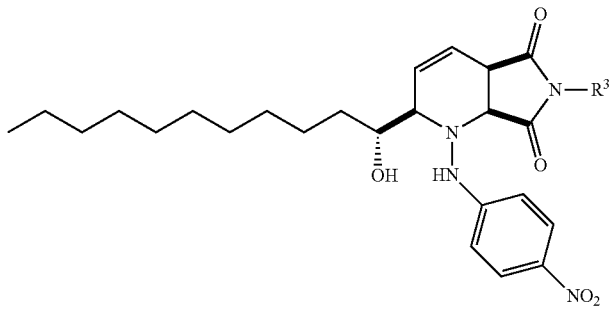
| Compound | R³ | $K_d$ (μM) | $IC_{50}$ (μM) | cLogP |
|---|---|---|---|---|
| A12B4C28 | (C₆H₃-2-Cl-5-CN) | 0.19 | — | — |
| A12B4C29 | (C₆H₃-2-Cl-5-CO₂Me) | — | — | — |
| A12B4C30 | 2-Me-4-F-phenyl | — | — | — |
| A12B4C31 | (C₆H₃-3-OAc-4-Me) | 0.140 | 6.5 | 6.3 |
| A12B4C32 | (CH₂C₆H₄-4-OMe) | — | — | — |
| A12B4C33 | (CH₂CH₂Ph) | — | — | — |
| A12B4C34 | (CH₂CH₂CH₂Ph) | — | — | — |

TABLE B-continued
Modifying R³ when R⁴ is —C₁₀H₂₁
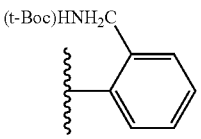
| Compound | R³ | $K_d$ (μM) | $IC_{50}$ (μM) | cLogP |
|---|---|---|---|---|
| A12B4C35 | 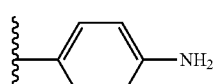 (C₆H₄-2-CH₂NH-t-Boc) | — | — | — |
| A12B4C37 | 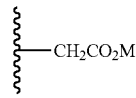 (C₆H₄-4-NH₂) | — | — | — |
| A12B4C38 | —CH₂CO₂Me | — | — | — |
| A12B4C39 | —CH₂CH₂CO₂Et | — | — | — |
| A12B4C40 | 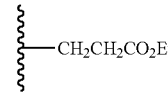 (CH₂C₆H₃-2,4-F₂) | — | — | — |
| A12B4C41 | 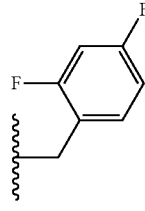 (C₆H₄-3-OH) | — | — | — |
| A12B4C42 | —CH₂CH₂NHPh | — | — | — |
| A12B4C44 | —NH-t-Boc | — | — | — |

TABLE B-continued
Modifying R³ when R⁴ is —C₁₀H₂₁
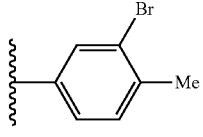
| Compound | R³ | $K_d$ (μM) | $IC_{50}$ (μM) | cLogP |
|---|---|---|---|---|
| A12B4C46 | 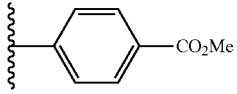<br>($C_6H_3$-3-Br-4-Me) | 0.36 | — | — |
| A12B4C47 | 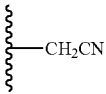<br>($C_6H_4$-4-$CO_2Me$) | 0.20 | — | — |
| A12B4C48 | —$CH_2CN$ | — | — | — |
| A12B4C49 | 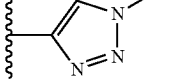<br>(4-Ph-2,3,4-triazolyl) | 0.18 | — | — |
| A12B4C50 | 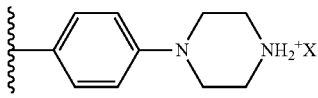<br>(4-piperidinyl with 4-NH) | 0.105 | 11.9 | 2.7 |
| A12B4C51 | 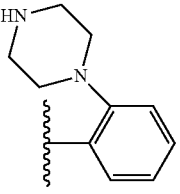<br>(2-piperidinyl with 4-NH) | 0.28 | — | — |
| A12B4C53 | 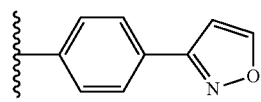<br>($C_6H_4$-4-(3-(1,2-oxazolyl)) | 0.19 | 5.3 | 5.8 |

TABLE B-continued
Modifying $R^3$ when $R^4$ is —$C_{10}H_{21}$
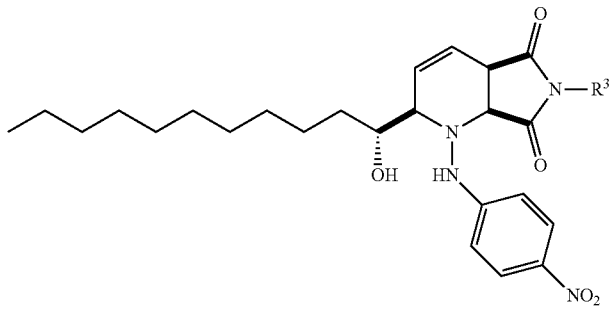
| Compound | $R^3$ | $K_d$ (μM) | $IC_{50}$ (μM) | cLogP |
|---|---|---|---|---|
| A12B4C60 | (CH$_2$-(2-pyridyl)) | 0.16 | — | — |
| A12B4C61 | (CH$_2$-(3-pyridyl)) | 0.420 | — | — |
| A12B4C62 | (CH$_2$-(4-pyridyl)) | 0.250 | — | — |
| A12B4C63 | (naphthyl-CH$_2$) | 0.160 | 7 | — |
| A12B4C65 | (C$_6$H$_4$-4-N$_3$) | 0.14 | — | — |
| A12B4C66 | (C$_6$H$_4$-4-morpholino) | 0.18 | — | — |

TABLE B-continued

Modifying R³ when R⁴ is —C₁₀H₂₁

| Compound | R³ | $K_d$ (µM) | $IC_{50}$ (µM) | cLogP |
|---|---|---|---|---|
| A12B4C67 | (4-benzoylphenyl) | 0.23 | — | — |
| A12B4C68 | (C₆H₄-4-piperidunyl-N-Me) | 0.20 | — | — |

TABLE C

Modifying N R¹R² when R³ is —C₆H₅ and R⁴ is —C₁₀H₂₁

| Compound | N R¹R² | $K_d$ (µM) | $IC_{50}$ (µM) | cLogP |
|---|---|---|---|---|
| A12B12C3 | (NHC₆H₄-4-CN) | — | 39.4 | — |
| A12B26C3 | (NHC₆H₄-4-SO₂NH₂) | — | — | — |

TABLE C-continued
Modifying N R¹R² when R³ is —C₆H₅ and R⁴ is —C₁₀H₂₁
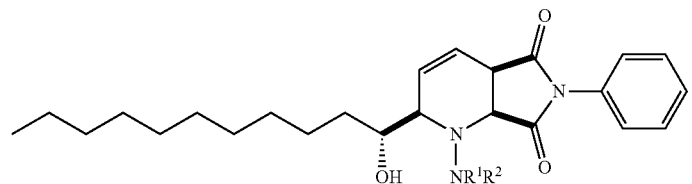
| Compound | N R¹R² | $K_d$ (µM) | $IC_{50}$ (µM) | cLogP |
|---|---|---|---|---|
| A12B27C3 | (NHC₆H₄-4-Cl) | 0.38 | 6.1 | 1.8 |
| A12B29C3 | (NHC₆H₄-4-SO₂Me) | — | — | — |
| A12B32C3 | (NHC₆H₄-4-(3,2-oxazolyl)) | 0.155 | — | — |
| A12B35C3 | (NHC₆H₄-3,4-F) | — | — | — |
| A12B36C3 | (NHC₆H₄-4-OCF₃) | — | — | — |

TABLE D
Modifying the scaffolding core
| Compound | Structure | $K_d$ (μM) | $IC_{50}$ (μM) | cLogP |
|---|---|---|---|---|
| A12B4C3 (COCF₃ ester) | 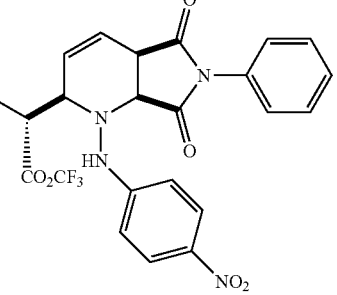 | 0.23 | — | — |
| SBH-05-129 | 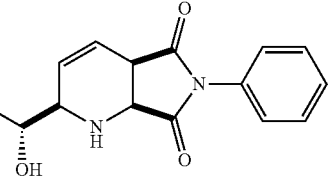 | 0.14 | — | — |
| A12B37C3 | 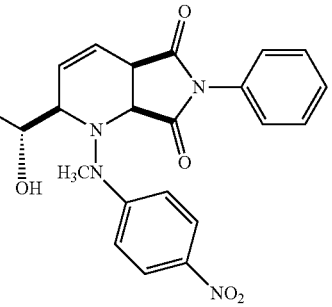 | 0.135 | 12 | 6.4 |
| A83C63 (no hydrazine) | 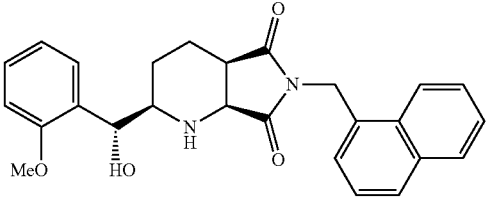 [SMILES: COc1ccccc1[C@@H](O)[C@H]1CC[C@H]2C(=O)N(Cc3cccc4ccccc34)C(=O)[C@H]2N1] | 0.10 | 15 | — |
| SBH-03-189 | 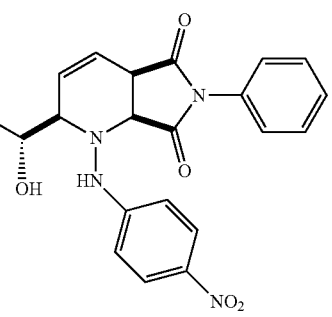 | — | — | — |
TVH-01-171 Kd 0.22

TABLE E

Hybrids of compounds from Tables A-D

| Compound | Structure | $K_d$ (μM) | $IC_{50}$ (μM) | cLogP |
|---|---|---|---|---|
| A44B27C5 | 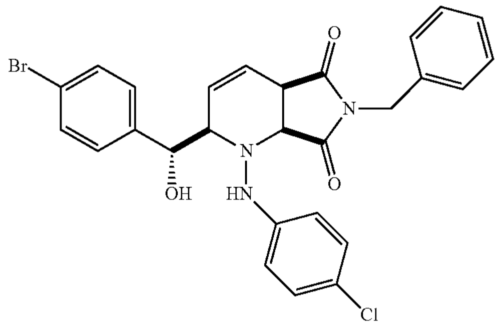 | 0.29 | — | — |
| A44B27C3 | 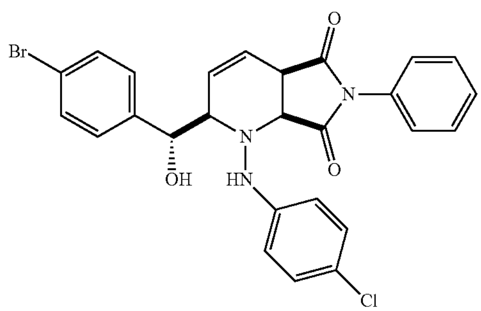 | 0.15 | 18 | 4.4 |
| A83BxxC63 (EWG = CN, CO$_2$Me) | 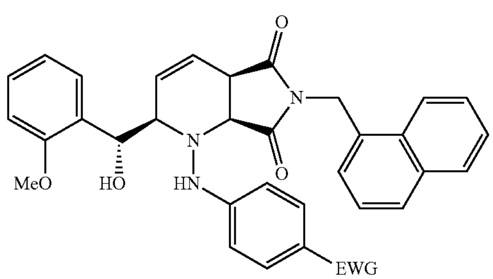 | 0.07-0.09 | — | — |
| A44B4C60 | 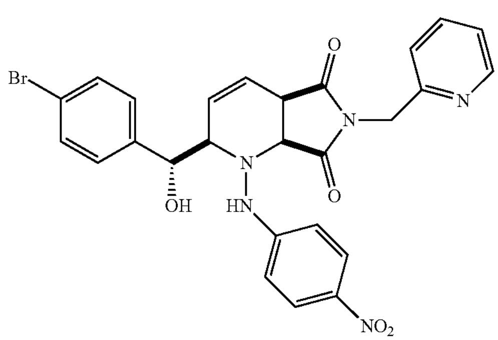 | 0.16/0.23 | 22 | — |

TABLE E-continued

Hybrids of compounds from Tables A-D

| Compound | Structure | $K_d$ (μM) | $IC_{50}$ (μM) | cLogP |
|---|---|---|---|---|
| A44B4C50 | 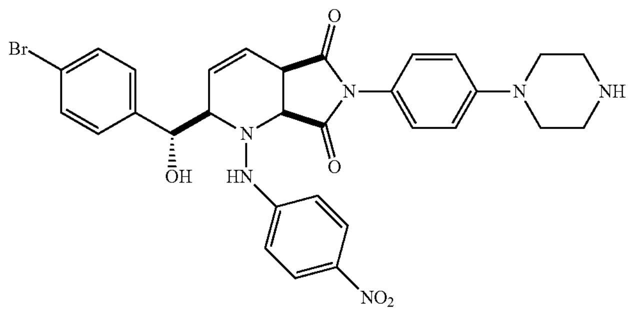 | 0.135 | 13 | 1.8 |
| A44B29C3 | 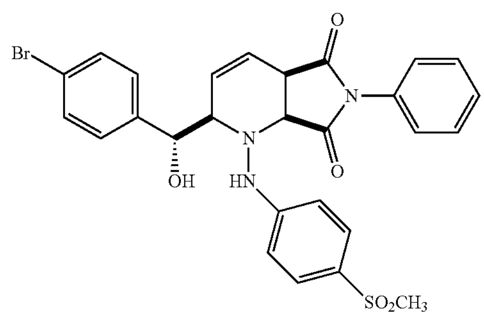 | 0.15 | — | — |
| A44B29C5 | 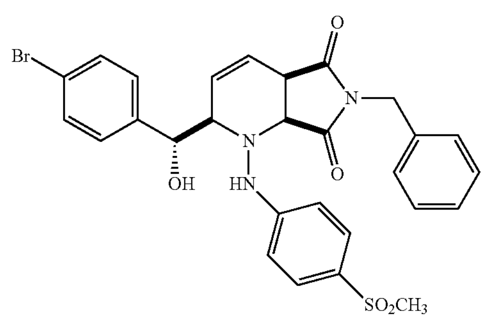 | 0.17 | — | — |
| A44B29C60 | 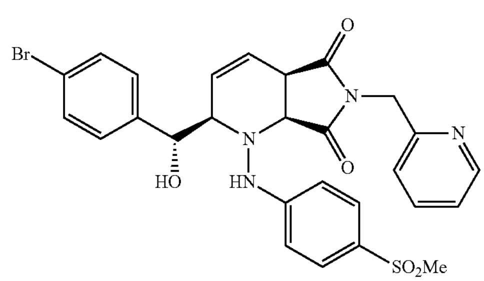 [SMILES: CS(=O)(=O)c1ccc(NN2[C@@H]([C@H](O)c3ccc(Br)cc3)C=C[C@H]3C(=O)N(Cc4ccccn4)C(=O)[C@H]32)cc1] | 0.12 | >40 | — |
| A83B29C63 | 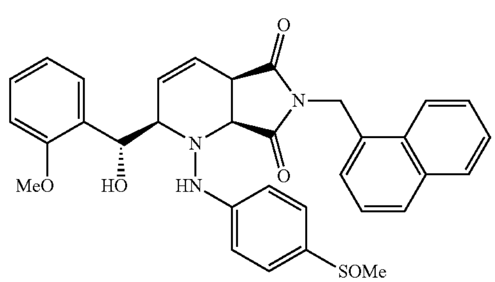 | 0.14 | 20 | 3.7 |

TABLE E-continued

Hybrids of compounds from Tables A-D

| Compound | Structure | $K_d$ (μM) | $IC_{50}$ (μM) | cLogP |
|---|---|---|---|---|
| A44B29C50 | 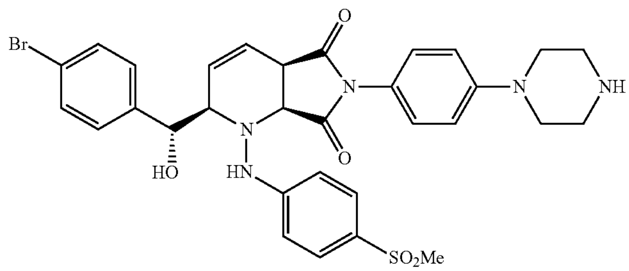 [SMILES: CS(=O)(=O)c1ccc(NN2[C@@H]([C@H](O)c3ccc(Br)cc3)C=C[C@H]3C(=O)N(c4ccc(N5CCNCC5)cc4)C(=O)[C@H]32)cc1] | 0.085 | 6.2 | 2.1 |
| A12B29C60 | 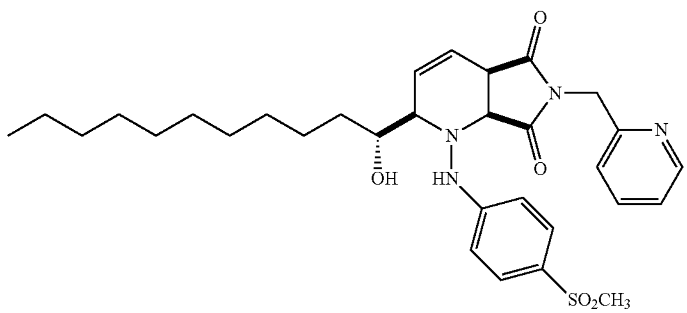 | 0.33 | 34 | — |
| A83B4C61 | 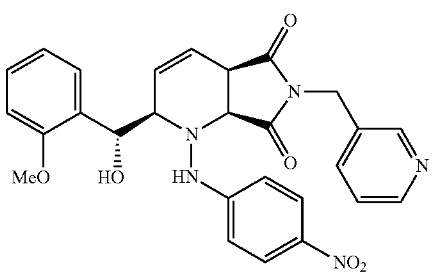 [SMILES: COc1ccccc1[C@@H](O)[C@H]1C=C[C@H]2C(=O)N(Cc3cccnc3)C(=O)[C@H]2N1Nc1ccc([N+](=O)[O-])cc1] | 0.280 | — | 2 |
| A83B4C63 | 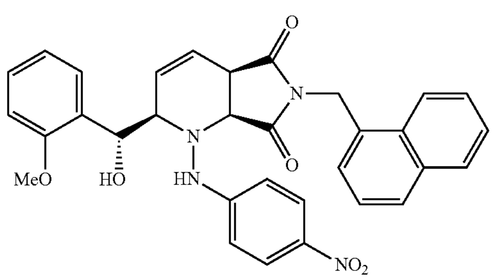 [SMILES: COc1ccccc1[C@@H](O)[C@H]1C=C[C@H]2C(=O)N(Cc3cccc4ccccc34)C(=O)[C@H]2N1Nc1ccc([N+](=O)[O-])cc1] | 0.090 | 9.8 | 4.3 |
| A83B1C63 | 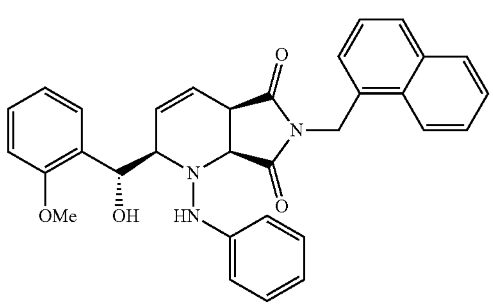 [SMILES: COc1ccccc1[C@@H](O)[C@H]1C=C[C@H]2C(=O)N(Cc3cccc4ccccc34)C(=O)[C@H]2N1Nc1ccccc1] | 0.095 | 8.4 | — |

TABLE E-continued

Hybrids of compounds from Tables A-D

| Compound | Structure | $K_d$ (μM) | $IC_{50}$ (μM) | cLogP |
|---|---|---|---|---|
| A83B4C2 | 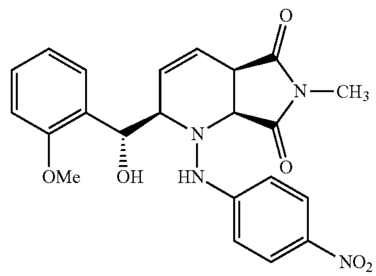 [SMILES: COc1ccccc1[C@@H](O)[C@H]1C=C[C@H]2C(=O)N(C)C(=O)[C@H]2N1Nc1ccc([N+](=O)[O-])cc1] | 0.2 | — | — |
| A83B4C64 | 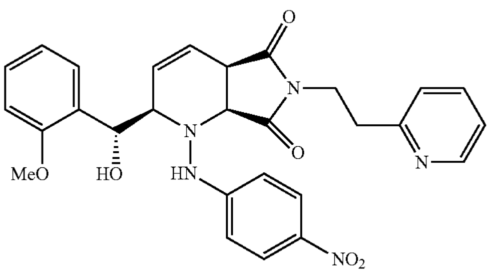 [SMILES: COc1ccccc1[C@@H](O)[C@H]1C=C[C@H]2C(=O)N(CCc3ccccn3)C(=O)[C@H]2N1Nc1ccc([N+](=O)[O-])cc1] | 0.22 | — | — |
| A83B4C69 | 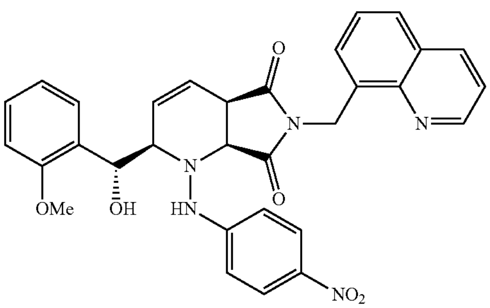 [SMILES: COc1ccccc1[C@@H](O)[C@H]1C=C[C@H]2C(=O)N(Cc3cccc4cccnc34)C(=O)[C@H]2N1Nc1ccc([N+](=O)[O-])cc1] | 0.13 | 16 | — |
| A83B37C63 | 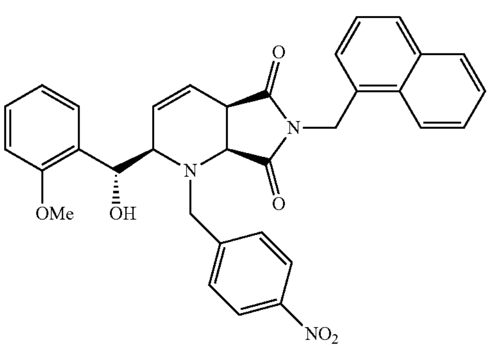 [SMILES: COc1ccccc1[C@@H](O)[C@H]1C=C[C@H]2C(=O)N(Cc3cccc4ccccc34)C(=O)[C@H]2N1Cc1ccc([N+](=O)[O-])cc1] | 0.145 | 19.4 | — |
| A83B38C63 | 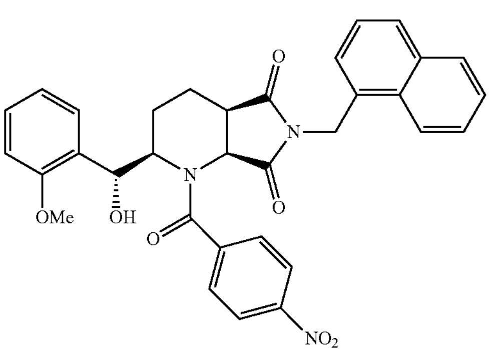 [SMILES: COc1ccccc1[C@@H](O)[C@H]1CC[C@H]2C(=O)N(Cc3cccc4ccccc34)C(=O)[C@H]2N1C(=O)c1ccc([N+](=O)[O-])cc1] | 0.135 | 10 | — |

TABLE E-continued

Hybrids of compounds from Tables A-D

| Compound | Structure | $K_d$ (µM) | $IC_{50}$ (µM) | cLogP |
|---|---|---|---|---|
| A44B4C66 | 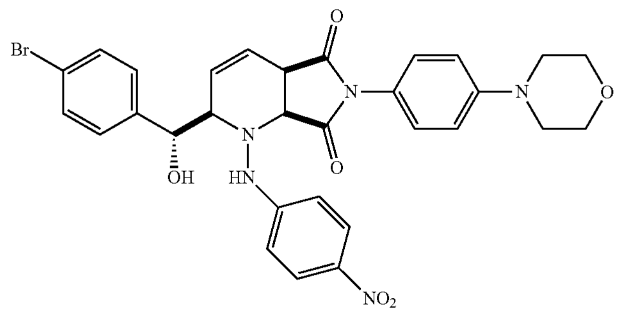 | 0.12/0.18 | 17 | — |
| A44B29C67 | 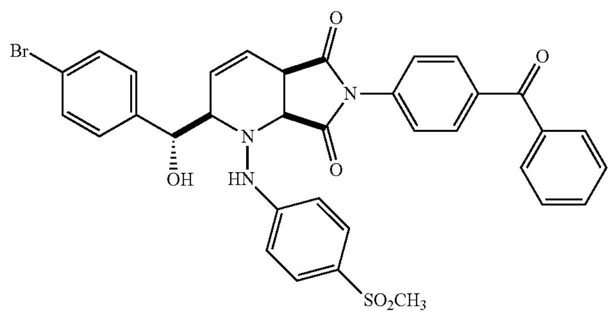 | — | — | — |
| A93/A94B29C3 | 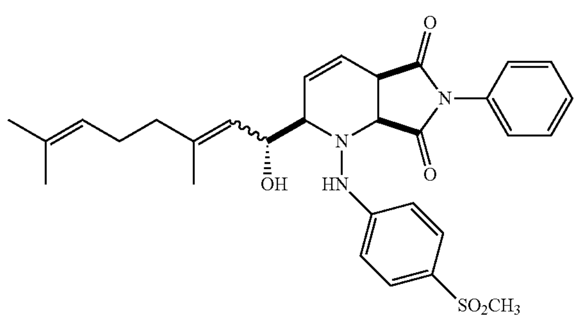 | 0.25 | — | — |

A76B4C5 0.140, 15 mM

| | Structural Characteristics of Compounds, Lipinski Parameters | | | |
|---|---|---|---|---|
| Number | M.W. | H-Bond Donors | H-Bond Acceptors | Rotatable Bonds |
| H5 | 534.66 | 2 | 7 | 14 |

Structural Characteristics of Compounds, Lipinski Parameters
| Number | M.W. | H-Bond Donors | H-Bond Acceptors | Rotatable Bonds |
|---|---|---|---|---|
| 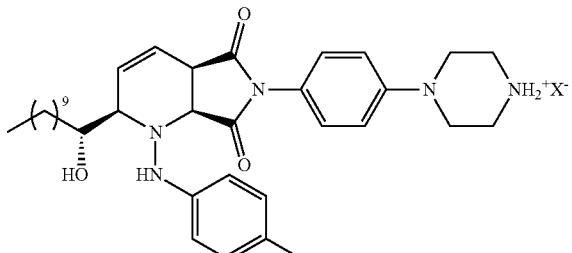<br>A12B4C50 | 618.78 | 3 | 9 | 15 |
| 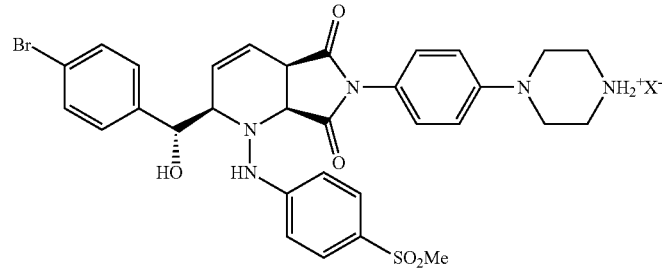<br>A442B29C50 | 666.59 | 3 | 9 | 7 |
| 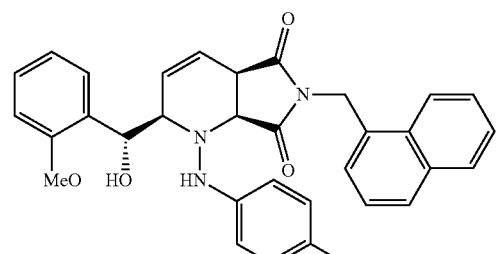<br>A83B4C63 | 564.60 | 2 | 8 | 8 |
| 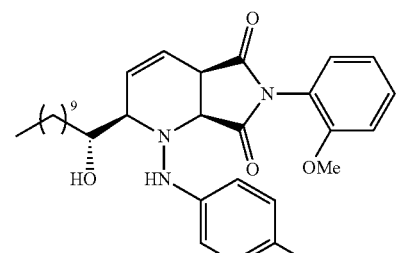<br>A12B4C15 | 564.68 | 2 | 8 | 15 |

-continued
Structural Characteristics of Compounds, Lipinski Parameters
| Number | M.W. | H-Bond Donors | H-Bond Acceptors | Rotatable Bonds |
|---|---|---|---|---|
|   A12B4C23 | 552.64 | 2 | 7 | 14 |
| 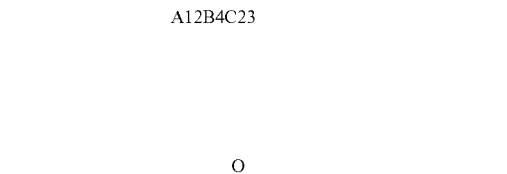  A44B4C66 | 667.58 | 2 | 9 | 7 |
| 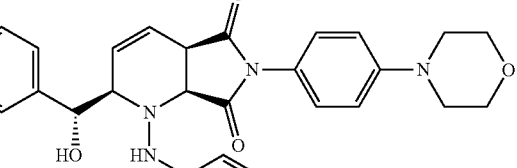  A12B4C53 | 601.70 | 2 | 8 | 15 |
| 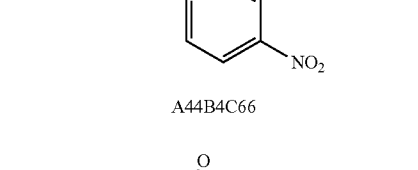  A12B4C31 | 606.72 | 2 | 8 | 16 |

Structural Characteristics of Compounds, Lipinski Parameters
| Number | M.W. | H-Bond Donors | H-Bond Acceptors | Rotatable Bonds |
|---|---|---|---|---|
| A12B37C3 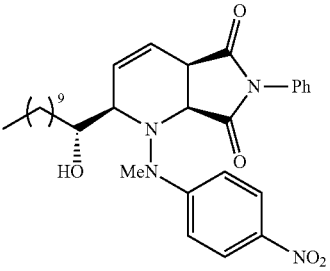 | 548.68 | 1 | 7 | 14 |
| A44B27C3 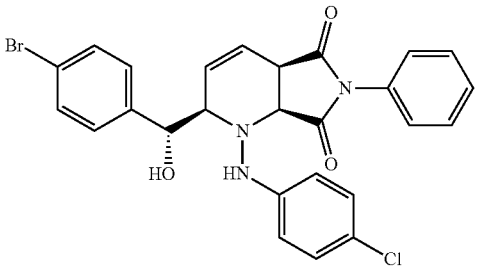 | 538.83 | 2 | 5 | 5 |
| A83B29C63 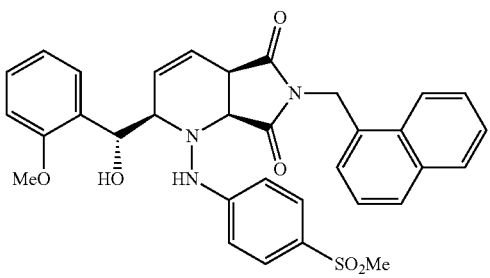 | 597.67 | 2 | 8 | 8 |
| A44B4C50 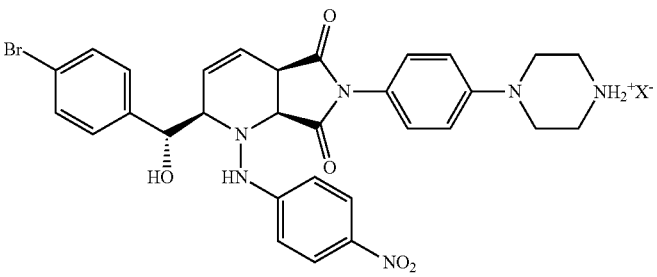 | 633.50 | 3 | 9 | 7 |

Structural Characteristics of Compounds, Lipinski Parameters

| Number | M.W. | H-Bond Donors | H-Bond Acceptors | Rotatable Bonds |
|---|---|---|---|---|
| A12B27C3 | 524.10 | 2 | 5 | 13 |
| A85B4C10 | 629.67 | 3 | 9 | 11 |

Figure 37:
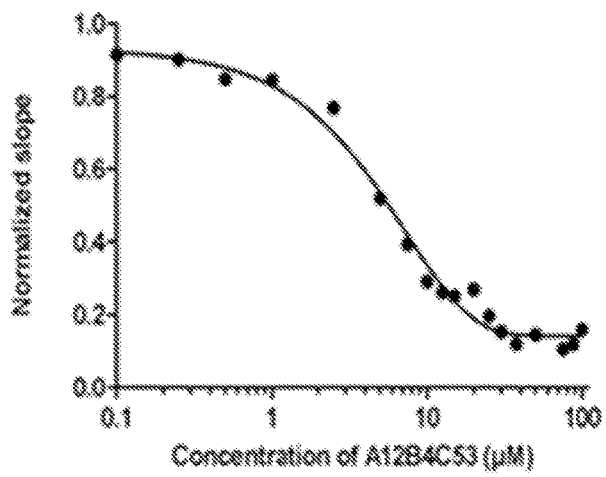
FIG. 37 shows binding affinities and IC$_{50}$ values of compound A12B4C53.

Example 1 B: Determining Binding Affinities and IC$_{50}$ Values (FIG. 37)

Binding Affinity (Kd) Values

Kd values were measured by steady-state fluorescence spectroscopy, by following protein tryptophan fluorescence quenching as a function of ligand concentration, as previously described (27; Freschauf, G. K., Mani, R. S., Mereniuk, T. R., Fanta, M., Virgen, C. A., Dianov, G. L., Grassot, J. M., Hall, D. G., and Weinfeld, M. Mechanism of action of an imido-piperidine inhibitor of human polynucleotide kinase/phosphatase. J. Biol. Chem. 285: 2351-2360 (2010).

IC$_{50}$ Determinations of Small Molecular Inhibitors of PNKP

IC$_{50}$ of the compounds as described herein was determined by the universal molecular beacon assay described by Song et al. Chem. Asian J. 2010, 5:1146-1151 (28), which combines use of a highly fluorescent oligonucleotide (U-MB), which when displaced from its template strand (UT), through a combination of PNKP and Klenow polymerase, forms a duplex structure thereby quenching the fluorescence. The substrate was generated by annealing the UT and U-MB oligonucleotides. UT is a 47-mer oligonucleotide, which formed an asymmetrical hairpin with a stable 6-base duplex bearing a phosphate on the recessed 3'-terminus. The UT sequence was: 5'-CTC TCT CTC TCT CTC TCT CTC CGG GAG TTG CGC ACC TAA AGG GTG CG/3Phos/-3' (SEQ ID NO: 1). U-MB was a 30-mer oligonucleotide bearing 5'-fluorescein (FAM) and 3'-dimethyl-aminoazobenzenesulfonic acid (DAB) groups, which annealed to UT to leave a 5'-nucleotide gap between the 3'-phosphate of UT and 5'-FAM of U-MB. The U-MB sequence was: 5'-/56FAM/CCC GGA GAG AGA GAG AGA GAG AGA GCC GGG/3Dab/-3 (SEQ ID NO: 2). By adding dNTPS and the Klenow polymerase to the reaction mixture, the phosphatase activity of PNKP can be monitored by measuring loss of fluorescence over time as U-MB is displaced from UT.

The oligonucleotides were purchased from IDT (San Diego, Calif.). For annealing, the oligonucleotides (50 µM each) were heated in annealing buffer (10 mM Tris (pH 8.0), 50 mM NaCl, 0.5 mM EDTA, 1 mM MgCl$_2$) at 100° C. for 5 minutes and allowed to cool to room temperature and then diluted in annealing buffer to a concentration of 2 µM. Prior to addition of substrate, reactions were set up in triplicate (19 µl volume each) in a 384-well plate containing reaction buffer (70 mM Tris-HCl (pH 7.4), 5 mM DTT, 10 mM MgCl$_2$), 0.4 mM dNTPs (New England Biolabs, Ipswich, Mass.), 0.25 units Klenow DNA polymerase (New England Biolabs), 12.5 ng PNKP, 1 µl test compound dissolved in DMSO. The final concentration of test compound in the reaction mixture ranged from 0.1 µM to 100 µM. This mixture was incubated for 5 min at room temperature before addition of the substrate (1 µl of 2 µM solution). The plate was placed immediately in a FLUOstar OPTIMA fluorescence plate reader (BMG Labtech), controlled by OPTIMA Version 2.2 software and fluorescence was continuously monitored over 20 min with excitation at 485 nm and emission at 520 nm (see FIG. 1). Two controls were included. In the first heat inactivated PNKP replaced the active enzyme and in the second, a control template oligonucleotide lacking the 3'-phosphate was used to ensure that the test compounds did not inhibit Klenow polymerase.

Figure 2:
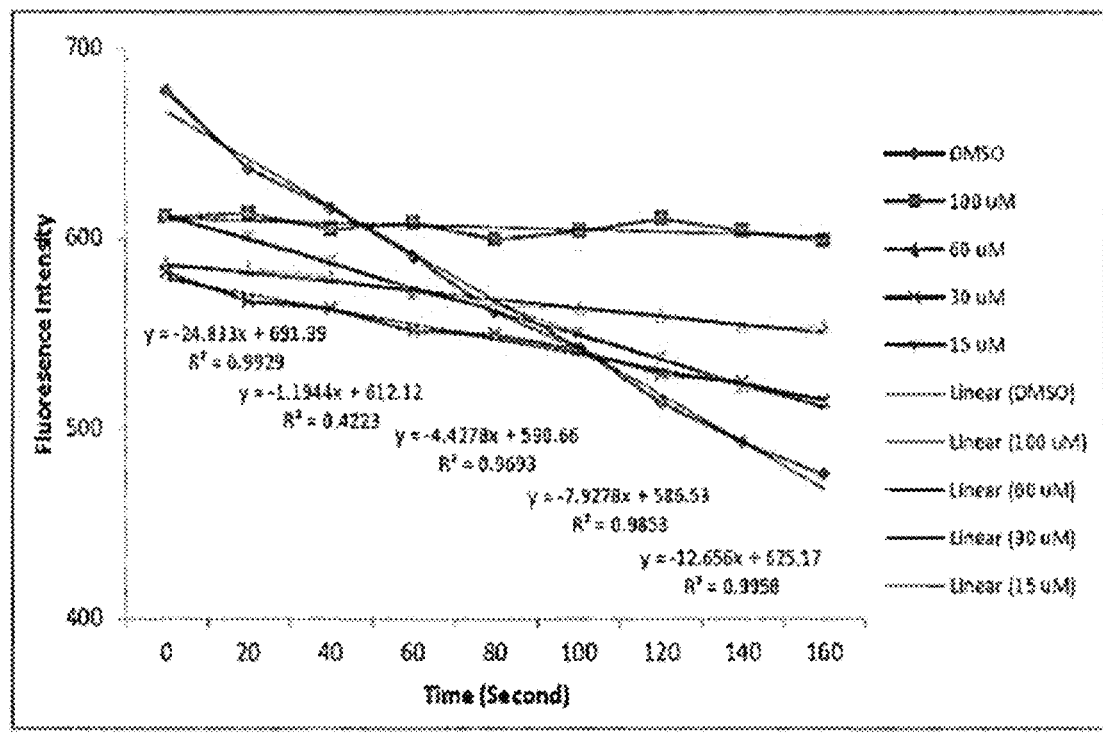
FIG. 2 is a graph depicting slope calculation.
Figure 3:
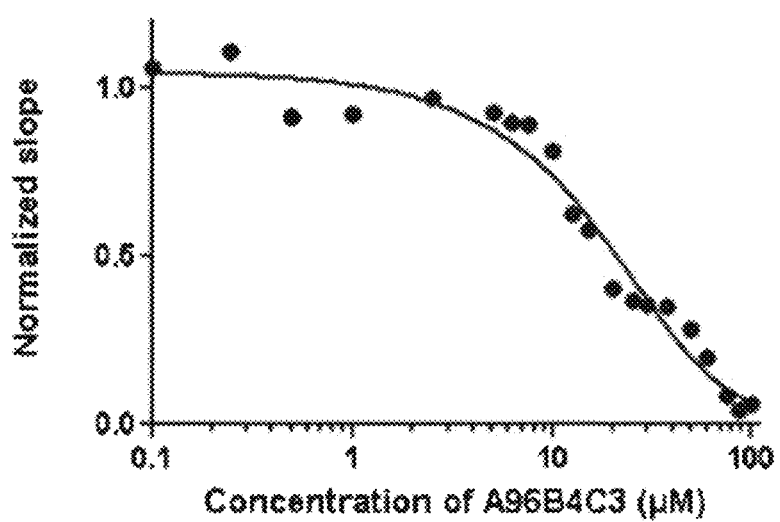
FIG. 3 is a graph depicting a nonlinear regression curve.

For analysis, the slope for the linear portion of each curve was calculated and normalized to the slope of DMSO alone control curve. Normalized slope for each concentration was then analyzed using GraphPad Prism Software and fitted to a nonlinear regression curve using Dose-response—Inhibition equation of Log(inhibitor) vs. Response—Variable slope (four parameters) to obtain the $IC_{50}$ value (see FIG. 2-4)

In vivo (cell sensitization was measured by clonogenic assay using HCT116 colorectal cancer cell line with either increasing doses of ionizing radiation or irinotecan.

CETSA was measured by modification to originally described assay (Jafari et al. Nat. Protoc. 2014, 9:2100-2122).

Example 1C: Synthetic Procedures and Characterization

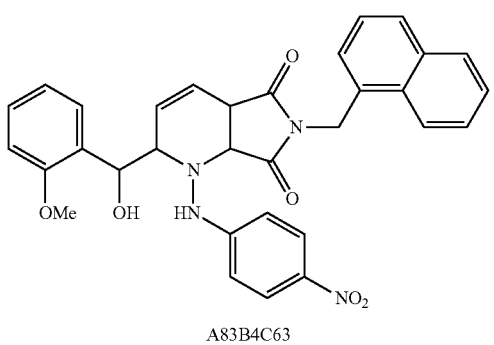 [SMILES: COc1ccccc1C(O)C1C=CC2C(=O)N(Cc3cccc4ccccc34)C(=O)C2N1Nc1ccc([N+](=O)[O-])cc1]

A83B4C63

2-[hydroxy(2-methoxyphenyl)methyl]-6-(naphthalen-1-ylmethyl)-1-[(4-nitrophenyl)amino]2H,4aH,7aH-pyrrolo[3,4-b]pyridine-5,7-dione $^1$H NMR (700 MHz; $C_5D_6$): δ8.64 (d, J=7.8, 1H), 7.95 (d, J=8.2, 2H), 7.85 (d, J=6.3, 1H), 7.60 (d, J=8.1, 1H), 7.55 (d, J=6.2, 1H), 7.45 (d, J=0.5, 1H), 7.23 (dd. J=9.1, 5.1, 2H), 7.00 (t, J=7.4, 1H), 6.80 (s, 1H), 6.33 (d, J=7.6, 1H), 5.64 (br s, 1H), 5.11 (ddd, J=10.2, 4.6, 1.9, 1H), 5.02 (br s, 1H), 4.92 (d, J=14.3, 1H), 4.66 (dd, J=8.1, 4.1, 1H), 3.75 (br s, 1H), 2.95 (s, 3H), 2.71 (br s, 1H); $^{13}$C NMR (125 MHz $CDCl_3$): δ174.3, 156.0, 140.1, 134.1, 133.8, 133.5, 131.4, 130.2, 129.19, 129.17, 128.7, 127.7, 127.2, 126.7, 126.1, 125.9, 125.2, 123.6, 121.0, 111.5, 110.5, 55.1, 50.9, 40.6, 29.7; IR (microscope, $cm^{-1}$): 3523.28 (br), 3291.61 (br), 3191.27, 3046.49, 2936.94, 2837.33, 2624.75, 2430.88, 1779.09, 1701.45, 1593.84, 1497.17, 1477.38, 1465.04, 1437.71, 1397.43, 1375.38, 1319.36; HRMS (ESI): for $C_{32}H_{38}N_4O_6$ calcd. 563.1936; found 563.1931.

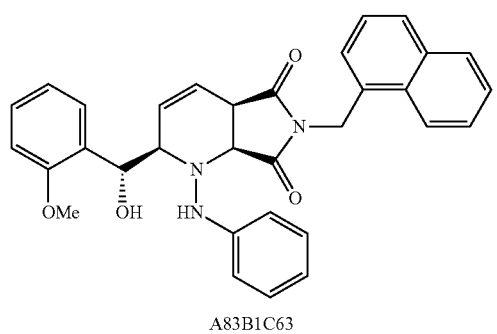 [SMILES: COc1ccccc1[C@@H](O)[C@H]1C=C[C@H]2C(=O)N(Cc3cccc4ccccc34)C(=O)[C@H]2N1Nc1ccccc1]

A83B1C63

A83B1C63:
The crude was purified by flash chromatography (1:4, EtOAc:hexanes) to obtain A83B1C63 analog (0.31 g, 60% yield, 90% purity). The analog was further purified by semipreparative HPLC (86 mg, >99% purity).

Brown-pinkish solid, $R_f$=0.14 (1:4, EtOAc:hexanes).

Figure 5:
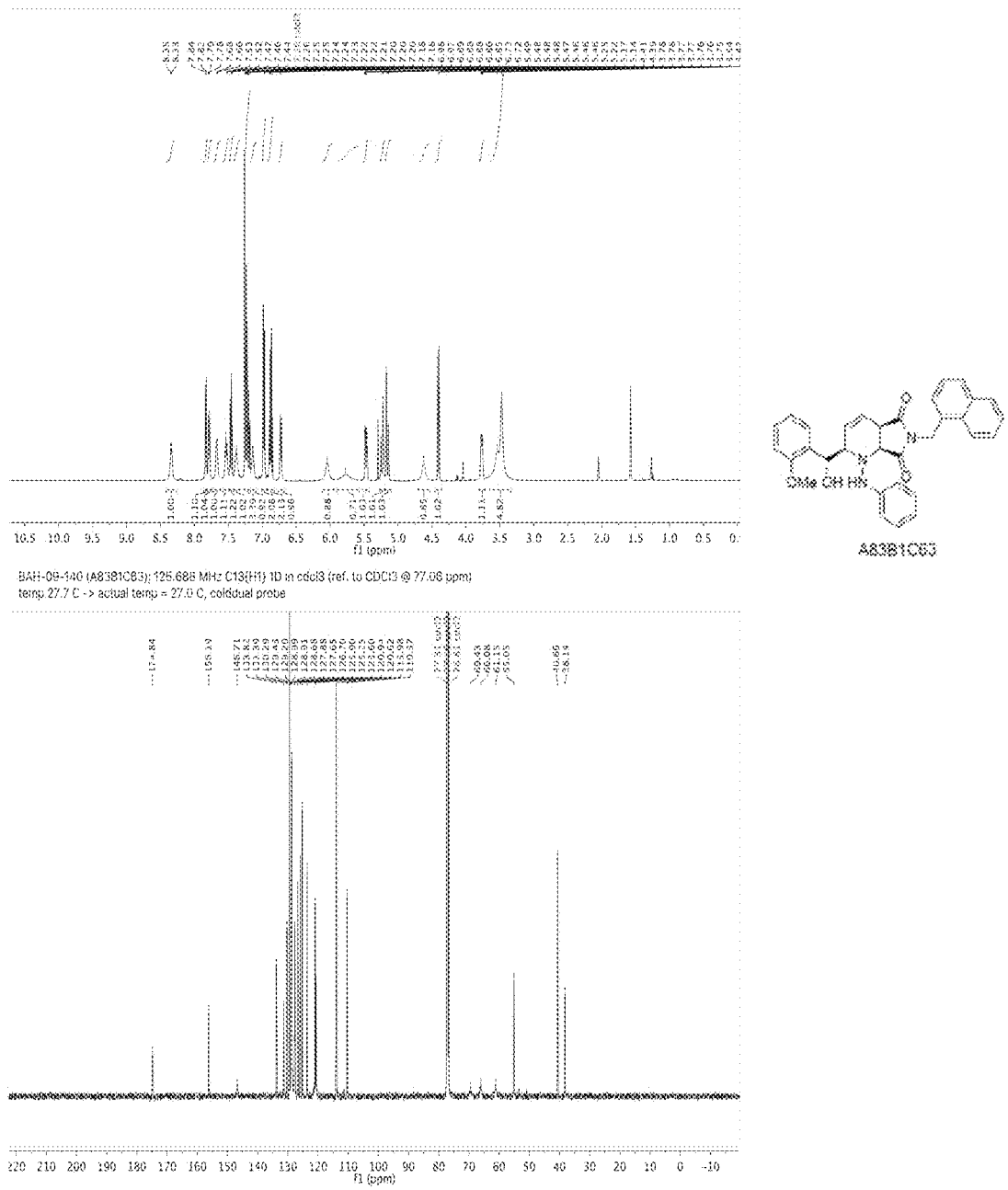
FIG. 5 depicts NMR spectra of compound A83B1C63 in chloroform-d.

$^1$H NMR δ/ppm: (500 MHz, $CDCl_3$) 8.34 (d, J=8.5 Hz, 1H), 7.83 (d, J=8.2 Hz, 1H), 7.78 (d, J=8.2 Hz, 1H), 7.67 (d, J=6.9 Hz, 1H), 7.53 (app t, J=7.8 Hz, 1H), 7.46 (app t, J=7.5 Hz, 1H), 7.42-7.33 (m, 1H), 7.26-7.17 (comp m, 3H), 7.16-7.10 (m, 1H), 6.98 (d, J=7.3 Hz, 2H), 6.93-6.82 (comp m, 2H), 6.73 (d, J=8.3 Hz, 1H), 6.04 (bs, 1H), 5.77 (bs, 1H), 5.47 (ddd, J=10.3, 4.5, 2.2 Hz, 1H), 5.23, 5.16 (ABq, $J_{AB}$=14.6 Hz, 2H), 4.62 (bs, 1H), 4.40 (d, J=8.5 Hz, 1H), 3.77 (ddd, J=9.2, 4.0, 2.0 Hz, 1H), 3.51 (comp m, 5H). See FIG. 5.

$^{13}$C NMR δ/ppm: (126 MHz, $CDCl_3$) 174.8, 156.2, 146.7, 133.8, 131.4, 130.3, 129.4, 129.2, 129.0, 128.9, 128.6, 127.9, 127.6, 126.7, 125.9, 125.2, 123.6, 120.9, 120.6, 114.0, 110.4, 69.4, 66.1, 61.2, 55.0, 40.7, 38.1.

Figure 6:
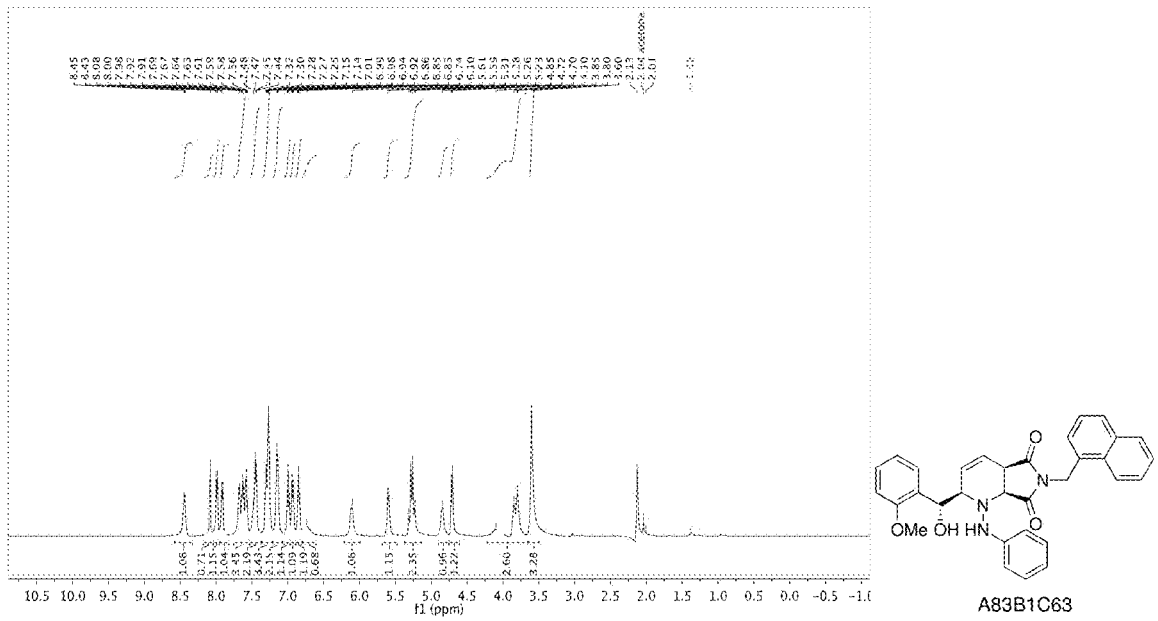
FIG. 6 depicts NMR spectra of compound A83B1C63 in acetone-d.
Figure 6:
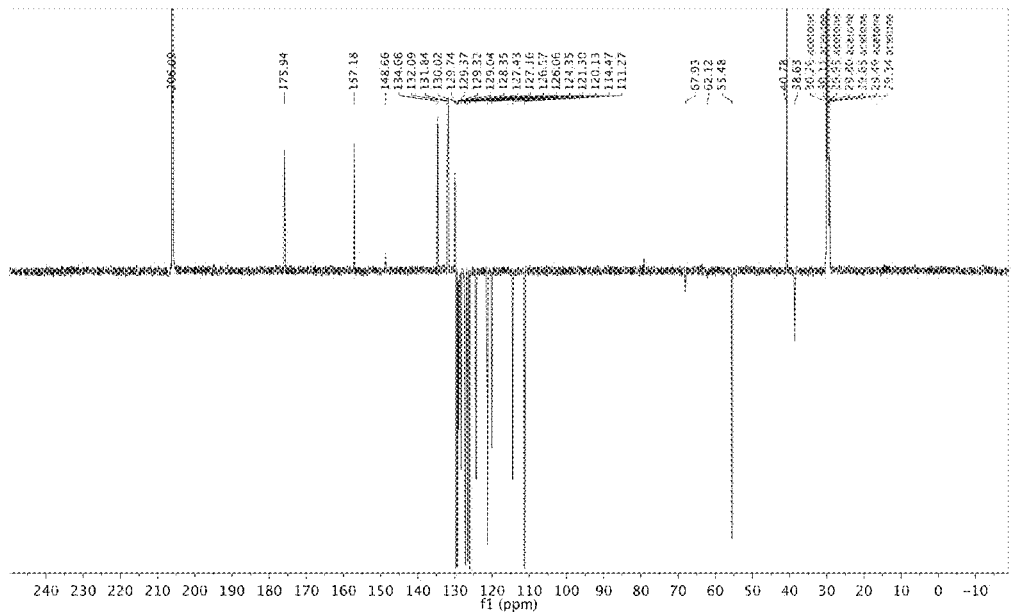

$^1$H NMR δ/ppm: (500 MHz, Acetone-$d_6$) 8.44 (d, J=8.2 Hz, 1H), 8.08 (s, 1H), 7.99 (d, J=8.1 Hz, 1H), 7.91 (d, J=8.2 Hz, 1H), 7.73-7.54 (comp m, 3H), 7.52-7.39 (comp m, 2H), 7.35-7.21 (comp m, 3H), 7.15 (d, J=8.1 Hz, 2H), 6.99 (app t, J=7.5 Hz, 1H), 6.93 (d, J=8.3 Hz, 1H), 6.85 (app t, J=7.4 Hz, 1H), 6.74 (bs, 1H), 6.10 (bs, 1H), 5.60 (d, J=6.4 Hz, 1H), 5.30, 5.24 (ABq, $J_{AB}$=15.2 Hz, 2H), 4.85 (bs, 1H), 4.71 (d, J=8.6 Hz, 1H), 4.22-3.67 (comp m, 3H), 3.60 (s, 3H). See FIG. 6.

$^{13}$C NMR δ/ppm: (126 MHz, Acetone-$d_6$, APT) 175.9 (CO), 157.2, 148.7, 134.7, 132.1, 131.8 (C), 130.0, 129.7, 129.4, 129.3, 129.0, 128.4, 127.4, 127.2, 126.6, 126.1, 124.4, 121.3, 120.1, 114.5, 111.3 (CH), 67.9, 62.1 (CH), 55.5 ($OCH_3$), 40.8 ($CH_2$), 38.6 (CH).

IR (Microscope, $cm^{-1}$) 3527, 3285, 3049, 3009, 2938, 2838, 1778, 1706, 1602, 1494, 1397.

HRMS (ESI-TOF) for $C_{32}H_{30}N_3O_4$ $(M+H)^+$: calcd.: 520.2231; found: 520.2242; for $C_{32}H_{29}N_3NaO_4$ $(M+Na)^+$: calcd.: 542.205; found: 542.2051.

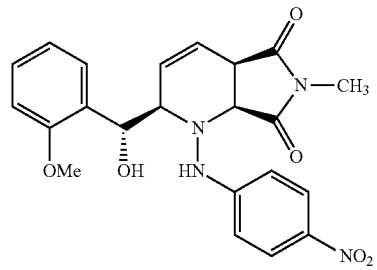

A83B4C2

A83B4C2:
The crude was purified by flash chromatography (1:1, EtOAc:hexanes) to obtain A83B4C2 analog (0.23 g, 53% yield, 94% purity). The analog was further purified by semipreparative HPLC (0.16 g, >99% purity).

White-yellowish solid, $R_f$=0.22 (1:1, EtOAc:hexanes).

Figure 7:
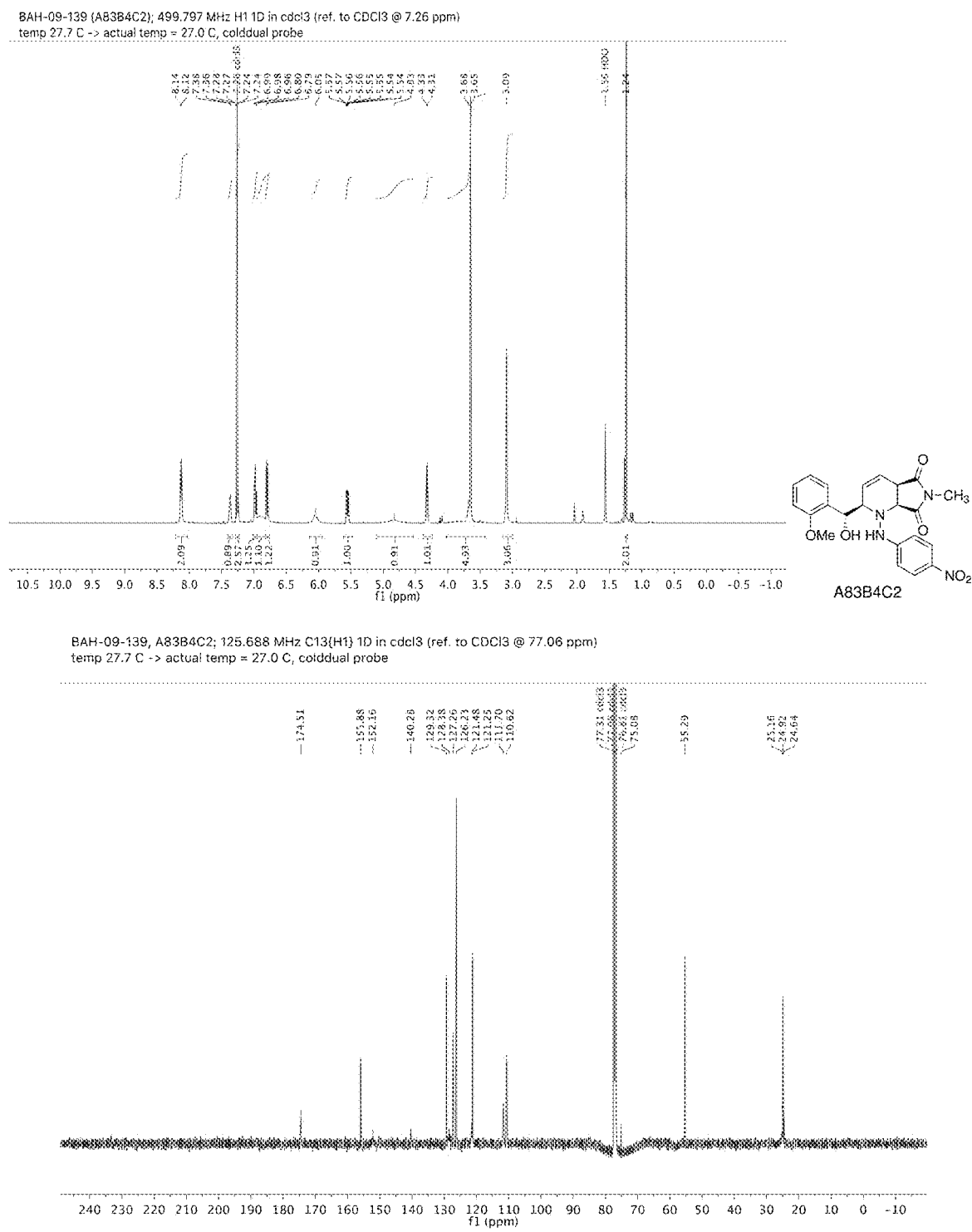
FIG. 7 depicts NMR spectra of compound A83B4C2 in chloroform-d.

$^1$H NMR δ/ppm: (500 MHz, $CDCl_3$) 8.12 (d, J=8.8 Hz, 2H), 7.37 (d, J=7.6 Hz, 1H), 7.29-7.23 (comp m, 2H), 7.07-6.70 (comp m, 4H), 6.05 (bs, 1H), 5.55 (ddd, J=10.3, 4.9, 2.1 Hz, 1H), 4.83 (bs, 1H), 4.32 (d, J=8.7 Hz, 1H), 3.96-3.50 (comp m, 5H), 3.09 (s, 3H). See FIG. 7.

$^{13}$C NMR δ/ppm: (126 MHz, $CDCl_3$) 174.5, 155.9, 152.2, 140.3, 129.3, 128.4, 127.3, 126.2, 121.5, 121.2, 111.7, 110.6, 75.1, 55.3, 25.2, 24.9, 24.6.

Figure 8:
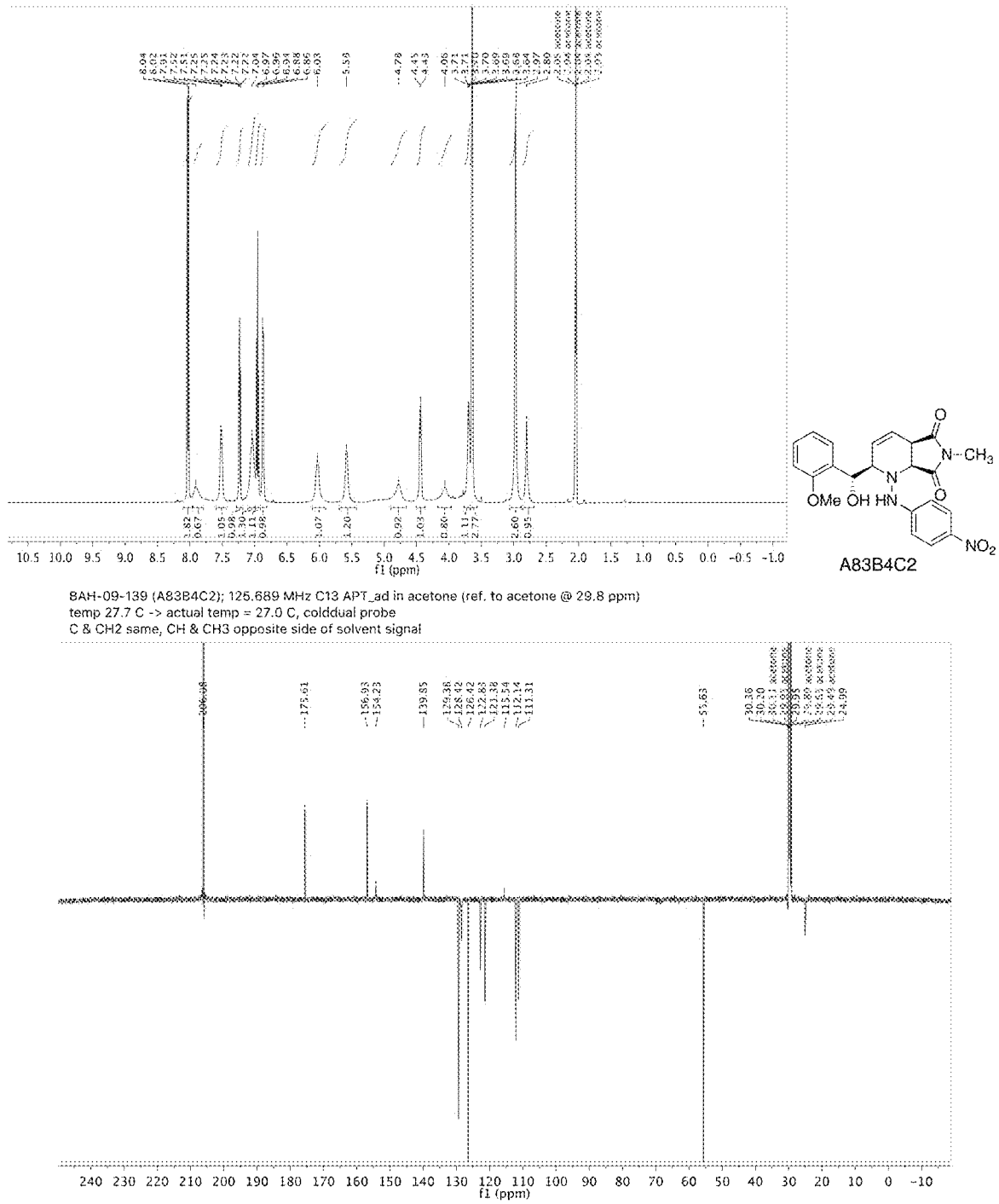
FIG. 8 depicts NMR spectra of compound A83B4C2 in acetone-d.

¹H NMR δ/ppm: (500 MHz, Acetone-$d_6$) 8.03 (d, J=9.5 Hz, 2H), 7.90 (bs, 1H), 7.52 (d, J=7.2 Hz, 1H), 7.28-7.18 (m, 1H), 7.04 (bs, 1H), 6.96 (app t, J=7.4 Hz, 1H), 6.87 (d, J=8.3 Hz, 1H), 6.03 (bs, 1H), 5.58 (bs, 1H), 4.78 (bs, 1H), 4.44 (d, J=8.3 Hz, 1H), 4.06 (bs, 1H), 3.76-3.68 (m, 1H), 3.64 (s, 3H), 2.97 (s, 3H), 2.86-2.72 (m, 1H). See FIG. 8.

¹³C NMR δ/ppm: (126 MHz, Acetone-$d_6$, APT) 175.6 (CO), 156.9, 154.2, 139.8 (C), 129.4, 128.4, 126.4, 122.8, 121.4 (CH), 115.5 (C), 112.1, 111.3 (CH), 55.6 (OCH$_3$), 30.4, 30.2, 30.0, 29.49 (CH), 25.0 (CH$_3$).

IR (Microscope, cm⁻¹) 3516, 3301, 2928, 2852, 2427, 1780, 1704, 1598, 1500, 1326, 1112.

HRMS (ESI-TOF) for $C_{22}H_{21}N_4O_6$ (M−H)⁻: calcd.: 437.1467; found: 437.1464.

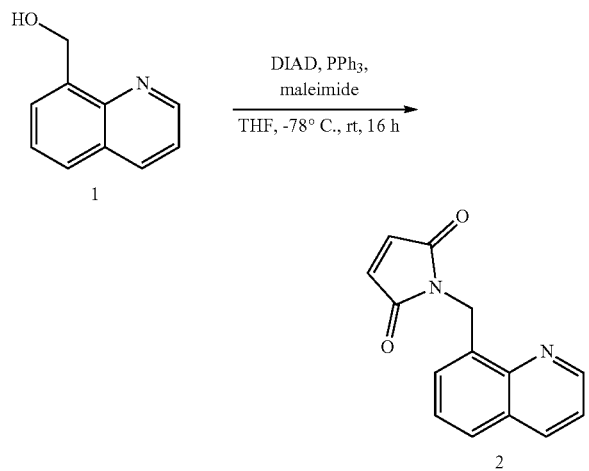

Compound 2:

Compound 1 was synthesized based on the literature example [Xu, Y.; Young, M. C.; Wang, C.; Magness, D. M.; Dong, G. Angew. Chem. Int. Ed. 2016, 55 (31), 9084-9087]. Triphenylphosphine (1.0 equiv, 0.66 g, 2.5 mmol) was dissolved in dry THF (20 ml) and the solution was cooled to −78° C. DIAD (1.0 equiv, 0.49 ml, 2.5 mmol) was then added dropwise to the solution and the reaction mixture was stirred for 15 min at −78° C. The solution of compound 1 (1.5 equiv, 0.6 g, 3.8 mmol) in dry THF (15 ml) was added slowly to the reaction mixture, which was stirred for 5 min at −78° C. Lastly, the solution of maleimide (1.0 equiv, 0.24 g, 2.5 mmol) in dry THF (5 ml) was added, and the reaction mixture was stirred at room temperature for 16 h, after which it was concentrated in vacuo. The crude was dissolved in dichloromethane (50 ml) and extracted with HCl solution (1 M, 3×20 ml). Then the combined acidic aqueous phase was neutralized (pH 7) with solid NaHCO$_3$. The neutral aqueous solution was extracted with EtOAc (3×30 ml), and the combined organic extracts were dried over Na$_2$SO$_4$, filtered and concentrated. The crude residue was purified by flash chromatography (1:4 to 1:1, EtOAc:hexanes) to obtain compound 2 (0.24 g, 41% yield).

Pale-white solid, $R_f$=0.45 (1:1, EtOAc:hexanes).

Figure 9:
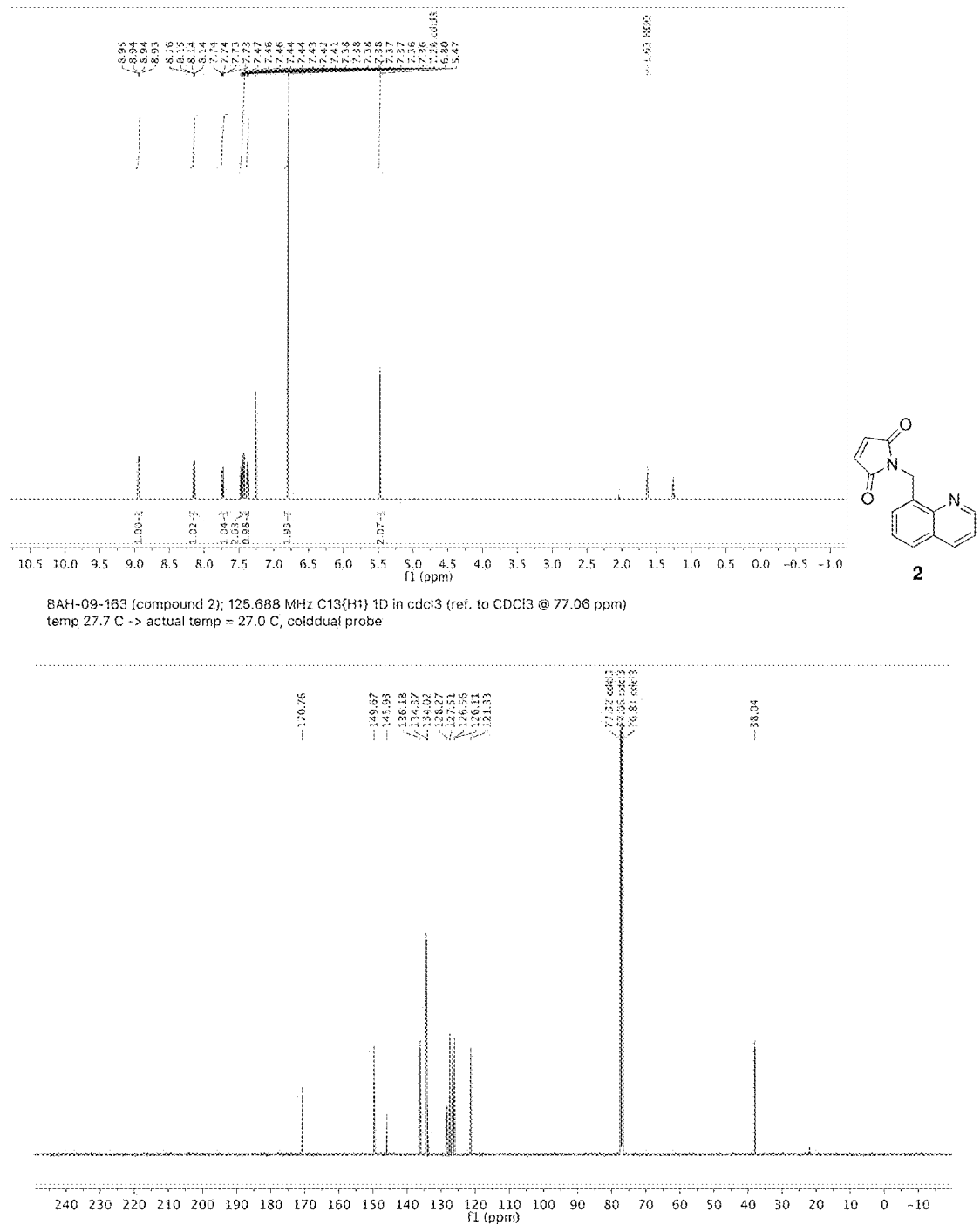
FIG. 9 depicts NMR spectra of compound 2.

¹H NMR δ/ppm: (500 MHz, CDCl$_3$) 8.94 (dd, J=4.2, 1.8 Hz, 1H), 8.15 (dd, J=8.3, 1.8 Hz, 1H), 7.78-7.67 (m, 1H), 7.48-7.41 (comp m, 2H), 7.39-7.35 (m, 1H), 6.80 (s, 2H), 5.47 (s, 2H). See FIG. 9.

¹³C NMR δ/ppm: (126 MHz, CDCl$_3$) 170.8, 149.7, 145.9, 136.2, 134.4, 134.0, 128.3, 127.5, 126.6, 126.1, 121.3, 38.0.

IR (Microscope, cm⁻¹) 3097, 3014, 2982, 2935, 1773, 1709, 1499, 1425, 1406, 1149.

HRMS (ESI-TOF) for $C_{14}H_{11}N_2O_2$(M+H)⁺: calcd.: 239.0815; found: 239.0816; for $C_{14}H_{10}N_2NaO_2$ (M+Na)⁺: calcd.: 261.0634; found: 261.0637.

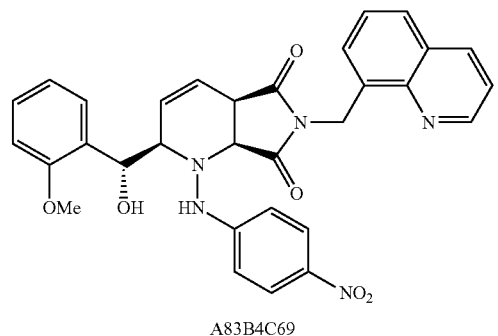 [SMILES: COc1ccccc1[C@@H](O)[C@H]1C=C[C@H]2C(=O)N(Cc3cccc4cccnc34)C(=O)[C@H]2N1Nc1ccc([N+](=O)[O-])cc1]

A83B4C69

A83B4C69:

The crude was purified by flash chromatography (1:1, EtOAc:hexanes) to obtain A83B4C69 analog (60 mg, 80% purity). The analog was further purified by semipreparative HPLC (33 mg, 12% yield, 96% purity).

Yellow solid, $R_f$=0.21 (1:1, EtOAc:hexanes).

Figure 10:
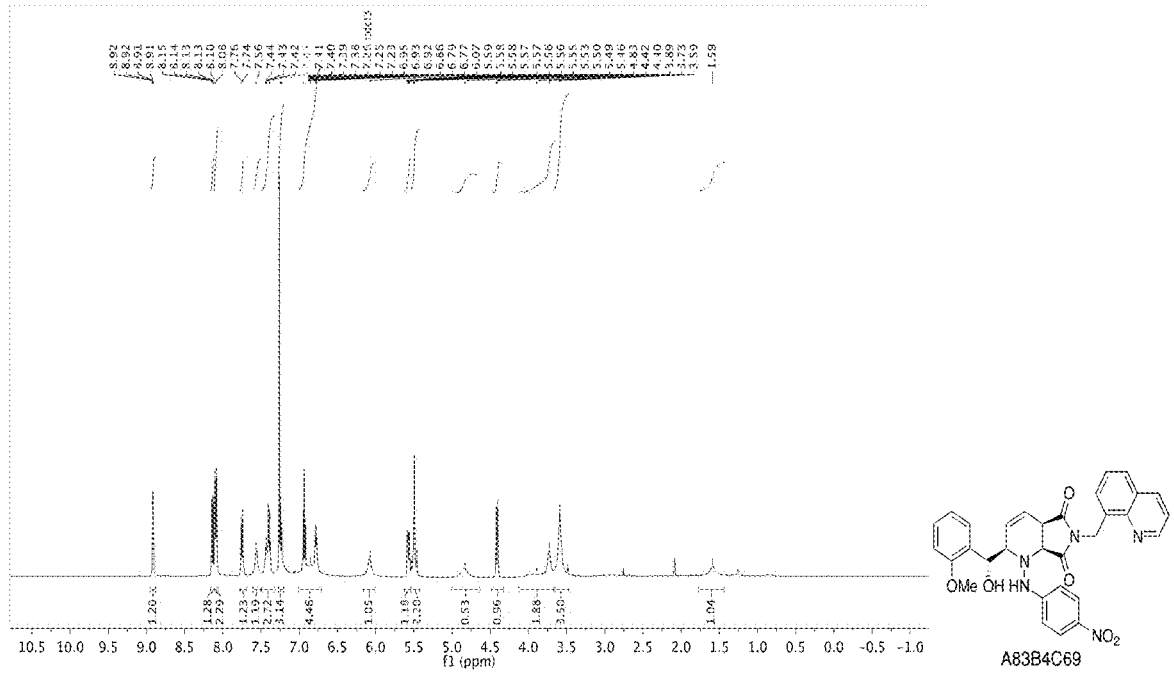
FIG. 10 depicts NMR spectra of compound A83B4C69 in chloroform-d.
Figure 10:
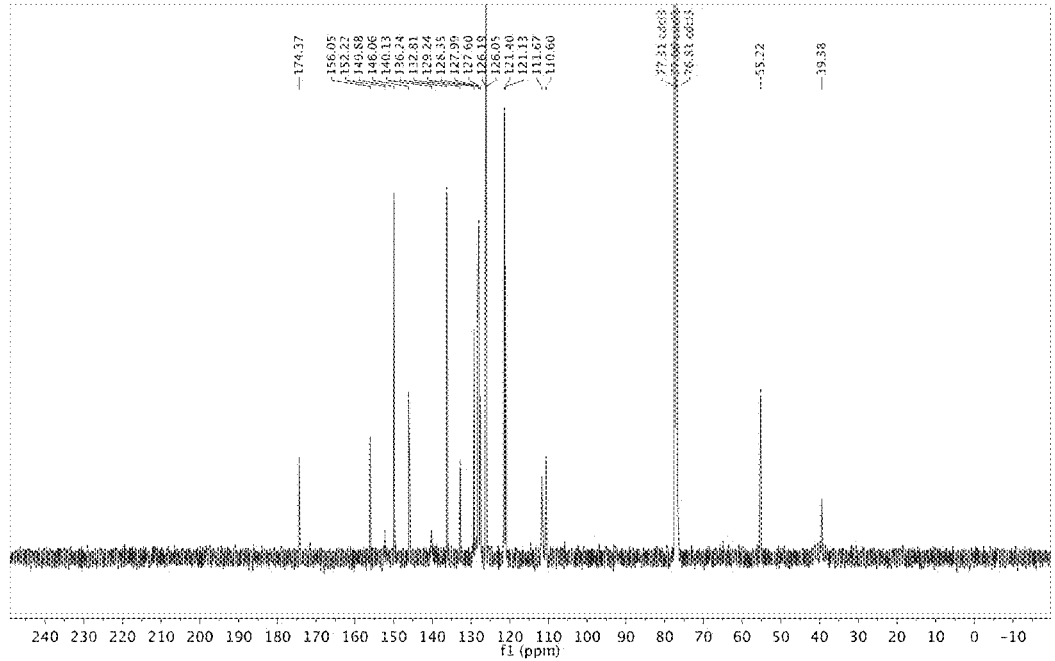

¹H NMR δ/ppm: (500 MHz, CDCl$_3$) 8.92 (dd, J=4.2, 1.8 Hz, 1H), 8.14 (dd, J=8.3, 1.8 Hz, 1H), 8.09 (d, J=8.8 Hz, 2H), 7.75 (d, J=8.1 Hz, 1H), 7.56 (s, 1H), 7.48-7.36 (m, 2H), 7.24 (comp m, 3H), 7.01-6.71 (comp m, 4H), 6.07 (s, 1H), 5.57 (ddd, J=10.3, 4.7, 2.2 Hz, 1H), 5.50 (comp m, 2H), 4.83 (bs, 1H) 4.41 (d, J=8.8 Hz, 1H), 4.11-3.66 (comp m, 2H), 3.59 (s, 3H), 1.59 (bs, 1H). See FIG. 10.

¹³C NMR δ/ppm: (126 MHz, CDCl$_3$) 174.4, 156.0, 152.2, 149.9, 146.1, 140.1, 136.2, 132.8, 129.2, 128.4, 128.0, 127.6, 126.2, 126.0, 121.4, 121.1, 111.7, 110.6, 55.2, 39.4.

Figure 11:
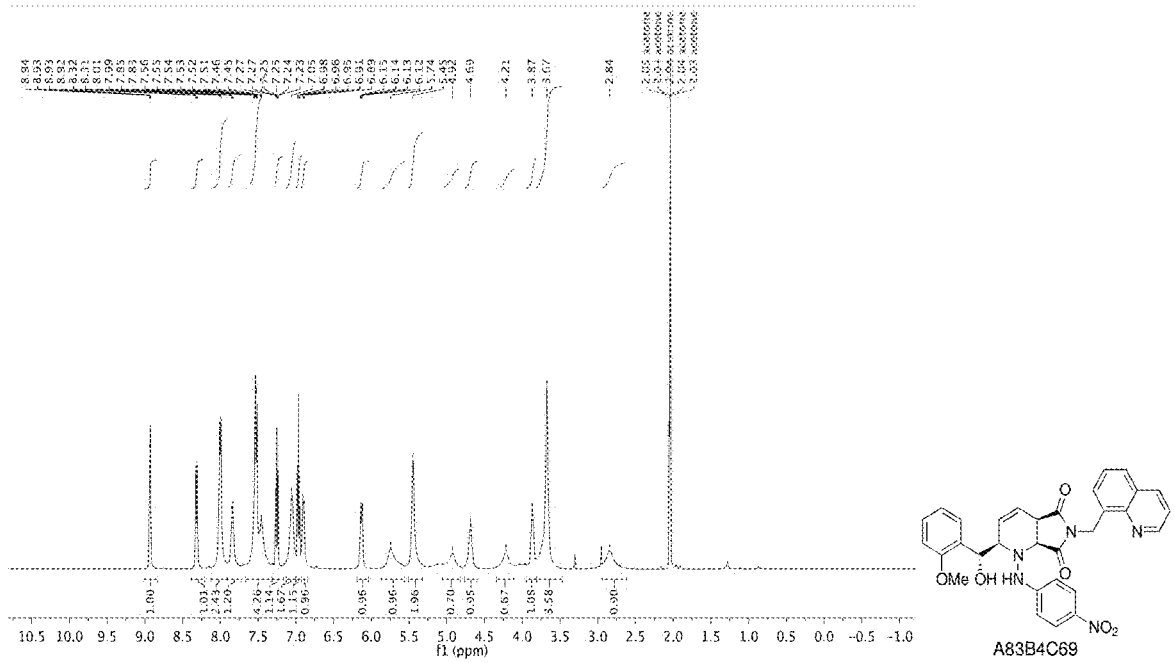
FIG. 11 depicts NMR spectra of compound A83B4C69 in acetone-d.
Figure 11:
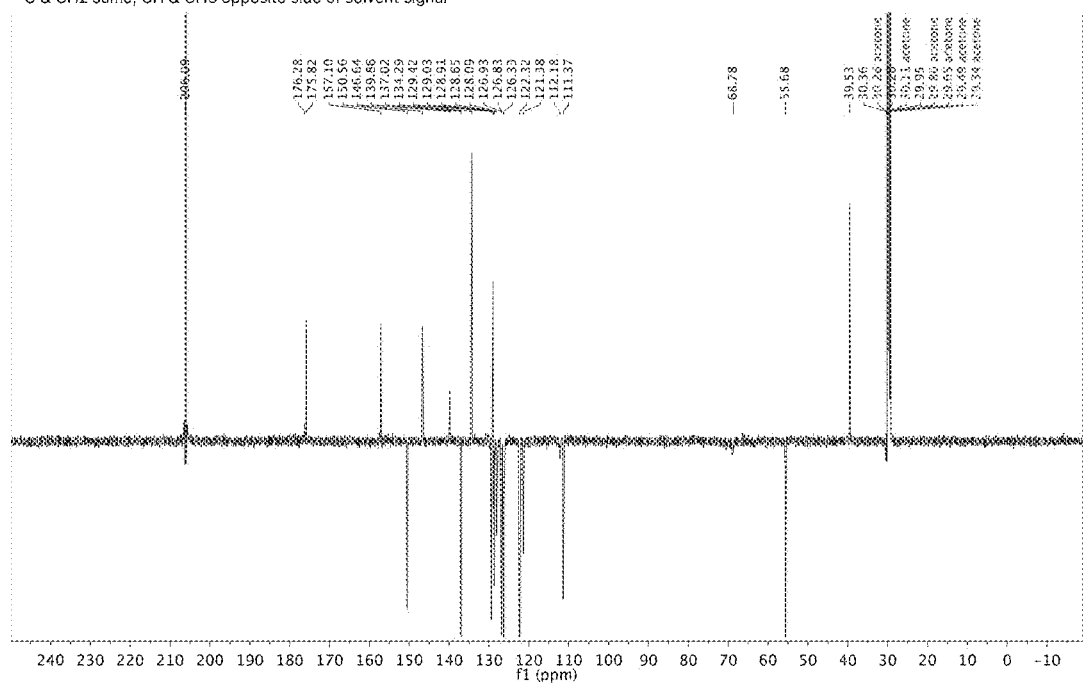

¹H NMR δ/ppm: (500 MHz, Acetone-$d_6$) 8.93 (dd, J=4.1, 1.8 Hz, 1H), 8.32 (d, J=8.0 Hz, 1H), 8.00 (d, J=9.0 Hz, 2H), 7.84 (d, J=7.8 Hz, 1H), 7.66-7.32 (comp m, 4H), 7.25 (app td, J=7.9, 1.8 Hz, 1H), 7.05 (bs, 2H), 6.96 (app t, J=7.5 Hz, 1H), 6.90 (d, J=8.3 Hz, 1H), 6.13 (dd, J=11.0, 4.2 Hz, 1H), 5.74 (bs, 1H), 5.45 (s, 2H), 4.92 (bs, 1H), 4.69 (s, 1H), 4.21 (bs, 1H), 3.87 (s, 1H), 3.67 (app s, 4H), 2.84 (s, 1H). See FIG. 11.

¹³C NMR δ/ppm: (126 MHz, Acetone-$d_6$, APT) 176.3, 175.8 (CO), 157.1 (C), 150.6 (CH), 146.6, 139.9 (C), 137.0 (CH), 134.3 (C), 129.4 (CH), 129.0 (C), 128.9, 128.6, 128.1, 126.9, 126.8, 126.3, 122.3, 121.4, 112.2, 111.4 (CH), 68.8 (CH), 55.7 (OCH$_3$), 39.5 (CH$_2$), 30.4, 30.2, 30.0 (CH).

IR (Microscope, cm⁻¹) 3514, 3300, 3046, 2937, 2837, 2254, 1781, 1708, 1598, 1500, 1326, 1112.

HRMS (ESI-TOF) for $C_{31}H_{28}N_5O_6$ (M+H)⁺: calcd.: 566.2034; found: 566.203.

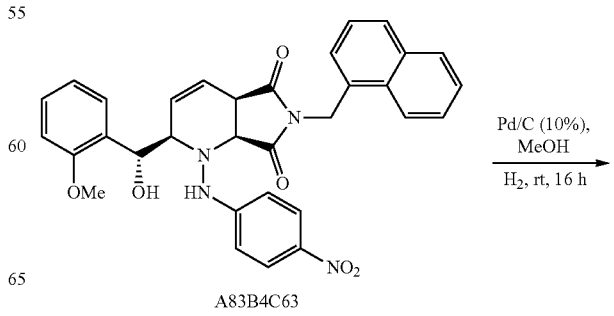

A83B4C63

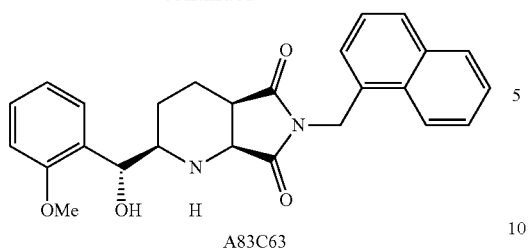

A83C63

A83C63:

Analog A83B4C63 (0.17 g, 0.32 mmol) was dissolved in methanol (10 ml) under nitrogen in a single-neck round bottom flask. Adapter with both vacuum and nitrogen inlet was placed on the flask. The reaction mixture was degassed for 30 min by bubbling nitrogen through the solution. Then, 10 wt % palladium on carbon (32 mg) was added to the reaction mixture. Finally, nitrogen was replaced with hydrogen filled balloon and the reaction mixture was stirred for 16 h at room temperature. The reaction mixture was filtered through celite and the filtrate was concentrated in vacuo. The crude was purified by flash chromatography (1:1, EtOAc:hexanes) to obtain A83C63 (72 mg, 52% yield).

Light brown solid, $R_f$=0.29 (1:1, EtOAc:hexanes).

Figure 12:
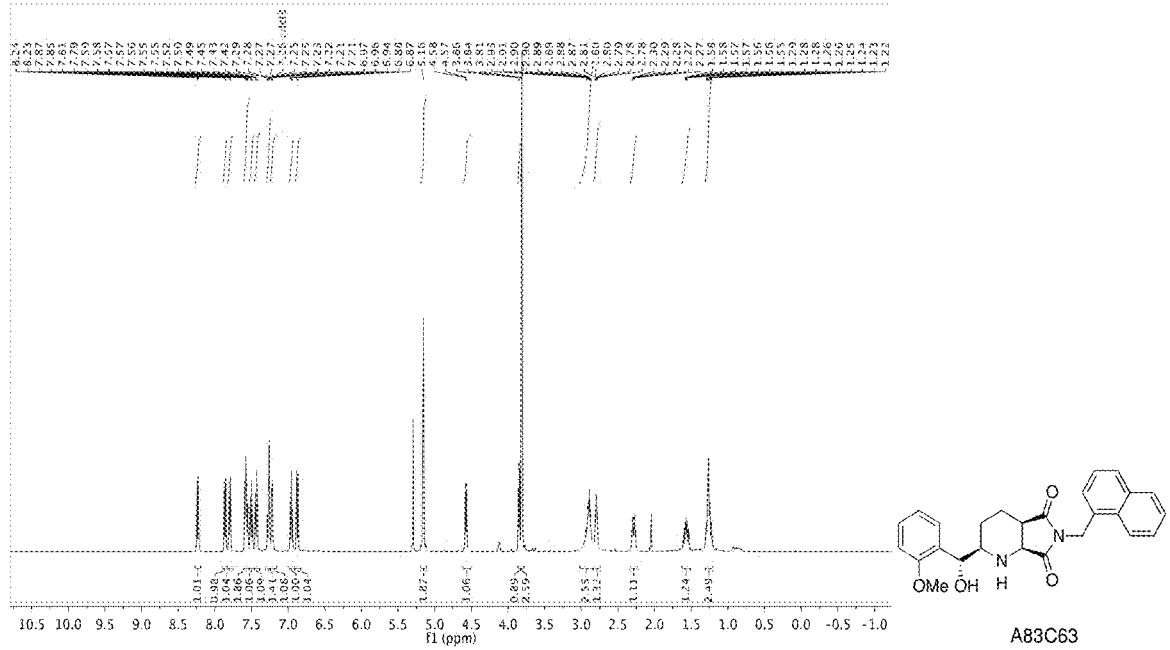
FIG. 12 depicts NMR spectra of compound A83C63.
Figure 12:
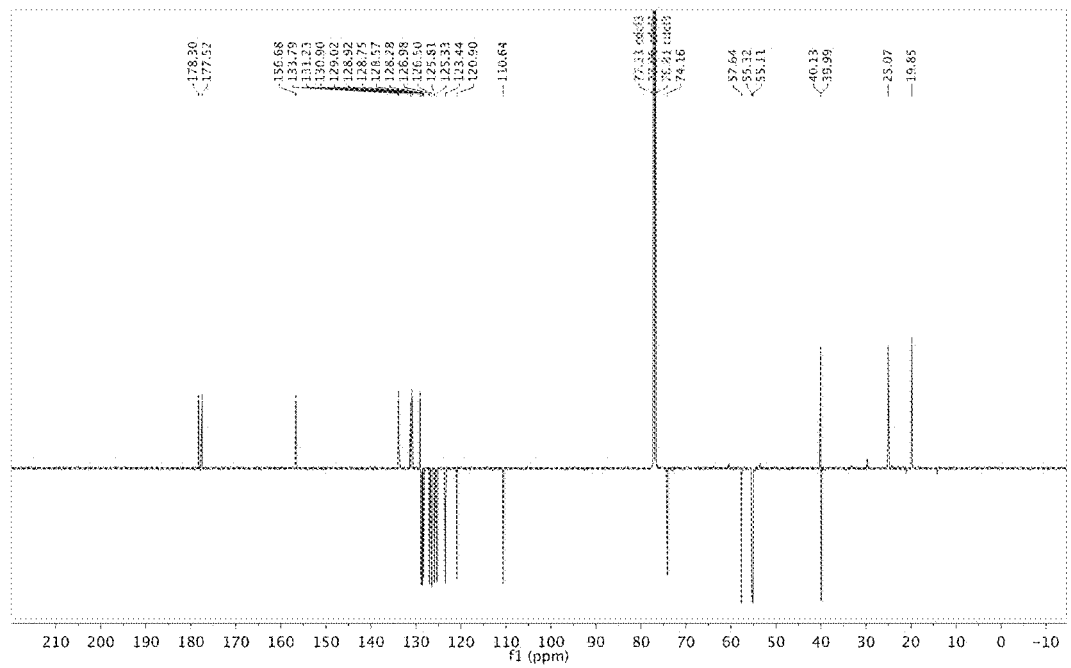

$^1$H NMR δ/ppm: (500 MHz, CDCl$_3$) 8.24 (d, J=8.5 Hz, 1H), 7.86 (d, J=8.1 Hz, 1H), 7.80 (d, J=8.2 Hz, 1H), 7.61-7.53 (comp m, 2H), 7.50 (app t, J=7.5 Hz, 1H), 7.43 (app t, J=7.7 Hz, 1H), 7.27 (app td, J=7.9, 1.7 Hz, 1H), 7.22 (dd, J=7.6, 1.7 Hz, 1H), 6.96 (app t, J=7.4 Hz, 1H), 6.88 (d, J=8.2 Hz, 1H), 5.16 (s, 2H), 4.57 (d, J=7.4 Hz, 1H), 3.85 (d, J=6.4 Hz, 1H), 3.81 (s, 3H), 3.02-2.84 (comp m, 3H), 2.79 (app td, J=6.7, 2.9 Hz, 1H), 2.33-2.24 (m, 1H), 1.63-1.51 (m, 1H), 1.33-1.19 (comp m, 2H). See FIG. 12.

$^{13}$C NMR δ/ppm: (126 MHz, CDCl$_3$, APT) 178.3, 177.5 (CO), 156.7, 133.8, 131.2, 130.9, 129.0 (C), 128.9, 128.8, 128.6, 128.3, 127.0, 126.5, 125.8, 125.3, 123.4, 120.9, 110.6 (CH), 74.2, 57.6, 55.3, 55.1, 40.1 (CH$_2$), 40.0 (CH), 25.1, 19.8 (CH$_2$).

IR (Microscope, cm$^{-1}$) 3474, 3339, 3051, 3006, 2925, 2855, 2838, 2250, 1781, 1709, 1600, 1492, 1399, 1243.

HRMS (ESI-TOF) for C$_{26}$H$_{27}$N$_2$O$_4$ (M+H)$^+$: calcd.: 431.1965; found: 431.1962; for C$_{26}$H$_{26}$N$_2$NaO$_4$ (M+Na)$^+$: calcd.: 453.1785; found: 453.1788.

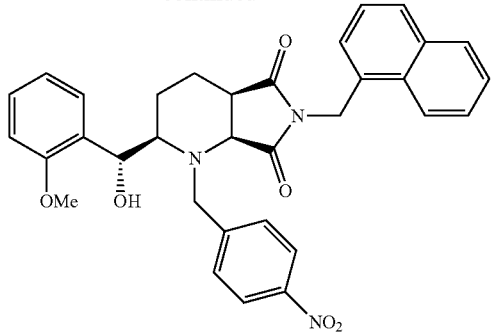

A83B37C63

A83B37C63:

To A83C63 (1.0 equiv, 26 mg, 0.060 mmol) in acetonitrile (2.0 ml), p-nitrobenzyl bromide (1.1 equiv, 14 mg, 0.066 mmol), K$_2$CO$_3$ (1.5 equiv, 15 mg, 0.090 mmol) and n-Bu$_4$NI (0.3 equiv, 6.6 mg, 0.018 mmol) were added at room temperature under nitrogen balloon. Then, the reaction mixture was stirred at reflux for 3 h. After the removal of the solvent in vacuo, the reaction mixture was directly purified by flash chromatography (1:1, EtOAc:hexanes) to obtain A83B37C63 (12.2 mg, 68% purity). The analog was further purified by semipreparative HPLC (6 mg, 18% yield, 99% purity).

Pale-white solid, $R_f$=0.53 (1:1, EtOAc:hexanes).

Figure 13:
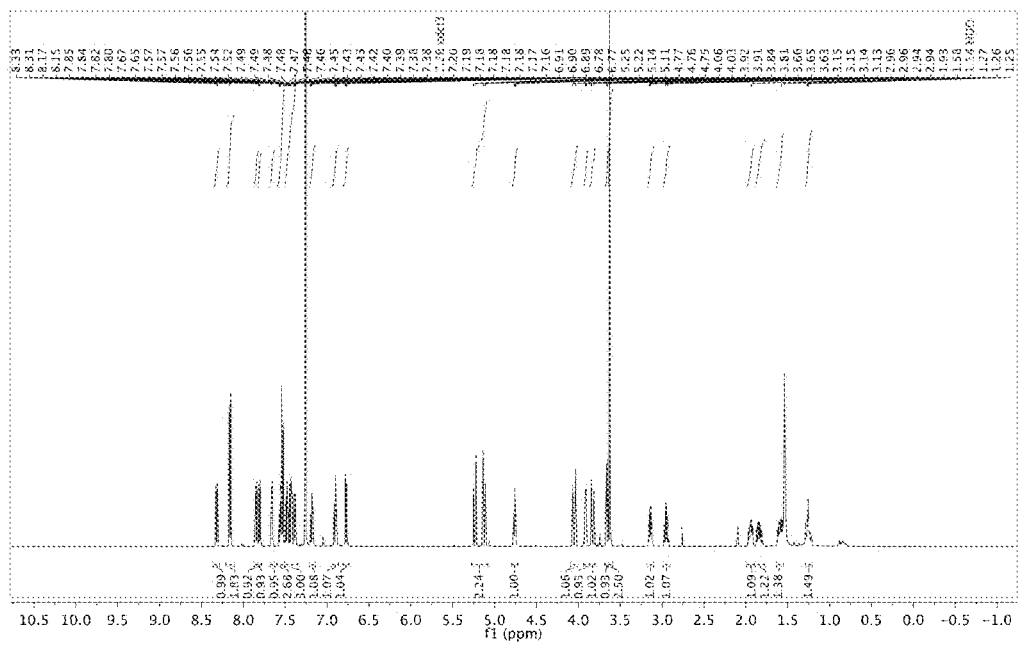
FIG. 13 depicts NMR spectra of compound A83B37C63.
Figure 13:
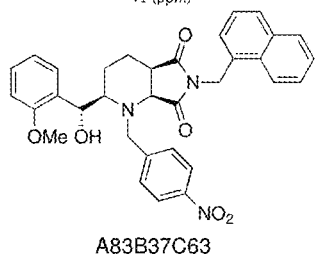

$^1$H NMR δ/ppm: (500 MHz, CDCl$_3$) 8.32 (d, J=8.5 Hz, 1H), 8.16 (d, J=8.7 Hz, 2H), 7.85 (d, J=7.9 Hz, 1H), 7.81 (d, J=8.2 Hz, 1H), 7.66 (d, J=6.7 Hz, 1H), 7.60-7.51 (comp m, 3H), 7.50-7.35 (comp m, 3H), 7.18 (ddd, J=8.3, 7.4, 1.7 Hz, 1H), 6.90 (app t, J=7.0 Hz, 1H), 6.77 (d, J=7.2 Hz, 1H), 5.28, 5.13 (ABq, J$_{AB}$=15.0, 2H), 4.76 (app t, J=6.2 Hz, 1H), 4.05 (d, J=15.1 Hz, 1H), 3.91 (d, J=6.5 Hz, 1H), 3.83 (d, J=15.0 Hz, 1H), 3.66 (d, J=8.4 Hz, 1H), 3.63 (s, 3H), 3.17-3.10 (m, 1H), 2.99-2.91 (m, 1H), 1.99-1.90 (m, 1H), 1.88-1.78 (m, 1H), 1.63-1.53 (m, 1H), 1.29-1.21 (m, 1H). See FIG. 13.

IR (Microscope, cm$^{-1}$) 3467, 3052, 2927, 2854, 2250, 1778, 1706, 1600, 1520, 1345.

HRMS (ESI-TOF) for C$_{33}$H$_{32}$N$_3$O$_6$(M+H)$^+$: calcd.: 566.2286; found: 566.2273; for C$_{33}$H$_{31}$N$_3$NaO$_6$ (M+Na)$^+$: calcd.: 588.2105; found: 588.2104.

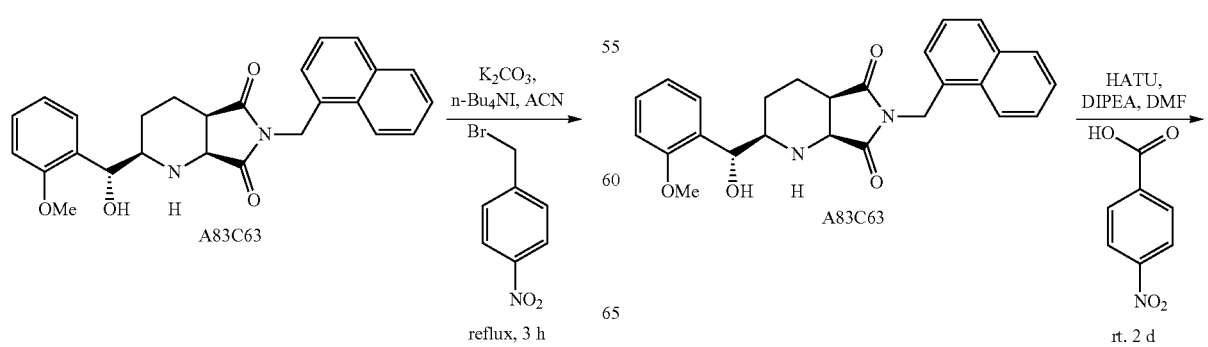

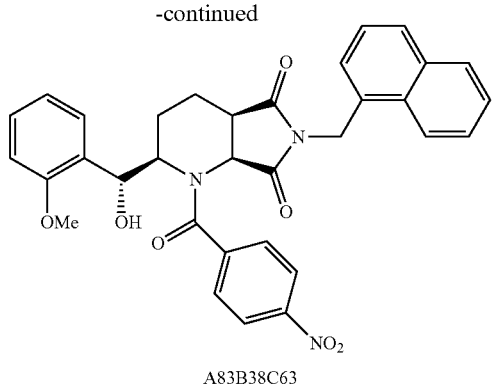

A83B38C63

A83B38C63:

p-Nitrobenzoic acid (1.0 equiv, 13 mg, 0.080 mmol) and HATU coupling reagent (1.0 equiv, 30 mg, 0.080 mmol) were dissolved in dry DMF (0.5 ml) at room temperature under argon balloon. Then, the solution of compound A83C63 (1.0 equiv, 34 mg, 0.08 mmol) in dry DMF (0.5 ml) and DIPEA (3.2 equiv, 45 µl, 0.26 mmol) were added. The reaction mixture was then stirred for 2 d at room temperature, concentrated in vacuo. The crude residue was purified by semipreparative HPLC (2.7 mg, 6% yield).

Light yellow-white solid.

Figure 14:
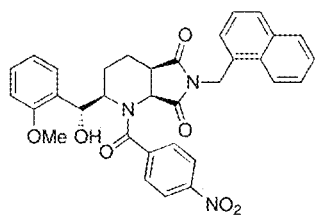
FIG. 14 depicts NMR spectra of compound A83B38C63.
Figure 14:
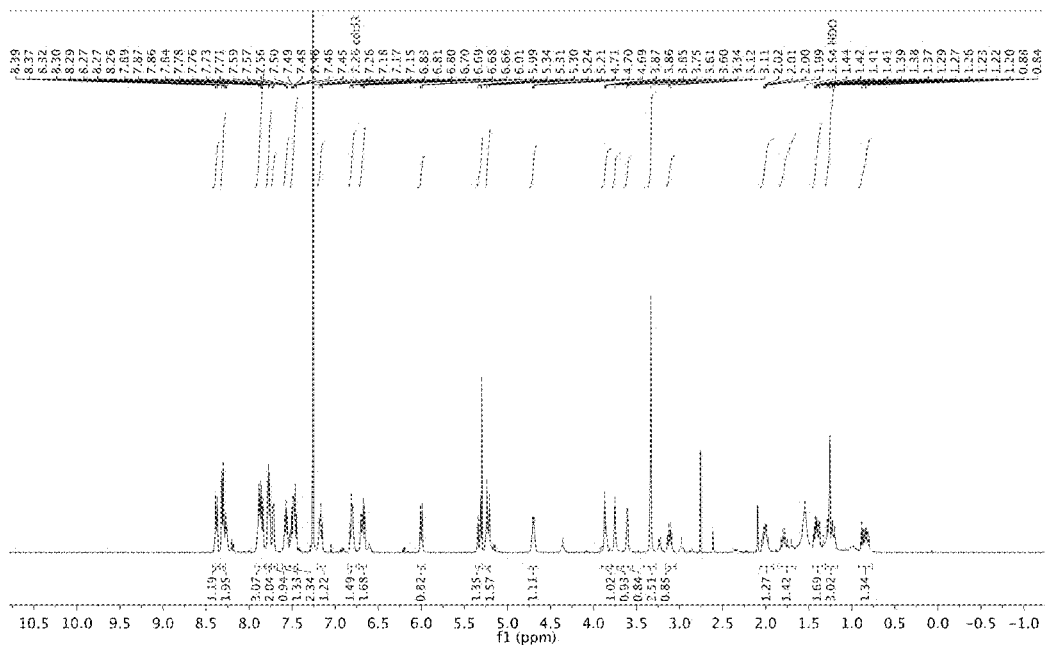

$^1$H NMR δ/ppm: Please see the spectra below. It is hard to assign peaks because this analog appeared to contain two related compounds. See FIG. 14.

IR (Microscope, cm$^-$) 3476, 3106, 3050, 2925, 2854, 1782, 1710, 1645, 1601, 1524, 1398, 1348.

HRMS (ESI-TOF) for $C_{33}H_{29}N_3NaO_7$ (M+Na)$^+$: calcd.: 602.1898; found: 602.1902.

Example 1 References

1. Madhusudan S, Middleton M R. The emerging role of DNA repair proteins as predictive, prognostic and therapeutic targets in cancer. Cancer Treat Rev 2005; 31: 603-17.
2. O'Connor M J, Martin N M, Smith G C. Targeted cancer therapies based on the inhibition of DNA strand break repair. Oncogene 2007; 26: 7816-24.
3. Drew Y, Calvert H. The potential of PARP inhibitors in genetic breast and ovarian cancers. Ann N Y Acad Sci 2008; 1138: 136-45.
4. Madhusudan S, Smart F, Shrimpton P, et al. Isolation of a small molecule inhibitor of DNA base excision repair. Nucleic Acids Res 2005; 33: 4711-24.
5. Marchand C, Lea W A, Jadhav A, et al. Identification of phosphotyrosine mimetic inhibitors of human tyrosyl-DNA phosphodiesterase I by a novel AlphaScreen high-throughput assay. Mol Cancer Ther 2009; 8: 240-8.
6. Hickson I, Zhao Y, Richardson C J, et al. Identification and characterization of a novel and specific inhibitor of the ataxia-telangiectasia mutated kinase ATM. Cancer Res 2004; 64: 9152-9.
7. Zhao Y, Thomas H D, Batey M A, et al. Preclinical evaluation of a potent novel DNA-dependent protein kinase inhibitor NU7441. Cancer Res 2006; 66: 5354-62.
8. Plummer R, Jones C, Middleton M, et al. Phase I study of the poly(ADP-ribose) polymerase inhibitor, AG014699, in combination with temozolomide in patients with advanced solid tumors. Clin Cancer Res 2008; 14: 7917-23.
9. Henner W D, Rodriguez L O, Hecht S M, Haseltine W A. gamma Ray induced deoxyribonucleic acid strand breaks. 3' Glycolate termini. J Biol Chem 1983; 258: 711-3.
10. Lennartz M, Coquerelle T, Bopp A, Hagen U. Oxygen-effect on strand breaks and specific end-groups in DNA of irradiated thymocytes. Int J Radiat Biol Relat Stud Phys Chem Med 1975; 27: 577-87.
11. Friedberg E C, Walker G C, Siede W, Wood R D, Schultz R A, Ellenberger T. DNA Repair and Mutagenesis. 2nd ed. Washington, D.C.: ASM Press; 2006.
12. Krokan H E, Nilsen H, Skorpen F, Otterlei M, Slupphaug G. Base excision repair of DNA in mammalian cells. FEBS Lett 2000; 476: 73-7.
13. Jilani A, Ramotar D, Slack C, et al. Molecular cloning of the human gene, PNKP, encoding a polynucleotide kinase 3'-phosphatase and evidence for its role in repair of DNA strand breaks caused by oxidative damage. J Biol Chem 1999; 274: 24176-86.
14. Karimi-Busheri F, Daly G, Robins P, et al. Molecular characterization of a human DNA kinase. J Biol Chem 1999; 274: 24187-94.
15. Whitehouse C J, Taylor R M, Thistlethwaite A, et al. XRCC1 stimulates human polynucleotide kinase activity at damaged DNA termini and accelerates DNA single-strand break repair. Cell 2001; 104: 107-17.
16. Loizou J I, EI-Khamisy S F, Zlatanou A, et al. The protein kinase CK2 facilitates repair of chromosomal DNA single-strand breaks. Cell 2004; 117: 17-28.
17. Mani R S, Fanta M, Karimi-Busheri F, et al. XRCC1 stimulates polynucleotide kinase by enhancing its damage discrimination and displacement from DNA repair intermediates. J Biol Chem 2007; 282: 28004-13.
18. Chappell C, Hanakahi L A, Karimi-Busheri F, Weinfeld M, West S C. Involvement of human polynucleotide kinase in double-strand break repair by non-homologous end joining. Embo J 2002; 21: 2827-32.
19. Koch C A, Agyei R, Galicia S, et al. Xrcc4 physically links DNA end processing by polynucleotide kinase to DNA ligation by DNA ligase IV. Embo J 2004; 23: 3874-85.
20. Karimi-Busheri F, Rasouli-Nia A, Allalunis-Turner J, Weinfeld M. Human polynucleotide kinase participates in repair of DNA double-strand breaks by nonhomologous end joining but not homologous recombination. Cancer Res 2007; 67: 6619-25.
21. Wiederhold L, Leppard J B, Kedar P, et al. AP endonuclease-independent DNA base excision repair in human cells. Mol Cell 2004; 15: 209-20.
22. Das A, Wiederhold L, Leppard J B, et al. NEIL2-initiated, APE-independent repair of oxidized bases in DNA: Evidence for a repair complex in human cells. DNA Repair (Amst) 2006; 5: 1439-48.
23. Plo I, Liao Z Y, Barcelo J M, et al. Association of XRCC1 and tyrosyl DNA phosphodiesterase (Tdp1) for the repair of topoisomerase I-mediated DNA lesions. DNA Repair (Amst) 2003; 2: 1087-100.
24. Rasouli-Nia A, Karimi-Busheri F, Weinfeld M. Stable down-regulation of human polynucleotide kinase enhances spontaneous mutation frequency and sensitizes cells to genotoxic agents. Proc Natl Acad Sci USA 2004; 101: 6905-10.
25. Bernstein N K, Williams R S, Rakovszky M L, et al. The molecular architecture of the mammalian DNA repair enzyme, polynucleotide kinase. Mol Cell 2005; 17: 657-70.
26. Dobson C J, Allinson S L. The phosphatase activity of mammalian polynucleotide kinase takes precedence over its kinase activity in repair of single strand breaks. Nucleic Acids Res 2006; 34: 2230-7.
27. Freschauf, G. K., Mani, R. S., Mereniuk, T. R., Fanta, M., Virgen, C. A., Dianov, G. L., Grassot, J. M., Hall, D. G., and Weinfeld, M. Mechanism of action of an imido-piperidine inhibitor of human polynucleotide kinase/phosphatase. J. Biol. Chem. 285: 2351-2360 (2010).
28. Song, C., Zhang, C., and Zhao, M. P. Development of a high-throughput screening platform for DNA 3'-phosphatases and their inhibitors based on a universal molecular beacon and quantitative real-time PCR. Chem Asian J. 5: 1146-1151 (2010).

Example 2

We previously identified compound A12B4C3 as an inhibitor of the PNKP 3'-phosphatase activity from a library of polysubstituted imidopiperidines (8, 9). Further modification of this scaffold structure has led to the synthesis of two more potent inhibitors of PNKP, A12B4C50 and A83B4C63 (Table 1). However, since these inhibitors have low water solubility, we investigated the use of polymeric micelles as solubilizers for these compounds. Micelles provide the additional benefits of protecting their constituents from metabolism by serum factors until they are delivered to cells and have the potential to enhance targeting of the encapsulated compound to cancer cells rather than normal tissues (10-12).

TABLE 1

Characteristics of the polymeric micelles under study.

| Compound | Structure | Formulation | Size ± SD (nm) | *PDI ± SD | $^a$EE % | $^b$DL % |
|---|---|---|---|---|---|---|
| A83B4C63 | 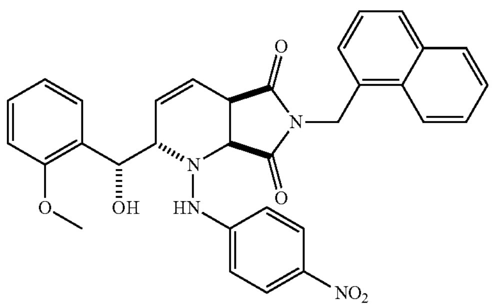 | PEO-b-PCL-A83B4C63 | 62 ± 3.4 | 0.37 ± 0.007 | 93.8 ± 0.051 | 4.9 |
| | | PEO-b-PBCL-A83B4C63 | 99.9 ± 0.8 | 0.23 ± 0.015 | 96.2 | 9.1 |
| | | GE11-PEO-b-PBCL-A83B4C63 | 47.5 ± 0.3 | 0.26 ± 0.00 | 95.6 | 10.1 |
| A12B4C50 | 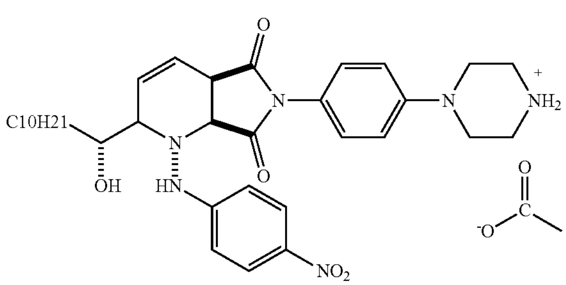 | PEO-b-PCL-A12B4C50 | 71.3 ± 0.1 | 0.18 ± 0.00 | 100 | 5 |
| | | PEO-b-PCCL-A12B4C50 | 33.8 ± 0.3 | 0.25 ± 0.000 | 92 ± 16.0 | 5 |
| | | GE11-PEO-b-PCCL-A12B4C50 | 58.8 ± 0.4 | 0.29 ± 0.00 | 75 | 7.7 |
| DiI | | PEO-b-PECL-DiI | 70.7 ± 0.9 | 0.23 ± 0.01 | 100 | 1 |
| | | GE11-PEO-b-PBCL-DiI | 62.7 ± 0.6 | 0.19 ± 0.000 | 78.8 | 1 |

*PDL polydispersity Index $^a$Encapsulation Efficiency($EE$ %) = $\frac{\text{the amount of encapsulated inhibitor}}{\text{the initial amount of inhibitor added}} \times 100$ $^b$Drug Loading($DL$ %) = $\frac{\text{the amount of encapsulated inhibitor}}{\text{the total amount of polymer}} \times 100$ Polymeric micelles are self-assembled amphiphilic block copolymers that are used for encapsulation of poorly soluble drugs, sustained-release and targeted drug delivery (13-17). The advantage of these delivery systems arises from their unique chemical composition, which is characterized by a hydrophilic block that is chemically attached to a hydrophobic block. In aqueous solution, polymeric micelles form core/shell structures at or above the critical micelle concentration (15, 18). Upon micellization, the hydrophobic core can serve as a reservoir for hydrophobic compounds, which are loaded by physical or chemical means depending on the specific functionalities or chemical compatibility of the core-forming block and the encapsulated compound (Scheme 1).

Schemes:

Scheme 1. Synthesis of polysubstituted imidopiperidine compounds.

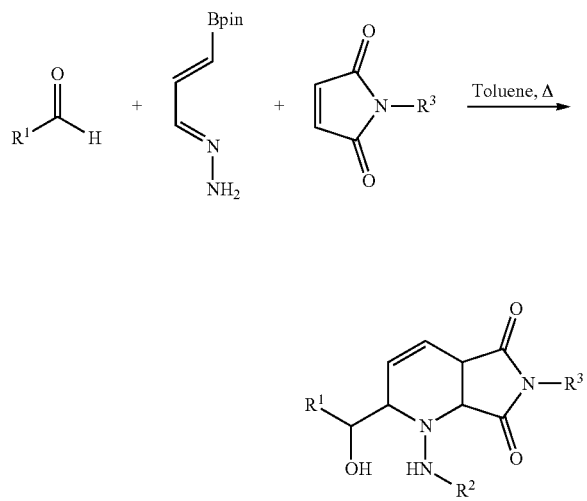

Refer to Table 1 for the illusteration of groups $R^1$, $R^2$ and $R^3$.

Furthermore, the size of the micelles is a critical feature of the formulation, since the range for optimal tumor accumulation is perceived to be 20-100 nm (19, 20). A series of micelle-forming block copolymers based on methoxy poly(ethylene oxide)-b-poly(ε-caprolactone) (PEO-b-PCL), methoxy poly(ethylene oxide)-b-poly(α-benzyl carboxylate-ε-caprolactone) (PEO-b-PBCL), and methoxy poly(ethylene oxide)-b-poly(α-carboxylate-ε-caprolactone) (PEO-b-PCCL) were used, to provide a range of different core structures for efficient accommodation of hit molecules under study in the micellar system (15, 21).

Polymeric micelles passively deliver drugs to tumor tissues utilizing the enhanced permeability and retention (EPR) effect. To further enhance the selective targeting ability of polymeric micelles, targeting ligands can be attached to the surface of the micelles. Typically, ligands such as antibodies, peptides, small molecules and aptamers are used to target surface receptors that are overexpressed on cancer cells and absent or minimally expressed on healthy cells (22, 23). Epidermal growth factor receptor (EGFR) overexpression is frequently found in tumors such as colorectal, breast and lung cancer (24-26). It is a cellular transmembrane receptor with tyrosine kinase enzymatic activity that plays a key role in cell proliferation, survival and differentiation. A dodecapeptide, (YHWYGYTPQNVI; SEQ ID NO: 3), identified by phage display screening and designated as GE11, has been found to be a selective and efficient EGFR allosteric ligand (27-29). GE11 binds specifically to EGFR with a dissociation constant of $\approx$ 22 nM, and with much lower mitogenic activity than EGF itself (30).

Another strategy to selectively target tumors is the application of synthetic lethality. Synthetic lethality is defined as a condition where the simultaneous disruption of two genes or their cognate proteins, but not either gene/protein alone, leads to cell death (31, 32). Phosphatase and tensin homolog (PTEN), which is one of the most frequently disrupted tumor suppressors in cancer, has been studied extensively as a synthetic lethal partner for several proteins including PNKP (33-36).

Here we describe the encapsulation and characterization of A12B4C50 and A83B4C63 inside micelles composed of PEO-b-PCCL and PEO-b-PBCL, respectively. We examined the ability of the encapsulated inhibitors to radiosensitize and chemosensitize cancer cells in vitro. GE11 peptide was used to construct an active targeting peptide-micelle conjugate toward EGFR-overexpressing colorectal cancer cells. We monitored the intracellular delivery of dye-encapsulated GE11-polymeric micelles in tumor cells with different EGFR expression levels, and the enhanced sensitization of EGFR-overexpressing cells by PNKP inhibitors encapsulated in GE11-polymeric micelles. Finally, we also tested the capacity of encapsulated PNKP inhibitors to engender a synthetic lethal response in PTEN-deficient cells.

In one aspect, there is provided a compound of formula (I), wherein formula (I) has the structure,

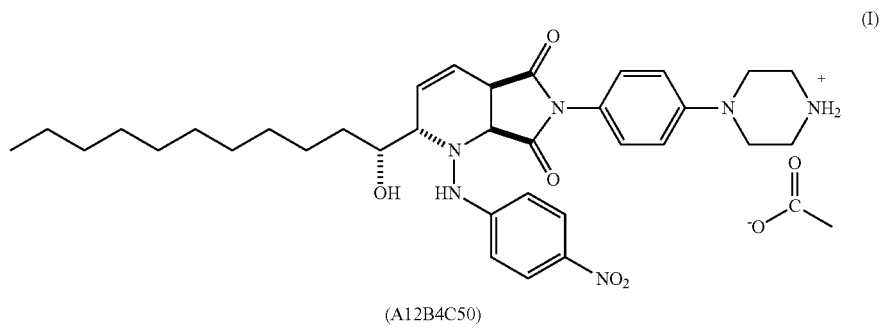

(A12B4C50)

or enantiomers, prodrugs, derivatives, and pharmaceutically acceptable salts thereof.

In one aspect, there is provided a compound of formula (II), wherein formula (II) has the structure,

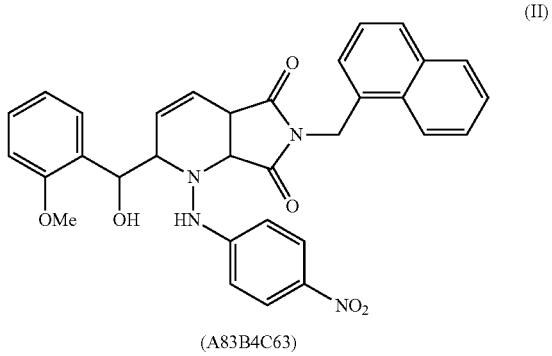 [SMILES: COc1ccccc1C(O)C1C=CC2C(=O)N(Cc3cccc4ccccc34)C(=O)C2N1Nc1ccc([N+](=O)[O-])cc1]

(A83B4C63)

or enantiomers, prodrugs, derivatives, and pharmaceutically acceptable salts thereof.

The compounds described herein may be capable of forming a variety of different salts with various inorganic and organic acids. Such salts are pharmaceutically acceptable for administration to a subject.

The aim of this study is to develop nano-delivery systems for the encapsulation of novel imidopiperidine-based inhibitors of 3'-phosphatase activity of polynucleotide phosphatase/kinase (PNKP) and to establish the validity of GE11 as a suitable ligand for targeted delivery of encapsulated drugs to colorectal cancer cells overexpressing epidermal growth factor receptor (EGFR). For this purpose, newly identified hit compounds with potent PNKP inhibitory activity, i.e., A12B4C50 and A83B4C63, were encapsulated in polymeric micelles of different poly(ethylene oxide)-b-poly (ε-caprolactone) (PEO-b-PCL)-based structures having various pendent groups on the PCL block. The level of encapsulated compounds were measured by High-performance liquid chromatography (HPLC) and the cumulative in vitro release was investigated using dialysis of the released drug followed by HPLC assay. Targeted delivery to EGFR-expressing cells following conjugation of GE11 peptide to the polymeric micelles was investigated by cellular uptake of DiI dye. The non-specific toxicity of the PNKP inhibitors towards HCT116 human colorectal cancer cells was assessed by MTS assay. At non-toxic levels, both free and encapsulated inhibitors were tested for their capacity to sensitize HCT116 cells to radiation and irinotecan by colony forming assay. Free and encapsulated inhibitors were also tested for their ability to cause synthetic lethality in PTEN-deficient HCT116 cells. Our results showed, among different block copolymers, efficient loading of A12B4C50 and A83B4C63 was achieved in PEO-b-PCLs with pendent carboxyl and benzyl carboxylate groups, respectively. The cumulative release of A12B4C50 and A83B4C63 from their respective optimum micellar formulations within 24 h was 54 and 48%, respectively. A positive correlation between the level of EGFR expression by three different colorectal cancer cell lines, i.e. HCT116, HT29 and SW620 cells, and the uptake of encapsulated DiI in GE11 modified polymeric micelles was observed. The encapsulated inhibitors were able to sensitize HCT116 cell to radiation and irinotecan at a level of 4 μM for A12B4C50 and 6 μM for A83B4C63. The encapsulated PNKP inhibitors were found to be capable of inducing synthetic lethality in HCT116 PTEN-deficient cells at a level of 4 μM for both A12B4C50 and A83B4C63. Modification of nano-carriers with GE11 enhanced did not affect the cytotoxic activity of encapsulated inhibitors of PNKP in HC116 colorectal cancer cells that overexpress EGFR as monotherapy or in combination with radiation or irinotecan. Our results show the potential of nano-encapsulated inhibitors of PNKP as either mono or combined therapeutic agents for colorectal cancer.

Materials and Methods

Materials

Methoxy-polyethylene oxide (PEO) (average molecular weight of 5000 g/mol), and palladium on charcoal were purchased from Sigma (St. Louis, Mo.). ε-Caprolactone was purchased from Lancaster Synthesis (Lancashire, UK). α-Benzyl carboxylate-ε-caprolactone monomer was synthesized by Alberta Research Chemicals Inc. (Edmonton, AB). Stannous octoate was purchased from MP Biomedicals Inc. (Tuttlingen, Germany). GE11 peptide was kindly provided by Dr. Rania Soudy (Faculty of Pharmacy and Pharmaceutical Sciences, University of Alberta). Fluorescent probes, 1,1'-Dioctadecyl-3,3,3',3'-tetramethylindocarbocyanine perchlorate (DiI) and Hoechst 33342, were purchased from Molecular Probes (Waltham, Mass., USA). Antibodies used included monoclonal antibodies against PNKP (37), anti-EGFR antibodies [EP38Y] (cat. #ab52894 and ab193244, Abcam Inc., Toronto, CA), lamin B (cat. #sc-6127, Santa Cruz Biotechnology, Santa Cruz, Calif.) and actin (cat. #sc-1616, Santa Cruz Biotechnology, Santa Cruz, Calif.).

Cell Lines

HCT116, HT29 and SW620 cells were purchased from the American Type Culture Collection (ATCC). HCT116 PNKP knock-out cells were prepared by CRISPR technology by Dr. Yaping Yu (Molecular Biology Services, University of Calgary). The identity of HCT116 cells, both in their original and modified forms, was confirmed by ATCC. (The correct identity of HCT116 cells was last confirmed by STR testing on Mar. 13, 2017). The HCT116 PTEN knock-out variants were generously provided by Dr. Todd Waldman (Georgetown University, Washington D.C.). The presence or absence of PNKP, PTEN and EGFR expression was confirmed by western blot. Cell lines were cultured at 37° C. in 5% $CO_2$ in a humidified incubator in a 1:1 mixture of Dulbecco's modified Eagle medium and F12 (DMEM/F12) supplemented with 10% FBS, 50 U/mL penicillin, 50 mg/mL streptomycin, 2 mmol/L L-glutamine, 0.1 mmol/L nonessential amino acids, and 1 mmol/L sodium pyruvate. All culture supplements were purchased from Invitrogen (Burlington, ON, CA).

Synthesis of Polysubstituted Imidopiperidine Compounds

Figure 24A:
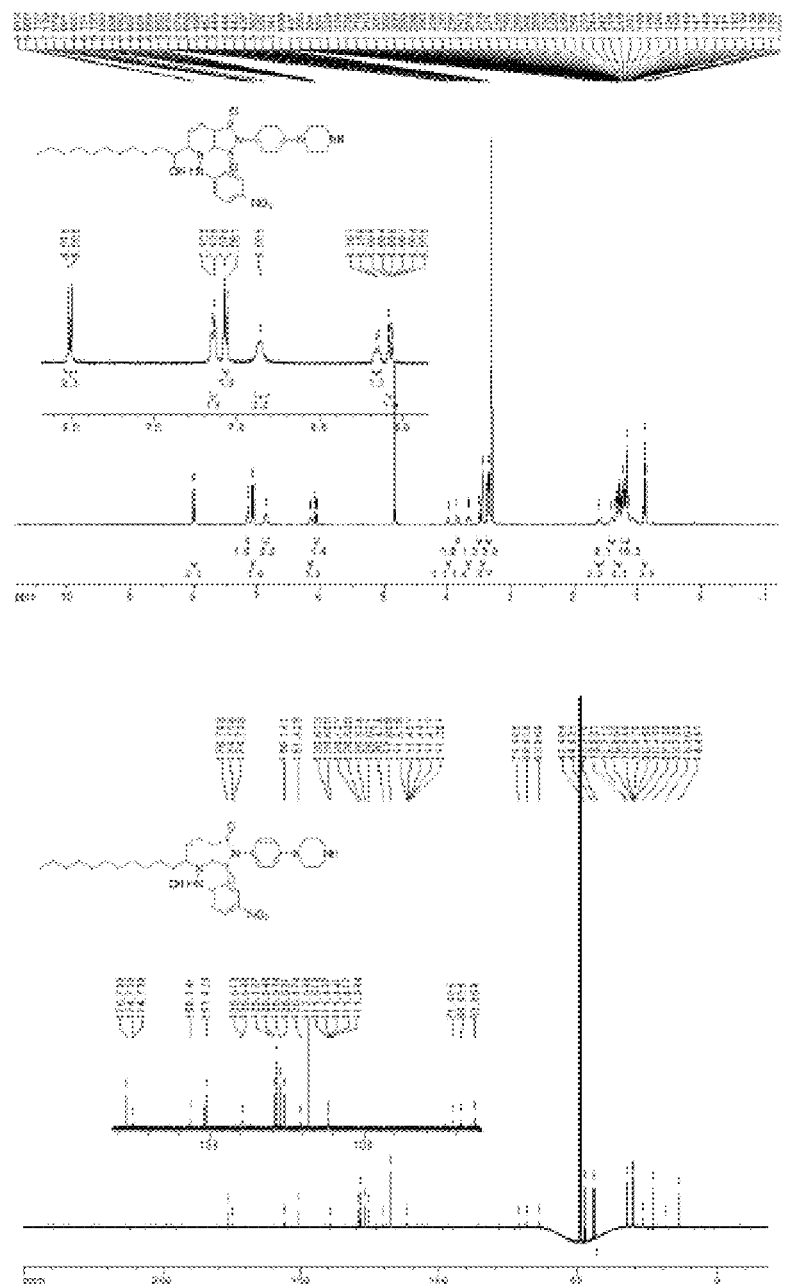
FIG. 24. NMR Spectra of A12B4C50. Top: $^1$H NMR (CD3OD, 500 Mhz). Bottom: $^{13}$C NMR (CD3OD, 125 MHz).
Figure 24B:
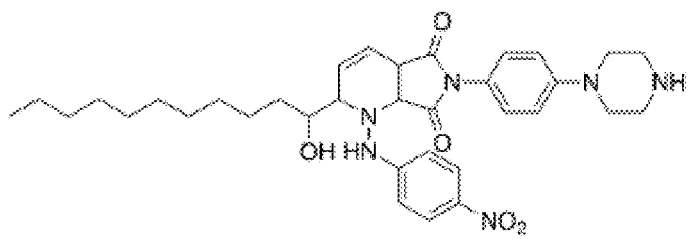
Figure 25A:
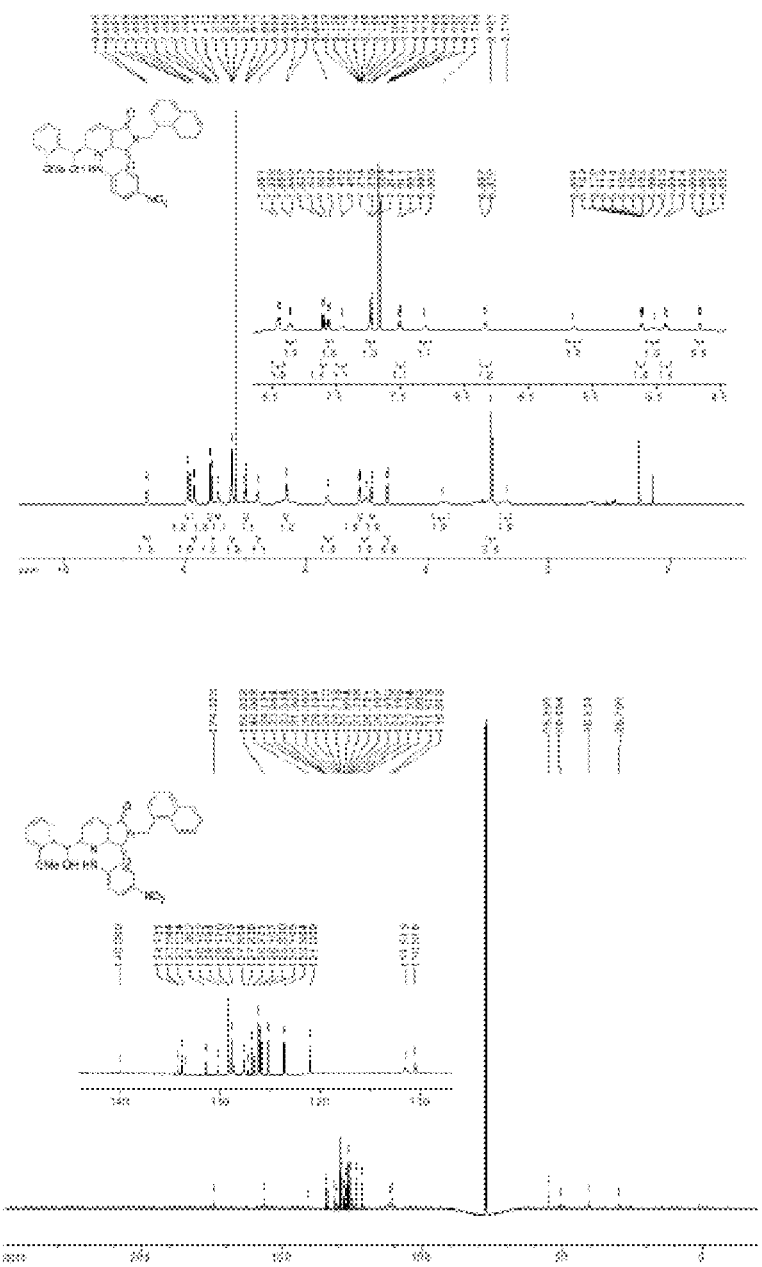
FIG. 25. NMR Spectra of A83B4C63. Top: $^1$H NMR (C6D6, 700 Mhz). Bottom: $^{13}$C NMR (CDCl$_3$, 125 MHz).
Figure 25B:
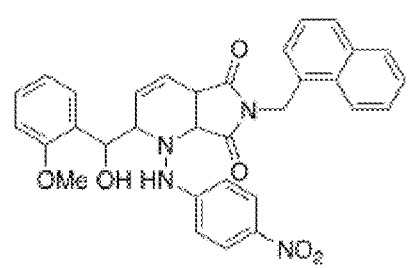
Figure 26:
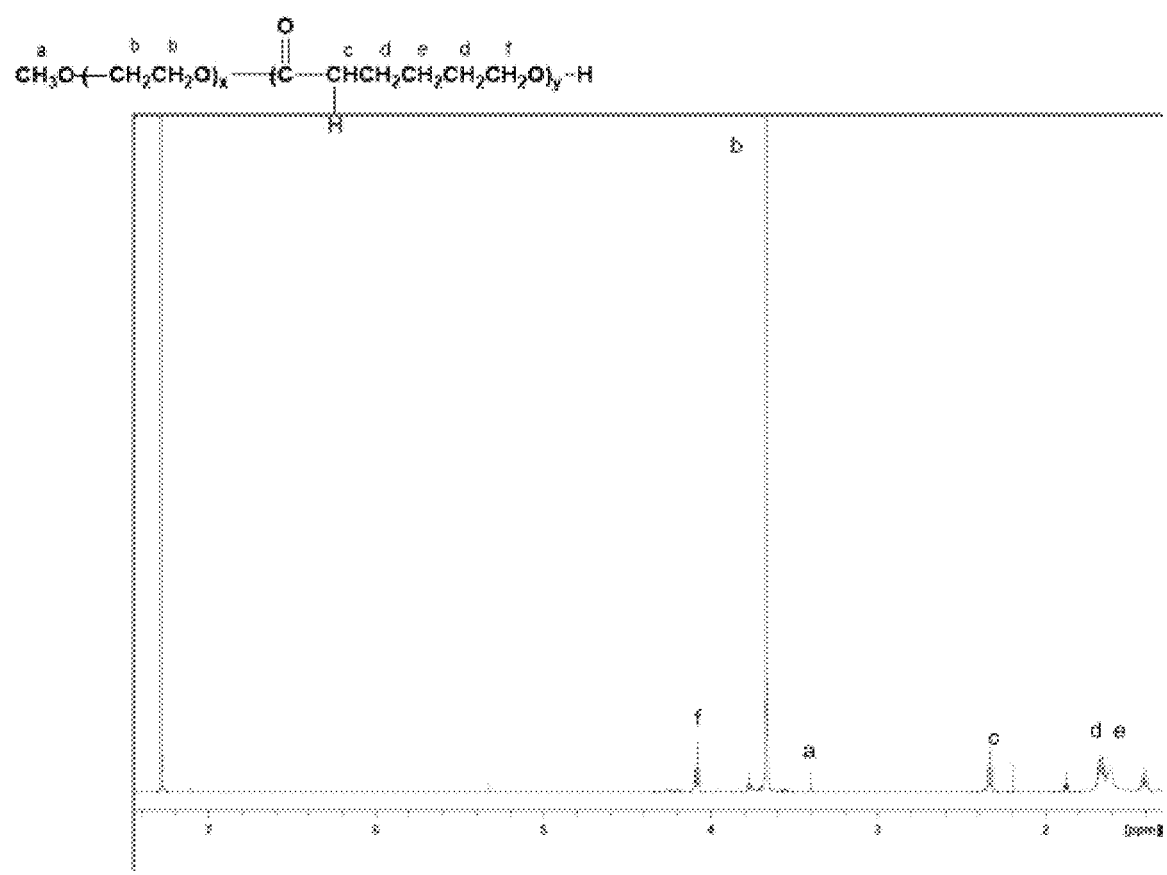
FIG. 26. $^1$H NMR spectrum of PEO-b-PCL block copolymer in CDCl$_3$ and peak assignments.
Figure 27:
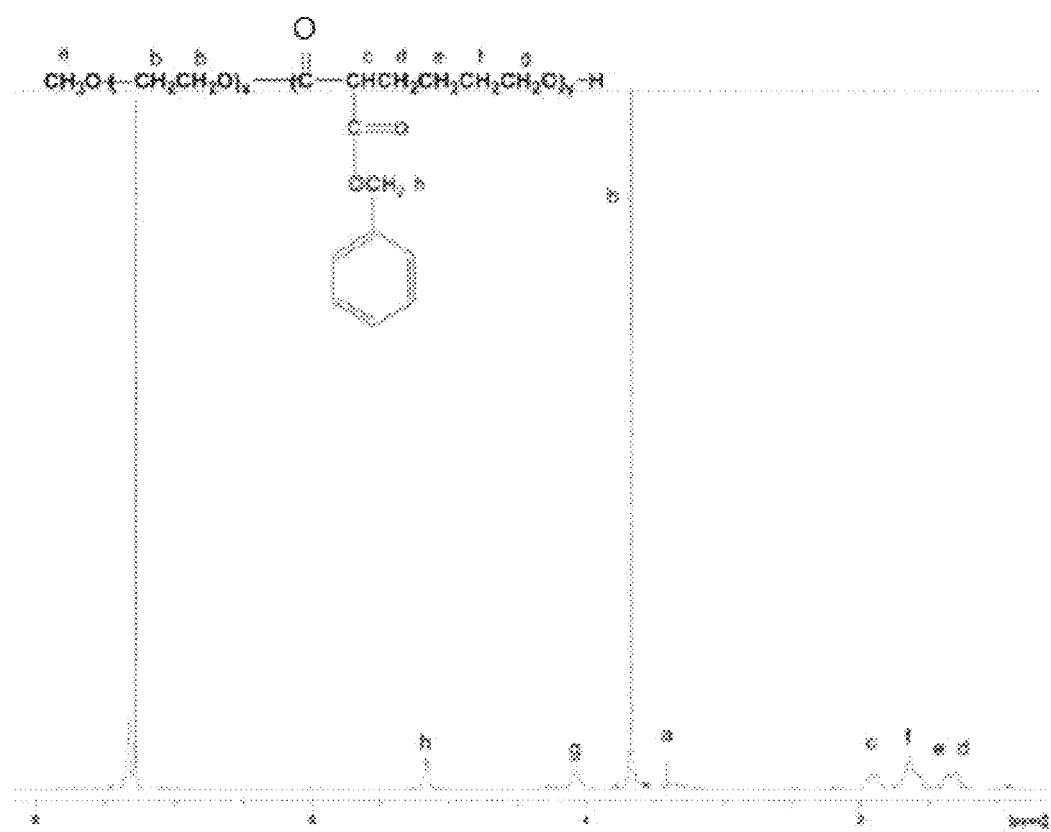
FIG. 27. $^1$H NMR spectrum of PEO-b-PBCL block copolymer in CDCl$_3$ and peak assignments.
Figure 28:
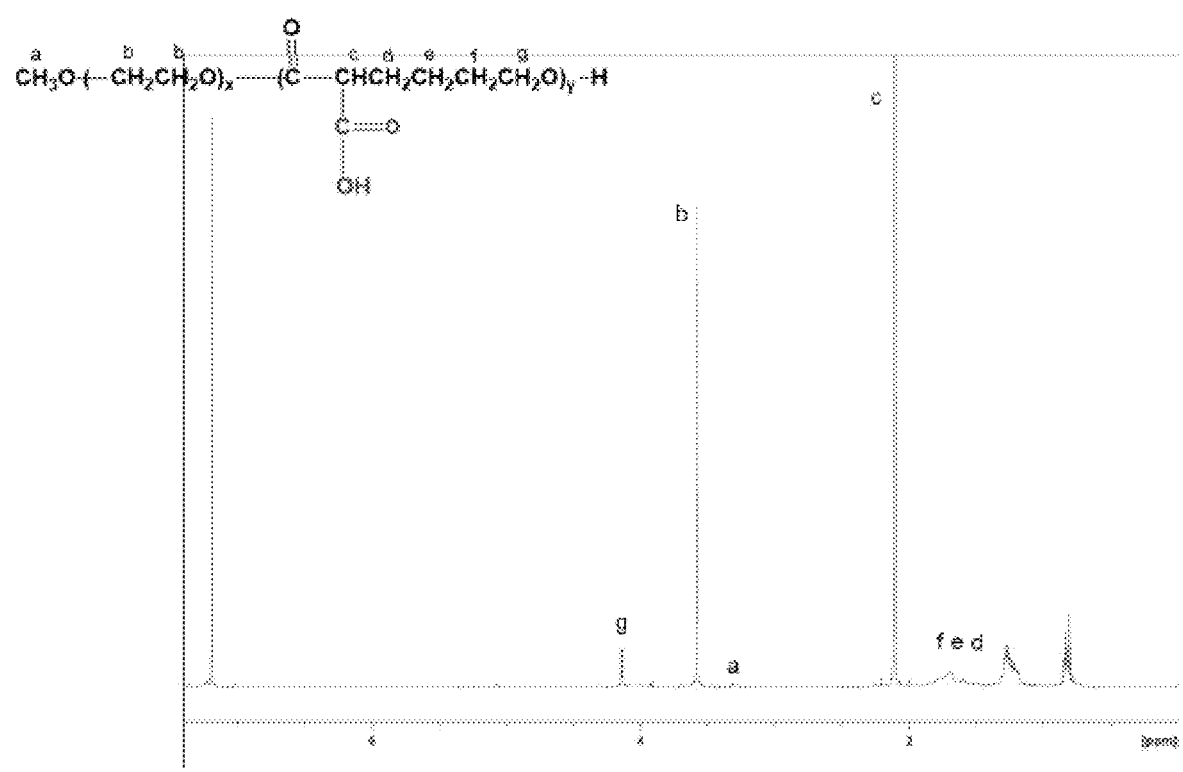
FIG. 28. $^1$H NMR spectrum of PEO-b-PCCL block copolymer in CDCl$_3$ and peak assignments.
Figure 29:
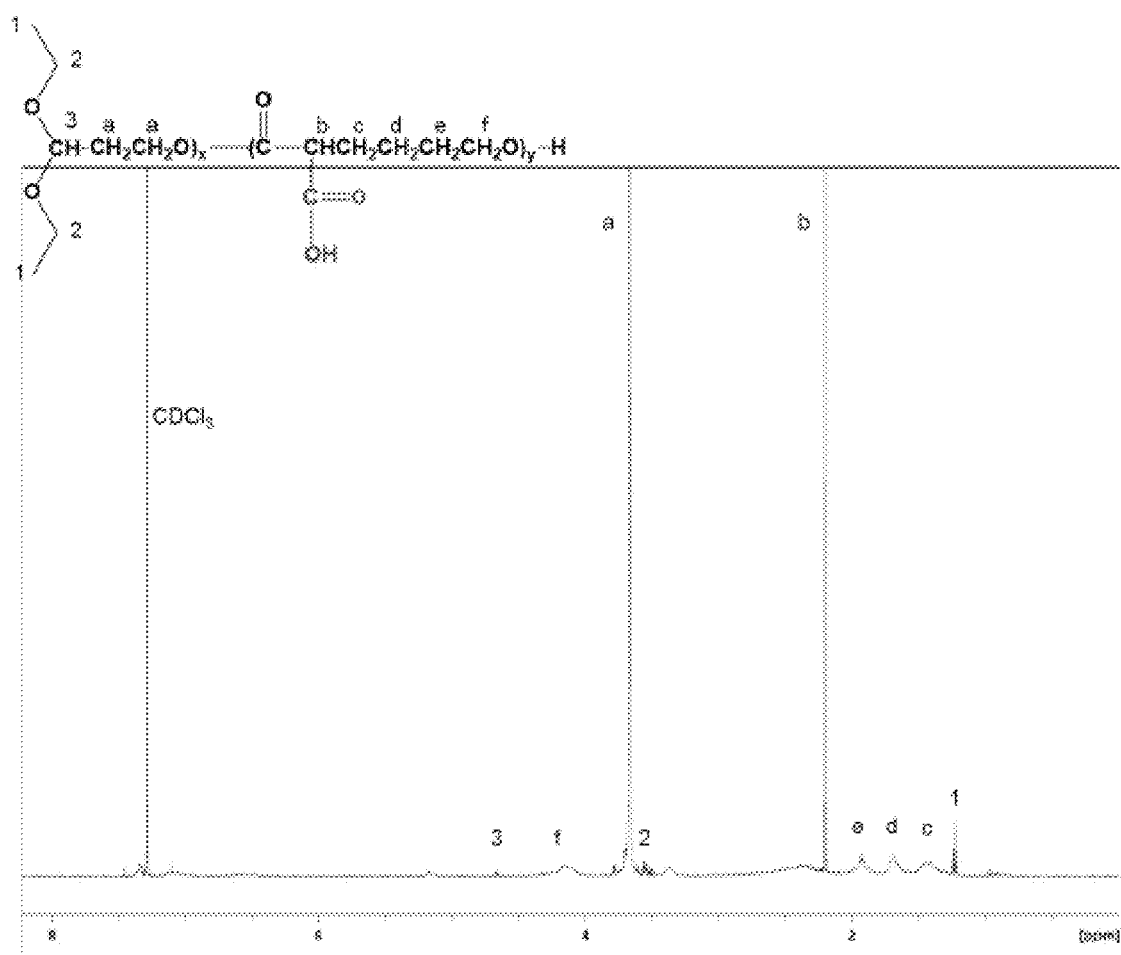
FIG. 29. $^1$H NMR spectrum of act-PEO-b-PCCL block copolymer in CDCl$_3$ and peak assignments.
Figure 30:
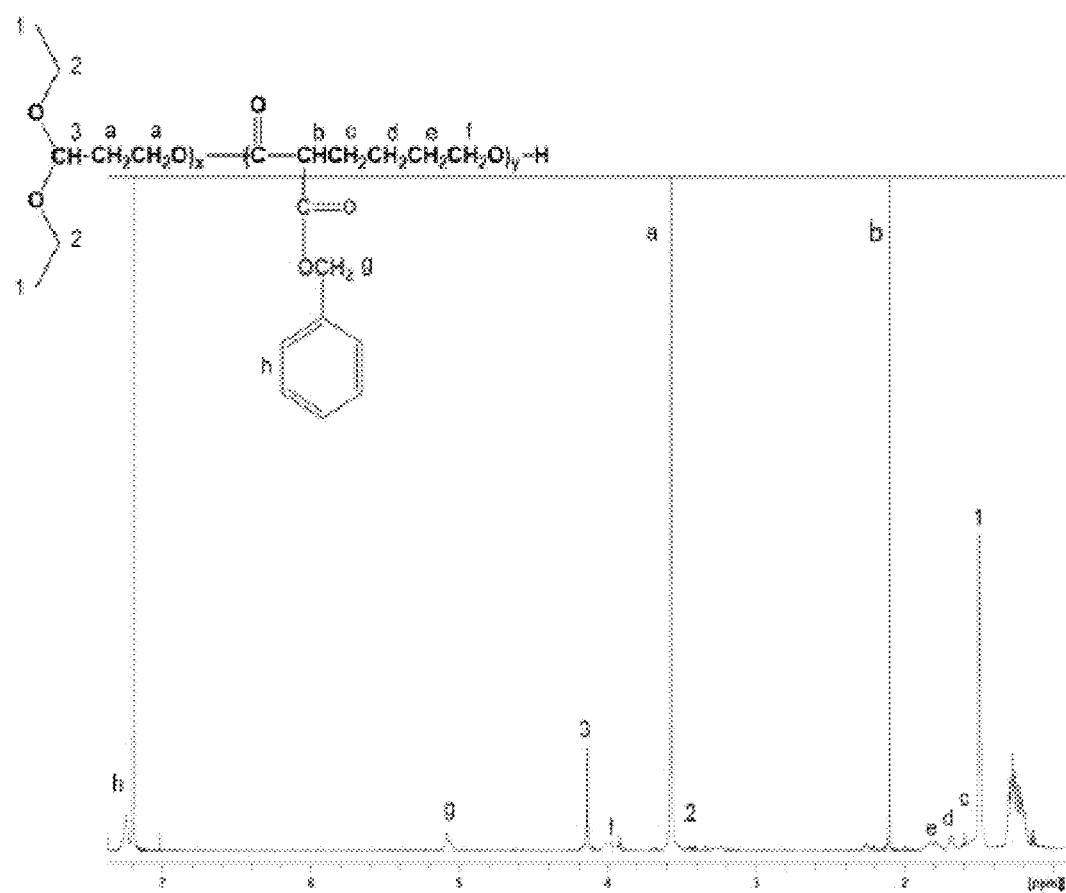
FIG. 30. $^1$H NMR spectrum of act-PEO-b-PBCL block copolymer in CDCl$_3$ and peak assignments.

Compounds A12B4C50 and A83B4C63 (Table 1) were prepared according to the previously reported one-pot procedure shown in Scheme 1 (38). The heterodiene (1 equiv) and maleimide (1.5-2 equiv) were dissolved in toluene in a screw-cap reaction vial. The aldehyde (2 equiv) was added and the vial was sealed and heated to 85° C. for three days. After cooling to room temperature, the solvent was removed under reduced pressure. The residue was purified by flash column chromatography (ethyl acetate/hexane solvent system) to afford yellow solids (40-70% yield). The compounds were further purified by semipreparative HPLC to purities of 95-99%. Purified compounds were characterized by NMR, IR, and mass spectrometry (FIGS. 24 & 25).

Synthesis of Block Copolymers

Block copolymers of PEO-b-PCL and PEO-b-PBCL with different degrees of polymerization for the PCL and PBCL segment were synthesized by ring-opening polymerization of ε-caprolactone or α-benzyl carboxylate-ε-caprolactone, respectively, using methoxy-PEO (MW: 5000 g/mol) as an initiator and stannous octoate as a catalyst according to a method described previously (39-41).

Block copolymers of PEO-b-PCCL were synthesized by catalytic debenzylation of PEO-b-PBCL in the presence of $H_2$ to obtain PEO-b-PCCL according to a method described previously (41).

Synthesis and Characterization of GE11-PEO-b-PBCL Conjugates

Preparation of GE11-PEO-b-PBCL conjugates was carried out in three steps. The first step involved the synthesis of aldehyde-PEO-b-PBCL adopting a previously reported method (42). Briefly, acetal-PEO-b-PBCL was first synthesized through one-pot anionic ring-opening polymerization of ethylene oxide using initiator 3,3 diethoxy-1-propanol (DEP) and potassium naphthalenide solution in THF at room temperature under argon, followed by ε-caprolactone addition. Second, acetal-PEO-b-PBCL was allowed to self-assemble into micelles using a water/acetone mixture, after which the acetone was evaporated. The acetal groups on the surface of the micelles were converted to aldehyde through the dropwise addition of HCl (0.5 mol/L) at room temperature, adjusting the pH of the medium to 2. After being stirred for 2 h, the mixture was neutralized with NaOH (0.5 mol/L) to stop the reaction. The third step involved the conjugation of GE11 peptide to the aldehyde-PEO-b-PBCL micelles. Briefly, GE11 peptide was added and stirred with the polymeric micelles at a 1:3 molar ratio (peptide:CHO-PEO-b-PBCL) at room temperature. After 2 h, NaBH3CN (10 equiv) was added to the reaction mixture to reduce the Schiff's base. After 24 h, the micellar solution was purified by dialysis against water (MWCO, 3.5 kDa). The relative amount of conjugated peptide was determined using HPLC. Reversed phase chromatography was carried out on a Microsorb-MV 5 μm $C_{18}$-100 Å column (4.6 mm×250 mm, Phenomenex, Torrance, Calif., USA) with 20 μL of sample injected and eluted using the following conditions: (1) 100% A (0.1% trifluroacetic acid aqueous solution) and 0% B (acetonitrile) for 5 min; (2) linear gradient from 100% A to 60% A and 0% B to 40% B over 15 min; (3) linear gradient from 60% A to 0% A and 40% B to 100% B over 22 min. Gradient elution was performed at a flow rate of 1 mL/min using a Varian Prostar 210 HPLC System. Detection was performed at 214 nm using a Varian 335 detector (Varian Inc., Palo Alto, Calif., USA). The resulting GE11-PEO-b-PBCL conjugates were freeze-dried and stored at −20° C. until use.

Characterization of the Prepared Block Copolymers and Polymeric Micelles

The prepared block copolymers were characterized for their average molecular weights by $^1$H NMR (600 MHz Avance III—Bruker, East Milton, ON, CA) using deuterated chloroform ($CDCl_3$) as solvent and tetramethylsilane as an internal reference standard. Inhibitors-loaded micelles were prepared by dissolving inhibitors (1 mg) and block copolymers (10-20 mg) in acetone. The solution was added to double distilled water (10 mL) in a dropwise manner and stirred overnight, the organic solvent was removed under vacuum. The obtained micellar solution was then centrifuged at 11,600×g for 5 min to remove the free unencapsulated inhibitors. The average diameter and size distribution of the prepared micelles were estimated by dynamic light scattering (DLS) using a Malvern Zetasizer 3000 (Malvern Instruments Ltd, Malvern, UK). An aqueous droplet (20 μL) of the micellar solution with a polymer concentration of 1 mg/mL was placed on a copper-coated grid. The polymeric micellar solution was negatively stained by 1% phosphotungstic acid ($H_3PO_4$ $12WO_3.24H_2O$). After 5 min, the excess fluid was removed by filter paper and the grid was inserted in Transmission electron microscopy (TEM) (FEI Morgagni 268, North America NanoPort, Oreg., USA) machine for image analysis.

In Vitro Release of Encapsulated PNKP Inhibitors

The in vitro release of encapsulated PNKP inhibitors was studied using a dialysis method. Each dialysis bag (Spectrapor dialysis tubing, MWCO 3.5 kDa, Spectrum Laboratories, Rancho Dominguez, Calif.), containing 2 mL of the micellar formulation or free drug dissolved in acetone, was placed into 300 mL of distilled water maintained at 37° C. in a shaking water bath (65 rpm, Julabo SW 22 shaking water bath, Seelbach, Germany). At selected time intervals, aliquots of 200 μL from the inside of the dialysis bag were collected. The amount of PNKP inhibitor was analyzed using a Varian Prostar 210 HPLC system. Reversed phase chromatography was carried out with a Microsorb-MV 5 μm $C_{18}$-100 Å column (4.6 mm×250 mm) with 20 μL of sample injected and eluted under isocratic conditions with a solution of 0.1% trifluroacetic acid/acetonitrile (1:1 v/v) at a flow rate of 1.0 mL/min at room temperature. Detection was performed at 380 and 280 nm for A12B4C50 and A83B4C63, respectively using a Varian 335 Photodiode Array HPLC detector (Varian Inc., Palo Alto, Calif., USA).

Cell Proliferation Assay

To determine the maximum dose of each PNKP inhibitor that did not affect cell growth rate, we used the CellTiter 96® Non-Radioactive Cell Proliferation Assay (MTS), (Promega). Approximately $1×10^5$ HCT116 cells were plated in triplicate in a 96-well plate with different concentrations of the inhibitors as free or polymeric micellar formulation. Free inhibitor was dissolved in DMSO in a way to keep the final concentration of DMSO<1%. After 72 h, 11 μL of the pre-mixed optimized dye solution (tetrazolium dye) was added to each well and cells were incubated for 4 more hours at 37° C. The absorbance recorded at 490 nm on a FLUOstar Optima® plate reader (BMG Labtech Inc., Durham, N.C.) was used as a representation of the relative number of metabolically active cells in the culture.

Clonogenic Survival Assay

Cells, seeded in 60-mm dishes 24 hours in advance, were treated with PNKP inhibitors for 9-14 consecutive days at nontoxic concentrations. Colonies were then stained with a crystal violet (Sigma, Oakville, ON, CA) stain containing 25% methanol for 30 min, after which the plates were washed in warm water and left to dry overnight. Colonies consisting of 50 cells or more were counted using an automated colony counter (Oxford Optronix, Abingdon, UK).

To determine the radiation response, cells were treated with 0, 2, 4, or 6 Gy γ-radiation ($^{60}$Co Gammacell, AECL, Chalk River, ON, CA) in the absence of PNKP inhibitor or in its presence as free or polymeric micellar formulation. Similarly, to determine the irinotecan response, cells were treated with 0, 2, 3, or 4 μM of irinotecan in the absence of PNKP inhibitor or in its presence as free or polymeric micellar formulation.

Determination of Polymeric Micellar Uptake by Different Colorectal Cancer Cells

Physical entrapment of the hydrophobic fluorescent probe Dil was used to prepare fluorescently labeled polymeric micelles for cellular uptake investigation. Briefly, 30 μg Dil and 3 mg of the block copolymer were dissolved in acetone (0.5 mL). This solution was added to 3 mL of water in a drop-wise manner followed by evaporation of the organic solvent under vacuum. The micellar solution was then centrifuged at 11,600×g to remove the unencapsulated DiI. The level of encapsulation efficiency was determined by measuring the fluorescence at 550/565 nm (excitation/emission) (using a FLUOstar Optima® plate reader (BMG Labtech Inc., Durham, N.C.). The release of DiI from micelles was conducted in PBS buffer containing lipid vesicles as the receiver phase of the released DiI as described previously (43).

To determine cellular uptake by confocal microscopy, HCT116, HT29, and SW620 cells ($1 \times 10^5$) were cultured on a coverslip at 37° C. for 24 h. The medium was removed and replaced with 1 mL of fresh medium containing free DiI, PEO-b-PBCL-DiI and GE11-PEO-b-PBCL-DiI at a concentration of 10 µg/mL encapsulated in micelles. The cells were incubated for 3 h at 37° C. After incubation, the medium was removed and the cells were washed three times with 1 mL of PBS. The cells were fixed with ice cold methanol for 5 min. Methanol was removed by washing with PBS three times. The coverslips were put on slides containing anti-EGFR antibody to stain the membrane for 60 min. The cells were then washed three times with washing buffer and incubated with Hoechst 33342 to stain the nuclei for 5 min. The fixed cells were imaged by confocal laser scanning microscopy (Zeiss 510 LSMNLO, Jena, Germany) performed using a 40× oil immersion lens. Confocal stacks were processed using Carl Zeiss LSM 5 Image software.

Cellular uptake was also measured by determining the fluorescence of DiI using a well plate reader FLUOstar Optima (BMG Labtech Inc., Guelph ON). HCT116, HT29 and SW620 cells were seeded into a 96-well plate ($1 \times 10^4$ cells/well) containing 100 µL of media. 24 h later, DiI loaded polymeric micelles were added and incubated with the cells for 3 h at 37° C. For the competition experiments, HCT116 cells were pre-incubated with excess free peptide (1 mg/mL) for 30 min to saturate receptors and to inhibit the binding and internalization of peptide conjugated micelles. Following the incubation period, medium was removed and cells were washed with PBS three times. Internalized DiI levels were assessed by fluorescence emission intensity at 565 nm.

Statistical Analysis

Plots show an average of at least three independent biological replicates. Experimental groups were compared using a two-tail unpaired Student's t-test. The software used was GraphPad Prism5 software (La Jolla, Calif., USA). A value of $P<0.05$ was considered as statistically significant in all experiments.

Results

Polymer Synthesis and Micelle Characterization

Figure 15:
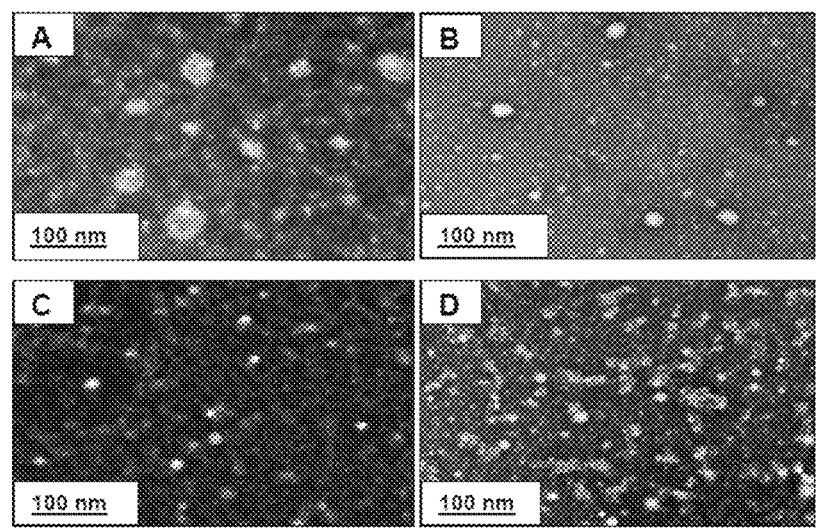
FIG. 15. TEM of loaded polymeric micelles. (A) PEO-b-PCCL-A12B4C50 (B) PEO-b-PBCL A83B4C63 (C) GE11-PEO-b-PCCL-A12B4C50 and (D) GE11-PEO-b-PBCL-A83B4C63. An aqueous droplet (20 μL) of the micellar solution with a polymer concentration of 1 mg/mL was placed on a copper-coated grid. Then a drop of 1% solution of phosphotungstic acid was added to provide the negative stain. After 5 min, the excess fluid was removed by filter paper and the grid was inserted in the TEM for image analysis.

Polymers PEO-b-PCL, PEO-b-PBCL, PEO-b-PCCL, acetal-PEO-b-PBCL and acetal-PEO-b-PCCL were synthesized and characterized using our previously established method (44). The structures were confirmed by NMR, which showed all of the characteristic peaks for PEO, PCL, PBCL, PCCL and acetal segments (FIGS. 26-30). Polymers were assembled into micelles using a co-solvent evaporation method where acetone was used as an organic solvent in the presence of inhibitor or DiI. Micelle formation was confirmed by studying the size distribution and polydispersity index (PDI) using dynamic light scattering (DLS) measurements. We found that the size of all micelles is <100 nm and the PDI measurements, a value representing the homogeneity of micellar solution, were similar except for PEO-b-PCL-A83B4C63 which shows a higher PDI value (0.37) indicating a more disperse solution. We also achieved a high encapsulation efficiency with these micelles which ranges between 75-100%. The characteristics of the polymeric micelles are summarized in Table 1. In addition, the morphology of the micelles was confirmed by TEM. The TEM image showed a spherical morphology and it also showed a similar trend in the size of polymeric micelles like what was observed from DLS (FIG. 15).

In Vitro Release of PNKP Inhibitors from Polymeric Micelles

Figure 16:
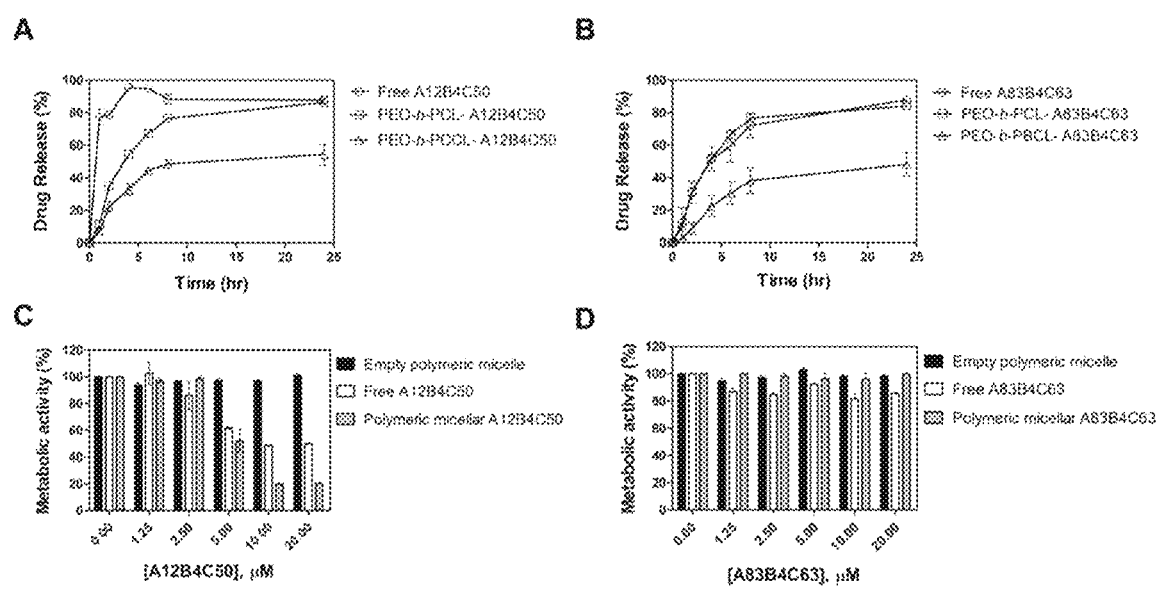
FIG. 16. In vitro release from dialysis tubing for free versus encapsulated (A) A12B4C50 and (B) A83B4C63 in aqueous solution at 37° C. At fixed time intervals, a sample of 120 μL was withdrawn and was analyzed by HPLC to determine the amount of released drug. Each point represents the mean±SD (n=3). In vitro cytotoxicity of (C) A12B4C50 and (D) A83B4C63 measured by MTS assay after 72 h of drug incubation at 37° C. HCT116 cells ($1 \times 10^5$) were plated in triplicate in a 96-well plate with different concentrations of inhibitors. After 72 h, a tetrazolium dye solution was added to each well and cells were incubated for 4 h at 37° C. Absorbance was recorded at 490 nm. Each point represents the mean±SD (n=3).

The results of the in vitro release of A12B4C50 and A83B4C63 from PEO-b-PCCL and PEO-b-PBCL are presented in FIGS. 16A and 16B, respectively. Free A12B4C50 and A83B4C63 were released from the dialysis bag at a rapid rate, 94.8% and 59.4% within 6 h, respectively, while only 44.5% of A12B4C50 was released from PEO-b-PCCL micelles and 30.6% of A83B4C63 was released from PEO-b-PBCL micelles. In contrast, PEO-b-PCL micelles released 67.2% and 66.5% of A12B4C50 and A83B4C63, respectively, within the same time frame.

Inhibition of Cell Growth by the Hit Compounds and their Polymeric Micellar Formulations.

Figure 17:
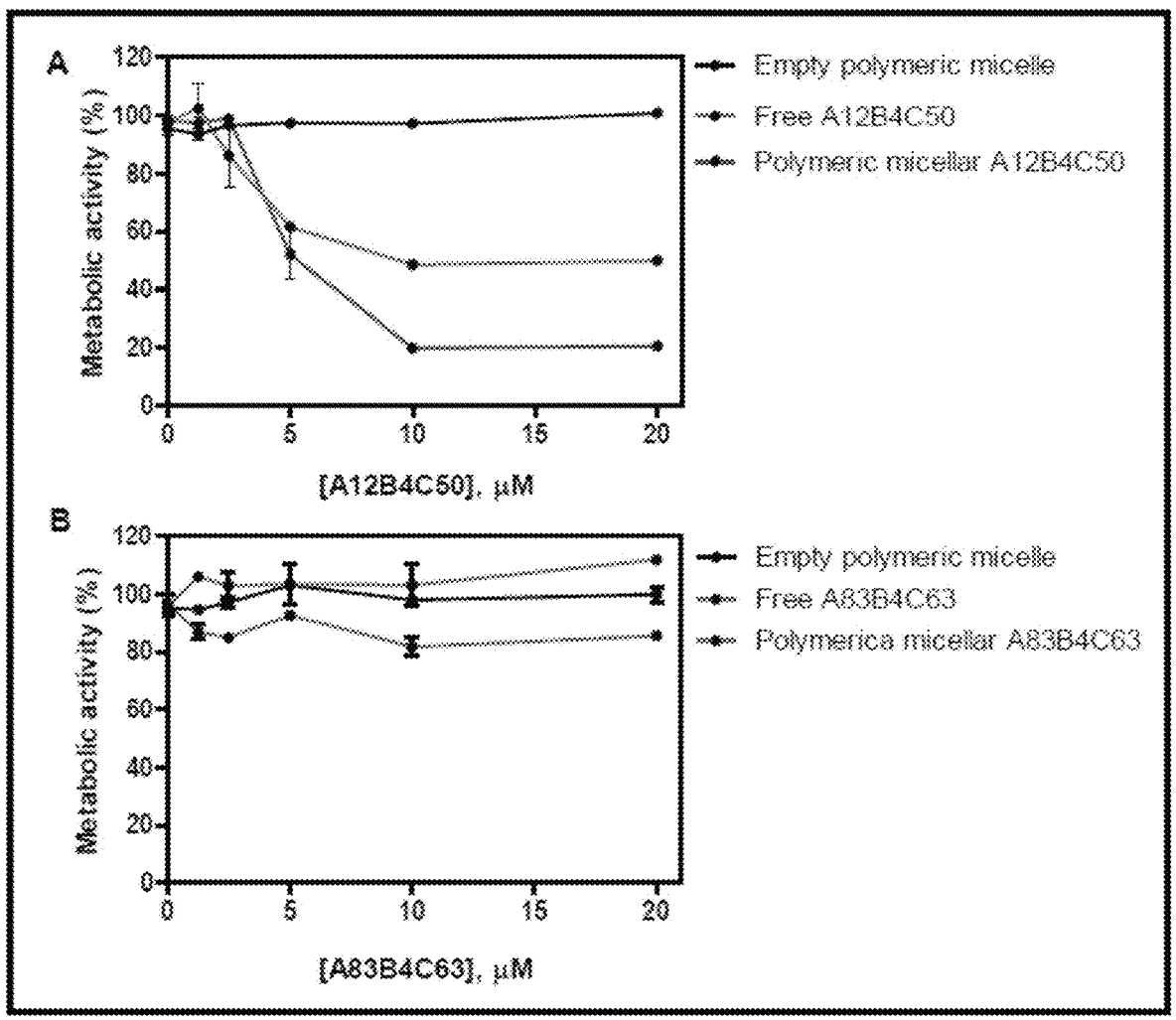
FIG. 17. In vitro cytotoxicity of (A) A12B4C50 and (B) A83B4C63 measured by MTS assay after 72 h of drug incubation at 37° C. HCT116 cells ($1 \times 10^5$) were plated in triplicate in a 96-well plate with different concentrations of inhibitors. After 72 h, a tetrazolium dye solution was added to each well and cells were incubated for 4 h at 37° C. Absorbance was recorded at 490 nm. Each point represents the mean±SD (n=3).

To determine the maximum concentrations of the PNKP inhibitors that could be employed in the subsequent clonogenic survival assays, we used the MTS assay to assess non-specific inhibition of colorectal cancer cell growth induced by the free and encapsulated PNKP inhibitors. HCT116 colorectal cancer cells were exposed to serial dilutions of empty polymeric micelles, free PNKP inhibitor and encapsulated PNKP inhibitor and assayed after 72 h, as shown in FIG. 17, free and encapsulated A12B4C50 affected cell growth at concentrations >5 µM, thus limiting the usable concentration of this compound to ≤5 µM in the clonogenic survival assays. On the other hand, A83B4C63 could be used at concentrations <20 µM. Furthermore, there was no toxicity associated with the empty PEO-b-PCCL and PEO-b-PBCL micelles.

Cellular Radio/Chemosensitization by PNKP Inhibitors

Figure 18:
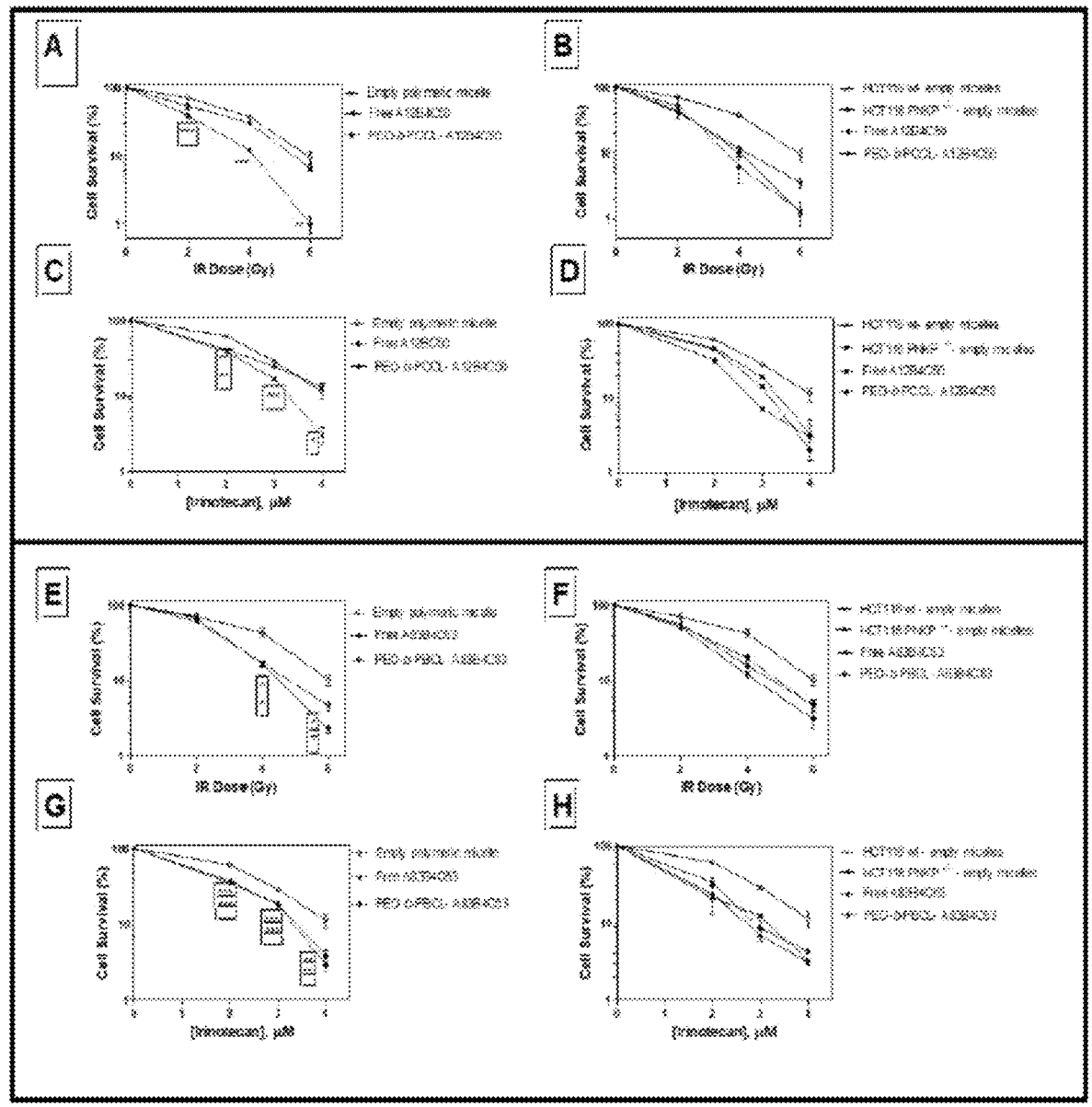
FIG. 18. Radio/chemosensitization by free and encapsulated A12B4C50 or A83B4C63. Cells, treated with 4 μM A12B4C50 and 6 μM A83B4C63 24 hours in advance, were subjected to radiation or irinotecan and survival was assessed by clonogenic survival assay. (A, C, E and G) HCT116 wild-type cells were sensitized to radiation and irinotecan by encapsulated PNKP inhibitors. (B, D, F and H) PNKP inhibitors failed to sensitize HCT116 PNKP-knock out cells (HCT116PNKP-/-) to radiation or irinotecan. (I) Western blot showing PNKP protein levels in wild-type and PNKP-knock out HCT116 cells. Each point represents mean±SD (n=3). All marked points were compared to control group and are statistically significant at (* $P \leq 0.05$), ( $P \leq 0.01$) and (* $P \leq 0.001$).
Figure 18:
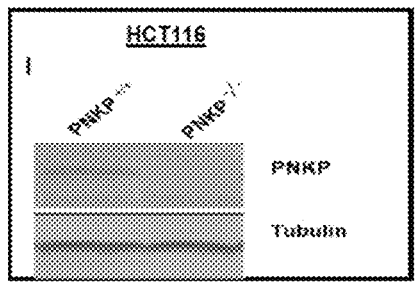
Figure 31:
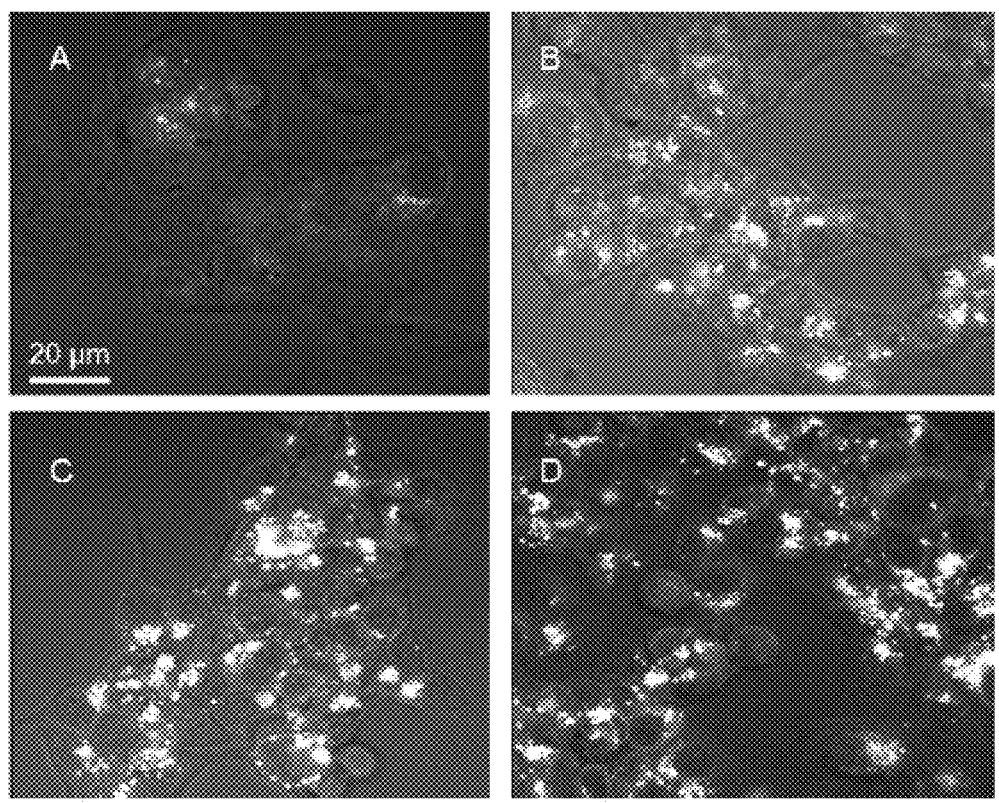
FIG. 31. Live cell fluorescence microscopy images of A12B4C50 accumulation in HCT116 after 4 h incubation. (A) Control cells. (B) Free A12B4C50. (C) PEO-b-PCCL-A12B4C50. (D) GE11-PEO-b-PBCL-A12B4C50. Bright signals indicate fluorescence of A12B4C50 (excitation wavelength 380 nm and emission wavelength 405 nm).

To examine the capacity of A12B4C50 and A83B4C63 to act as sensitizers to radiation or the topoisomerase poison, irinotecan, clonogenic survival assays were performed to measure the response of HCT116 cells and HCT116 PNKP-knock out cells (generated by CRISPR technology) in the presence and absence (empty polymeric micelles were added instead) of A12B4C50 and A83B4C63. The cells were incubated with 4 µM and 6 µM of free and encapsulated A12B4C50 and A83B4C63, respectively, for 24 h prior to exposure to radiation or addition of irinotecan. The survival curves (FIGS. 18A, C, E and G) indicated that exposure to encapsulated A12B4C50 and A83B4C63 significantly increased the sensitivity of HCT116 cells to radiation and irinotecan, and this response was nearly identical to that seen with HCT116 PNKP-knock out cells treated with either radiation or irinotecan alone. However, only free A83B4C63 was able to sensitize HCT116 cells to either radiation or irinotecan. Free A12B4C50 failed to sensitize HCT116 cells to either treatment. This could be due to the poor internalization of free A12B4C50 in HCT116 cells, which was confirmed by fluorescence microscopy (FIG. 31). Furthermore, A12B4C50 and A83B4C63 (free or encapsulated) failed to further sensitize the HCT116 PNKP-knock out cells to either radiation or irinotecan (FIGS. 18B, D, F and H).

In Vitro Release of PNKP Inhibitors from GE11-Conjugated Polymeric Micelles

Figure 19:
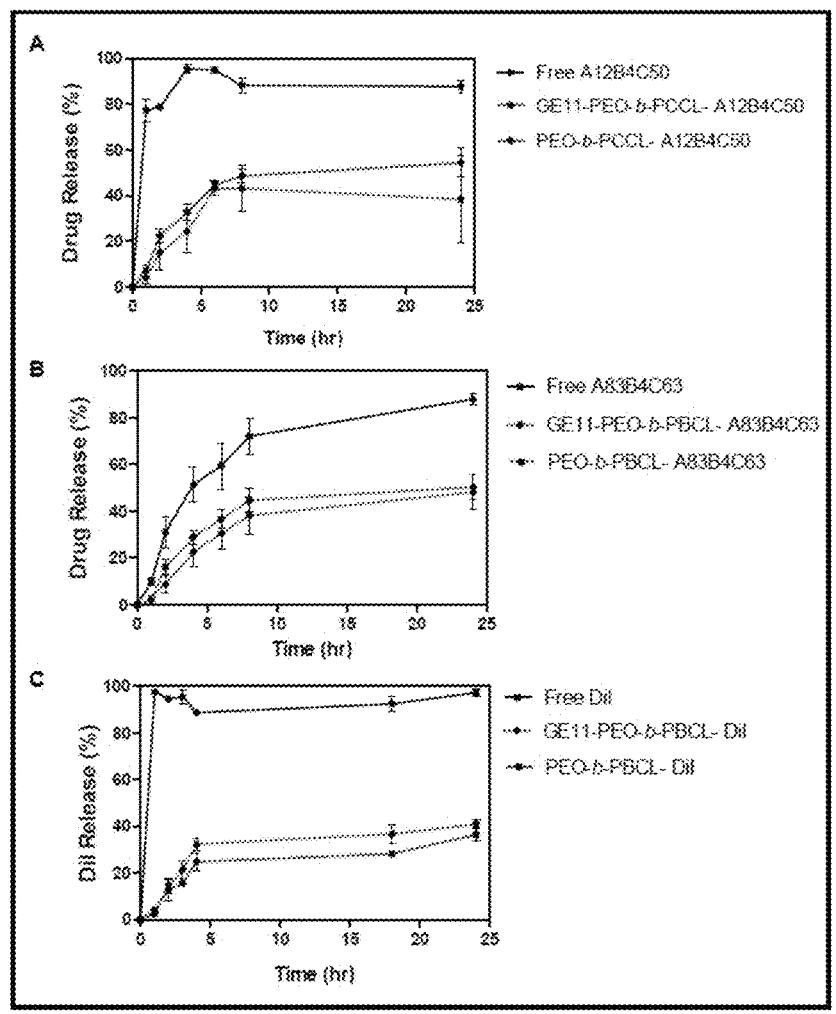
FIG. 19. In vitro release from dialysis tubing (MWCO 3.5 kDa) of (A) A12B4C50, (B) A83B4C63 and (C) DiI from GE11-conjugated polymeric micelles in comparison to plain micelles and free drug (reported previously in FIG. 2) in aqueous solution at 37° C. At fixed time intervals, a sample of 120 μL was withdrawn and analyzed by HPLC to determine the amount of released drug. Each point represents the mean±SD (n=3).

To prepare GE11-micelle conjugates, the peptide was chemically conjugated to the aldehydic groups on the surface of the polymeric micelles through their N-terminal groups as described previously (45). Using this method, GE11-PEO-b-PBCL and GE11-PEO-b-PCCL were obtained. Free peptide after the completion of the reaction was removed by extensive dialysis. The progress of the reaction was monitored by HPLC at 24, 48, and 96 h. The reaction progress revealed almost 100% conjugation after 96 h. FIGS. 19A & 19B show that the attachment of GE11 on the surface of either PEO-b-PCCL or PEO-b-PBCL did not perturb the slow release of A12B4C50 and A83B4C63 seen with the unmodified micelles.

To study the influence of GE11 on cellular uptake in cells expressing different levels of EGFR, we encapsulated Dil dye in PEO-b-PBCL to be used as a general model for targeted polymeric micelles. FIG. 5C shows that Dil dye has a slow controlled release from both plain and GE11-modified polymeric micelles. This further confirmed that GE11 attachment to the surface of the micelles did not alter the release of the encapsulated compounds.

Cellular Uptake of Encapsulated Compounds

Figure 20:
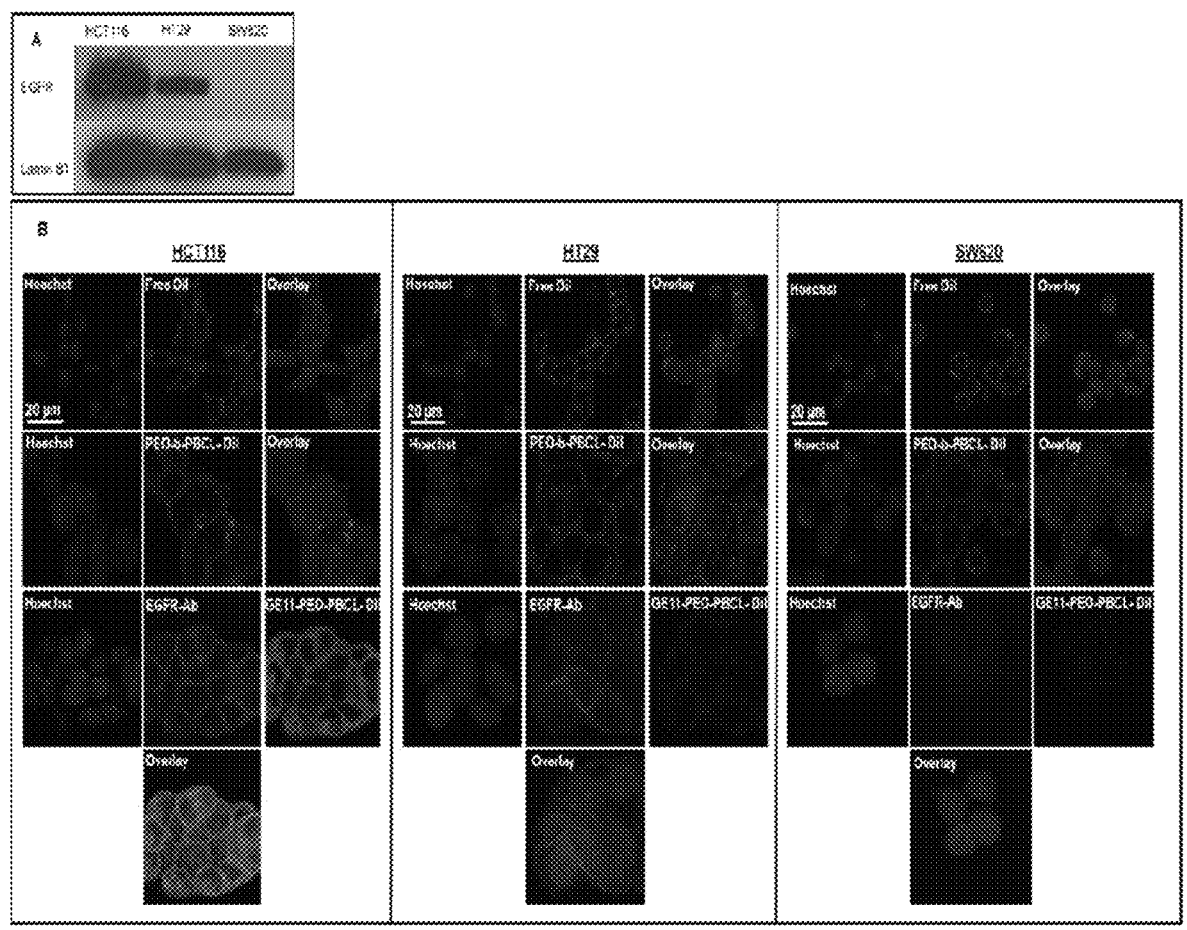
FIG. 20. Cellular uptake of DiI-encapsulated polymeric micelles. (A) Western blotting shows different expression levels of EGFR in HCT116, HT29 and SW620 cells. (B) In vitro fluorescence microscopy images of DiI accumulation in HCT116, HT29 and SW620 cells. After 3 h incubation with free DiI, PEO-b-PBCL-DiI and GE11-PEO-b-PBCL-DiI. Red fluorescence indicates DiI. Blue fluorescence indicates Hoechst dye. Green fluorescence indicates EGFR immunostaining.

To evaluate the relationship between EGFR expression and the effectiveness of GE11-conjugated micelles, we monitored the cellular uptake of Dil by three colorectal cancer cell lines expressing different levels of EGFR. Western blot analysis revealed that HCT116 cells express relatively high levels of EGFR compared to HT29 cells, while the EGFR signal from SW620 cells was undetectable (FIG. 20A), in line with previous reports (46). HCT116, HT29 and SW620 cells were incubated with free Dil, PEO-b-PBCL-Dil and GE11-PEO-b-PBCL-Dil for 3 h. Fluorescence microscopy (FIG. 20B) revealed that the Dil was mainly localized in the cytoplasmic compartment. HCT116 cells treated with GE11-PEO-b-PBCL-Dil showed more intense Dil fluorescence signals than HT29 and SW620.

Figure 21:
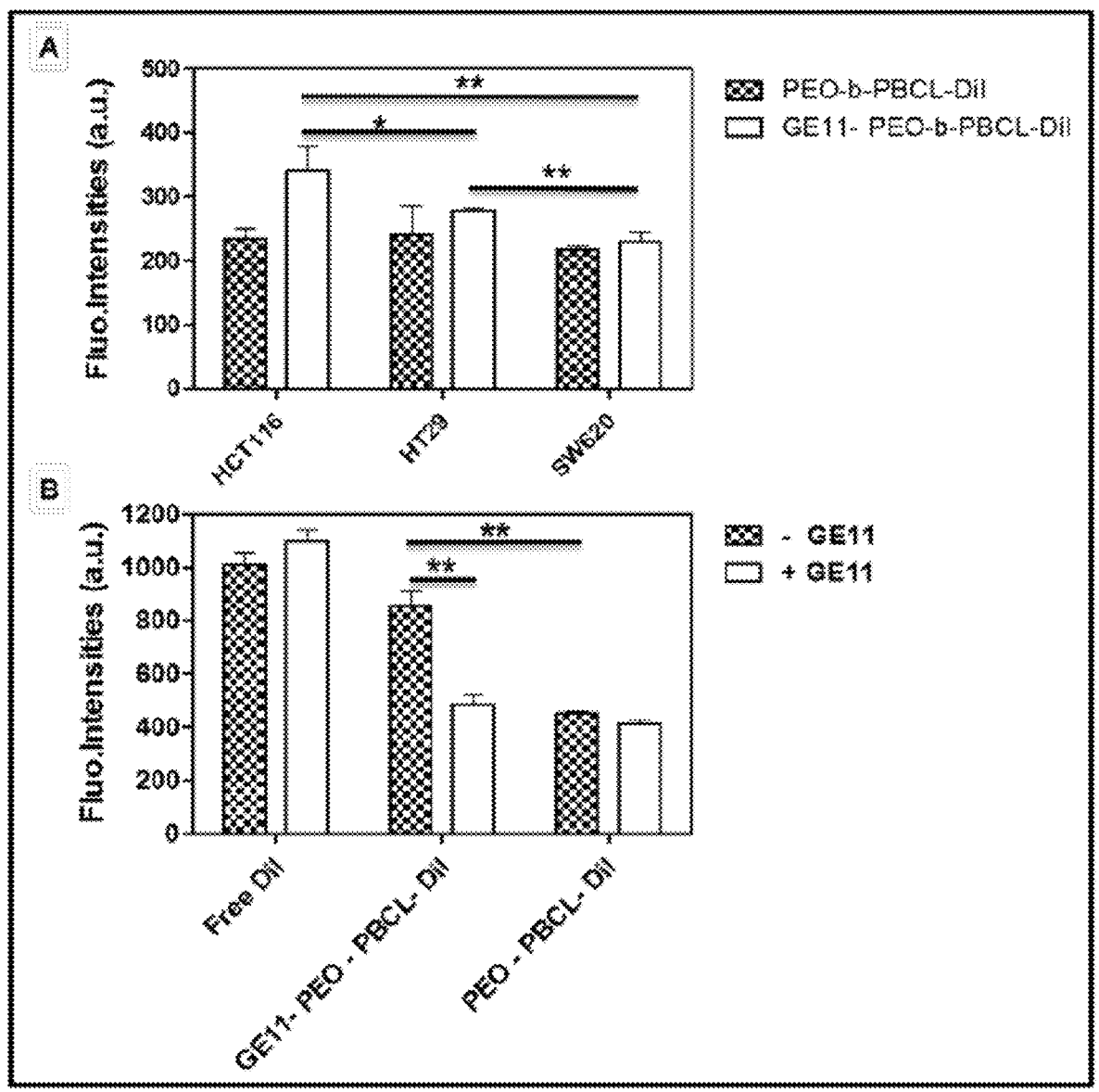
FIG. 21. (A) In vitro cell uptake of PEO-b-PBCL-DiI and GE11-PEO-b-PBCL-DiI by HCT116, HT29 and SW620 cells. (B) In vitro cell uptake of free DiI, GE11-PEO-b-PBCL-DiI and PEO-b-PBCL-DiI with (+) or without (−) pre-treatment with excess of free GE11 peptide. Each point represents mean±SD (n=3). (* $P \leq 0.05$) and (** $P \leq 0.01$).

To obtain quantifiable data, fluorescence intensities of Dil uptake were measured using a plate reader. After 3 h incubation we observed enhanced cellular uptake of GE11-PEO-b-PBCL-Dil micelles by HCT116 cells in comparison to HT29 and SW620 cells (FIG. 21A). In addition, the cellular uptake by HCT116 cells of GE11-PEO-b-PBCL-Dil was higher than PEO-b-PBCL-Dil by HCT116 cells. These data are in accord with our cell imaging observations.

To investigate the possible role of receptor mediated cell uptake of GE11-PEO-b-PBCL-Dil, we pretreated HCT116 cells with 1 mg/mL free GE11 to compete with the conjugated micelles. As shown in FIG. 21B, the free GE11 significantly reduced the cellular uptake of GE11-PEO-b-PBCL-Dil by HCT116 cells. In comparison, the uptake of PEO-b-PBCL-Dil by HCT116 cells did not change significantly following pre-treatment with free GE11.

Figure 22:
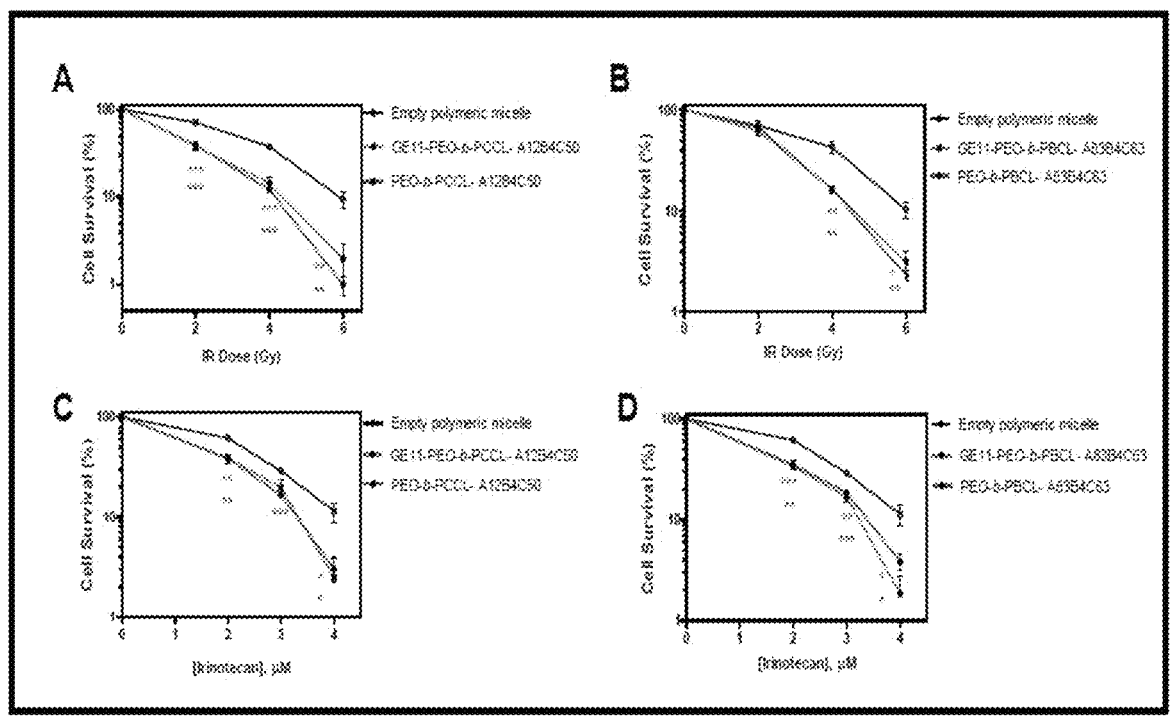
FIG. 22. Radio/chemosensitization of HCT116 wild-type cells by A12B4C50 and A83B4C63 encapsulated in GE11-PEO-b-PCCL and GE11-PEO-b-PBCL, respectively. Cells, treated with increasing concentrations of PNKP inhibitors 24 hours in advance, were subjected to radiation or irinotecan and survival was assessed by clonogenic survival assay. Data of empty polymeric micelles, PEO-b-PBCL-A83B4C63 and PEO-b-PCCL-A12B4C50 were reported previously in FIG. 4. Each point represents mean±SD (n=3). All marked points were compared to control group and are statistically significant at (* $P \leq 0.05$), ( $P \leq 0.01$) and (* $P \leq 0.001$).

Cellular Radio/Chemosensitization by PNKP Inhibitors Encapsulated in GE11-Conjucated Micelles Clonogenic survival assays were performed to examine the capacity of GE11-PEO-b-PCCL-A12B4C50 and GE11-PEO-b-PBCL-A83B4C63 to act as radio- and chemo-sensitizers. HCT116 cells were incubated with GE11-PEO-b-PCCL-A12B4C50 and GE11-PEO-b-PBCL-A83B4C63 for 24 h prior to irradiation or exposure to irinotecan. The survival curves (FIG. 22) indicated that both GE11-PEO-b-PCCL-A12B4C50 and GE11-PEO-b-PBCL-A83B4C63 significantly increased the sensitivity of HCT116 cells to radiation and irinotecan, and this response was almost identical to that seen with PEO-b-PCCL-A12B4C50 and PEO-b-PBCL-A83B4C63.

Figure 23:
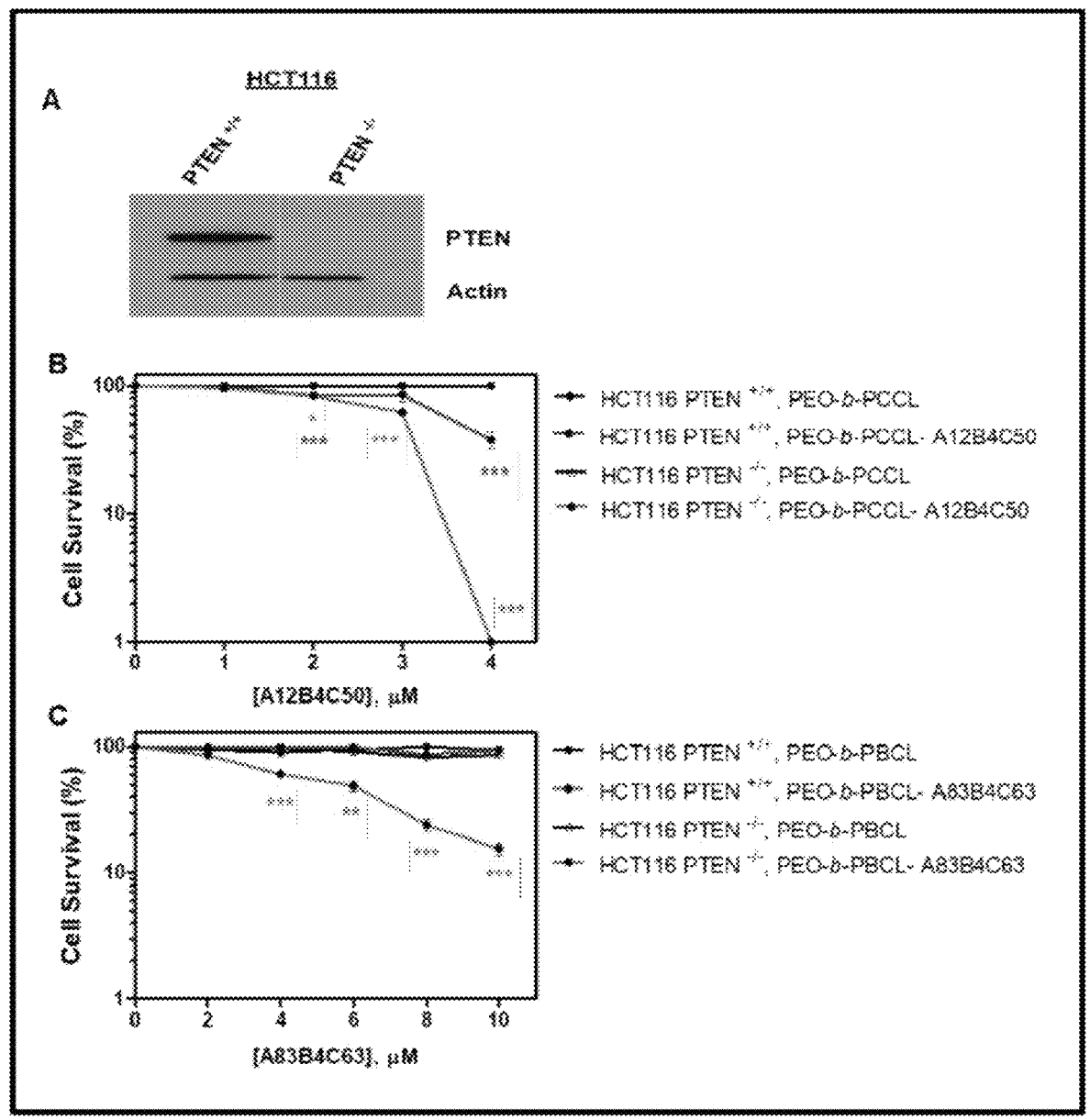
FIG. 23. Clonogenic survival assays of PTEN-deficient cells treated with encapsulated PNKP inhibitors. (A) Western blot confirms disruption of PTEN in HCT116 cells. (B & C) Cells were subjected to increasing concentrations of PNKP inhibitors encapsulated in polymeric micelles as well as empty polymeric micelles for control sets for 9-14 consecutive days. Colonies consisting of 50 cells or more were counted using an automated colony counter. Each point represents mean±SD (n=3). All marked points were compared to control (HCT116 PTEN-/-, PEO-b-PBCL/PEO-b-PCCL) group and are statistically significant at (* $P \leq 0.05$), ( $P \leq 0.01$) and (* $P \leq 0.001$).

Synthetic Lethal Targeting of PTEN-Deficient Cancer Cells Using Encapsulated PNKP Inhibitors To investigate whether the new encapsulated PNKP 3'-phosphatase inhibitors could induce a synthetic lethal response in PTEN-deficient cells, we performed clonogenic survival assays with both HCT116 PTEN+/+ and HCT116 PTEN−/− cells. As shown in FIG. 23, the combined disruption of both PTEN and PNKP led to a lethal response with increasing dose of PNKP inhibitor. However, the disruption of PNKP (chemically by inhibitors) or PTEN (genetically) individually was not lethal. These findings confirm our previous observation that a synthetic lethal relationship exists between PTEN and PNKP.

Figure 32:
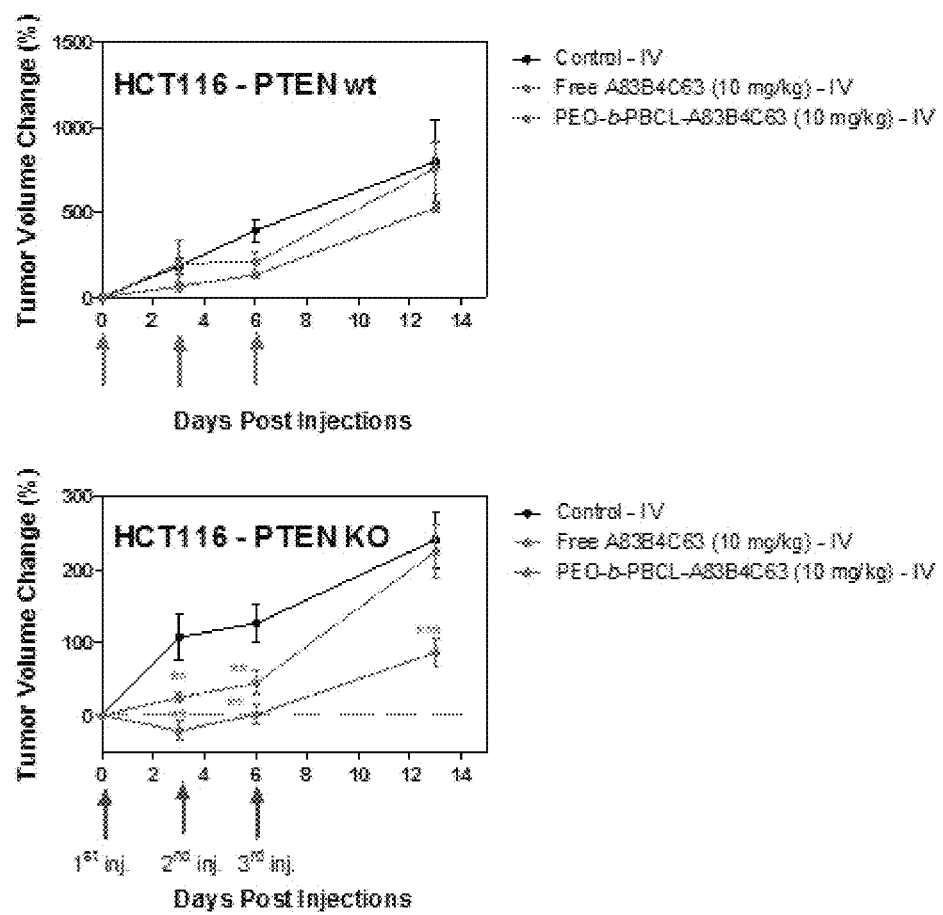
FIG. 32 depicts the response of subcutaneous xenograft tumours derived from injection of HCT116 wild type (wt) and PTEN knockout colorectal cells in mice to treatment with free and encapsulated with A83B4C63.

In FIG. 32, we have injected 500,000 HCT116 colorectal cancer cells subcutaneously in the right flank of NIHIII mice. Once tumors became palpable, free A83B4C63 drug dissolved with the aid of Cremophor EL/ethanol or ExCell formulation of A83B4C63 or Dextrose 5% (as control) were injected to mice intravenously via tail vein, three times 2 days apart. Tumour volume was then calculated from the measurement of tumour dimensions and used to plot change in tumour volume over time. The data show that A83B4C63 is not as effective in the PTEN positive tumour model as it is in the PTEN negative tumour model, indicating that A83B4C63 is synthetically lethal to PTEN negative cells, and has minimal non-specific (PNKP non-related) toxic effects in cancer cells expressing wild type PTEN.

Figure 33:
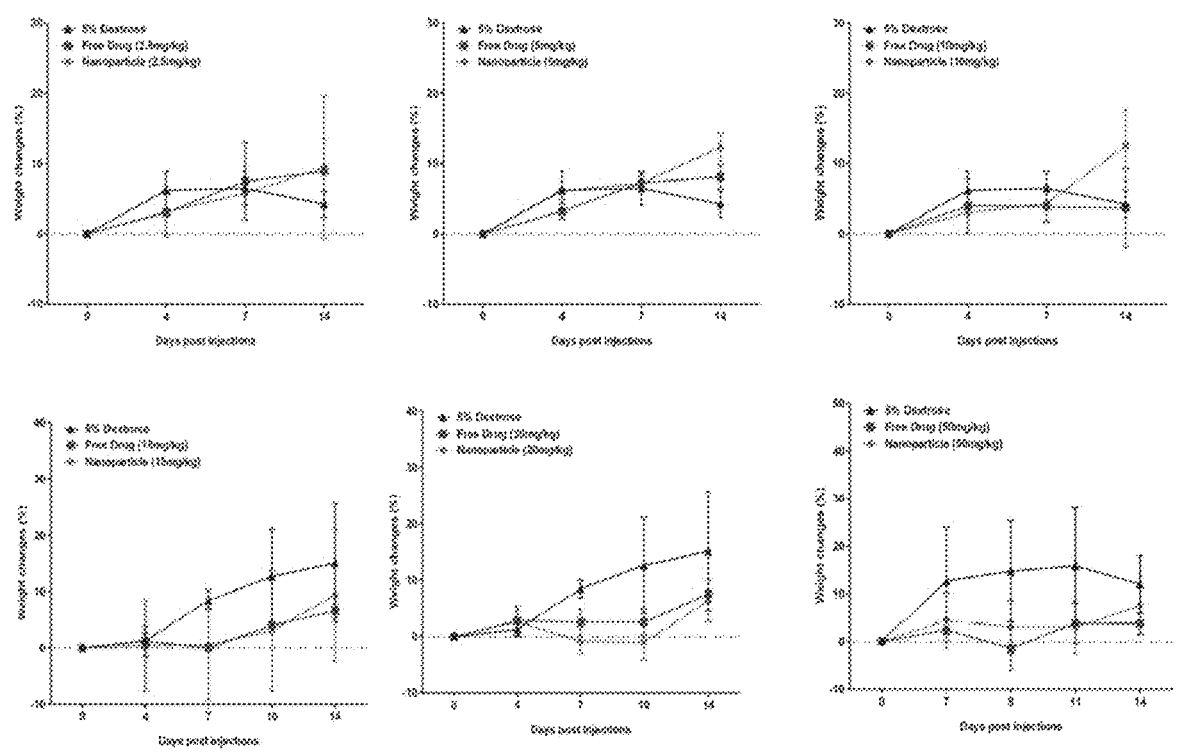
FIG. 33 depicts determination of MTD in CD-1 mice.
Figure 34A:
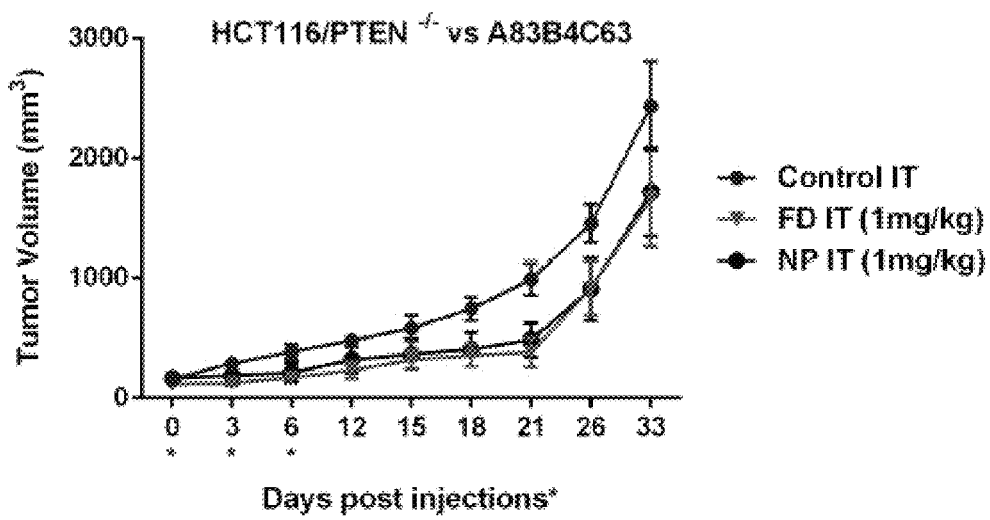
FIG. 34 depicts in vivo activity (inter-tumoural (IT) injection).
Figure 34B:
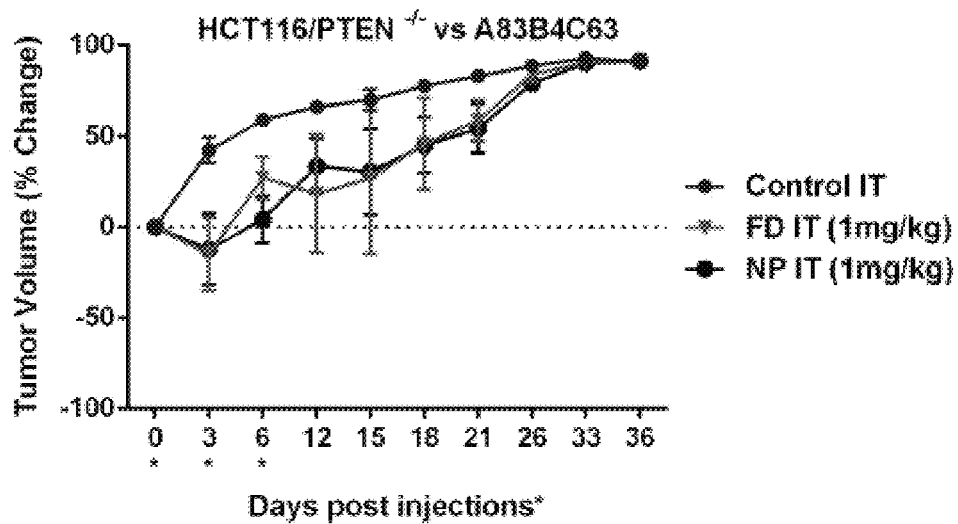
Figure 34C:
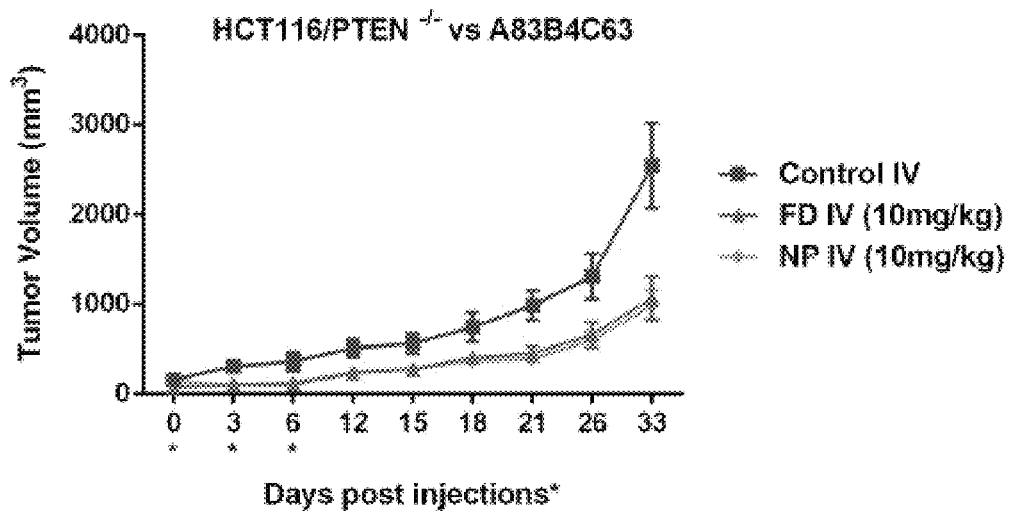
Figure 34D:
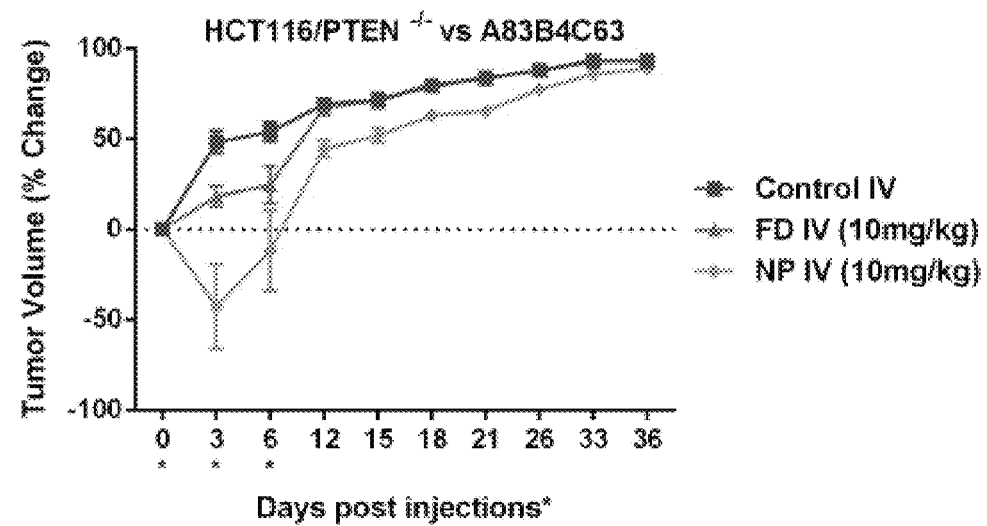
Figure 35:
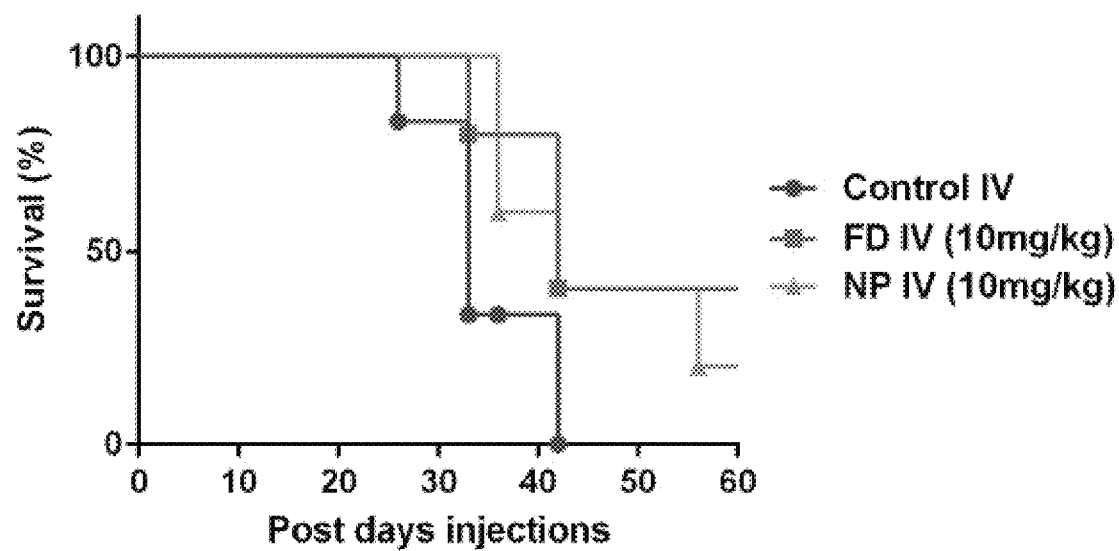
FIG. 35 depicts survival data.
Figure 36:
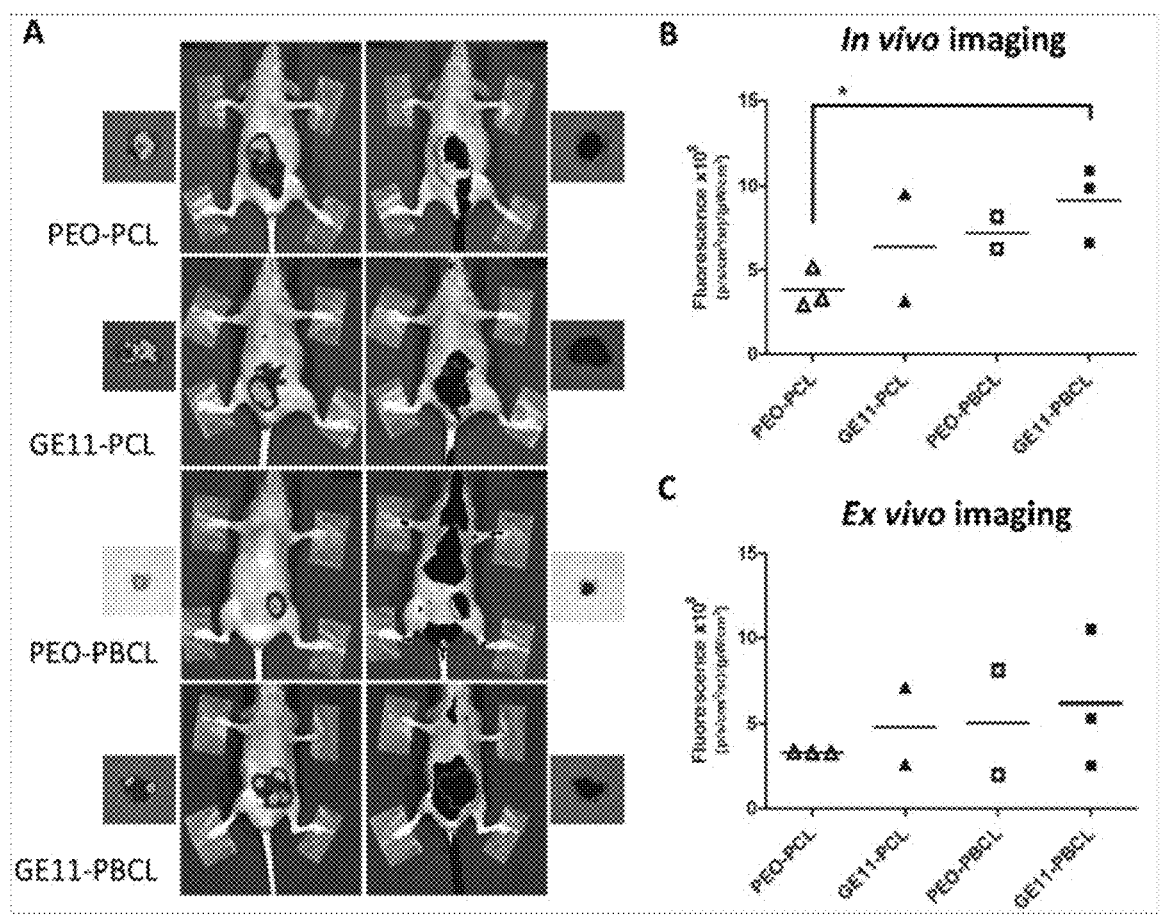
FIG. 36 depicts in vivo distribution of nano-carrier.

FIG. 32 depicts the response of subcutaneous xenograft tumours derived from injection of HCT116 wild type (wt) and PTEN knockout colorectal cells in mice to treatment with free and encapsulated with A83B4C63. FIG. 33 depicts determination of MTD in CD-1 mice. FIG. 34 depicts in vivo activity (inter-tumoural (IT) injection). FIG. 35 depicts survival data. FIG. 36 depicts in vivo distribution of nanocarrier.

Discussion

Despite recent advances in radio/chemotherapy, a large proportion of colorectal cancer patients do not achieve objective responses due to the existence of intrinsic and acquired resistance to these therapies. Identification of molecular mechanisms that reduce the efficacy of conventional therapy, and targeting these pathways, is essential for improving radiation and chemotherapy responses in cancer patients. DNA repair pathways play a major role in tumor resistance towards radio/chemotherapy. This gave rise to the hypothesis that inhibition of DNA repair may result in increased efficacy of existing therapies and, more recently, to the idea that some tumor cells may carry additional defects that make them sensitive to DNA repair inhibitors as single therapeutic agents (47). PNKP, a DNA repair enzyme that possesses 5'-kinase and 3'-phosphatase activity represents a candidate target for achieving this goal. Our previous studies indicated that depletion of PNKP activity by shRNA or a small molecule inhibitor of its phosphatase activity, sensitizes cells to ionizing radiation and camptothecin (7-9). Moreover, reduction of PNKP increases the spontaneous mutation frequency, indicating that it is required for the repair of endogenous DNA damage induced by reactive oxygen species (ROS) (7). The imidopiperidine, A12B4C3, was the first PNKP phosphatase inhibitor discovered in our lab (48, 49). A12B4C50 and A83B4C63 represent the development of second generation and more potent inhibitors of PNKP derived from the parent compound A12B4C3.

In this study, we describe the encapsulation of A12B4C50 and A83B4C63 inside polymeric micelles. Many emerging cancer drugs suffer from nonspecific distribution, rapid clearance and toxicity, which hinders their further preclinical evaluation and advancement in drug development process. Specifically, since our molecules of interest aim to inhibit a DNA repair enzyme, it is essential to target these carriers to tumor tissue and spare normal tissue from their exposure and effects. The benefits of using polymeric micelles as drug carriers include their ability to increase the water solubility of hydrophobic drugs, extend the circulation of drugs in the blood, eliminate fast renal excretion and increase tumor drug accumulation (50). A series of block copolymers based on PEO-b-PCL, bearing side groups of benzyl carboxylate (PEO-b-PBCL) or free carboxyl (PEO-b-PCCL) on the PCL backbone were used for this study. A12B4C50 and A83B4C63 were efficiently loaded in PEO-b-PCCL and PEO-b-PBCL nanoparticles, respectively. These polymer formulations were found to be superior to the more commonly used PEO-b-PCL micelles because the release of the compounds was considerably slower from the new polymeric micelles with pendent groups on the PCL block; 54.3 and 48.2% drug release from polymeric micellar formulations of A12B4C50 and A83B4C63 within 24 h in comparison to 86.2 and 84.2% release of A12B4C50 and A83B4C63 from PEO-b-PCL formulations.

The newly synthesized inhibitors were tested for their ability to sensitize HCT116 cells to either radiation or irinotecan. While free A83B4C63 was able to sensitize HCT116 cells to both radiation and irinotecan, free A12B4C50 failed to sensitize HCT116 cells to either treatment. We investigated the internalization of A12B4C50 by fluorescence microscopy by monitoring the fluorescence of A12B4C50 (excitation wavelength 380 nm and emission wavelength 405 nm) (Supplementary FIG. S8) and found that there is poor cellular uptake of free A12B4C50 by HCT116 cells compared to PEO-b-PCCL-A12B4C50 and GE11-PEO-b-PCCL-A12B4C50. This could explain the poor sensitization effect of free A12B4C50 compared to the encapsulated A12B4C50. Furthermore, PEO-b-PCCL-A12B4C50 and PEO-b-PBCL-A83B4C63 were able to effectively sensitize wild-type HCT116 cells to radiation and irinotecan, but importantly, failed to sensitize the HCT116 PNKP-knockout cells. This is an indication that the new inhibitors sensitize cells primarily through inhibition of PNKP 3'-phosphatase activity and not an alternative, unidentified protein.

PEO-b-PCCL and PEO-b-PBCL polymeric micelles are expected to provide A12B4C50 and A83B4C63, respectively, the capacity for so-called "passive" targeting of tumor. This approach is based on the fact that many tumors exhibit an EPR effect due to a leaky vasculature and poor or absent lymphatic drainage, which allows particles of diameter 20-200 nm to preferentially enter tumor tissue (50). PEO-b-PCCL-A12B4C50 and PEO-b-PBCL-A83B4C63 sizes are within this range as was shown by DLS and TEM analysis.

To achieve active targeting of our polymeric micelles and enhance their interaction with cancer cells, we covalently attached GE11 peptide to the surface of PEO-b-PCCL and PEO-b-PBCL. GE11 has an affinity for EGFR, which is expressed at a high level by HCT116 cells in comparison to HT29 cells, while SW60 cells express no EGFR. Cellular uptake analysis showed higher cellular internalization of Dil dye by HCT116 cells in comparison to HT29 and SW620 cells. Free Dil and PEO-b-PBCL-Dil internalization was similar in all cells. However, GE11-PEO-b-PBCL-Dil internalized in HCT116 cells more than HT29 and SW620 due to the high expression of EGFR by HCT116 cells. To confirm that the internalization is a receptor mediated process, we pre-treated HCT116 cells with an excess of free GE11, which resulted in reduced internalization of GE11-PEO-b-PBCL-Dil. Finally, GE11-PEO-b-PCCL-A12B4C50 and GE11-PEO-b-PBCL-A83B4C63 were able to sensitize HCT116 cell to radiation and irinotecan in a similar manner to that of the unmodified micelles. This was despite higher uptake of GE11 modified micelles compared to plain micelles by HCT116 cells, as determined in our earlier cell uptake studies and is most likely due to the release of encapsulated drug from the micellar carrier during the incubation with the cells (9-14 days) undermining the effect of GE11 modification. Collectively, these data indicate that GE11 is a suitable ligand to target the over-expression of EFGR in cancer cells, and that such conjugated polymeric micelles may provide PNKP inhibitors with selective targeting for future in vivo studies.

Since the discovery of a synthetic lethal partnership between PARP1 and BRCA1/2, synthetic lethality has become the most desired strategy clinically for targeting DNA repair inhibition (51-54). Previously, in our lab, genetic screening for possible synthetic lethal partners with PNKP led to the identification of two tumour suppressor proteins, SHP-1 and PTEN (33, 34). We have shown in this report that PEO-b-PCCL-A12B4C50 and PEO-b-PBCL-A83B4C63 cause synthetic lethality in HCT116 PTEN−/− cells (FIG. 23). It was also observed that A83B4C63 is more specifically toxic to PTEN-deficient cells than A12B4C50, which showed toxicity to HCT116 PTEN+/+ indicating a possible synthetic sickness relationship. These data are in line with what was observed in the MTS study, which showed greater toxicity of A12B4C50 than A83B4C63. Applying this approach could allow us to use PNKP inhibitors as a single agent selectively targeting PTEN-deficient tumors.

In conclusion, we have demonstrated that potent and specific nano-encapsulated PNKP phosphatase inhibitors could further enhance radiation and irinotecan therapy in colorectal cancer cells, and that PTEN-deficient tumors may be susceptible to encapsulated PNKP inhibitors administered as single therapeutic agents.

Abbreviations

BER Base excision repair
Dil 1,1'-Dioctadecyl-3,3,3',3'-tetramethylindocarbocyanine perchlorate
DLS Dynamic light scattering
EGFR Epidermal growth factor receptor
EPR Enhanced permeability and retention
HPLC High-performance liquid chromatography
Neil Endonuclease VIII-like
PDI Polydispersity index
PEO-b-PBCL Poly(ethylene oxide)-b-poly(α-benzyl carboxylate-ε-caprolactone)
PEO-b-PCL Poly(ethylene oxide)-b-poly(ε-caprolactone)
PEO-b-PCCL Poly(ethylene oxide)-b-poly(α-carboxylate-ε-caprolactone)
PNKP Polynucleotide kinase/phosphatase
PTEN Phosphatase and tensin homolog
ROS Reactive oxygen species
TEM Transmission electron microscopy
Top I Topoisomerase I Example 2 References 1. Jilani A, Ramotar D, Slack C, Ong C, Yang X M, Scherer S W, et al. Molecular cloning of the human gene, PNKP, encoding a polynucleotide kinase 3'-phosphatase and evidence for its role in repair of DNA strand breaks caused by oxidative damage. J Biol Chem 1999; 274:24176-86.
2. Karimi-Busheri F, Daly G, Robins P, Canas B, Pappin D J, Sgouros J, et al. Molecular characterization of a human DNA kinase. J Biol Chem 1999; 274:24187-94.
3. Bernstein N K, Williams R S, Rakovszky M L, Cui D, Green R, Karimi-Busheri F, et al. The molecular architecture of the mammalian DNA repair enzyme, polynucleotide kinase. Mol Cell 2005; 17:657-70.
4. Weinfeld M, Mani R S, Abdou I, Aceytuno R D, Glover J N. Tidying up loose ends: The role of polynucleotide kinase/phosphatase in DNA strand break repair. Trends Biochem Sci 2011; 36:262-71.
5. Andres S N, Schellenberg M J, Wallace B D, Tumbale P, Williams R S. Recognition and repair of chemically heterogeneous structures at DNA ends. Environ Mol Mutagen 2015; 56:1-21.
6. Shire Z, Jiang B, Abdou I, Weinfeld M. Processing strand break termini in the DNA single-strand break repair pathway. In: Wilson III DM, editor. The Base excision repair pathway: Molecular Mechanisms and Role in Disease Development and Therapeutic Design. London: World Scientific; 2017. p. 281-321.
7. Rasouli-Nia A, Karimi-Busheri F, Weinfeld M. Stable down-regulation of human polynucleotide kinase enhances spontaneous mutation frequency and sensitizes cells to genotoxic agents. Proc Natl Acad Sci USA 2004; 101:6905-10.
8. Freschauf G K, Karimi-Busheri F, Ulaczyk-Lesanko A, Mereniuk T R, Ahrens A, Koshy J M, et al. Identification of a small molecule inhibitor of the human DNA repair enzyme polynucleotide kinase/phosphatase. Cancer Res 2009; 69:7739-46.
9. Freschauf G K, Mani R S, Mereniuk T R, Fanta M, Virgen C A, Dianov G L, et al. Mechanism of action of an imidopiperidine inhibitor of human polynucleotide kinase/phosphatase. J Biol Chem 2010; 285:2351-60.
10. Adams M L, Lavasanifar A, Kwon G S. Amphiphilic block copolymers for drug delivery. J Pharm Sci 2003; 92:1343-55.
11. Perez-Herrero E, Fernandez-Medarde A. Advanced targeted therapies in cancer: Drug nanocarriers, the future of chemotherapy. Eur J Pharm Biopharm 2015; 93:52-79.
12. Houdaihed L, Evans J C, Allen C. Overcoming the road blocks: Advancement of block copolymer micelles for cancer therapy in the clinic. Mol Pharm. 2017; 8:2503-2517
13. Matsumura Y. Polymeric micellar delivery systems in oncology. Jpn J Clin Oncol 2008; 38:793-802.
14. Lu Y, Park K. Polymeric micelles and alternative nanonized delivery vehicles for poorly soluble drugs. Int J Pharm 2013; 453:198-214.
15. Garg S M, Vakili M R, Lavasanifar A. Polymeric micelles based on poly(ethylene oxide) and alpha-carbon substituted poly(varepsilon-caprolactone): An in vitro study on the effect of core forming block on polymeric micellar stability, biocompatibility, and immunogenicity. Colloids Surf B Biointerfaces 2015; 132:161-70.
16. Nishiyama N, Matsumura Y, Kataoka K. Development of polymeric micelles for targeting intractable cancers. Cancer Sci 2016; 107:867-74.
17. Yousefpour Marzbali M, Yari Khosroushahi A. Polymeric micelles as mighty nanocarriers for cancer gene therapy: A review. Cancer Chemother Pharmacol 2017; 79:637-49.
18. Zhang Y, Ren T, Gou J, Zhang L, Tao X, Tian B, et al. Strategies for improving the payload of small molecular drugs in polymeric micelles. J Control Release 2017; 261:352-66.
19. Honary S, Lavasanifar A. The effect of self-assembly conditions on the size of di- and tri-block copolymer micelles: Solicitation from response surface methodology. Pharm Dev Technol 2015; 20:957-65.
20. Talelli M, Barz M, Rijcken C J, Kiessling F, Hennink W E, Lammers T. Core-crosslinked polymeric micelles: Principles, preparation, biomedical applications and clinical translation. Nano Today 2015; 10:93-117.
21. Xiong X B, Falamarzian A, Garg S M, Lavasanifar A. Engineering of amphiphilic block copolymers for polymeric micellar drug and gene delivery. J Control Release 2011; 155:248-61.
22. Srinivasan M, Rajabi M, Mousa S A. Multifunctional nanomaterials and their applications in drug delivery and cancer therapy. Nanomaterials (Basel) 2015; 5:1690-703.
23. Dai W, Wang X, Song G, Liu T, He B, Zhang H, et al. Combination antitumor therapy with targeted dual-nanomedicines. Adv Drug Deliv Rev 2017; pii: S0169-409X (17)30031-5.
24. Hsu J L, Hung M C. The role of HER2, EGFR, and other receptor tyrosine kinases in breast cancer. Cancer Metastasis Rev 2016; 35:575-88.
25. Hung M S, Chen I C, Lin P Y, Lung J H, Li Y C, Lin Y C, et al. Epidermal growth factor receptor mutation enhances expression of vascular endothelial growth factor in lung cancer. Oncol Lett 2016; 12:4598-604.
26. Marmol I, Sanchez-de-Diego C, Pradilla Dieste A, Cerrada E, Rodriguez Yoldi M J. Colorectal carcinoma: A general overview and future perspectives in colorectal cancer. Int J Mol Sci 2017; 18:10.3390/ijmsl 8010197.
27. Tang H, Chen X, Rui M, Sun W, Chen J, Peng J, et al. Effects of surface displayed targeting ligand GE11 on liposome distribution and extravasation in tumor. Mol Pharm 2014; 11:3242-50.
28. Colzani B, Speranza G, Dorati R, Conti B, Modena T, Bruni G, et al. Design of smart GE11-PLGA/PEG-PLGA blend nanoparticulate platforms for parenteral administration of hydrophilic macromolecular drugs: Synthesis, preparation and in vitro/ex vivo characterization. Int J Pharm 2016; 511:1112-23.
29. Hu D, Mezghrani O, Zhang L, Chen Y, Ke X, Ci T. GE11 peptide modified and reduction-responsive hyaluronic acid-based nanoparticles induced higher efficacy of doxorubicin for breast carcinoma therapy. Int J Nanomedicine 2016; 11:5125-47.
30. Fan M, Yang D, Liang X, Ao J, Li Z, Wang H, et al. Design and biological activity of epidermal growth factor receptor-targeted peptide doxorubicin conjugate. Biomed Pharmacother 2015; 70:268-73.
31. Nijman S M. Synthetic lethality: General principles, utility and detection using genetic screens in human cells. FEBS Lett 2011; 585:1-6.
32. Leung A W, de Silva T, Bally M B, Lockwood W W. Synthetic lethality in lung cancer and translation to clinical therapies. Mol Cancer 2016; 15:61.
33. Mereniuk T R, Maranchuk R A, Schindler A, Penner-Chea J, Freschauf G K, Hegazy S, et al. Genetic screening for synthetic lethal partners of polynucleotide kinase/phosphatase: Potential for targeting SHP-1-depleted cancers. Cancer Res 2012; 72:5934-44.
34. Mereniuk T R, El Gendy M A, Mendes-Pereira A M, Lord C J, Ghosh S, Foley E, et al. Synthetic lethal targeting of PTEN-deficient cancer cells using selective disruption of polynucleotide kinase/phosphatase. Mol Cancer Ther 2013; 12:2135-44.
35. Liu Y, Hu X, Han C, Wang L, Zhang X, He X, et al. Targeting tumor suppressor genes for cancer therapy. Bioessays 2015; 37:1277-86.
36. Jackson R A, Chen E S. Synthetic lethal approaches for assessing combinatorial efficacy of chemotherapeutic drugs. Pharmacol Ther 2016; 162:69-85.

37. Fanta M, Zhang H, Bernstein N, Glover M, Karimi-Busheri F, Weinfeld M. Production, characterization, and epitope mapping of monoclonal antibodies against human polydeoxyribonucleotide kinase. Hybridoma 2001; 20:237-42.
38. Toure B B, Hoveyda H R, Tailor J, Ulaczyk-Lesanko A, Hall D G. A three-component reaction for diversity-oriented synthesis of polysubstituted piperidines: Solution and solid-phase optimization of the first tandem aza[4+2]/allylboration. Chemistry 2003; 9:466-74.
39. Aliabadi H M, Mahmud A, Sharifabadi A D, Lavasanifar A. Micelles of methoxy poly(ethylene oxide)-b-poly(epsilon-caprolactone) as vehicles for the solubilization and controlled delivery of cyclosporine A. J Control Release 2005; 104:301-11.
40. Mahmud A, Lavasanifar A. The effect of block copolymer structure on the internalization of polymeric micelles by human breast cancer cells. Colloids Surf B Biointerfaces 2005; 45:82-9.
41. Garg S M, Vakili M R, Lavasanifar A. Polymeric micelles based on poly(ethylene oxide) and alpha-carbon substituted poly(varepsilon-caprolactone): An in vitro study on the effect of core forming block on polymeric micellar stability, biocompatibility, and immunogenicity. Colloids Surf B Biointerfaces 2015; 132:161-70.
42. Xiong X B, Mahmud A, Uludag H, Lavasanifar A. Conjugation of arginine-glycine-aspartic acid peptides to poly(ethylene oxide)-b-poly(epsilon-caprolactone) micelles for enhanced intracellular drug delivery to metastatic tumor cells. Biomacromolecules 2007; 8:874-84.
43. Lavasanifar A, Samuel J, Kwon G S. The effect of fatty acid substitution on the in vitro release of amphotericin B from micelles composed of poly(ethylene oxide)-block-poly(N-hexyl stearate-L-aspartamide). J Control Release 2002; 79:165-72.
44. Mahmud A, Xiong X-, Lavasanifar A. Novel self-associating POly(ethylene oxide)-block-poly(ε-caprolactone) block copolymers with functional side groups on the polyester block for drug delivery. Macromolecules 2006; 39:9419-28.
45. Mathews A S, Ahmed S, Shahin M, Lavasanifar A, Kaur K. Peptide modified polymeric micelles specific for breast cancer cells. Bioconjug Chem 2013; 24:560-70.
46. Balin-Gauthier D, Delord J P, Rochaix P, Mallard V, Thomas F, Hennebelle I, et al. In vivo and in vitro antitumor activity of oxaliplatin in combination with cetuximab in human colorectal tumor cell lines expressing different level of EGFR. Cancer Chemother Pharmacol 2006; 57:709-18.
47. Curtin N J. Inhibiting the DNA damage response as a therapeutic manoeuvre in cancer. Br J Pharmacol 2013; 169:1745-65.
48. Freschauf G K, Karimi-Busheri F, Ulaczyk-Lesanko A, Mereniuk T R, Ahrens A, Koshy J M, et al. Identification of a small molecule inhibitor of the human DNA repair enzyme polynucleotide kinase/phosphatase. Cancer Res 2009; 69:7739-46.
49. Freschauf G K, Mani R S, Mereniuk T R, Fanta M, Virgen C A, Dianov G L, et al. Mechanism of action of an imidopiperidine inhibitor of human polynucleotide kinase/phosphatase. J Biol Chem 2010; 285:2351-60.
50. Ulbrich K, Hola K, Subr V, Bakandritsos A, Tucek J, Zboril R. Targeted drug delivery with polymers and magnetic nanoparticles: Covalent and noncovalent approaches, release control, and clinical studies. Chem Rev 2016; 116:5338-431.
51. Stover E H, Konstantinopoulos P A, Matulonis U A, Swisher E M. Biomarkers of response and resistance to DNA repair targeted therapies. Clin Cancer Res 2016; 22:5651-60.
52. Brown J S, O'Carrigan B, Jackson S P, Yap T A. Targeting DNA repair in cancer: Beyond PARP inhibitors. Cancer Discov 2017; 7:20-37.
53. Srivas R, Shen J P, Yang C C, Sun S M, Li J, Gross A M, et al. A network of conserved synthetic lethal interactions for exploration of precision cancer therapy. Mol Cell 2016; 63:514-25.
54. Gavande N S, VanderVere-Carozza P S, Hinshaw H D, Jalal S I, Sears C R, Pawelczak K S, et al. DNA repair targeted therapy: The past or future of cancer treatment?Pharmacol Ther 2016; 160:65-83.

The embodiments described herein are intended to be examples only. Alterations, modifications and variations can be effected to the particular embodiments by those of skill in the art. The scope of the claims should not be limited by the particular embodiments set forth herein, but should be construed in a manner consistent with the specification as a whole.

All publications, patents and patent applications mentioned in this Specification are indicative of the level of skill those skilled in the art to which this invention pertains and are herein incorporated by reference to the same extent as if each individual publication patent, or patent application was specifically and individually indicated to be incorporated by reference.

The invention being thus described, it will be obvious that the same may be varied in many ways. Such variations are not to be regarded as a departure from the spirit and scope of the invention, and all such modification as would be obvious to one skilled in the art are intended to be included within the scope of the following claims.

What is claimed is:

1. A compound of formula (IIb)

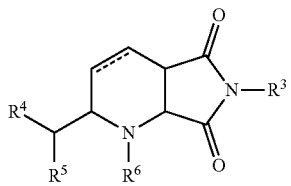

a stereoisomer, a racemate, a tautomer, a pharmaceutically acceptable salt, a solvate, or a functional derivative thereof, wherein

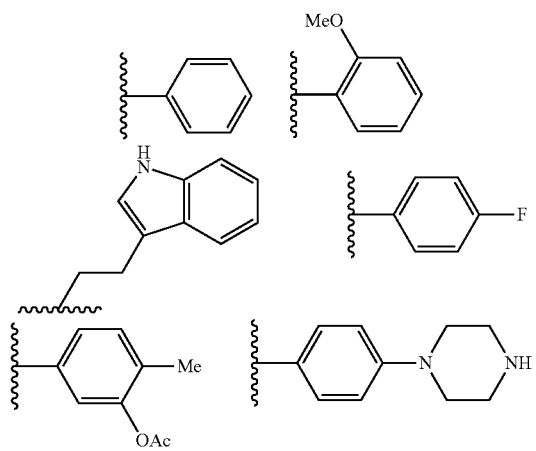

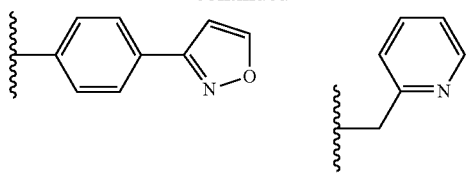

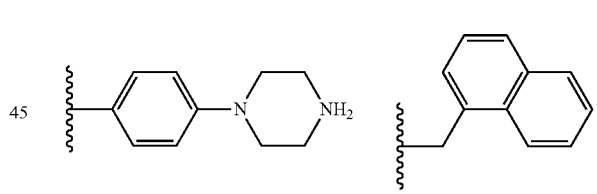

each of which is optionally substituted;

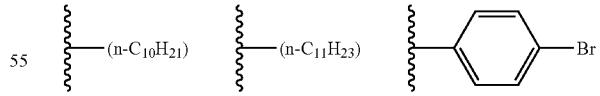

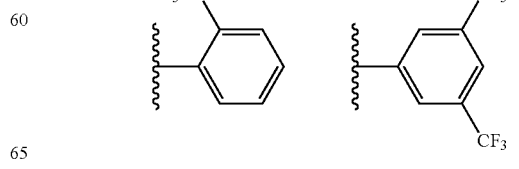

each of which is optionally substituted;
R⁵ is OH;
R⁶ is (NR¹R²), where R¹ and R² together are

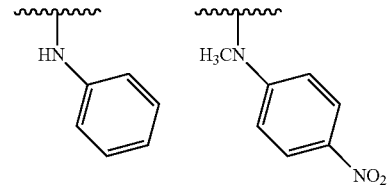

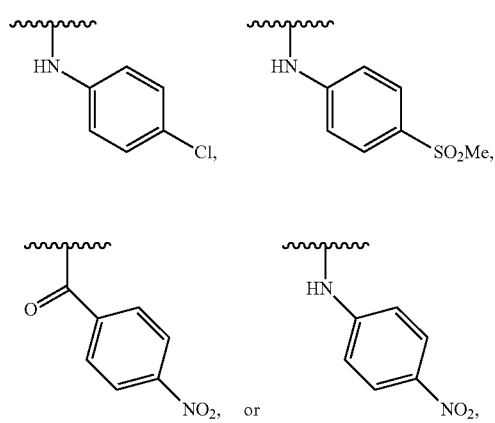

where the dashed line represents an optional double bond; and with the proviso that, when the double bond is present and
(i) R³ is —C₆H₅, R⁵ is —OH, and R⁶ is (NR¹R²), where R¹ is H and R² is —C₆H₄-4-NO₂, R⁴ is not —C₁₀H₂₁;
(ii) R³ is —C₆H₅, R⁵ is —OH, and R⁶ is (NR¹R²), where R¹ is H and R² is —C₆H₄-4-NO₂, R⁴ is not —C₆H₅;
(iii) R³ is —C₆H₅, R⁵ is —OH, and R⁶ is (NR¹R²), where R¹ is H and R² is —C₆H₄-4-NO₂, R⁴ is not —C₆H₂-3,4,5-(OCH₃)₃;
(iv) R⁵ is —OH, R⁶ is (NR¹R²), where R¹ is H and R² is —BOC, and R⁴ is —CH(C₆H₅)₂, R³ is not —CH₃; or
(v) R⁵ is —OH, R⁶ is (NR¹R²), where R¹ is H and R² is —C₆H₅, and R⁴ is -(2-thienyl), R³ is not —CH₃.

2. A compound of formula (Va)

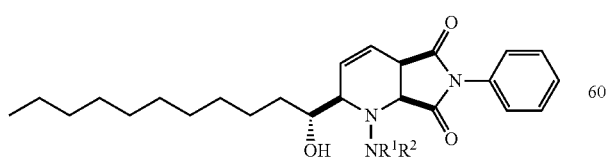

a stereoisomer, a racemate, a tautomer, a pharmaceutically acceptable salt, a solvate, or a functional derivative thereof, wherein
R¹ and R² together are

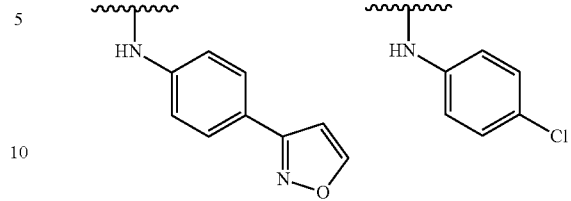

3. The compound of claim 2, having the formula (Vb)

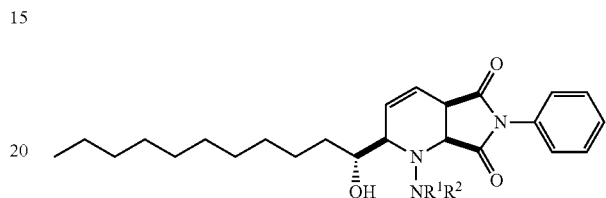

a stereoisomer, a racemate, a tautomer, a pharmaceutically acceptable salt, a solvate, or a functional derivative thereof,
wherein
R¹ and R² together are

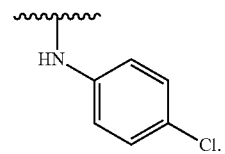 [SMILES: *Nc1ccc(Cl)cc1]

4. A compound having the structure

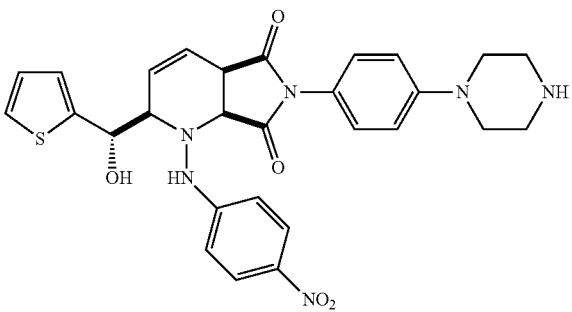

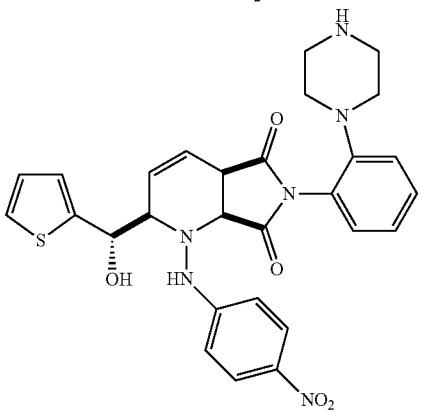

155
-continued
156
-continued
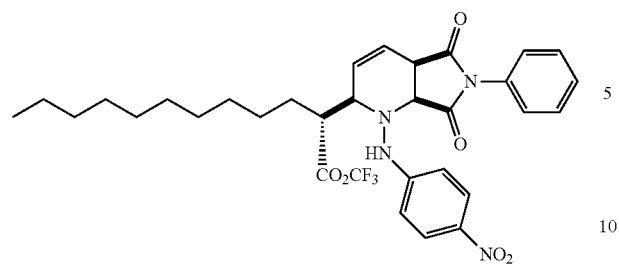
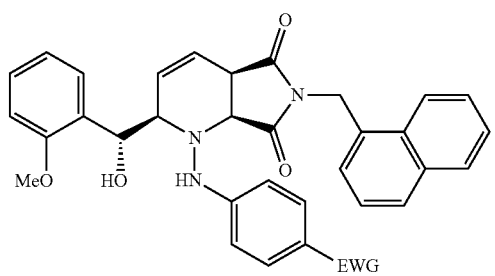
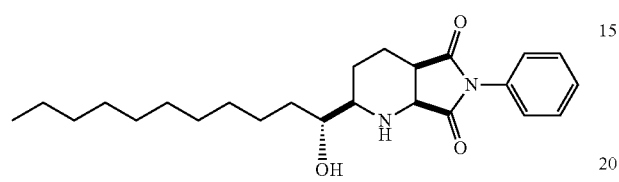
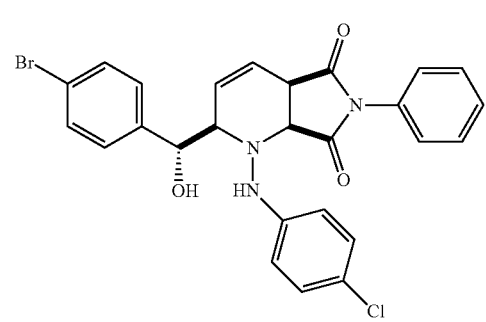
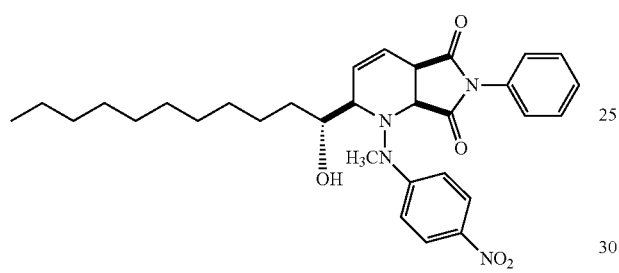
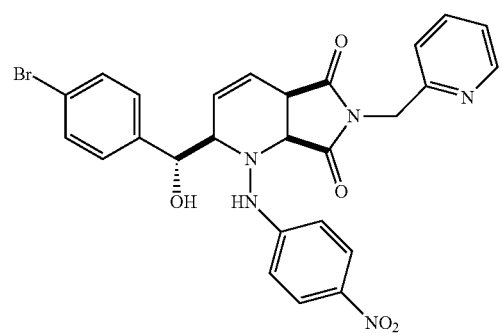
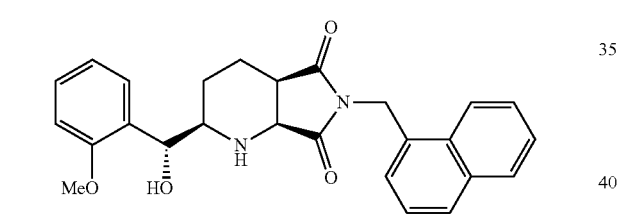
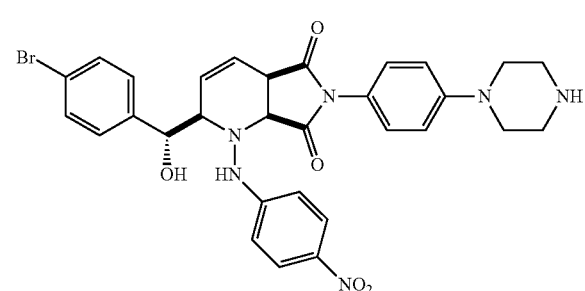
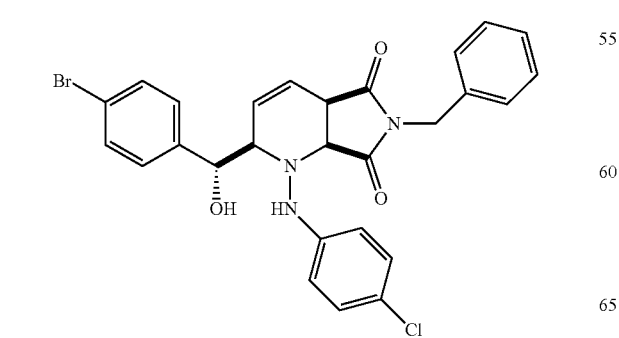
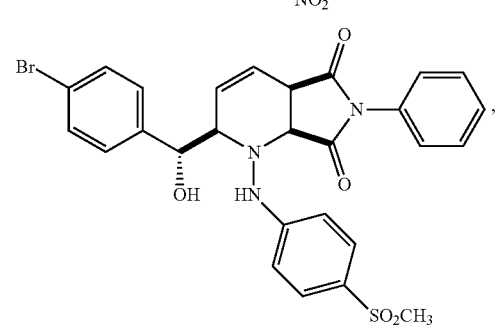

157
-continued
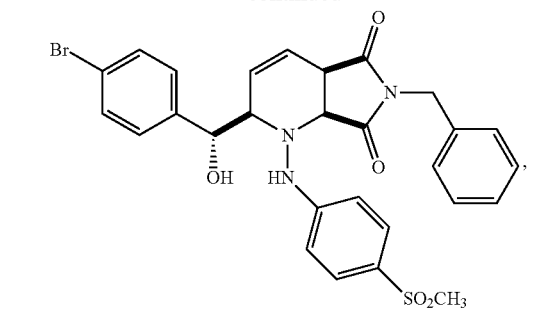
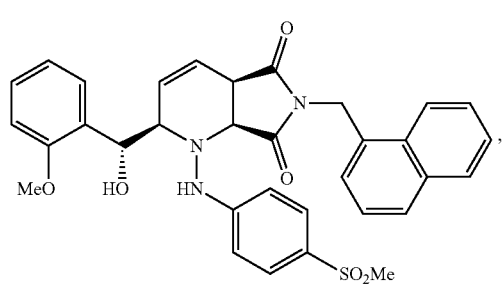
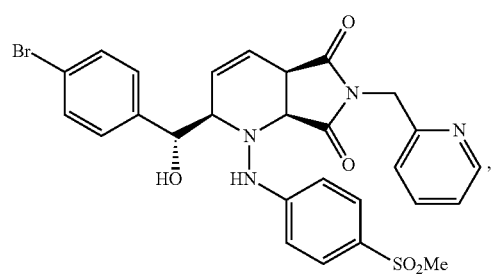
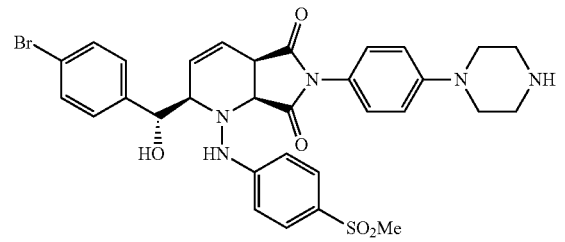
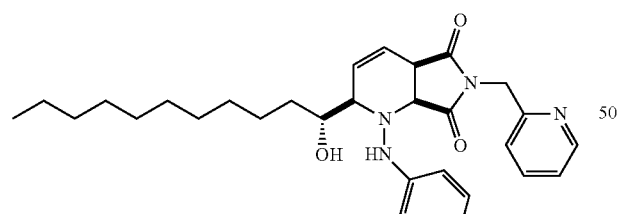
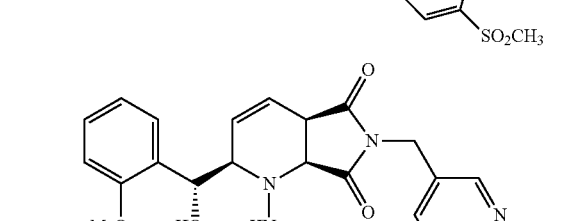
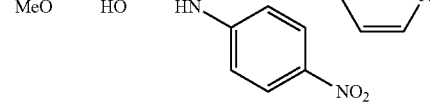
158
-continued
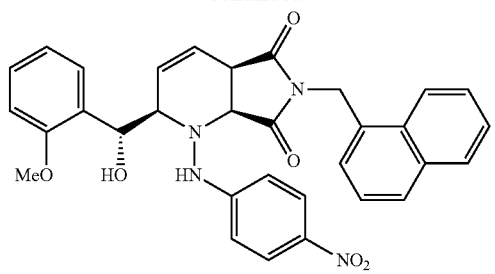
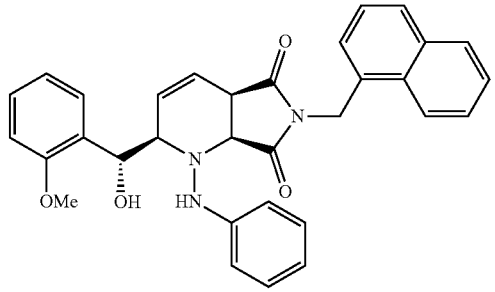
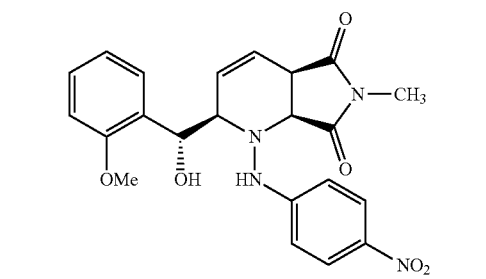
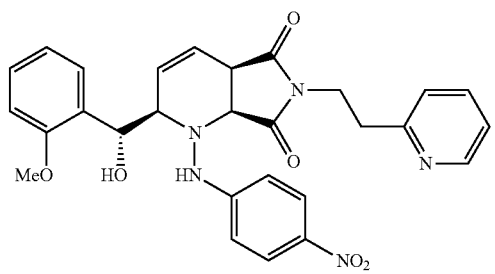
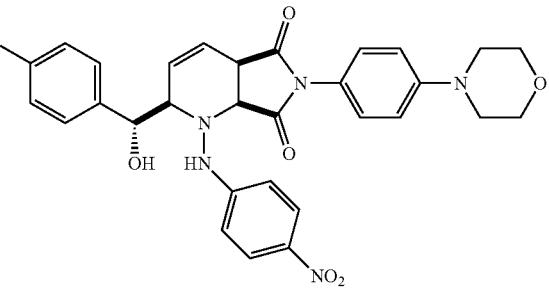
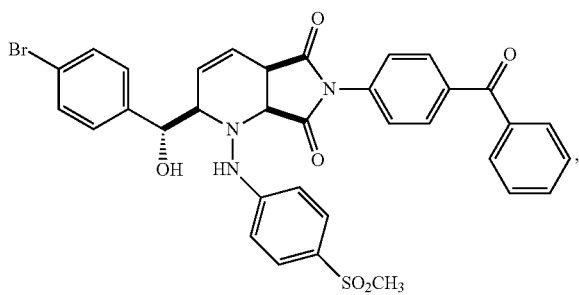

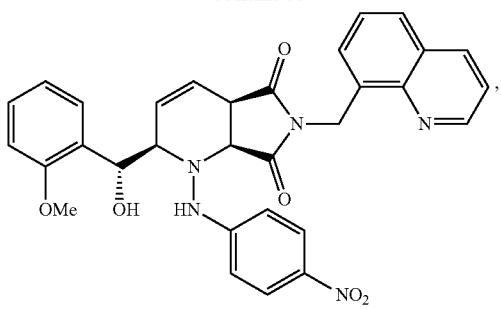

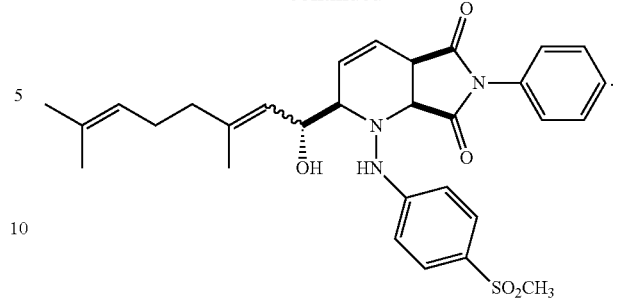

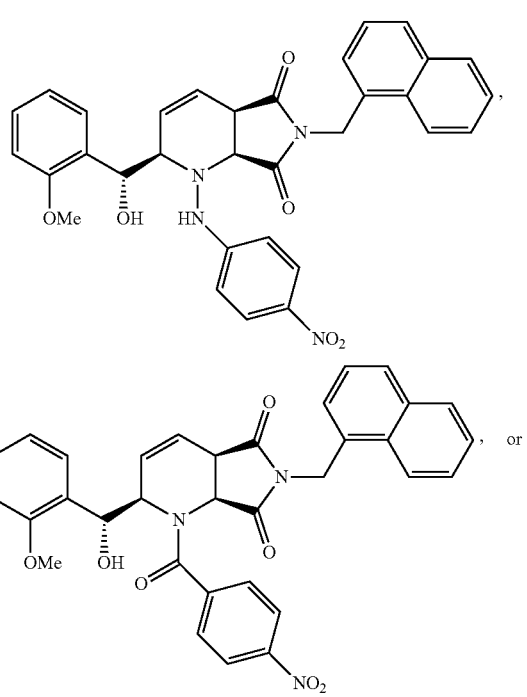

5. A pharmaceutical composition comprising a micelle, a nano-carrier, a nanoparticle, or a lipid vesicle and a compound of claim 1.

6. The pharmaceutical composition of claim 5, wherein said micelle comprises PEO-b-PBCL, PEO-PCL, PEO-PDLA, and/or PEO-PLGA.

7. The pharmaceutical composition of claim 6, wherein said micelle further comprises a targeting ligand.

8. The pharmaceutical composition of claim 7, wherein said targeting ligand is an antibody, a polypeptide, a small molecule, or an aptamer.

9. The pharmaceutical composition of claim 7, wherein said targeting ligand comprises or consists of a polypeptide having the amino acid sequence of SEQ ID NO: 3.

10. The pharmaceutical composition of claim 5, further comprising a topoisomerase I inhibitor.

11. A method of chemosensitizing or radio sensitizing a cancer cell in a mammal in need of chemotherapy or radiation therapy, comprising: administering to said mammal a compound of claim 1.

12. The method of claim 11, wherein said chemotherapy is treatment with a topoisomerase I inhibitor.

13. The method of claim 12, wherein said topoisomerase I inhibitor is irinotecan.

14. The method of claim 11, wherein said radiation therapy is external radiation therapy, internal radiation therapy or systemic radiation therapy.

15. The method of claim 11, wherein said patient has or is suspected of having a colorectal cancer.

\* \* \* \* \*

UNITED STATES PATENT AND TRADEMARK OFFICE
CERTIFICATE OF CORRECTION

PATENT NO. : 11,325,905 B2
APPLICATION NO. : 16/500885
DATED : May 10, 2022
INVENTOR(S) : Dennis Hall et al.

It is certified that error appears in the above-identified patent and that said Letters Patent is hereby corrected as shown below:

In the Specification

Column 2, Line 25, replace "(PARR)" with --PARP--

Column 58, Line 17, replace "cancer" with --cancer.--

Column 62, Line 6, replace "viability" with --viability.--

Column 63, Line 23, replace "cancer" with --cancer.--

Column 125, Line 50, replace "563.1931." with --563.1937.--

Signed and Sealed this
Fourth Day of October, 2022

Katherine Kelly Vidal
*Director of the United States Patent and Trademark Office*

SEQUENCE LISTING

<160> NUMBER OF SEQ ID NOS: 3

<210> SEQ ID NO 1
<211> LENGTH: 47
<212> TYPE: DNA
<213> ORGANISM: Artificial Sequence
<220> FEATURE:
<223> OTHER INFORMATION: UT Sequence
<220> FEATURE:
<221> NAME/KEY: phosphate on the recessed 3'-terminus
<222> LOCATION: (47)..(47)

<400> SEQUENCE: 1

```
ctctctctct ctctctctct ccgggagttg cgcacctaaa gggtgcg          47

<210> SEQ ID NO 2
<211> LENGTH: 30
<212> TYPE: DNA
<213> ORGANISM: Artificial Sequence
<220> FEATURE:
<223> OTHER INFORMATION: U-MB Sequence
<220> FEATURE:
<221> NAME/KEY: 5'-fluorescein (FAM)
<222> LOCATION: (1)..(1)
<220> FEATURE:
<221> NAME/KEY: 3' dimethylaminoazobenzenesulfonic acid (DAB)
<222> LOCATION: (30)..(30)

<400> SEQUENCE: 2
cccggagaga gagagagaga gagagccggg                              30

<210> SEQ ID NO 3
<211> LENGTH: 12
<212> TYPE: PRT
<213> ORGANISM: Artificial Sequence
<220> FEATURE:
<223> OTHER INFORMATION: synthetic peptide

<400> SEQUENCE: 3

Tyr His Trp Tyr Gly Tyr Thr Pro Gln Asn Val Ile
1               5                   10
```